US008653072B2

(12) United States Patent
Rhonnstad et al.

(10) Patent No.: US 8,653,072 B2
(45) Date of Patent: Feb. 18, 2014

(54) ESTROGEN RECEPTOR LIGANDS

(71) Applicants: Patrik Rhonnstad, Kungsor (SE); Elisabet Kallin, Tullinge (SE); Theresa Apelqvist, Grodinge (SE); Mattias Wennerstal, Hagersten (SE); Aiping Cheng, Huddinge (SE)

(72) Inventors: Patrik Rhonnstad, Kungsor (SE); Elisabet Kallin, Tullinge (SE); Theresa Apelqvist, Grodinge (SE); Mattias Wennerstal, Hagersten (SE); Aiping Cheng, Huddinge (SE)

(73) Assignee: Karo Bio AB, Huddinge (SE)

(*) Notice: Subject to any disclaimer, the term of this patent is extended or adjusted under 35 U.S.C. 154(b) by 0 days.

(21) Appl. No.: 13/739,124

(22) Filed: Jan. 11, 2013

(65) Prior Publication Data
US 2013/0131061 A1    May 23, 2013

Related U.S. Application Data

(62) Division of application No. 12/736,438, filed as application No. PCT/EP2009/054521 on Apr. 16, 2009, now Pat. No. 8,367,665.

(30) Foreign Application Priority Data

Apr. 16, 2008  (GB) .................................. 0806944.5
Dec. 22, 2008  (GB) .................................. 0823367.8

(51) Int. Cl.
*A61K 31/404*  (2006.01)
*A61K 31/4155* (2006.01)
*A61K 31/4178* (2006.01)
*A61K 31/4196* (2006.01)
*A61K 31/4245* (2006.01)
*A61K 31/42*   (2006.01)
*A61K 31/427*  (2006.01)
*A61K 31/4439* (2006.01)
*A61K 31/5377* (2006.01)
*A61K 31/454*  (2006.01)

(52) U.S. Cl.
USPC ........ 514/235.2; 514/339; 514/365; 514/378; 514/383; 514/397; 514/406; 514/414; 514/415; 514/418; 514/419

(58) Field of Classification Search
None
See application file for complete search history.

(56) References Cited

U.S. PATENT DOCUMENTS 3,799,943 A    3/1974   Bell et al.
3,878,225 A    4/1975   Allen et al.
4,056,624 A   11/1977   Lassman et al.
6,147,105 A   11/2000   Von Angerer et al.
7,772,271 B2   8/2010   Karp et al.
7,781,478 B2   8/2010   Karp et al.
7,868,037 B2   1/2011   Karp et al.
2003/0220377 A1 11/2003  Chesworth
2008/0096928 A9  4/2008  Karp et al.
2010/0292187 A1 11/2010  Karp et al.
2010/0305100 A1 12/2010  Karp et al.

FOREIGN PATENT DOCUMENTS

| DE | 27 21 085 A1 | 5/1977 |
| EP | 0 802 183 A1 | 10/1997 |
| JP | 2008-195642 | 8/2008 |
| JP | 2009-105642 | 8/2008 |
| WO | WO 96/03375 A1 | 2/1996 |
| WO | WO99/59581 | 11/1999 |
| WO | WO 00/00487 A1 | 1/2000 |
| WO | WO 00/51983 A1 | 9/2000 |
| WO | WO 00/59902 A2 | 10/2000 |
| WO | 2004052854 A2 | 6/2004 |
| WO | WO 2005/018636 A1 | 3/2005 |
| WO | WO 2007/047775 A1 | 4/2007 |
| WO | WO 2008/043567 A1 | 4/2008 |

OTHER PUBLICATIONS

Wang et al., J. Immunol. (2007) 179, pp. 5958-5965.*
Mewshaw, Richard E. et al., "ERβ ligands. Part 5: Synthesis and structure-activity relationships of a series 4'-hydroxyphenyl-aryl-carbaldehyde oxime derivatives," Bioorganic & Medicinal Chemistry Letters, vol. 17, pp. 902-906 (2007).
Narasimhan, S. et al., "A New Reaction of o-Benzoquinone with N-Acetyl-$_{DL}$-Tryptophan (a 3-Substituted Indole) & Characterisation of the Product," Indian Journal of Biochemistry & Biophysics, vol. 23, pp. 215-219 (1986).
Bell, Malcolm R. et al., "Basic Etheres of 1-(p-Hydroxyphenyo)-2-phenyl-1,2,3,4-tetrahydroquinoline and 1-(p-Hydroxyphenyl)-2-phenylindole. Antifertility Agents," Journal of Medicinal Chemistry, vol. 13, No. 4, pp. 664-668 (1970).

* cited by examiner

*Primary Examiner* — Joseph McKane
(74) *Attorney, Agent, or Firm* — Cantor Colburn LLP

(57) ABSTRACT

The invention provides a compound of formula (I) or a pharmaceutically acceptable ester, amide, carbamate, solvate or salt thereof, including a salt of such an ester, amide or carbamate, and a solvate of such an ester, amide, carbamate or salt. The invention also provides also provides the use of such compounds in the treatment or prophylaxis of a condition associated with a disease or disorder associated with estrogen receptor activity, wherein $R^1$, $R^2$, $R^3$, $R^5$ and $R^6$ are as defined in the specification.

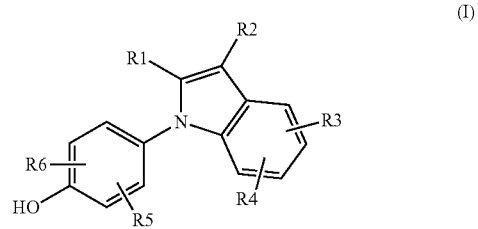

(I)

19 Claims, No Drawings

ESTROGEN RECEPTOR LIGANDS

CROSS-REFERENCE TO RELATED APPLICATIONS

This application is a Divisional of U.S. patent application Ser. No. 12/736,438 filed Nov. 4, 2010, now U.S. Pat. No. 8,367,665 issued Feb. 5, 2013, which is a U.S. National Stage application of International Patent Application No. PCT/EP2009/054521 filed Apr. 16, 2009, which claims the benefit of GB 0806944.5 filed Apr. 16, 2008 and GB 0823367.8 filed Dec. 22, 2008. All of these applications are incorporated by reference in their entireties.

FIELD OF INVENTION

This invention relates to compounds which are estrogen receptor ligands and are preferably selective for the estrogen receptor β isoform, to methods of preparing such compounds and to methods for using such compounds in treatment of diseases related to the estrogen receptor such as depressive disorders, anxiety disorders, Alzheimer's disease, cognitive disorders, osteoporosis, elevated blood triglyceride levels, atherosclerosis, endometriosis, urinary incontinence, autoimmune disease, and cancer of the lung, colon, breast, uterus and prostate.

BACKGROUND OF INVENTION

The estrogen receptor (ER) is a ligand activated mammalian transcription factor involved in the up and down regulation of gene expression. The natural hormone for the estrogen receptor is β-17-estradiol (E2) and closely related metabolites. Binding of estradiol to the estrogen receptor causes a dimerization of the receptor and the dimer in turn binds to estrogen response elements (ERE's) on DNA. The ER/DNA complex recruits other transcription factors responsible for the transcription of DNA downstream from the ERE into mRNA which is eventually translated into protein. Alternatively the interaction of ER with DNA may be indirect through the intermediacy of other transcription factors, most notably fos and jun. Since the expression of a large number of genes is regulated by the estrogen receptor and since the estrogen receptor is expressed in many cell types, modulation of the estrogen receptor through binding of either natural hormones or synthetic ER ligands can have profound effects on the physiology and pathophysiology of the organism.

Historically it has been believed there was only one estrogen receptor. However a second subtype (ER-β) has been discovered. While both the "classical" ER-α and the more recently discovered ER-β are widely distributed in different tissues, they nevertheless display markedly different cell type and tissue distributions. Therefore synthetic ligands which are either ER-α or ER-β selective may preserve the beneficial effects of estrogen while reducing the risk of undesirable side effects.

Estrogens are critical for sexual development in females. In addition, estrogens play an important role in maintaining bone density, regulation of blood lipid levels, and appear to have neuroprotective effects. Consequently decreased estrogen production in post-menopausal women is associated with a number of diseases such as osteoporosis, atherosclerosis, depression and cognitive disorders. Conversely certain types of proliferative diseases such as breast and uterine cancer and endometriosis are stimulated by estrogens and therefore anti-estrogens (i.e., estrogen antagonists) have utility in the prevention and treatment of these types of disorders.

The efficacy of the natural estrogen, 17β-estradiol, for the treatment of various forms of depressive illness has also been demonstrated and it has been suggested that the anti-depressant activity of estrogen may be mediated via regulation of tryptophan hydroxylase activity and subsequent serotonin synthesis (See, e.g., Lu N Z, Shlaes T A, Cundlah C, Dziennis S E, Lyle R E, Bethea C L, "Ovarian steroid action on tryptophan hydroxylase protein and serotonin compared to localization of ovarian steroid receptors in midbrain of guinea pigs." Endocrine 11:257-267, 1999). The pleiotropic nature of natural estrogen precludes its widespread, more chronic use due to the increased risk of proliferative effects on breast, uterine and ovarian tissues. The identification of the estrogen receptor, ERβ, has provided a means by which to identify more selective estrogen agents which have the desired anti-depressant activity in the absence of the proliferative effects which are mediated by ERα. Thus, it has been shown that therapeutic agents having ERβ-selectivity are potentially effective in the treatment of depression.

What is needed in the art are compounds that can produce the same positive responses as estrogen replacement therapy without the negative side effects. Also needed are estrogen-like compounds that exert selective effects on different tissues of the body.

WO 2006/019831 discloses certain indole derivatives having utility in the prevention or treatment of Hepatitis C viral infection. WO 2005/018636 discloses certain indole derivative having estrogen receptor modulator activity, all said indoles being oximes.

The compounds of the present invention are ligands for estrogen receptors and as such may be useful for treatment or prevention of a variety of conditions related to estrogen functioning including bone loss, bone fractures, osteoporosis, cartilage degeneration, endometriosis, uterine fibroid disease, hot flashes, increased levels of LDL cholesterol, cardiovascular disease, impairment of cognitive functioning, age-related mild cognitive impairment, cerebral degenerative disorders, restenosis, gynecomastia, vascular smooth muscle cell proliferation, obesity, incontinence, anxiety, depression, peri-menopausal depression, post-partum depression, premenstrual syndrome, manic depression, dementia, obsessive compulsive behavior, attention deficit disorder, attention deficit hyperactivity disorder, sleep disorders, irritability, impulsivity, anger management, hearing disorders, multiple sclerosis, Parkinson's disease, Alzheimer's disease, Huntington's disease, amyotrophic lateral sclerosis, spinal cord injury, stroke, autoimmune disease, inflammation, IBD, IBS, sexual dysfunction, hypertension, retinal degeneration, lung cancer, colon cancer, breast cancer, uterus cancer, prostate cancer and cholangiocarcinoma.

SUMMARY OF THE INVENTION

This invention provides a compound of formula (I) or a pharmaceutically acceptable ester, amide, carbamate, solvate or salt thereof, including a salt of such an ester, amide or carbamate, and a solvate of such an ester, amide, carbamate or salt,

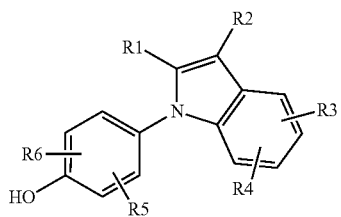

(I)

wherein R¹ is selected from the group consisting of halogen, cyano, nitro, OR$^A$, N(R$^B$)$_2$, —C(O)C$_{1-4}$alkyl, —SO$_2$C$_{1-4}$alkyl, C$_{1-6}$alkyl, C$_{2-6}$alkenyl, C$_{2-6}$alkynyl, haloC$_{1-6}$alkyl, dihaloC$_{1-6}$alkyl, trihaloC$_{1-6}$alkyl, haloC$_{2-6}$alkenyl, dihaloC$_{2-6}$alkenyl, trihaloC$_{2-6}$alkenyl, cyanoC$_{1-6}$alkyl, C$_{1-4}$alkoxyC$_{1-6}$ alkyl, C$_{3-8}$cycloalkyl, C$_{3-8}$cycloalkylC$_{1-6}$alkyl, phenyl, benzyl, and 5-10 membered heterocyclyl, wherein said phenyl, benzyl or heterocyclyl group can be either unsubstituted or substituted with from 1 to 3 substituents, each substituent being selected from the group consisting of OR$^A$, halogen, cyano, nitro, —C(O)C$_{1-4}$alkyl, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

R² is selected from the group consisting of halogen, cyano, nitro, OR$^A$, N(R$^B$)$_2$, N(OH)$_2$, —C(O)C$_{1-4}$alkyl optionally substituted with from 1 to 3 halogens, —SO$_2$C$_{1-4}$alkyl, —C(O)NH—OH, —C(NH$_2$)=N—OH, —C(CO$_2$H)=N—OH, —C(NH$_2$)=NH, —C(NHC$_{1-4}$alkyl)=NH, —C(O—C$_{1-4}$alkyl)=NH, —C(NH$_2$)=N—NH$_2$, —NH—C(NH$_2$)=NH, —NH—C(O)NH$_2$, —N=C(—NH—CH$_2$CH$_2$—NH—), —S—CN, —S—C(NH$_2$)=NH, —S—C(NH$_2$)=N—OH, —CO$_2$H, —CH$_2$—CO$_2$H, —CH(OH)CO$_2$H, —C(O)CO$_2$H, SO$_3$H, CH$_2$SO$_3$H, C$_{1-6}$alkyl, haloC$_{1-6}$alkyl, dihaloC$_{1-6}$alkyl, trihaloC$_{1-6}$alkyl, cyanoC$_{1-6}$alkyl, C$_{1-4}$alkoxyC$_{1-6}$alkyl, C$_{2-6}$alkenyl, C$_{2-6}$alkynyl, C$_{3-8}$cycloalkyl, C$_{3-8}$cycloalkylC$_{1-6}$alkyl, phenyl, benzyl and 5-10 membered heterocyclyl wherein said phenyl, benzyl or heterocyclyl group can be either unsubstituted or substituted with from 1 to 3 substituents each substituent being selected from the group consisting of OR$^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl; provided that if one of R¹ and R² represents halogen, the other must represent a group other than halogen;

each of R³, R⁴, R⁵ and R⁶ is independently selected from the group consisting of hydrogen, OR$^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

each R$^A$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, C$_{6-10}$aryl and C$_{6-10}$aryl C$_{1-6}$alkyl, each optionally substituted by from 1 to 3 halogen atoms; and each R$^B$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, C$_{6-10}$aryl and C$_{6-10}$ aryl C$_{1-6}$alkyl, each optionally substituted by from 1 to 3 halogen atoms;

with the proviso that the compound of formula (I) is not
4-[3-(4,5-Dihydro-1H-imidazol-2-yl)-2-(3,5-dimethyl-isoxazol-4-yl)-indol-1-yl]-phenol;
1-(4-Hydroxy-phenyl)-2-(4-methyl-imidazol-1-yl)-1H-indole-3-carbonitrile;
1-(4-Hydroxy-phenyl)-2-(1H-pyrazol-3-yl)-1H-indole-3-carbonitrile;
1-(3-Chloro-4-hydroxy-phenyl)-2-(1-methyl-1H-pyrazol-4-yl)-1H-indole-3-carbonitrile;
1-(4-Hydroxy-phenyl)-2-prop-1-ynyl-1H-indole-3-carboxylic acid amide; or
1-(4-Hydroxy-phenyl)-2-thiazol-2-yl-1H-indole-3-carboxylic acid.

Compounds of the invention have surprisingly been found to be ligands of the estrogen receptor. The compounds accordingly have use in the treatment or prophylaxis of conditions associated with estrogen receptor activity.

DETAILED DESCRIPTION OF INVENTION

The compounds of the invention may contain chiral (asymmetric) centers or the molecule as a whole may be chiral. The individual stereoisomers (enantiomers and diastereoisomers) and mixtures of these are within the scope of the present invention.

The present invention provides compounds that are estrogen receptor ligands. The term "estrogen receptor ligand" as used herein is intended to cover any moiety which binds to an estrogen receptor. The ligand may act as an agonist, a partial agonist, an antagonist or a partial antagonist. The ligand may be ERβ selective or display mixed ERα and ERβ activity. For example, the ligand may act both as an agonist or a partial agonist of ERβ and as an antagonist or a partial antagonist of ERα.

When R¹ represents a heterocyclyl group, this group may be saturated or unsaturated, and may contain one or more O, N and/or S atoms. It is preferably 5- or 6-membered. Suitable heterocyclyl groups include furyl, thienyl, pyrrolyl, pyrrolinyl, pyrrolidinyl, oxazolyl, isoxazolyl, thiazolyl, isothiazolyl, imidazolyl, imidazolinyl, imidazolidine, pyrazolyl, pyrazolinyl, pyrazolidinyl, pyridyl, morpholinyl, and piperidyl, with isoxazolyl being a particularly preferred heterocyclyl group. Preferred substituents for a heterocyclyl group include 1 to 3, for example 1 or 2, substituents, each substituent being selected from the group consisting of OR$^A$, halogen, cyano, —C(O)C$_{1-4}$alkyl, C$_{1-4}$alkyl, C$_{2-4}$alkenyl, C$_{2-4}$alkynyl, haloC$_{1-4}$alkyl, dihaloC$_{1-4}$alkyl and trihaloC$_{1-4}$alkyl. Especially preferred substituents are selected from halogen, cyano, C$_{1-4}$alkyl (especially methyl), —C(O)C$_{1-4}$alkyl, and OR$^A$ in which R$^A$ preferably represents a hydrogen atom or a C$_{1-4}$alkyl group. More especially preferred substituents are selected from halogen, cyano and C$_{1-4}$alkyl (especially methyl or ethyl).

Preferred substituents for a phenyl or benzyl group R¹ include those mentioned above for a heterocyclyl group R¹.

When R² represents a heterocyclyl group, this group may for example be one of the preferred groups mentioned above for R¹.

Preferred substituents for a phenyl or benzyl group R² include those mentioned above for a heterocyclyl group R¹.

Unless otherwise stated, each R$^A$ is preferably independently selected from the group consisting of hydrogen, C$_{1-4}$alkyl, C$_{2-4}$alkenyl, C$_{2-4}$alkynyl, C$_{3-6}$cycloalkyl, phenyl and benzyl. Preferably each R$^A$ independently represents hydrogen or C$_{1-4}$alkyl, especially methyl.

Unless otherwise stated, each R$^B$ is preferably independently selected from the group consisting of hydrogen and C$_{1-4}$alkyl.

Preferably R¹ is selected from the group consisting of OR$^A$, N(R$^B$)$_2$, —C(O)C$_{1-4}$alkyl, C$_{1-4}$alkyl, C$_{2-6}$alkenyl, C$_{2-6}$alkynyl, haloC$_{1-4}$alkyl, dihaloC$_{1-4}$alkyl, trihaloC$_{1-4}$alkyl, haloC$_{2-4}$alkenyl, dihaloC$_{2-4}$alkenyl, trihaloC$_{2-4}$alkenyl, phenyl, and 5-6 membered heterocyclyl, wherein said phenyl or heterocyclyl group can either be unsubstituted or substituted as above. More preferably, $R^1$ is selected from the group consisting of $OR^A$, $N(R^B)_2$, —$C(O)C_{1-4}$alkyl, $C_{2-4}$alkenyl, $C_{2-4}$alkynyl, phenyl, and 5-6 membered heterocyclyl, wherein said phenyl or heterocyclyl group can either be unsubstituted or substituted as above.

$R^2$ may for example be selected from one of the preferred groups mentioned above for $R^1$. In one embodiment of the invention, $R^2$ is selected from the group consisting of halogen, cyano, nitro, $OR^A$, $N(R^B)_2$, $N(OH)_2$, —$C(O)C_{1-4}$alkyl optionally substituted with from 1 to 3 halogens, —$SO_2C_{1-4}$alkyl, —$C(O)NH$—$OH$, —$C(NH_2)$=$N$—$OH$, —$C(CO_2H)$=$N$—$OH$, —$C(O$—$C_{1-4}$alkyl)=$NH$, —$C(NH_2)$=$N$—$NH_2$, —$NH$—$C(NH_2)$=$NH$, —$NH$—$C(O)NH_2$, —$N$=$C($—$NH$—$CH_2CH_2$—$NH$—$)$, —$S$—$CN$, —$S$—$C(NH_2)$=$NH$, —$S$—$C(NH_2)$=$N$—$OH$, —$CO_2H$, —$CH_2$—$CO_2H$, —$CH(OH)CO_2H$, —$C(O)CO_2H$, $SO_3H$, $CH_2SO_3H$, halo$C_{1-6}$alkyl, dihalo$C_{3-6}$alkyl, trihalo$C_{1-6}$alkyl, cyano$C_{1-6}$alkyl, $C_{3-4}$alkoxy$C_{1-6}$ alkyl, $C_{2-6}$alkenyl, $C_{2-6}$alkynyl, $C_{3-6}$cycloalkyl, $C_{3-8}$cycloalkyl$C_{1-6}$alkyl, phenyl, benzyl and 5-10 membered heterocyclyl wherein said phenyl, benzyl or heterocyclyl group can be either unsubstituted or substituted with from 1 to 3 substituents each substituent being selected from the group consisting of $OR^A$, halogen, cyano, nitro, $C_{3-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl.

In an alternative embodiment of the invention, $R^2$ is selected from the group consisting of halogen, nitro, $OR^A$, $N(R^B)_2$, —$C(O)C_{1-4}$alkyl optionally substituted with from 1 to 3 halogens, —$SO_2C_{1-4}$alkyl, —$C(O)NH$—$OH$, —$C(NH_2)$=$N$—$OH$, —$C(NH_2)$=$NH$, —$NH$—$C(NH_2)$=$NH$, —$NH$—$C(O)NH_2$, —$N$=$C($—$NH$—$CH_2CH_2$—$NH$—$)$, —$S$—$C(NH_2)$=$NH$, —$CO_2H$, —$CH_2$—$CO_2H$, $SO_3H$, $CH_2SO_3H$, $C_{1-6}$alkyl, halo$C_{1-6}$alkyl, dihalo$C_{1-6}$alkyl, trihalo$C_{1-6}$alkyl, cyano$C_{1-6}$alkyl, $C_{1-4}$alkoxy$C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, benzyl and 5-10 membered heterocyclyl wherein said phenyl, benzyl or heterocyclyl group can be either unsubstituted or substituted with from 1 to 3 substituents each substituent being selected from the group consisting of $OR^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl.

In a preferred embodiment of the invention, $R^2$ is selected from the group consisting of halogen, nitro, $OR^A$, $N(R^B)_2$, —$C(O)C_{1-4}$alkyl optionally substituted with from 1 to 3 halogens, —$SO_2C_{1-4}$alkyl, —$C(O)NH$—$OH$, —$C(NH_2)$=$N$—$OH$, —$NH$—$C(NH_2)$=$NH$, —$NH$—$C(O)NH_2$, —$N$=$C($—$NH$—$CH_2CH_2$—$NH$—$)$, —$S$—$C(NH_2)$=$NH$, —$CO_2H$, —$CH_2$—$CO_2H$, $C_{1-6}$alkyl, halo$C_{1-6}$alkyl, dihalo$C_{1-6}$alkyl, cyano$C_{1-6}$alkyl, $C_{1-4}$alkoxy$C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, benzyl and 5-10 membered heterocyclyl wherein said phenyl, benzyl or heterocyclyl group can be either unsubstituted or substituted with from 1 to 3 substituents each substituent being selected from the group consisting of $OR^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl. More preferably, $R^2$ is selected from the group consisting of —$C(O)C_{1-4}$alkyl (especially —$C(O)CH_3$), —$C(NH_2)$=$N$—$OH$, —$CO_2H$, —$CH_2$—$CO_2H$, $C_{1-4}$alkyl, $C_{2-4}$alkenyl, $C_{2-4}$alkynyl, and 5-6 membered heterocyclyl wherein said heterocyclyl group can either be unsubstituted or substituted as above. Most preferably, $R^2$ is selected from the group consisting of —$C(O)CH_3$), —$C(NH_2)$=$N$—$OH$, —$CO_2H$, and —$CH_2$—$CO_2H$, with —$C(NH_2)$=$N$—$OH$ being a particularly preferred $R^2$ group.

Preferably each of $R^3$, $R^4$, $R^5$ and $R^6$ is selected from the group consisting of hydrogen, $OR^A$, halogen, cyano, $C_{3-4}$alkyl, for example methyl, halo$C_{1-4}$alkyl, for example chloro- or fluoro-methyl, dihalo$C_{1-4}$alkyl, for example dichloro- or difluoromethyl, and trihalo$C_{1-4}$alkyl, for example trichloro- or trifluoromethyl. Preferably each of $R^3$, $R^4$, $R^5$ and $R^6$ is selected from the group consisting of hydrogen, OH, halogen, cyano, methyl, or trifluoromethyl. Most preferably at least one of $R^3$ and $R^4$ is hydrogen. Most preferably each of $R^5$ and $R^6$ independently represents hydrogen and/or halogen, especially fluorine.

Accordingly, in one preferred group of compounds of the invention, $R^1$ is selected from the group consisting of $OR^A$, $N(R^B)_2$, —$C(O)C_{1-4}$alkyl, $C_{1-6}$alkyl, $C_{2-6}$alkenyl, $C_{2-6}$alkynyl, halo$C_{1-4}$alkyl, dihalo$C_{1-4}$alkyl, trihalo$C_{1-4}$alkyl, halo$C_{2-4}$alkenyl, dihalo$C_{2-4}$alkenyl, trihalo$C_{2-4}$alkenyl, phenyl, and 5-6 membered heterocyclyl, wherein said phenyl or heterocyclyl group may be either unsubstituted or substituted as above; more preferably, $R^1$ is selected from the group consisting of $OR^A$, $N(R^B)_2$, —$C(O)C_{1-4}$alkyl, $C_{1-4}$alkyl, $C_{2-4}$alkenyl, $C_{2-4}$alkynyl, phenyl, and 5-6 membered heterocyclyl, wherein said phenyl or heterocyclyl group can either be unsubstituted or substituted as above;

$R^2$ is selected from the group consisting of —$C(O)C_{1-4}$alkyl (especially —$C(O)CH_3$), —$C(NH_2)$=$N$—$OH$, —$CO_2H$, —$CH_2$—$CO_2H$, $C_{1-4}$alkyl, $C_{2-4}$alkenyl, $C_{2-4}$alkynyl, and 5-6 membered heterocyclyl wherein said heterocyclyl group can be either unsubstituted or substituted as above;

each of $R^3$, $R^4$, $R^5$ and $R^6$ is selected from the group consisting of hydrogen, $OR^A$, halogen, cyano, $C_{1-4}$alkyl, halo$C_{1-4}$alkyl, dihalo$C_{1-4}$alkyl, and trihalo$C_{1-4}$alkyl, especially hydrogen, OH, halogen, cyano, methyl, or trifluoromethyl; especially, each of $R^5$ and $R^6$ represents hydrogen and/or halogen, especially fluorine;

each $R^A$ is preferably independently selected from the group consisting of hydrogen, $C_{1-4}$alkyl, $C_{2-4}$alkenyl, $C_{2-4}$alkynyl, $C_{3-6}$cycloalkyl, phenyl and benzyl, especially hydrogen and $C_{1-4}$alkyl, especially methyl; and each $R^B$ is independently selected from the group consisting of hydrogen and $C_{1-4}$alkyl.

In a further embodiment, this invention provides a compound of formula (I) or a pharmaceutically acceptable ester, amide, solvate or salt thereof, including a salt of such an ester or amide, and a solvate of such an ester, amide or salt,

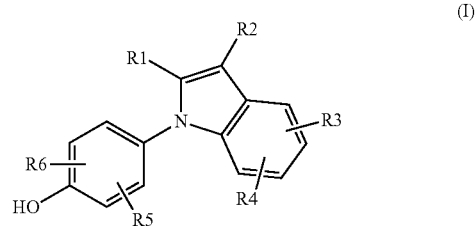

(I)

wherein $R^1$ is selected from the group consisting of halogen, cyano, nitro, $OR^A$, $N(R^B)_2$, —$C(O)C_{1-4}$alkyl, —$SO_2C_{1-4}$alkyl, $C_{1-6}$alkyl, $C_{2-6}$alkenyl, $C_{2-6}$alkynyl, halo$C_{1-6}$alkyl, dihalo$C_{1-6}$alkyl, trihalo$C_{1-6}$alkyl, halo $C_{2-6}$alkenyl, dihalo$C_{2-6}$alkenyl, trihalo$C_{2-6}$alkenyl, cyano$C_{1-6}$alkyl, $C_{1-4}$alkoxy$C_{1-6}$ alkyl, $C_{3-8}$cycloalkyl, $C_{3-8}$cycloalkyl$C_{1-6}$alkyl, phenyl, benzyl, and 5-10 membered heterocyclyl, wherein said phenyl, benzyl or heterocyclyl group can be either unsubstituted or substituted with from 1 to 3 substituents, each substituent being selected from the group consisting of $OR^A$, halogen, cyano, nitro, —$C(O)C_{1-4}$alkyl, $C_{1-6}$alkyl, $C_{2-6}$alkenyl, $C_{2-6}$alkynyl, halo$C_{1-6}$alkyl, dihalo $C_{1-6}$alkyl and trihalo$C_{1-6}$alkyl;

$R^2$ is selected from the group consisting of halogen, cyano, nitro, $OR^A$, $N(R^B)_2$, —C(O)C$_{1-4}$alkyl optionally substituted with from 1 to 3 halogens, —SO$_2$C$_{1-4}$alkyl, —C(O)NH—OH, —C(NH$_2$)=N—OH, —C(NH$_2$)=NH, —NH—C(NH$_2$)=NH, —NH—C(O)NH$_2$, —N=C(—NH—CH$_2$CH$_2$—NH—), —S—C(NH$_2$)=NH, —CO$_2$H, —CH$_2$—CO$_2$H, SO$_3$H, CH$_2$SO$_3$H, haloC$_{1-6}$alkyl, dihaloC$_{1-6}$alkyl, trihaloC$_{1-6}$alkyl, cyanoC$_{1-6}$alkyl, C$_{1-4}$alkoxyC$_{1-6}$ alkyl, C$_{2-6}$alkenyl, C$_{2-6}$alkynyl, C$_{3-8}$cycloalkyl, C$_{3-8}$cycloalkyl C$_{1-6}$alkyl, phenyl, benzyl and 5-10 membered heterocyclyl wherein said phenyl, benzyl or heterocyclyl group can be either unsubstituted or substituted with from 1 to 3 substituents each substituent being selected from the group consisting of $OR^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl; provided that if one of $R^1$ and $R^2$ represents halogen, the other must represent a group other than halogen; each of $R^3$, $R^4$, $R^5$ and $R^6$ is independently selected from the group consisting of hydrogen, $OR^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

each $R^A$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, C$_{6-10}$aryl and C$_{6-10}$arylC$_{1-6}$alkyl, each optionally substituted by from 1 to 3 halogen atoms; and each $R^B$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, C$_{6-10}$aryl and C$_{6-10}$arylC$_{1-6}$alkyl, each optionally substituted by from 1 to 3 halogen atoms;

with the proviso that the compound of formula (I) is not 4-[3-(4,5-Dihydro-1H-imidazol-2-yl)-2-(3,5-dimethyl-isoxazol-4-yl)-indol-1-yl]-phenol, Compounds of the formula I include, but are not limited to, the compounds specifically named in the Examples herein, In the Examples, the compound names were generated in accordance with IUPAC by the ACD Labs 8.0/name program, version 8.05 and/or with ISIS DRAW Autonom 2000 and/or ChemBioDraw Ultra version 11.0.

Depending upon the substituents present in compounds of the formula I, the compounds may form esters, amides, carbamates and/or salts. Salts and solvates of compounds of formula (I) which are suitable for use in medicine are those wherein a counterion or associated solvent is pharmaceutically acceptable. However, salts and solvates having non-pharmaceutically acceptable counterions or associated solvents are within the scope of the present invention, for example, for use as intermediates in the preparation of the compounds of formula (I) and their pharmaceutically acceptable salts, solvates and physiologically functional derivatives. By the term "physiologically functional derivative" is meant a chemical derivative of a compound of formula (I) having the same physiological function as the free compound of formula (I), for example, by being convertible in the body thereto. Esters, amides and carbamates are examples of physiologically functional derivatives.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as (C$_1$-C$_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

Compounds of formula (I) may have an appropriate group converted to an ester, an amide or a carbamate Thus typical ester and amide groups formed from an acid group in the compound of the formula I include —COOR$^B$, —CONR$^B_2$, —SO$_2$.OR$^B$, or —SO$_2$.NR$^B_2$, while typical ester and amide and carbamate groups formed from an —OH or —NHR$^B$ group in the compound of the formula I include —O.CO.R$^B$, —NR$^B$.COR$^B$, —NR$^B$.CO$_2$R$^B$—O.SO$_2$R$^B$, and —NR$^B$.SO$_2$R$^B$, where R$^B$ has one of the meanings given above.

Those skilled in the art of organic chemistry will appreciate that many organic compounds can form complexes with solvents in which they are reacted or from which they are precipitated or crystallized. These complexes are known as "solvates". For example, a complex with water is known as a "hydrate".

A compound which, upon administration to the recipient, is capable of being converted into a compound of formula (I) as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups. Among unbranched alkyl groups, there are preferred methyl, ethyl, n-propyl, iso-propyl, n-butyl groups. Among branched alkyl groups, there may be mentioned t-butyl, i-butyl, 1-ethylpropyl and 1-ethylbutyl groups.

As used herein, the term "alkoxy" means the group O-alkyl, where "alkyl" is used as described above. Examples of alkoxy groups include methoxy and ethoxy groups. Other examples include propoxy and butoxy.

As used herein, the term "alkenyl" means both straight and branched chain unsaturated hydrocarbon groups with at least one carbon carbon double bond. Examples of alkenyl groups include ethenyl, propenyl, butenyl, pentenyl and hexenyl. Preferred alkenyl groups include ethenyl, 1-propenyl and 2-propenyl.

As used herein, the term "alkynyl" means both straight and branched chain unsaturated hydrocarbon groups with at least one carbon carbon triple bond. Examples of alkynyl groups include ethynyl, propynyl, butynyl, pentynyl and hexynyl. Preferred alkynyl groups include ethynyl 1-propynyl and 2-propynyl.

As used herein, the term "cycloalkyl" means a saturated group in a ring system. A cycloalkyl group can be monocyclic or bicyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo[2.2.1]hept-2-yl. Preferably, the cycloalkyl group is monocyclic.

As used herein, the term "aryl" means a monocyclic or bicyclic aromatic carbocyclic group. Examples of aryl groups include phenyl and naphthyl. A naphthyl group may be attached through the 1 or the 2 position. In a bicyclic aromatic group, one of the rings may, for example, be partially saturated. Examples of such groups include indanyl and tetrahydronaphthyl. Specifically, the term $C_{5-10}$ aryl is used herein to mean a group comprising from 5 to 10 carbon atoms in a monocyclic or bicyclic aromatic group. A particularly preferred $C_{5-10}$ aryl group is phenyl.

As used herein, the term "halogen" means fluorine, chlorine, bromine or iodine. Fluorine, chlorine and bromine are particularly preferred.

As used herein, the term "haloalkyl" means an alkyl group having a halogen substituent, the terms "alkyl" and "halogen" being understood to have the meanings outlined above. Similarly, the term "dihaloalkyl" means an alkyl group having two halogen substituents and the term "trihaloalkyl" means an alkyl group having three halogen substituents. Examples of haloalkyl groups include fluoromethyl, chloromethyl, bromomethyl, fluoromethyl, fluoropropyl and fluorobutyl groups; examples of dihaloalkyl groups include difluoromethyl and difluoroethyl groups; examples of trihaloalkyl groups include trifluoromethyl and trifluoroethyl groups.

As used herein, the term "heterocyclyl" means an aromatic or a non-aromatic cyclic group of carbon atoms wherein from one to three of the carbon atoms is/are replaced by one or more heteroatoms independently selected from nitrogen, oxygen or sulfur. A heterocyclyl group may, for example, be monocyclic or bicyclic. In a bicyclic heterocyclyl group there may be one or more heteroatoms in each ring, or only in one of the rings. A heteroatom is preferably O or N. Heterocyclyl groups containing a suitable nitrogen atom include the corresponding N-oxides.

Examples of monocyclic non-aromatic heterocyclyl groups (also referred to as monocyclic heterocycloalkyl rings) include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl.

Examples of bicyclic heterocyclyl groups in which one of the rings is non-aromatic include dihydrobenzofuranyl, indanyl, indolinyl, isoindolinyl, tetrahydroisoquinolinyl, tetrahydroquinolyl and benzoazepanyl.

Examples of monocyclic aromatic heterocyclyl groups (also referred to as monocyclic heteroaryl groups) include furanyl, thienyl, pyrrolyl, oxazolyl, thiazolyl, imidazolyl, oxadiazolyl; thiadiazolyl, pyridyl, triazolyl, triazinyl, pyridazyl, isothiazolyl, isoxazolyl, pyrazinyl, pyrazolyl and pyrimidinyl.

Examples of bicyclic aromatic heterocyclyl groups (also referred to as bicyclic heteroaryl groups) include quinoxalinyl, quinazolinyl, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridiyl, pyridopyrimidinyl, isoquinolinyl and benzodroxazole.

Examples of preferred heterocyclyl groups include piperidinyl, tetrahydrofuranyl, tetrahydropyranyl, pyridyl, pyrimidinyl and indolyl. Preferred heterocyclyl groups also include thienyl, thiazolyl, furanyl, pyrazolyl, pyrrolyl, isoxazolyl and imidazolyl.

As used herein the term "cycloalkylalkyl" means a group cycloalkyl-alkyl-attached through the alkyl group, "cycloalkyl" and "alkyl" being understood to have the meanings outlined above.

As mentioned above, the compounds of the invention have activity as estrogen receptor ligands. The compounds of the invention have activity as estrogen receptor modulators, and may be agonists, partial agonists, antagonists, or partial antagonists of the estrogen receptor. Particularly preferred compounds of the invention have activity as an agonist or a partial agonist of ERβ. Preferred compounds of this type are selective agonists of the estrogen receptor-beta (ERβ).

The compounds of the invention may thus be used in the treatment of diseases or disorders associated with estrogen receptor activity. In particular, the compounds of the invention that are agonists or partial agonists of the estrogen receptor may be used in the treatment of diseases or disorders for which selective agonists or partial agonists of the estrogen receptor are indicated. The compounds of the invention that are antagonists or partial antagonists of the estrogen receptor may be used in the treatment of diseases or disorders for which selective antagonists or partial antagonists of the estrogen receptor are indicated.

Clinical conditions for which an agonist or partial agonist is indicated include, but are not limited to, bone loss, bone fractures, osteoporosis, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression, autoimmune disease, inflammation, IBD, IBS, sexual dysfunction, hypertension, retinal degeneration, and lung, colon, breast, uterus, and prostate cancer, and/or disorders related to estrogen functioning.

The compounds of the invention find particular application in the treatment or prophylaxis of the following: bone loss, bone fractures, osteoporosis, cartilage degeneration, endometriosis, uterine fibroid disease, hot flashes, increased levels of LDL cholesterol, cardiovascular disease, impairment of cognitive functioning, age-related mild cognitive impairment, cerebral degenerative disorders, restenosis, gynecomastia, vascular smooth muscle cell proliferation, obesity, incontinence, anxiety, depression, perimenopausal depression, post-partum depression, premenstrual syndrome, manic depression, dementia, obsessive compulsive behavior, attention deficit disorder, attention deficit hyperactivity disorder, sleep disorders, irritability, impulsivity, anger management, hearing disorders, multiple sclerosis, Parkinson's disease, Alzheimer's disease, Huntington's disease, amyotrophic lateral sclerosis, spinal cord injury, stroke, autoimmune disease, inflammation, IBD, IBS, sexual dysfunction, hypertension, retinal degeneration, lung cancer, colon cancer, breast cancer, uterus cancer, prostate cancer and the bile duct cancer form named cholangiocarcinoma.

In one embodiment of the invention, the present compounds finds particular application in the treatment or prophylaxis of depression, perimenopausal depression, post-partum depression, premenstrual syndrome and manic depression.

The treatment or prophylaxis of hot flashes (or hot flushes) in males, is preferable for patients that has had an androgen ablation for treatment of prostate cancer.

The phrase "depression" includes but is not limited to, major depressive disorder, dysthymic disorder, bipolar disorder, cyclothymic disorder, mood disorder due to a general medical condition, substance-induced mood misorder, seasonal affective disorder (SAD), postpartum depression and premenstrual dysphoric disorder.

The invention also provides a method for the treatment or prophylaxis of a condition in a mammal mediated by an estrogen receptor, which comprises administering to the mammal a therapeutically effective amount of a compound according to the invention. Clinical conditions mediated by an estrogen receptor that may be treated by the method of the invention are preferably those described above.

The invention also provides the use of a compound according to the invention, for the manufacture of a medicament for the treatment or prophylaxis of a condition mediated by an estrogen receptor. Clinical conditions mediated by an estrogen receptor that may be treated by the method of the invention are preferably those described above.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

While it is possible for the active ingredient to be administered alone, it is preferable for it to be present in a pharmaceutical formulation or composition. Accordingly, the invention provides a pharmaceutical formulation comprising a compound according to the invention, and a pharmaceutically acceptable diluent, excipient or carrier (collectively referred to herein as "carrier" materials). Pharmaceutical compositions of the invention may take the form of a pharmaceutical formulation as described below.

The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered does pressurized aerosols), nebulizers or insufflators, rectal, intraperitoneal and topical (including dermal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage florins include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient in a medicament, it is also possible for the compound to be used in combination with one or more further active agents. Such further active agents may be further compounds according to the invention, or they may be different therapeutic agents, for example an antidepressant, an anxiolytic, an anti-psychotic, an agent useful in the prevention or treatment of osteoporosis, an agent useful in the prevention or treatment of cancer or other pharmaceutically active material. For example, the compounds of the instant invention may be effectively administered in combination with effective amounts of other agents such as an antidepressant, an anxiolytic, an anti-psychotic, an organic bisphosphonate or a cathepsin K inhibitor. In one preferred embodiment, the compounds of the invention may be effectively administered in combination with an effective amount of an antidepressant. Nonlimiting examples of antidepressants include noradrenaline reuptake inhibitors (NRI), selective serotonin reuptake inhibitors, monoamine oxidase inhibitors, tricyclic antidepressants (TCA), dopamine reuptake inhibitors (DRI), opioids, selective seretonic reuptake enhancers, tetracyclic antidepressants, reversible inhibitors of monoamine oxidase, melatonin agonists, serotonin and noradrenaline reuptake inhibitors (SNRI), corticotropin releasing factor antagonists, α-adrenoreceptor antagonists, 5HT1α receptor agonists and antagonists, lithium and atypical antipsychotics. Examples of antidepressants of the SSRI class include Fluoxetine and Sertraline; examples of antidepressants of the SNRI class Venlafaxine, Citalopram, Paroxetine, Escitalopram, Fluvoxamine; examples of antidepressants of the SNRI class include Duloxetine; examples of antidepressants of the DRI and NRI classes include Bupropion; examples of antidepressants of the TCA class include Amitriptyline and Dothiepin (Dosulepin). Examples of atypical antipsychotics include: Clozapine, Olanzapine, Risperidone, Quetiapine, Ziprasidone and Dopamine partial agonists. Nonlimiting examples of anxiolytics include benzodiazepines and non-benzodiazapines. Examples of benzodiazapines include lorazepam, alprazolam, and diazepam. Examples of non-benzodiazapines include Buspirone (Buspar®), barbiturates and meprobamate. One or more of those further anti-depressants may be used in combination.

Examples of anti-cancer agents include tamoxifene or an aromatase inhibitor, used in treatment of breast cancer.

In the event that hot flashes are induced by a particular treatment, a compound of the invention may be used in combination therapy with the agent of such treatment. Nonlimiting examples of such combination treatment therapies include: a compound of the invention in combination with tamoxifene treatment of breast cancer, a compound of the invention in combination with aromatase inhibitor treatment of breast cancer or a compound of the invention in combination with raloxifene treatment of osteoporosis.

Nonlimiting examples of above-mentioned organic bisphosphonates include adendronate, clodronate, etidronate, ibandronate, incadronate, minodronate, neridronate, risedronate, piridronate, pamidronate, tiludronate, zoledronate, pharmaceutically acceptable salts or esters thereof, and mixtures thereof. Preferred organic biphosphonates include alendronate and pharmaceutically acceptable salts and mixtures thereof. Most preferred is alendronate monosodium trihydrate.

The precise dosage of the bisphosphonate will vary with the dosing schedule, the oral potency of the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. An appropriate amount can be determined by routine experimentation from animal models and human clinical studies. Generally, an appropriate amount of bisphosphonate is chosen to obtain a bone resorption inhibiting effect, i.e. a bone resorption inhibiting amount of the bisphonsphonate is administered. For humans, an effective oral dose of bisphosphonate is typically from about 1.5 to about 6000 µg/kg of body weight and preferably about 10 to about 2000 µg/kg of body weight.

For human oral compositions comprising alendronate, pharmaceutically acceptable salts thereof, or pharmaceutically acceptable derivatives thereof, a unit dosage typically comprises from about 8.75 mg to about 140 mg of the alendronate compound, on an alendronic acid active weight basis, i.e. on the basis of the corresponding acid.

The compounds of the present invention can be used in combination with other agents useful for treating estrogen-mediated conditions. The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more other therapeutic agent(s), either concurrently or sequentially, the following combination ratios and dosage ranges are preferred:

When combined with an antidepressant, an anxiolytic, an anti-psychotic, an organic bisphosphonate or a cathepsin K inhibitor, the compounds of formula (I) may be employed in a weight ratio to the additional agent within the range from about 10:1 to about 1:10.

The compounds of the invention as described above also find use, optionally in labelled form, as a diagnostic agent for the diagnosis of conditions associated with malfunction of the estrogen receptor. For example, such a compound may be radioactively labelled.

The compounds of the invention as described above, optionally in labelled form, also find use as a reference compound in methods of discovering other agonists, partial agonists, antagonists or partial antagonists of the estrogen receptor. Thus, the invention provides a method of discovering a ligand of the estrogen receptor which comprises use of a compound of the invention or a compound of the invention in labelled form, as a reference compound. For example, such a method may involve a competitive binding experiment in which binding of a compound of the invention to the estrogen receptor is reduced by the presence of a further compound which has estrogen receptor-binding characteristics, for example stronger estrogen receptor-binding characteristics than the compound of the invention in question.

Numerous synthetic routes to the compounds of the present invention can be devised by any person skilled in the art and the possible synthetic routes described below do not limit the invention. Many methods exist in the literature for the synthesis of indoles, for example: *Indoles Part One*, W. J. Houlihan (ed.), 1972; *Indoles*, Sundberg, R. J., 1996; *Heterocyclic Chemistry*, Joule, J. A.; Mills, K. 2000; *Chem. Rev.*, 2005, 105, 2873-2920; *Org. Lett.* 2006, 8, 5919-5922; and *Bioorg. Med. Chem. Lett.*, 2007, 17, 902-906. A number of possible synthetic routes are shown schematically below. Where appropriate, any initially produced compound according to the invention can be converted into another compound according to the invention by known methods.

General Method 1

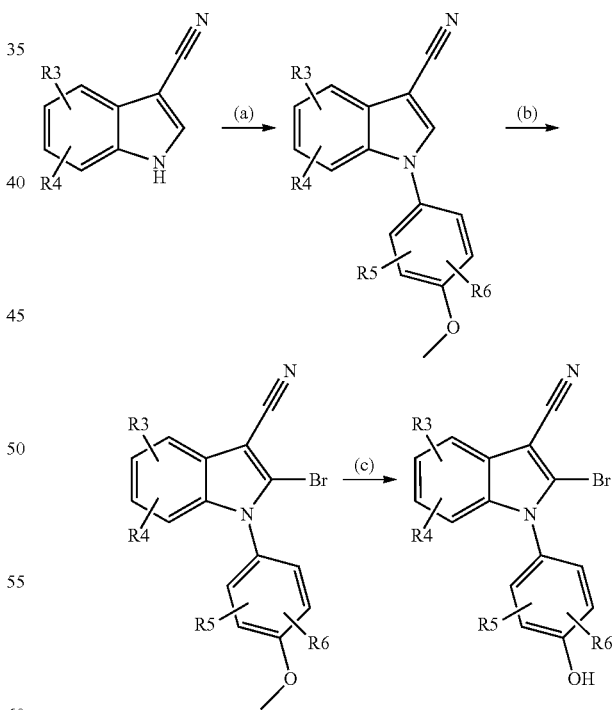

(a) Aryliodide, Potassium phosphate, N,N'-dimethylethylenediamine, CuI, Toluene;
(b) t-BuLi, 1,2-dibromotetrachloroethane, THF; (c) BBr₃, DCM General Method 1 as shown in the reaction scheme above was used for the synthesis of the following Examples:

Examples 46-159 and 211—full experimental details of the individual steps of the general method applicable for the synthesis of the final compounds of Examples 46-159 and 211 are described in Examples 1-5, 16 and 38-40.

Examples 160-162 and 196-210—full experimental details of the individual steps of the general method applicable for the synthesis of the final compounds of Examples 160-162 and 196-210 are described in Examples 1-4, 8, 16 and 38-40.

Examples 169 and 173-195—full experimental details of the individual steps of the general method applicable for the synthesis of the final compounds of Examples 169 and 173-195 are described in Examples 1-4, 8, 10-13, 14-16, 20, 25, 38-40 and 45.

Examples 233-270—full experimental details of the individual steps of the general method applicable for the synthesis of the final compounds of Examples 233-270 are described in Examples 1-4, 10-11, 14-16, 38-40 and 45.

General Method 2

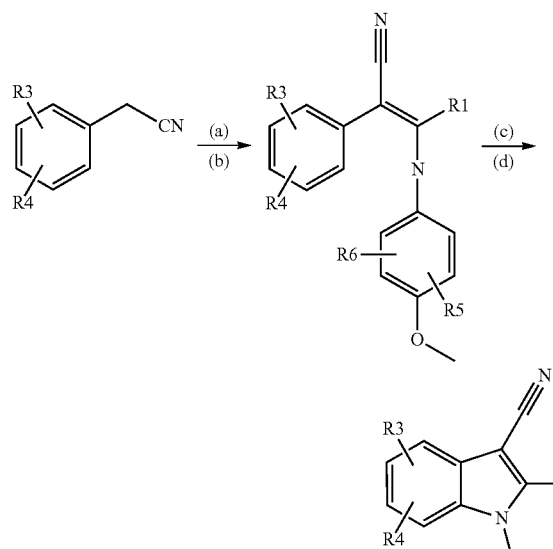

(a) NaH, R1-alkylester, THF; (b) Aniline, AcOH; (c) PIFA, $CH_2Cl_2$; (d) BBr$_3$, $CH_2Cl_2$.

General Method 2 as shown in the reaction scheme above was used for the synthesis of Example 6.

General Method 3

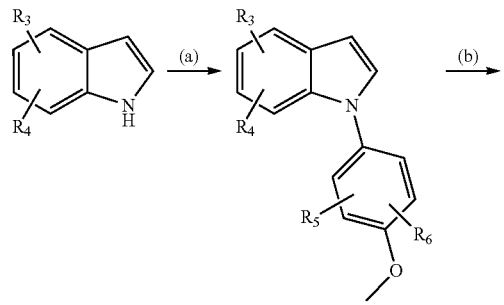

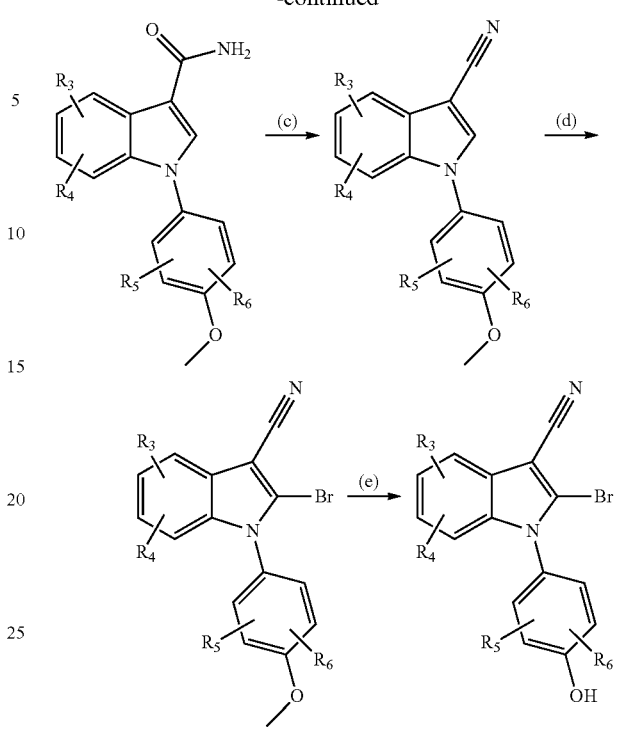

(a) Aryliodide, Potassium phosphate, N,N′-dimethylethylenediamin, CuI, Toluene; (b) Chlorosulphonyl isocyanate, 1,2-dichloorethane, THF; (c) Phosphorus oxychloride; (d) t-BuLi, 1,2-dibromotetrachloroethane, THF; (e) BF$_3$SMe$_2$, DCM General Method 3 as shown in the reaction scheme above was used for the synthesis of Examples 212-232 and 271. Full experimental details of the individual steps of the general method applicable for the synthesis of the final compounds of Examples 212-232 and 271 are described in Examples 2-4, 8, 16, 24 and 38-40.

General Method 4

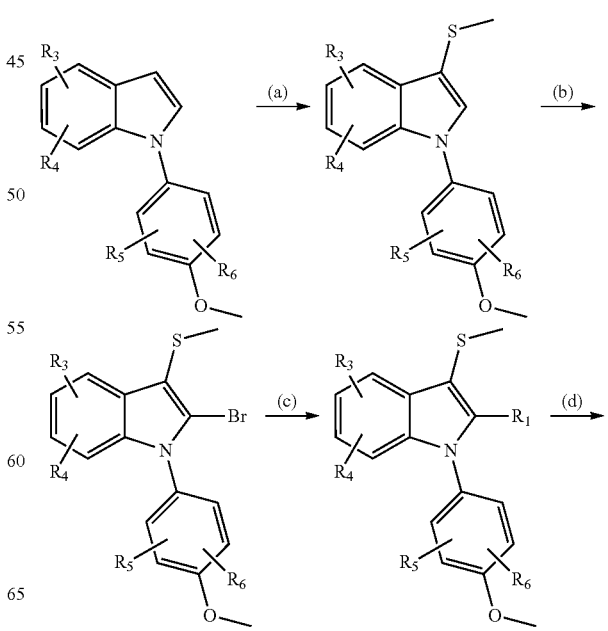

-continued

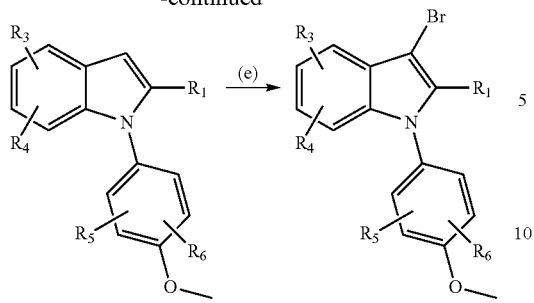

(a) 2-(methylthio)isoindoline-1,3-dione, MgBr, DMA; (b) NBS, DMF; (c) R₁boronic acid, Pd(PPh₃)₄, NaI, NaCO₃, DME, H₂O (d) 2-Mercaptobenzoic acid, TFA; (e) NBS, DMF General Method 4 as shown in the reaction scheme above was used for the synthesis of Examples 163-168 and 170-172. Full experimental details of the individual steps of the general method applicable for the synthesis of the final compounds of Examples 163-168 and 170-172 are described in Examples 2-4, 9, 20-21.

General Method 5

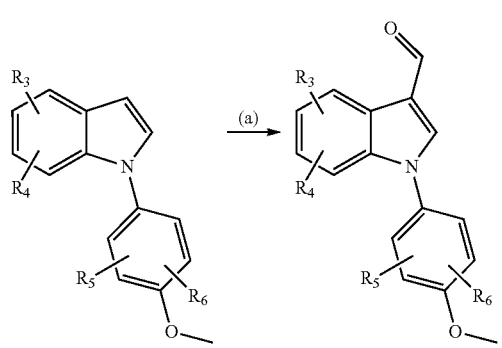

General Method 5 as shown in the reaction scheme above is also potentially applicable for synthesising the compounds of the invention. An appropriate 3-cyano-N-arylindole could be obtained from an N-arylindole via formylation as shown in step (a), for example by means of a Vilsmeier-Haack reaction, followed by reaction of the aldehyde with hydroxylamine hydrochloride and subsequent elimination using acetic anhydride as shown in step (b).

The following Examples illustrate the invention.

Example 1

2-Bromo-1-(4-hydroxy-phenyl)-1H-indole-3-carbonitrile (E1)

Scheme 1

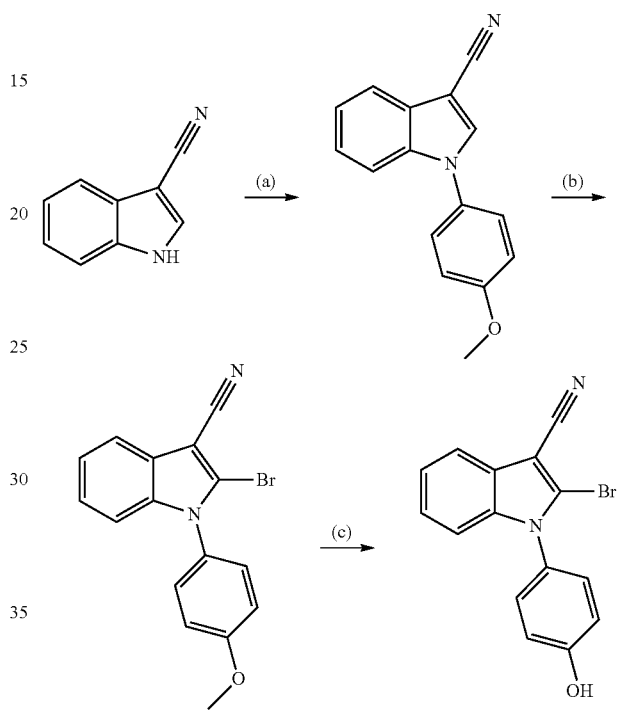

(a) 4-Iodoanisole, Potassium phosphate, N,N'-dimethylethylenediamine, CuI, Toluene; (b) t-BuLi, 1,2-dibromotetrachloroethane, THF; (c) BBr₃, DCM Step (a):

1 eq 3-Cyanoindole, 2 eq 4-iodoanisole, 2.1 eq potassium phosphate, 4.5 eq N,N'-dimethylethylenediamine and 0.2 eq copper(I) iodide were mixed in an oven-dried vial and toluene was added. The mixture was stirred under $N_2$-atmosphere at 110° C. over night. The reaction mixture was cooled to rt, filtered and evaporated in vacuo. The crude product was purified on silica using n-heptane:EtOAc (4:1) as mobile phase.

Step (b):

1-(4-Methoxy-phenyl)-1H-indole-3-carbonitrile was dissolved in dry THF and cooled to −78° C., 1.1 eq t-BuLi was added drop wise and the mixture was stirred for one hour. A solution of 1.3 eq 1,2-dibromotetrachloroethane in dry THF was added and the mixture was stirred for 4 hours while slowly warming it up to rt and then quenched by addition of $H_2O$. The reaction mixture was diluted with DCM, phases were separated and the organic phase was evaporated in vacuo. The crude product was purified on silica using n-heptane:DCM (1:1) as mobile phase.

Step (c):

2-Bromo-1-(4-methoxy-phenyl)-1H-indole-3-carbonitrile was dissolved in dry DCM and cooled to 0° C. 5 eq BBr₃ (1.0 M solution in hexane) was added and the mixture was stirred over night. Still at 0° C., the reaction was quenched with the addition of MeOH. The mixture was diluted with H₂O and the phases were partitioned. The organic phase was concentrated and the crude product purified on silica using n-heptane:EtOAc (4:1) as mobile phase. ES/MS m/z: 313, 315 (M+H), 311, 313 (M−H); ¹H NMR (acetone-d6, 500 MHz): 7.69 (m, 1H), 7.38-7.30 (m, 4H) and 7.16-7.10 (m, 3H).

Example 2

1-(4-Hydroxy-phenyl)-2-thiophen-3-yl-1H-indole-3-carbonitrile (E2)

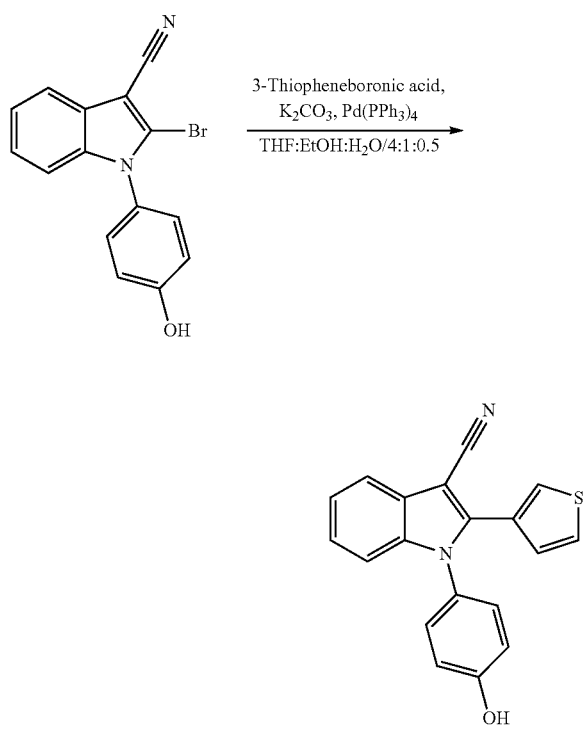

Scheme 2

To 2-bromo-1-(4-hydroxy-phenyl)-1H-indole-3-carbonitrile (Example 1) was added 2 eq 3-thiopheneboronic acid, 2.1 eq potassium carbonate and 10 mol % tetrakis(triphenylphosphine) palladium. THF:EtOH:H₂O (4:1:0.5) was added and the vial was flushed with nitrogen, sealed and stirred at 100° C. for 48 hours. The reaction mixture was cooled to rt, diluted with H₂O, extracted with EtOAc and filtered through silica. The organic phase was evaporated to dryness and the crude product was subjected to reversed phase preparative HPLC. Appropriate fractions were combined, evaporated, and identified by ¹H-NMR and LC/MS. Purity was determined by analytical HPLC. ES/MS m/z: 317.9 (M+H), 314.8 (M−H); ¹H NMR (acetone-d6, 500 MHz): 7.73 (m, 1H), 7.62 (dd, 1H, J=1.3, 2.9 Hz), 7.54 (dd, 1H, J=2.9, 5.0 Hz), 7.37-7.30 (m, 2H), 7.26 (m, 2H), 7.18 (m, 1H), 7.15 (dd, 1H, J=1.3, 5.0 Hz) and 7.03 (m, 2H).

Example 3

2-(3-Cyano-furan-2-yl)-1-(4-hydroxy-phenyl)-1H-indole-3-carbonitrile (E3)

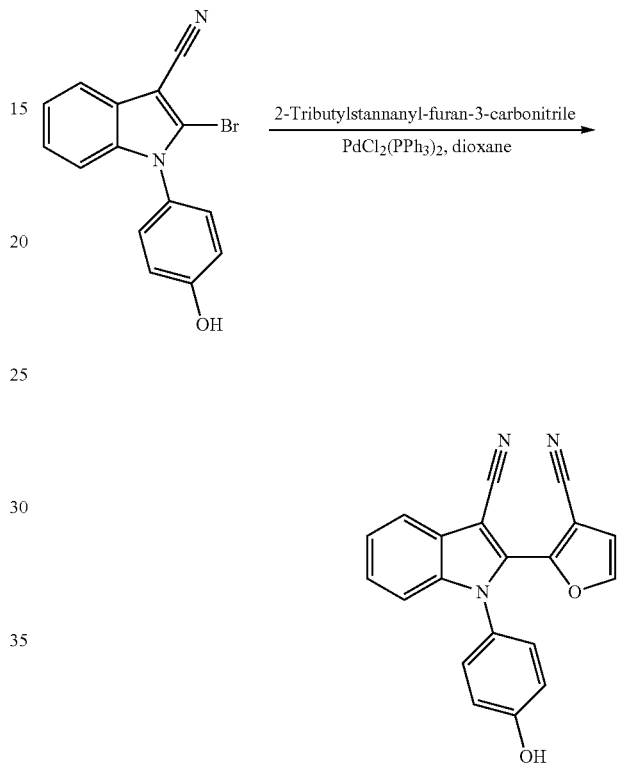

Scheme 3

2-Bromo-1-(4-hydroxy-phenyl)-1H-indole-3-carbonitrile (Example 1, 40 mg, 0.13 mmol, 1 eq), 2-tributylstannanyl-furan-3-carbonitrile (63.5 mg, 0.17 mmol, 1.3 eq) and dichlorobis(triphenylphosphine)palladium(II) (9 mg, 0.01 mmol, 0.1 eq) were weighed into a microwave vial. Dioxane (1 ml) was added, the vial was flushed with nitrogen and capped. The reaction mixture was irradiated at 130 degrees for 30 min in the microwave and then the solution was filtered. Saturated aqueous ammonium chloride solution (5 ml) was added and the mixture was extracted several times with DCM. The combined DCM phases were passed through a phase separation membrane and evaporated. The crude product was purified by a quick silica gel flash chromatography, using n-heptane:ethyl acetate (7:3) gradient, to remove the remaining tin reagent rests. Appropriate fractions were collected and evaporated, dissolved in acetonitrile (1 ml), and purified by preparative HPLC to give 33 mg (79% yield) 99% pure product, as determined by analytical HPLC. (Column: Reprosil Pur 120 ODS-3 (C18), 30×100 mm, 5 μm. Mobile phase A: Formic acid 0.05%, Mobile phase B: ACN. Gradient 20% A-100% B. ES/MS m/z: 326.1 (M+H), 324.1 (M−H); ¹H NMR (acetone-d6, 500 MHz): 7.89 (d, 1H, J=2.2 Hz), 7.85 (m, 1H), 7.48-7.43 (m, 2H), 7.34 (m, 1H), 7.32 (m, 2H) and 7.04-7.01 (m, 3H).

Example 4

1-(4-Hydroxy-phenyl)-2-pyrrol-1-yl-1H-indole-3-carbonitrile (E4)

Scheme 4

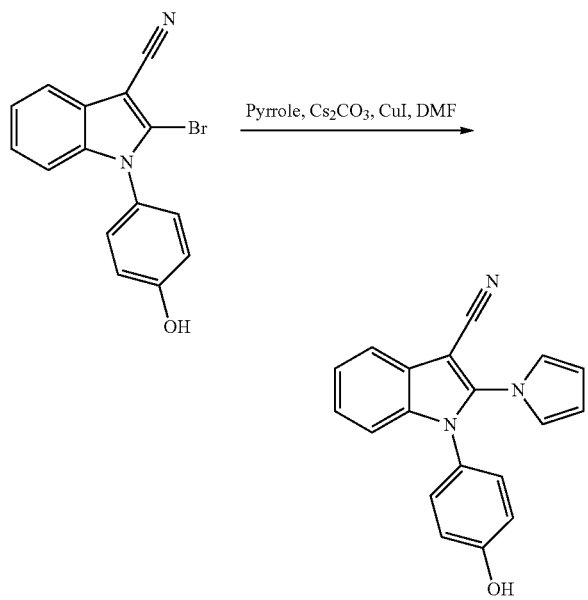

2-Bromo-1-(4-hydroxy-phenyl)-1H-indole-3-carbonitrile (Example 1), 1.4 eq pyrrole, 2 eq cesium carbonate and 20 mol % copper(I) iodide was mixed in a oven-dried vial, DMF was added and the mixture was flushed with nitrogen. The vial was sealed and stirred at 120° C. for 48 hours. The reaction-mixture was cooled to rt, diluted with EtOAc and filtered through silica. The crude mixture was evaporated to dryness and subjected to reversed phase preparative HPLC. Appropriate fractions were combined and evaporated, and identified by $^1$H-NMR and LC/MS. Purity was determined by analytical HPLC. ES/MS m/z: 300.2 (M+H), 298.3 (M−H); $^1$H NMR (acetone-d6, 500 MHz): 7.74 (m, 1H), 7.41-7.35 (m, 2H), 7.27 (m, 2H), 7.23 (m, 1H), 6.98 (m, 2H), 6.95 (t, 2H, J=2.2 Hz) and 6.23 (t, 2H, J=2.2 Hz).

Example 5

2-Dimethylamino-1-(4-hydroxy-phenyl)-1H-indole-3-carbonitrile (E5)

Scheme 5

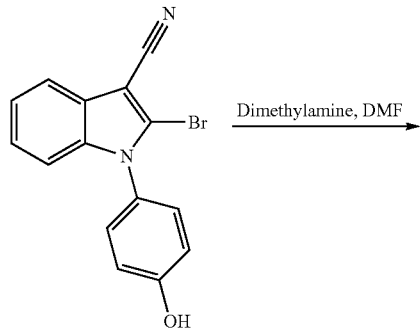

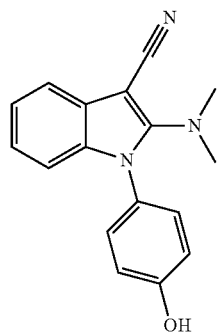

2-Bromo-1-(4-hydroxy-phenyl)-1H-indole-3-carbonitrile (Example 1) was mixed with excess dimethylamine in DMF (1:3) and the mixture was stirred in a sealed vial at 80° C. over night. The reaction-mixture was cooled to rt, diluted with H$_2$O and DCM and then the phases were separated. The organic phase was evaporated to dryness and subjected to reversed phase preparative HPLC. Appropriate fractions were combined and evaporated, and identified by $^1$H-NMR and LC/MS. Purity was determined by analytical HPLC, ES/MS m/z: 278.1 (M+H), 276.1 (M−H); $^1$H NMR (acetone-d6, 500 MHz): 7.42 (m, 1H), 7.33 (m, 2H), 7.17 (m, 1H), 7.09-7.05 (m, 3H), 6.95 (m, 1H) and 2.93 (s, 6H).

Example 6

1-(4-Hydroxy-phenyl)-2-isopropyl-1H-indole-3-carbonitrile (E6)

Scheme 6

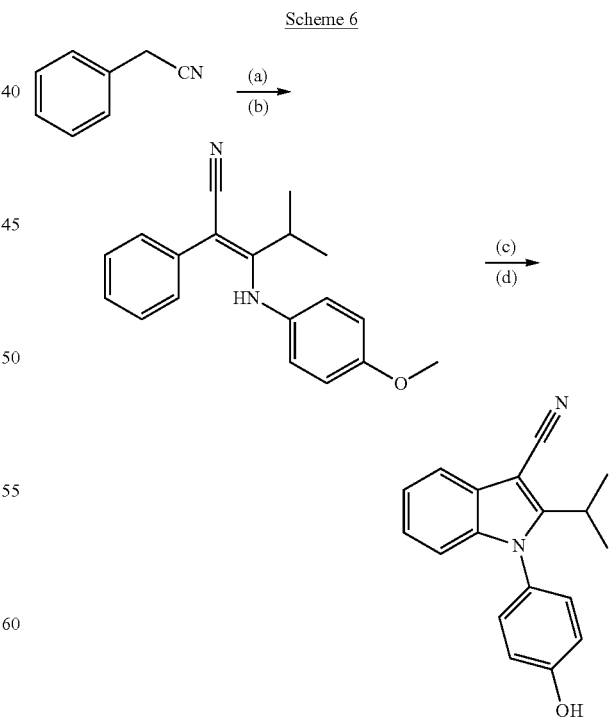

(a) NaH, Ethyl isobutyrate, THF; (b) 4-Methoxyaniline, AcOH; (c) PIFA, CH$_2$Cl$_2$; (d) BBr$_3$, CH$_2$Cl$_2$ Step (a):

Benzylcyanide (1500 mg, 12.8 mmol) was dissolved in 150 ml dry THF and cooled down to 0° C. The solution was stirred at that temperature while NaH (60% in mineral oil, 663 mg) was added slowly. After the addition was completed, the mixture was stirred at 0° C. for 30 min and then the ice bath was removed and stirring continued at RT for 120 min. Ethyl isobutyrate (1785 mg, 15.4 mmol) was added at once and the reaction mixture heated at 60° C. for 2 h. The THF was removed in vacuo and the residue was then poured into ice-water. HCl 6M was added with stirring until neutral pH was reached. The mixture was extracted with EtOAc, dried over $MgSO_4$ and concentrated in vacuo. The compound was purified by flash chromatography [silica; n-heptane-EtOAc (9:1)] to afford 4-methyl-3-oxo-2-phenyl-pentanenitrile (460 mg, 19%).

Step (b):

4-Methyl-3-oxo-2-phenyl-pentanenitrile (100 mg, 0.53 mmol) and 4-methoxyaniline were dissolved in AcOH 100% (1 ml). The mixture was heated at 160° C. during 30 min in the microwave. The solvent was co-evaporated with toluene in vacuo. The residue dissolved in $CH_2Cl_2$ and filtered through a silica plug. The solvent was removed and the mixture obtained was used directly in the next step without further purification.

Step (c):

The mixture obtained from step (b) (65 mg) and PEA (26 mg) were dissolved in $CH_2Cl_2$ (dry, 1.5 ml) and stirred at RT overnight. The mixture was extracted in $NaHCO_3/CH_2Cl_2$ using a phase separator. The mixture was purified by preparative HPLC to afford the desired 2-isopropyl-1-(4-methoxy-phenyl)-1H-indole-3-carbonitrile (3 mg).

Step (d):

2-Isopropyl-1-(4-methoxy-phenyl)-1H-indole-3-carbonitrile (3 mg, 0.01 mmol) was dissolved in dry $CH_2Cl_2$ (0.5 ml) and stirred at 0° C. $BBr_3$ (1M in $CH_2Cl_2$, 50 μl) was added and the mixture left in the fridge with stirring overnight. Some drops of MeOH were added and stirred. The solvent was removed in vacuo and the mixture partitioned in $H_2O$/DCM. The organic phase was separated using a phase separator. The solvent was removed in vacuo and the mixture was chromatographed using a prepacked silica column (solvent: EtOAc:n-Heptane 3-7) to afford the desired 1-(4-hydroxy-phenyl)-2-isopropyl-1H-indole-3-carbonitrile (1.1 mg, 39%). $^1$H NMR (acetone-d6, 500 MHz): 7.64 (m, 1H), 7.32 (m, 2H), 7.28 (m, 1H), 7.22 (m, 1H), 7.11 (m, 2H), 6.98 (m, 1H), 3.07 (m, 1H) and 1.43 (d, 61-1, J=7.0 Hz).

Example 7

2-Acetyl-1-(4-hydroxy-phenyl)-1H-indole-3-carbonitrile (E7)

The title compound was synthesized by hydrolysis of 2-(1-Ethoxy-vinyl)-1-(4-hydroxy-phenyl)-1H-indole-3-carbonitrile. ES/MS m/z: 277.1 (M+H), 275.1 (M−H); $^1$H NMR (acetone-d6, 500 MHz): 7.84 (d, 1H, J=7.5 Hz), 7.49-7.42 (m, 2H), 7.32 (m, 2H), 7.18 (m, 111, J=8.0 Hz), 7.06 (m, 1H) and 2.46 (s, 3H).

Example 8

2-(3,5-Dimethyl-isoxazol-4-yl)-1-(4-hydroxy-phenyl)-1H-indole-3-carboxylic acid (E8)

Scheme 7

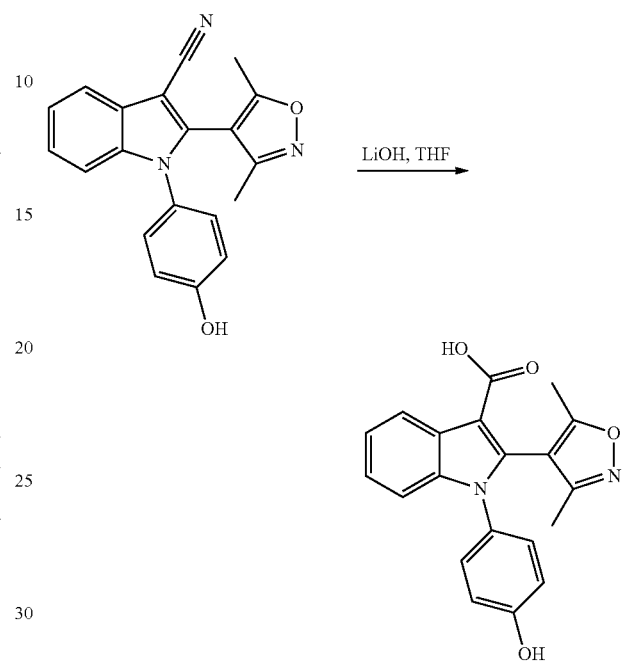

2-(3,5-Dimethyl-isoxazol-4-yl)-1-(4-hydroxy-phenyl)-1H-indole-3-carbonitrile (Example 51) was dissolved in a 1:2 mixture of THF and LiOH (aq, 2 M) and run in a microwave at 160° C. for one hour. The mixture was diluted with $H_2O$ and DCM, acidified to pH 1 with HCl (1 M) and the phases separated. The organic phase was concentrated in vacuo and purified with Chromatotrone using 5% MeOH in DCM as mobile phase. ES/MS m/z: 349.4 (M+H), 347.2 (M−H); NMR (acetone-d6, 500 MHz): 8.31 (m, 1H), 7.32-7.23 (m, 3H), 7.20 (m, 1H), 7.12 (br s, 1H), 6.97 (m, 2H), 2.16 (s, 3H) and 2.05 (s, 3H).

Example 9

1-[1-(4-Hydroxy-phenyl)-2-phenyl-1H-indol-3-yl]-ethanone (E9)

Scheme 8

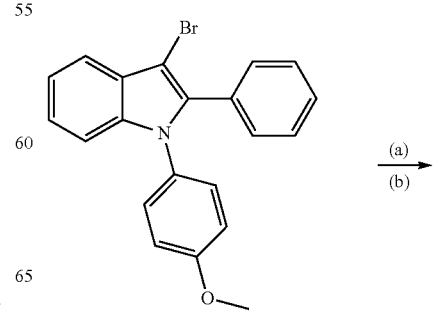

-continued

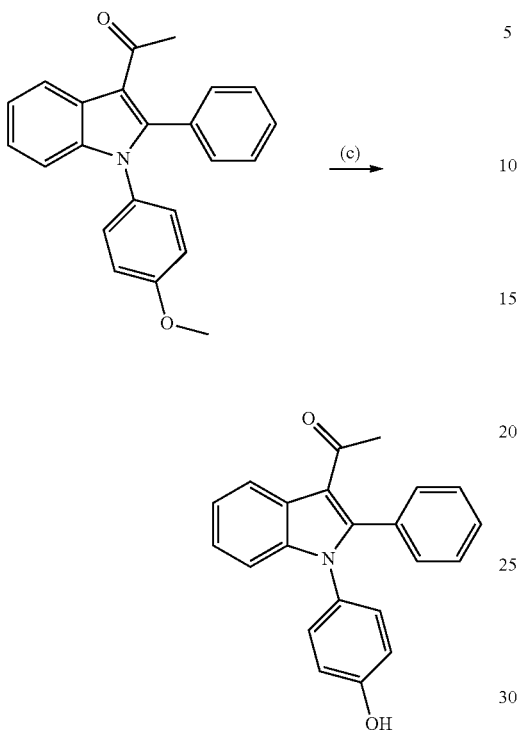

(a) Ethyleneglycol monovinylether, Pd(OAc)₂, dppp, KOAc, tBuNH₃Br, toluene/H2O 1:1; (b) 3M HCl; (c) BBr₃, DCM Steps (a) and (b):

1 eq. 3-Bromo-1-(4-methoxy-phenyl)-2-phenyl-1H-indole (synthesised from 1-(4-methoxyphenyl)-1H-indole by a method analogous to that used in steps (a), (b) and (c) of Example 21 followed by steps (a) and (b) of Example 22), 5 eq. ethylene glycol monovinyl ether, 5 mol % Pd(OAc)₂, mol % dppp, 1.3 eq. potassium acetate, 5 mol % tetrabutylammonium bromide were mixed with toluene/water in a microwave vial under nitrogen. The reaction was run in a microwave reactor at 150° C. for 20 min. 2 ml 3M HCl was added and the mixture was stirred at RT for 30 min. Water and DCM were added and the phases were separated. After evaporation of the solvents, the residue was purified by flash chromatography with heptane/EtOAc 9:1, Step (c):

The starting material was dissolved in dry DCM under nitrogen and was cooled to 0° C. BBr₃ was added and the temperature was allowed to reach RT for 2 h. The reaction was quenched with water and the phases were separated. After evaporation of the solvents, the residue was purified by preparative HPLC. ES/MS m/z: 328.16 (M+H), 326.2 (M−H); ¹H NMR (DMSO-d6, 500 MHz): 8.35 (m, 1H), 7.43 (m, 2H), 7.40-7.37 (m, 3H), 7.28 (m, 1H), 7.24 (m, 1H), 7.10 (m, 2H), 7.00 (m, 1H), 6.73 (m, 2H) and 1.88 (s, 3H).

Example 10

1-(4-Hydroxy-phenyl)-2-phenyl-1H-indole-3-carboxylic acid amide (E10)

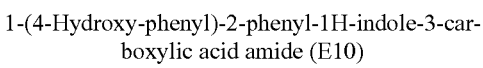

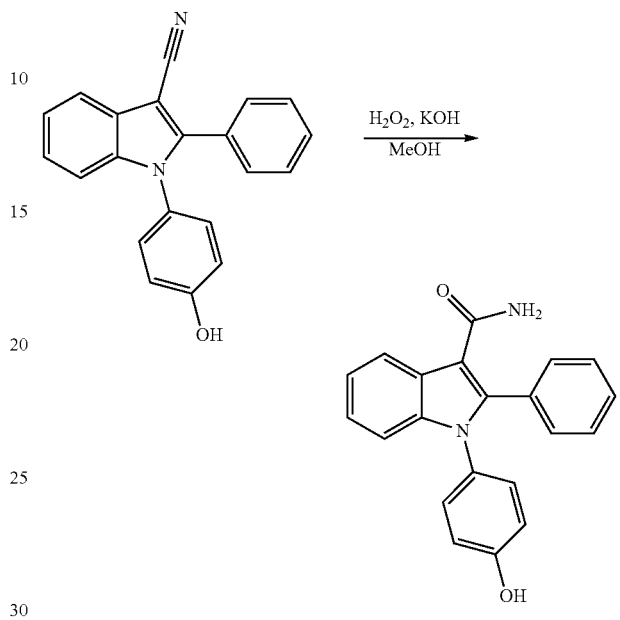

1-(4-Hydroxy-phenyl)-2-phenyl-1H-indole-3-carbonitrile (Example 46, 10 mg, 0.03 mmol) was dissolved in 1 ml of MeOH. H₂O₂ (1 ml, 35% by weight in H₂O) and 2M KOH (0.5 ml) were added and the reaction mixture was heated to reflux over night. The mixture was acidified with 1M HCl and EtOAc was added. The phases were separated and the organic solvents were evaporated. The crude product was purified by reversed phase preparative HPLC to give the title amide. ES/MS m/z: 329.1 (M+H), 327.13 (M−H); ¹H NMR (acetone-d6, 500 MHz): 8.34 (m, 1H), 7.46 (m, 2H), 7.40-7.37 (m, 3H), 7.24-7.18 (m, 2H), 7.12 (m, 2H), 7.07 (m, 1H) and 6.85 (m, 2H).

Example 11

(Z)-2-(3,5-dimethylisoxazol-4-yl)-N'-hydroxy-1-(4-hydroxyphenyl)-1H-indole-3-carboximidamide (E11)

Scheme 10

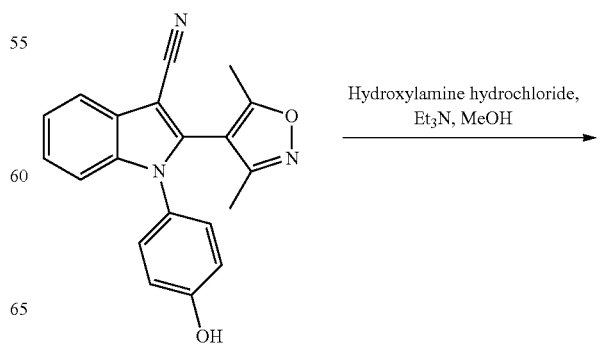

-continued

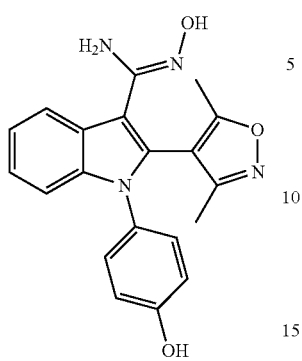

Under nitrogen atmosphere, a solution of 2-(3,5-dimethyl-isoxazol-4-yl)-1-(4-hydroxy-phenyl)-1H-indole-3-carbonitrile (Example 51), 12 eq hydroxylamine hydrochloride and 12 eq triethylamine in EtOH was heated at 100° C. for 24 hours. The reaction mixture was cooled to rt, diluted with methanol, precipitation filtered off and subjected to reversed phase preparative HPLC. Appropriate fractions were combined and evaporated, and identified by $^1$H-NMR and LC/MS. Purity was determined by analytical HPLC. ES/MS m/z: 363.5 (M+H), 361.6 (M−H); $^1$H NMR (acetone-d6, 500 MHz): 8.14-8.13 (s, OH), 8.08-8.04 (m, 1H), 7.23-7.14 (m, 3H), 7.15-7.06 (m, 2H), 6.96-6.91 (m, 2H), 5.18-5.07 (m, 2H), 2.16 (s, 3H), 2.00 (s, 3H).

Examples 12 and 13

[2-(3,5-Dimethyl-isoxazol-4-yl)-1-(4-hydroxy-phenyl)-1H-indol-3-yl]-carbamic acid tert-butyl ester (E12)

4-(3-Amino-2-(3,5-dimethylisoxazol-4-yl)-1H-indol-1-yl)phenol (E13)

-continued

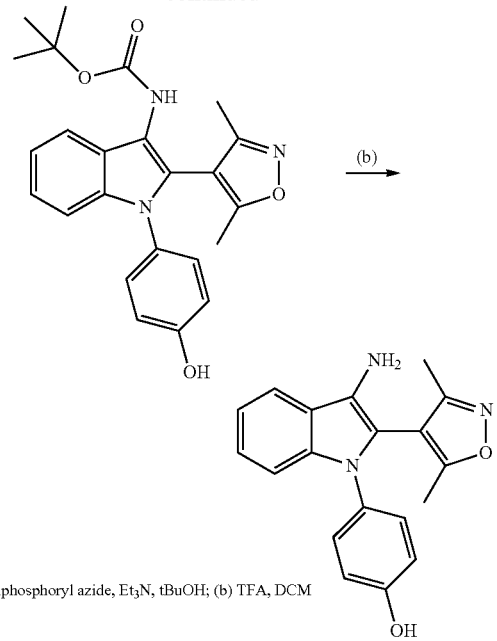

(a) Diphenylphosphoryl azide, Et₃N, tBuOH; (b) TFA, DCM

Step (a):
A mixture of 2-(3,5-dimethylisoxazol-4-yl)-1-(4-hydroxyphenyl)-1H-indole-3-carboxylic acid (Example 8), diphenylphosphoryl azide (1.1 eq) and triethyl amine (1.1 eq) in tert-BuOH was heated in microwave reactor at 90° C. for 1 hour. After cooling, the mixture was subjected to reversed phase preparative HPLC. Appropriate fractions were combined and evaporated, to provide [2-(3,5-dimethyl-isoxazol-4-yl)-1-(4-hydroxy-phenyl)-1H-indol-3-yl]-carbamic acid tert-butyl ester (E12). ES/MS m/z: 420.21 (M+H), 418.22 (M−H); $^1$H NMR (acetone-d6, 500 MHz): 7.61 (m, 1H), 7.26-7.13 (m, 5H), 6.93 (m, 2H), 2.22 (s, 3H), 1.89 (s, 3H) and 1.44 (s, 9H).

Step (b):
At rt, tert-butyl 2-(3,5-dimethylisoxazol-4-yl)-1-(4-hydroxyphenyl)-1H-indol-3-ylcarbamate was dissolved in DCM and treated with catalytic amount of TFA until the reaction was complete. The mixture was concentrated in vacuo and co-evaporated with MeOH. 4-(3-Amino-2-(3,5-dimethylisoxazol-4-yl)-1H-indol-1-yl)phenol (E13) was identified with LC/MS and purity determined by analytical HPLC. ES/MS m/z: 320.2 (M+H) and 318.2 (M−H).

Example 14

(Z)-2-(3,5-Dimethylisoxazol-4-yl)-7-fluoro-N'-hydroxy-1-(4-hydroxyphenyl)-1H-indole-3-carboximidamide (E14)

Scheme 11

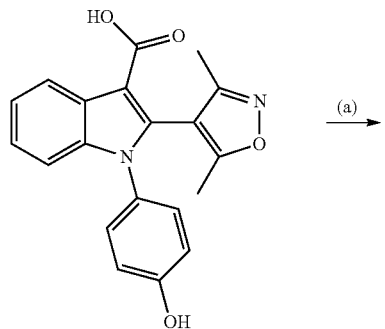

Scheme 12

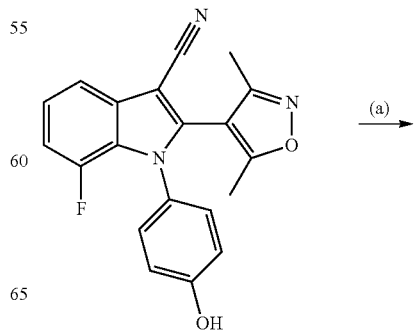

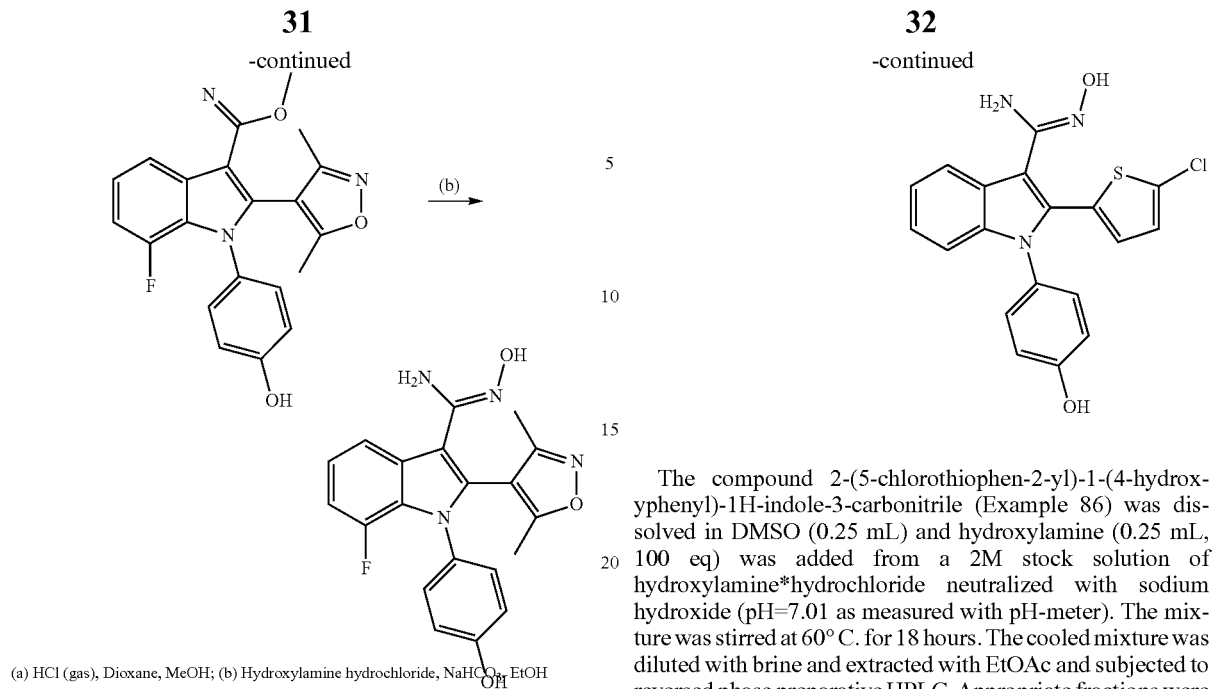

(a) HCl (gas), Dioxane, MeOH; (b) Hydroxylamine hydrochloride, NaHCO₃, EtOH

Step (a):

HCl gas was bubbled into a cooled (0° C.) solution of 2-(3,5-dimethylisoxazol-4-yl)-7-fluoro-1-(4-hydroxyphenyl)-1H-indole-3-carbonitrile (Example 230, 19 mg, 0.05 mmol) in dioxane (1.5 ml) and MeOH (0.5 ml) for 10 min. The tube was sealed, the temperature was allowed to warm to RT and the mixture was stirred over night. The solvents were evaporated in vacuo, Step (b):

To a stirring solution of hydroxylamine hydrochloride (19 mg, 0.27 mmol) in water, was added solid NaHCO₃ (23 mg, 0.27 mmol) at RT. The above amidate, dissolved in EtOH (1.5 ml), was added, and the solution was stirred at 90° C. in a sealed vial for 1 h. The mixture was purified by preparative HPLC to provide the title compound (Z)-2-(3,5-dimethylisoxazol-4-yl)-7-fluoro-N'-hydroxy-1-(4-hydroxyphenyl)-1H-indole-3-carboximidamide in 10% yield. ES/MS m/z: 381.1 (M+H), 279.2 (M–H); ¹H NMR (methanol-d4, 500 MHz): 7.68 (dd, 1H, J=8.1, 0.7 Hz), 7.13 (m, 1H), 7.08 (m, 2H), 6.93 (m, 1H), 6.77 (m, 2H), 2.16 (s, 3H) and 2.00 (s, 3H).

Example 15

(Z)-2-(5-chlorothiophen-2-yl)-N'-hydroxy-1-(4-hydroxyphenyl)-1H-indole-3-carboximidamide (E15)

Scheme 13

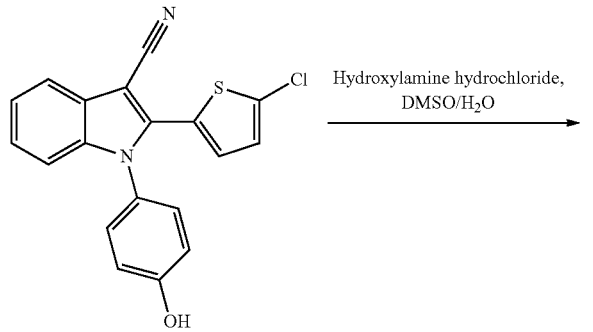

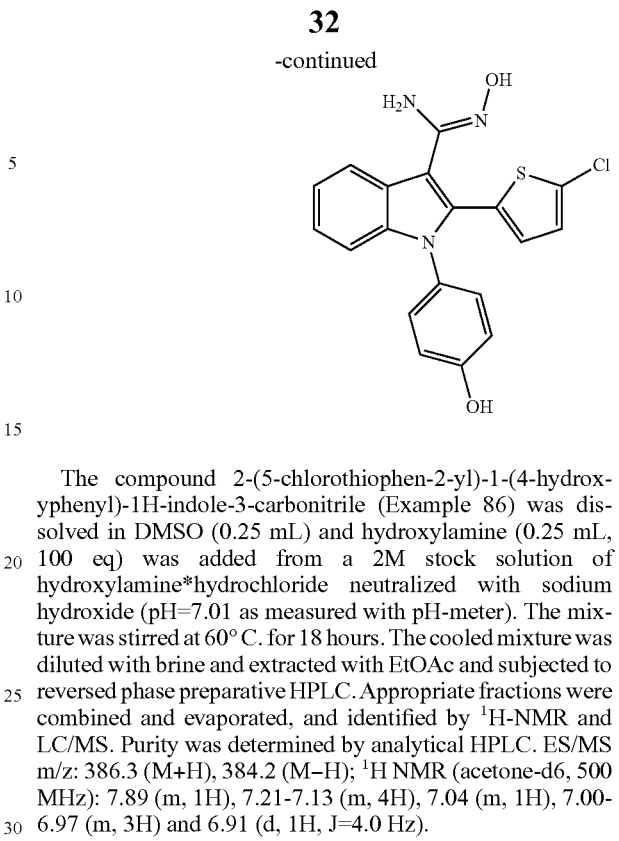

The compound 2-(5-chlorothiophen-2-yl)-1-(4-hydroxyphenyl)-1H-indole-3-carbonitrile (Example 86) was dissolved in DMSO (0.25 mL) and hydroxylamine (0.25 mL, 100 eq) was added from a 2M stock solution of hydroxylamine*hydrochloride neutralized with sodium hydroxide (pH=7.01 as measured with pH-meter). The mixture was stirred at 60° C. for 18 hours. The cooled mixture was diluted with brine and extracted with EtOAc and subjected to reversed phase preparative HPLC. Appropriate fractions were combined and evaporated, and identified by ¹H-NMR and LC/MS. Purity was determined by analytical HPLC. ES/MS m/z: 386.3 (M+H), 384.2 (M–H); ¹H NMR (acetone-d6, 500 MHz): 7.89 (m, 1H), 7.21-7.13 (m, 4H), 7.04 (m, 1H), 7.00-6.97 (m, 3H) and 6.91 (d, 1H, J=4.0 Hz).

Example 16

1-(2,3-Difluoro-4-hydroxyphenyl)-2-(3,5-dimethylisoxazol-4-yl)-1H-indole-3-carbonitrile (E16)

Scheme 14

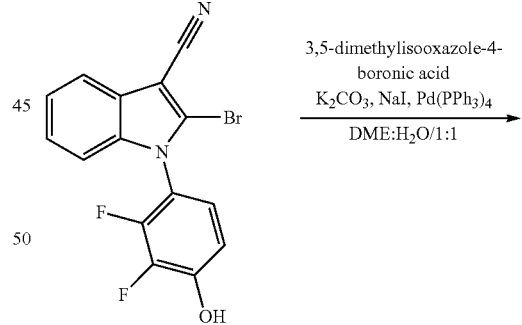

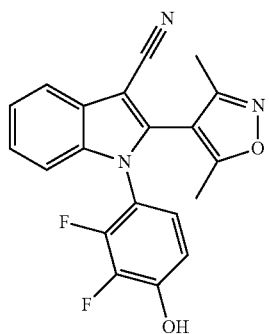

To 2-bromo-1-(2,3-difluoro-4-hydroxyphenyl)-1H-indole-3-carbonitrile (Example 103) was added 1.5 eq 3,5-dimethylisooxazole-4-boronic acid, 4 eq potassium carbonate, 2 eq sodium iodide and 10 mol % tetrakis(triphenylphosphine)palladium. DME:H$_2$O (1:1) was added and the vial was flushed with nitrogen, sealed and stirred at 150° C. for 10 min. The reaction mixture was cooled to rt, diluted with H$_2$O and extracted with DCM. The organic phase was evaporated to dryness and purified on silica column using 1:1 n-heptane:EtOAc as mobile phase. ES/MS m/z: 366.20 (M+H), 364.20 (M−H); NMR (CDCl$_3$, 500 MHz): 7.84 (d, 1H), 7.39 (m, 2H), 7.19 (d, 1H), 6.93 (broad m, 2H), 2.42 (s, 1.5H), 2.24 (s, 1.5H), 2.19 (s, 1.511), 2.01 (s, 1.5H)

Example 17

2-(3,5-Dimethylisoxazol-4-yl)-1-(4-hydroxyphenyl)-1H-indole-3 carbohydrazonamide (E17)

Scheme 15

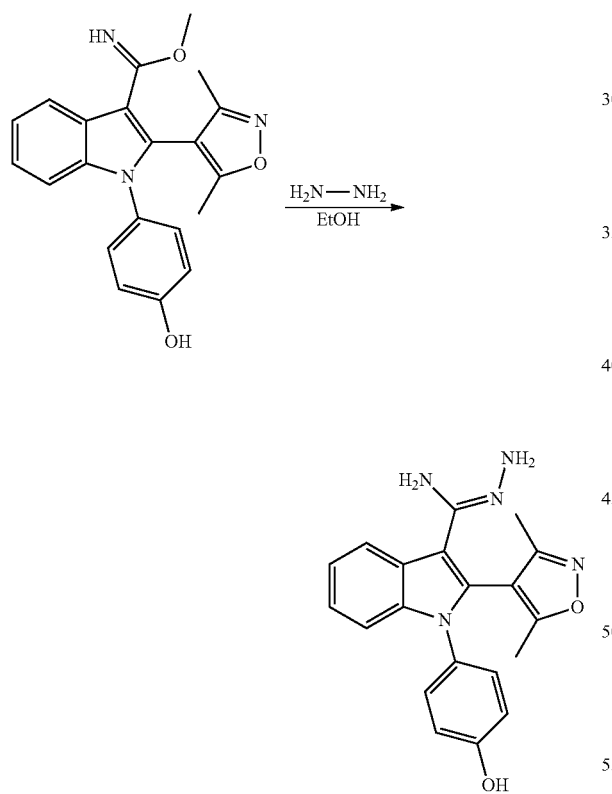

2-(3,5-Dimethylisoxazol-4-yl)-1-(4-hydroxyphenyl)-1H-indole-3-carbimidate (Example 184) was dissolved in EtOH and 10 eq hydrazine was added. The resulting mixture was stirred at 90° C. for 10 hours. The reaction mixture was diluted with EtOAc and washed with brine. The organic phase was evaporated to dryness in vacuo and then purified using reversed phase preparative HPLC. Fractions were combined, concentrated and the final product was identified by $^1$H-NMR and LC/MS. Purity was determined by analytical HPLC. ES/MS m/z: 362.21 (M+H), 360.28 (M−H); $^1$H NMR (methanol-d3, 500 MHz): 7.81 (m, 1H), 7.36-7.32 (m, 3H), 7.08 (m, 2H), 6.90 (m, 2H), 2.16 (s, 3H) and 1.96 (s, 3H).

Example 18

4-(2-(3,5-Dimethylisoxazol-4-yl)-3-(1,2,4-oxadiazol-3-yl)-1H-indol-1-yl)phenol (E18)

Scheme 16

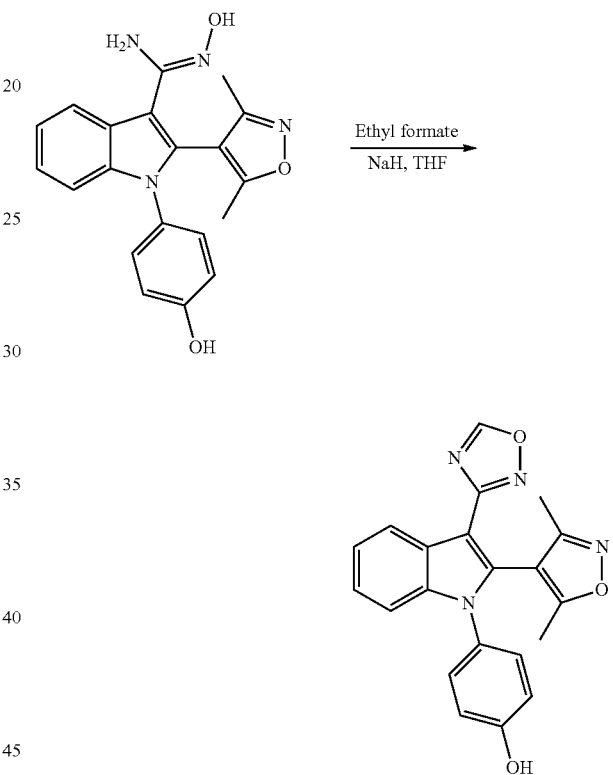

(Z)-2-(3,5-Dimethylisoxazol-4-yl)-N-hydroxy-1-(4-hydroxyphenyl)-1H-indole-3 carboximidamide (Example 11) was dissolved in THF containing 4-Å powdered molecular sieves. The mixture was stirred for 30 min under N$_2$. NaH (60% dispersion in mineral oil, 7.0 mg, 2.1 eq.) was added and the mixture was stirred at 60° C. for 20 min. After cooling to room temperature, ethyl formate (25.6 mg, 2.5 eq) in THF was added dropwise. The resulting mixture was heated at reflux for 1 h and then cooled to room temperature. The mixture was filtered and concentrated. The residue was filtered through silica and then purified using reversed phase HPLC to give 4-(2-(3,5-dimethylisoxazol-4-yl)-3-(1,2,4-oxadiazol-3-yl)-1H-indol-1-yl)phenol as a white powder: ES/MS m/z; 395.17 (M+H), 393.19 (M−H); NMR (acetone-d6, 500 MHz): 9.21 (s, 1H), 8.40 (m, 1H), 7.37-7.31 (m, 2H), 7.26-7.22 (m, 3H), 6.98 (m, 2H), 2.17 (s, 3H) and 1.98 (s, 3H).

Example 19

Methyl 2-(3,5-Dimethylisoxazol-4-yl)-1-(4-hydroxyphenyl)-1H-indole-3-carboxylate (E19)

Scheme 17

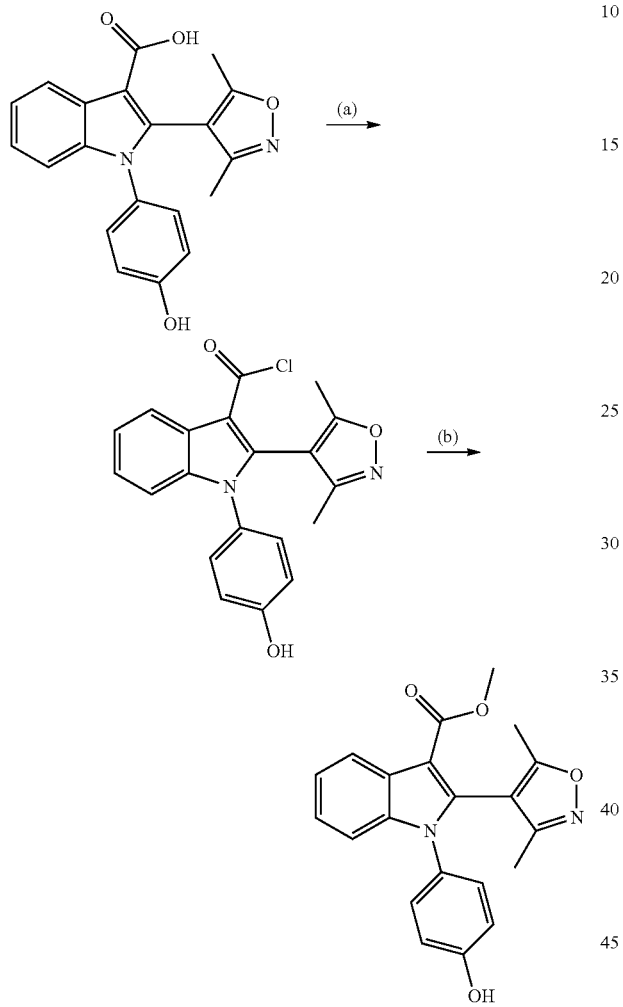

(a) Thionyl chloride, DMF; (b) Hydroxylamine, MeOH

Step (a):

2-(3,5-Dimethylisoxazol-4-yl)-1-(4-hydroxyphenyl)-1H-indole-3-carboxylic acid (Example 8, 6.0 mg, 0.02 mmol) was dissolved in 0.5 ml of thionyl chloride and 2 drops of DMF were added. The mixture was heated at 70° C. for 1 h and was then evaporated carefully in vacuo.

Step (b):

2-(3,5-Dimethylisoxazol-4-yl)-1-(4-hydroxyphenyl)-1H-indole-3-carbonyl chloride was dissolved in 0.5 ml of dry MeOH and the mixture was cooled on an ice-bath. Fresh hydroxylamine was prepared by pouring a MeOH solution (0.3 ml) of hydroxylamine hydrochloride (12 mg, 0.17 mmol) into a MeOH solution (0.3 ml) of KOH (19 mg, 0.33 mmol). The mixture was filtered through a syringe filter into the cooled acid chloride solution. After 5 min, the cooling bath was removed and the reaction was allowed to warm to RT and was stirred for 10 min Water, 1M HCl and EtOAc were added and the phases were separated. After evaporation of the solvents, the residue was purified by preparative HPLC to provide methyl 2-(3,5-dimethylisoxazol-4-yl)-1-(4-hydroxyphenyl)-1H-indole-3-carboxylate in 16% yield. ES/MS m/z: 363.11 (M+H), 361.13 (M−H); $^1$H NMR (methanol-$d_4$, 500 MHz): 8.21 (m, 1H), 7.32-7.26 (m, 2H), 7.20 (m, 1H), 7.13 (br s, 1H), 7.01 (br s, 1H), 6.88 (m, 2H), 3.83 (s, 3H), 2.12 (s, 3H) and 2.03 (s, 3H).

Example 20

2-(3,5-Dimethylisoxazol-4-yl)-N-hydroxy-1-(4-hydroxyphenyl)-1H-indole-3-carboxamide (E20)

Scheme 18

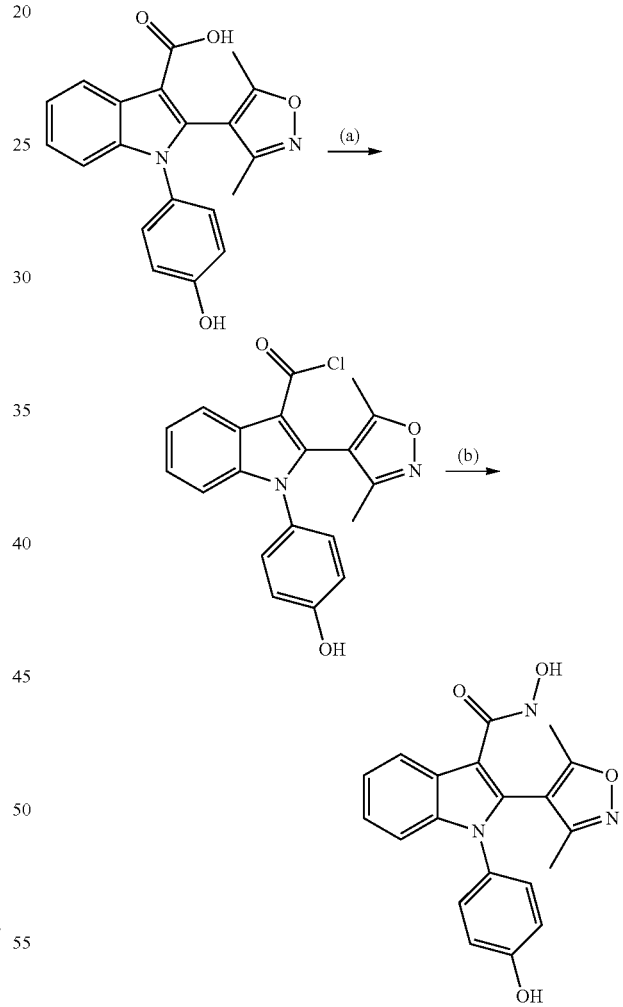

(a) Oxalyl dichloride, DMF, DCM; (b) Hydroxylamine, Et$_3$N, NMP

Step (a):

Oxalyl dichloride (75 μl, 0.86 mmol) and a drop of DMF were added to a cooled (0° C.) solution of 2-(3,5-dimethylisoxazol-4-yl)-1-(4-hydroxyphenyl)-1H-indole-3-carboxylic acid (Example 8, 30 mg, 0.09 mmol) in dry DCM. The temperature was allowed to warm to RT and stirred for 2 h. The solvents were evaporated.

Step (b):

A mixture of hydroxylamine hydrochloride (30 mg, 0.43 mmol) and triethylamine (60 μl, 0.43 mmol) in 3 ml of NMP was added to the crude product from step (a). The mixture was stirred at RT for 15 min. Water and EtOAc were added and the phases were separated. After evaporation of the solvents, the residue was purified by preparative HPLC to provide the title compound 2-(3,5-dimethylisoxazol-4-yl)-N-hydroxy-1-(4-hydroxyphenyl)-1H-indole-3-carboxamide in 32% yield. ES/MS m/z: 364.15 (M+H), 362.19 (M−H); $^1$H NMR (acetone-d6, 500 MHz): 7.40 (m, 1H), 6.80-6.70 (m, 3H), 6.62 (m, 2H), 6.39 (m, 2H), 1.65 (s, 3H) and 1.49 (s, 3H).

Example 21

4-[2-(3,5-Dimethyl-isoxazol-4-yl)-3-methanesulfonyl-indol-1-yl]-phenol (E21)

Scheme 19

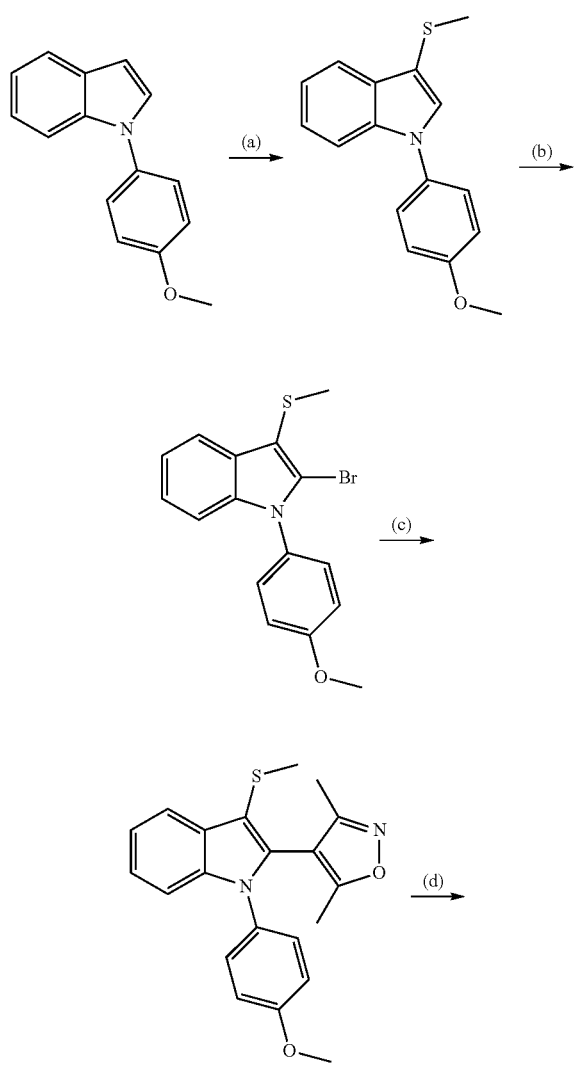

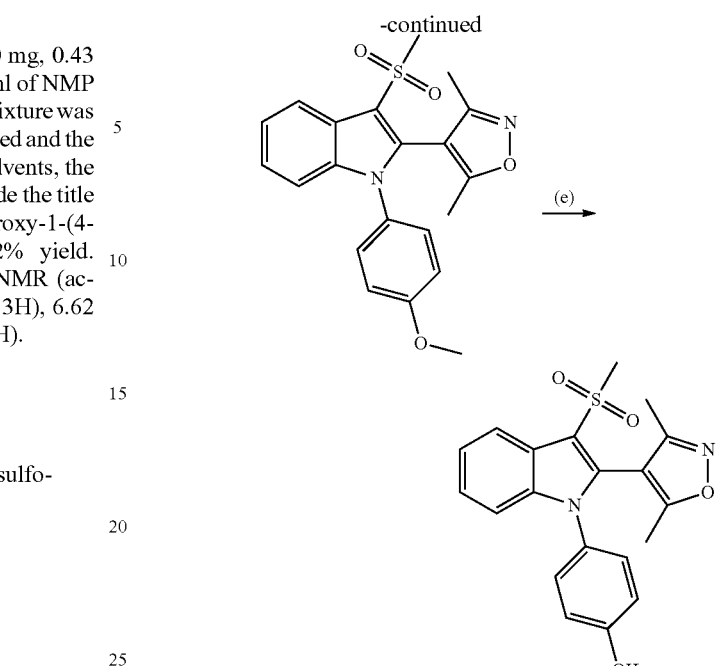

(a) 2-(methylthio)isoindoline-1,3-dione, MgBr, DMA; (b) NBS, DMF; (c) 3,5-dimethylisoxazole-4-ylboronic acid, Pd(PPh$_3$)$_4$, NaI, NaCO$_3$, DME, H$_2$O (d) Oxone, H$_2$O, MeOH; (e) BBr$_3$, DCM Step (a):

1-(4-methoxyphenyl)-1H-indole (synthesised from indole by an arylation process analogous to that described in step (a) of Example 1 [arylation process also described in *J. Org. Chem.* 2008, 73 (14), 5529-5535], 1.0 g, 4.48 mmol), 2-(methylthio)isoindoline-1,3-dione (0.95 g, 4.93 mmol) and magnesium bromide (8 mg, 0.045 mmol) were mixed in degassed DMA and stirred under an atmosphere of nitrogen at 90° C. for 90 min. 1M NaOH and EtOAc were added. The phases were separated and the organic solvents were evaporated. The residue was purified by flash chromatography with heptane/EtAc 20:1 to provide 1-(4-methoxyphenyl)-3-(methylthio)-1H-indole in 80% yield. ES/MS m/z: 270.11 (M+H).

Step (b):

NBS (529 mg, 2.97 mmol) was added to a cooled (0° C.) solution of 1-(4-methoxyphenyl)-3-(methylthio)-1H-indole (800 mg, 2.97 mmol) in 10 ml of DMF. The temperature was allowed to warm to RT and the mixture was stirred at RT for 30 min. Water and DCM were added and the phases were separated. After evaporation of the solvents, the residue was purified by flash chromatography with heptane/EtAc 20:1 to provide 2-bromo-1-(4-methoxyphenyl)-3-(methylthio)-1H-indole in 66% yield. ES/MS m/z: 348.04, 350.01 (M+H).

Step (c):

4-(1-(4-methoxyphenyl)-3-(methylthio)-1H-indol-2-yl)-3,5-dimethylisoxazole was synthesized from the product of step (b) using a procedure analogous to that described in Example 16.

Step (d):

Oxone (152 mg, 0.25 mmol) was mixed with water (1 ml) and added to a cooled (0° C.) mixture of 4-(1-(4-methoxyphenyl)-3-(methylthio)-1H-indol-2-yl)-3,5-dimethylisoxazole (30 mg, 0.08 mmol) in 2 ml of MeOH. The temperature was allowed to warm to RT and the slurry was stirred at RT over night. 1M HCl and EtOAc were added and the phases were separated. The organic phase was concentrated.

Step (e):

4-(1-(4-Methoxyphenyl)-3-(methylsulfonyl)-1H-indol-2-yl)-3,5-dimethylisoxazole was dissolved in 2 ml of dry DCM and cooled to −78° C. under nitrogen. BBr₃ (31 μl, 0.33 mmol) was added and the temperature was allowed to warm to RT for 2 h. Water and EtOAc were added and the phases were separated. After evaporation of the solvents, the residue was purified by preparative HPLC to provide 4-[2-(3,5-dimethyl-isoxazol-4-yl)-3-methanesulfonyl-indol-1-yl]-phenol in 27% yield. ES/MS m/z: 383.11 (M+H), 381.13 (M−H); ¹H NMR (acetone-d6, 500 MHz): 8.12 (m, 1H), 7.39-7.34 (m, 2H), 7.25-7.19 (m, 3H), 6.98 (m, 2H), 3.06 (s, 3H), 2.30 (s, 3H) and 2.09 (s, 3H).

Example 22

1-(2-(3,5-Dimethylisoxazol-4-yl)-1H-(4-hydroxyphenyl)-1H-indol-3-yl)-2,2,2-trifluoroethanone (E22)

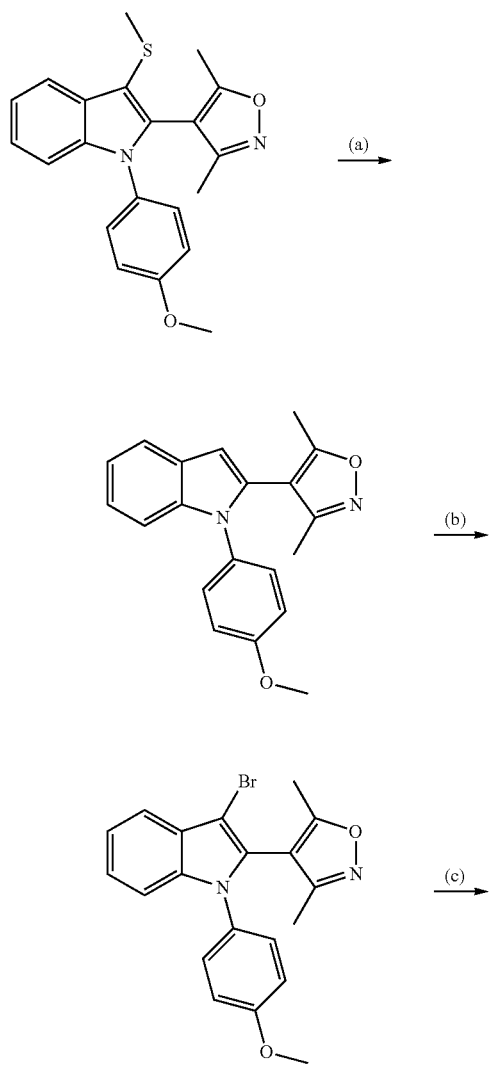

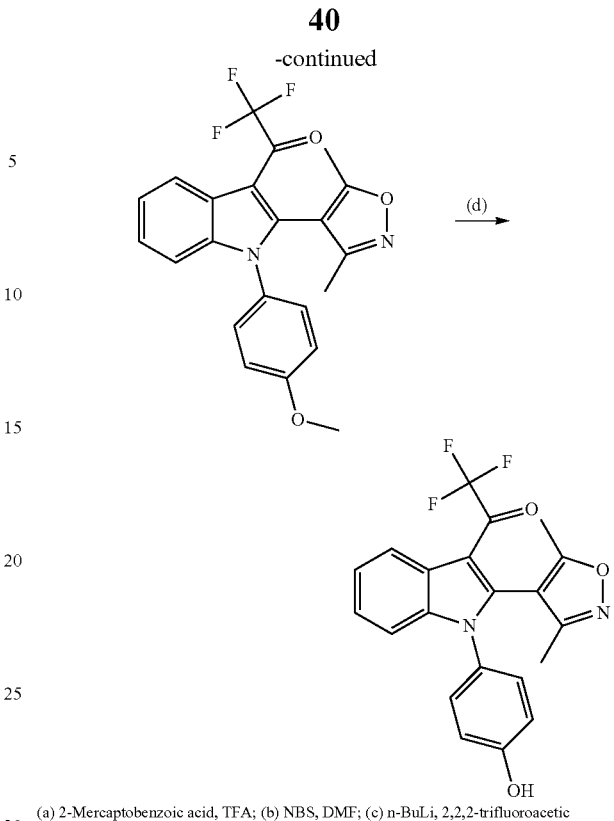

(a) 2-Mercaptobenzoic acid, TFA; (b) NBS, DMF; (c) n-BuLi, 2,2,2-trifluoroacetic anhydride, THF; (d) BBr₃, DCM Step (a):

4-(1-(4-Methoxyphenyl)-3-(methylthio)-1H-indol-2-yl)-3,5-dimethylisoxazole (the intermediate product of step (c) from the synthesis of Example 21, 140 mg, 0.38 mmol) and 2-mercaptobenzoic acid (118 mg, 0.77 mmol) were added to 5 ml of trifluoroacetic acid at RT. The mixture was stirred as a slurry at RT under an atmosphere of nitrogen over night. 2M NaOH and EtAc were added and the phases were separated. The solvents were evaporated and the residue was purified by flash chromatography with heptane/EtAc 4:1 as eluent to provide 4-(1-(4-methoxyphenyl)-1H-indol-2-yl)-3,5-dimethylisoxazole in 86% yield. ES/MS m/z: 319.1 (M+H)

Step (b):

NBS (59 mg, 0.33 mmol) was added to a cooled (0° C.) solution of 4-(1-(4-methoxyphenyl)-1H-indol-2-yl)-3,5-dimethylisoxazole (105 mg, 0.33 mmol) in 5 ml of DMF. The temperature was allowed to warm to RT and the mixture was stirred at RT for 30 min. DMF was evaporated. DCM and water were added and the phases were separated. After evaporation of the solvents, the residue was purified by flash chromatography with heptane/EtOAc 9:1 to provide 4-(3-bromo-1-(4-methoxyphenyl)-1H-indol-2-yl)-3,5-dimethylisoxazole in 98% yield. ES/MS m/z: 365.14 (M+H), 363.30 (M−H).

Step (c):

n-BuLi (10 μl, 0.03 mmol) was added to a cooled (−78° C.) solution of 4-(3-bromo-1-(4-methoxyphenyl)-1H-indol-2-yl)-3,5-dimethylisoxazole (10 mg, 0.03 mmol) under an atmosphere of nitrogen. After 5 min, 2,2,2-trifluoroacetic anhydride (7 μl, 0.05 mmol) was added. The temperature was allowed to warm to RT and the mixture was stirred over night. 1M NaHCO₃ and DCM were added, the phases were separated and the solvents were evaporated.

Step (d):

1-(2-(3,5-dimethylisoxazol-4-yl)-1-(4-methoxyphenyl)-1H-indol-3-yl)-2,2,2-trifluoroethanone was dissolved in dry DCM and the mixture was cooled on an ice-bath under an atmosphere of nitrogen. BBr₃ (17 µl, 0.1 mmol) was added and the temperature was allowed to warm to RT and the mixture was stirred over night. Water, DCM and some dioxane were added, the phases were separated and the solvents were evaporated. The residue was passed through a short plug of silica with EtOAc as eluent. The residue was purified by preparative HPLC to provide the title compound 1-(2-(3,5-dimethylisoxazol-4-yl)-1-(4-hydroxyphenyl)-1H-indol-3-yl)-2,2,2-trifluoroethanone in 46% yield. ES/MS m/z: 401.1 (M+H), 399.1 (M−H); ¹H NMR (methanol-d4, 500 MHz): 8.26 (m, 1H), 7.41-7.34 (m, 2H), 7.18 (m, 1H), 7.11 (m, 2H), 6.89 (m, 2H), 2.19 (s, 31-1) and 2.01 (s, 3H).

Example 23

4-[3-bromo-2-(3,5-dimethylisoxazol-4-yl)-1H-indole-1-yl]phenol (E23)

Scheme 21

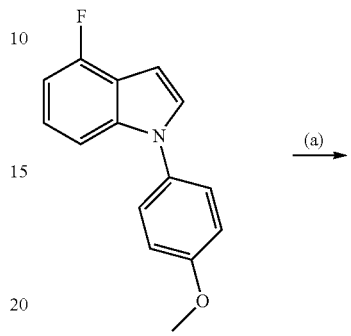

At 0° C., 10 eq of boron trifluoride-dimethyl sulfide was added to 4-[3-bromo-1-(4-methoxyphenyl)-1H-indol-2-yl]-3,5-dimethylisoxazole (the intermediate product of step (b) from the synthesis of Example 22), dissolved in DCM and stirred at ambient temperature over night. The mixture was diluted with EtOAc and washed with brine, the organic phase was concentrated and subjected to reversed phase preparative HPLC. Appropriate fractions were combined and evaporated, and identified by ES/MS m/z: 385.1 (M+H), 383.09 (M−H) and ¹H NMR (acetone-d6, 500 MHz): 7.60 (m, 1H), 7.31-7.23 (m, 3H), 7.17 (m, 2H), 6.95 (m, 2H), 2.28 (s, 3H) and 1.99 (s, 3H).

Example 24

2-bromo-4-fluoro-1-(4-hydroxyphenyl)-1H-indole-3-carbonitrile (E24)

Scheme 22

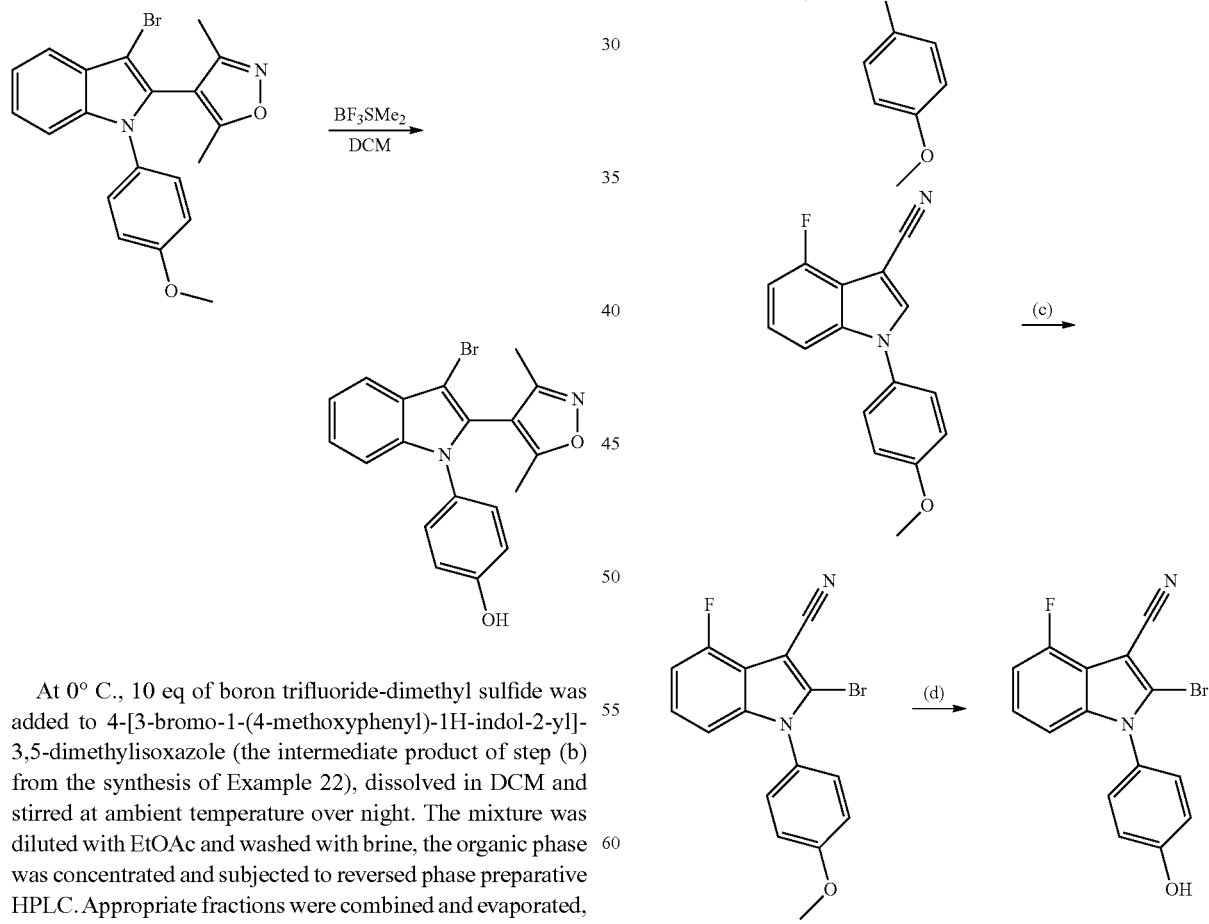

(a) Chlorosulfonyl isocyanate, 1,2-dichloroethane; (b) Phosphorus oxychloride; (c) t-BuLi, 1,2-dibromotetrachloroethane, THF; (d) BF₃SMe₂, DCM.

Step (a):

4-Fluoro-1-(4-methoxyphenyl)-1H-indole (synthesised from 4-fluoro-indole by an arylation process analogous to that described in step (a) of Example 1 [arylation process also described in *J. Org. Chem.* 2008, 73 (14), 5529-5535]) was dissolved in 1,2-dichloroethane and 1.2 eq of chlorosulfonyl isocyanate was added, and the mixture was stirred at room temperature for 2 hours. To the mixture was added water and the pH adjusted to neutral by addition of NaOH (aq, 1M), then the mixture was extracted with EtOAc. The organic phase was washed with brine and dried over $Na_2SO_4$. The crude product was purified on a Silica column using 50% EtOAc in n-heptane as mobile phase.

Step (b):

To 4-fluoro-1-(4-methoxyphenyl)-1H-indole-3-carboxamide was added 50 eq of phosphorus oxychloride and the reaction run neat at 60° C. for 2 hours. The mixture was cooled to rt and co-evaporated with toluene. The residue was diluted with EtOAc and washed first with sat. $NaHCO_3$, then brine, and the organic phase dried over $Na_2SO_4$. The crude product was purified on a Silica column using 10% EtOAC in n-heptane as mobile phase.

Step (c):

The intermediate was synthesized from the product of step (b) using a procedure analogous to that described in step (b) of Example 1.

Step (d):

The title compound 2-bromo-4-fluoro-1-(4-hydroxyphenyl)-1H-indole-3-carbonitrile was synthesized from the product of step (c) using a procedure analogous to that described in Example 23. ES/MS m/z: 333.04 (M+H), 331.04 (M−H); $^1$H NMR (acetone-d6, 500 MHz): 7.44 (dd, 1H, J=8.9, 2.6 Hz), 7.39 (m, 2H), 7.18 (dd, 1H, J=8.5, 4.2 Hz) and 7.15-7.09 (m, 3H).

Example 25

(Z)-2-(4-Fluorophenoxy)-N'-hydroxy-1-(4-hydroxyphenyl)-1H-indole-3-carboximidamide (E25)

Scheme 23

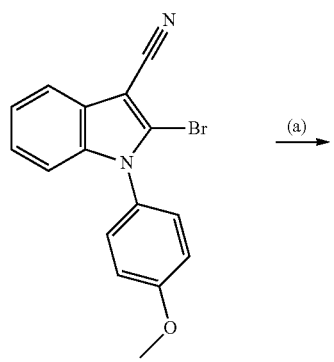

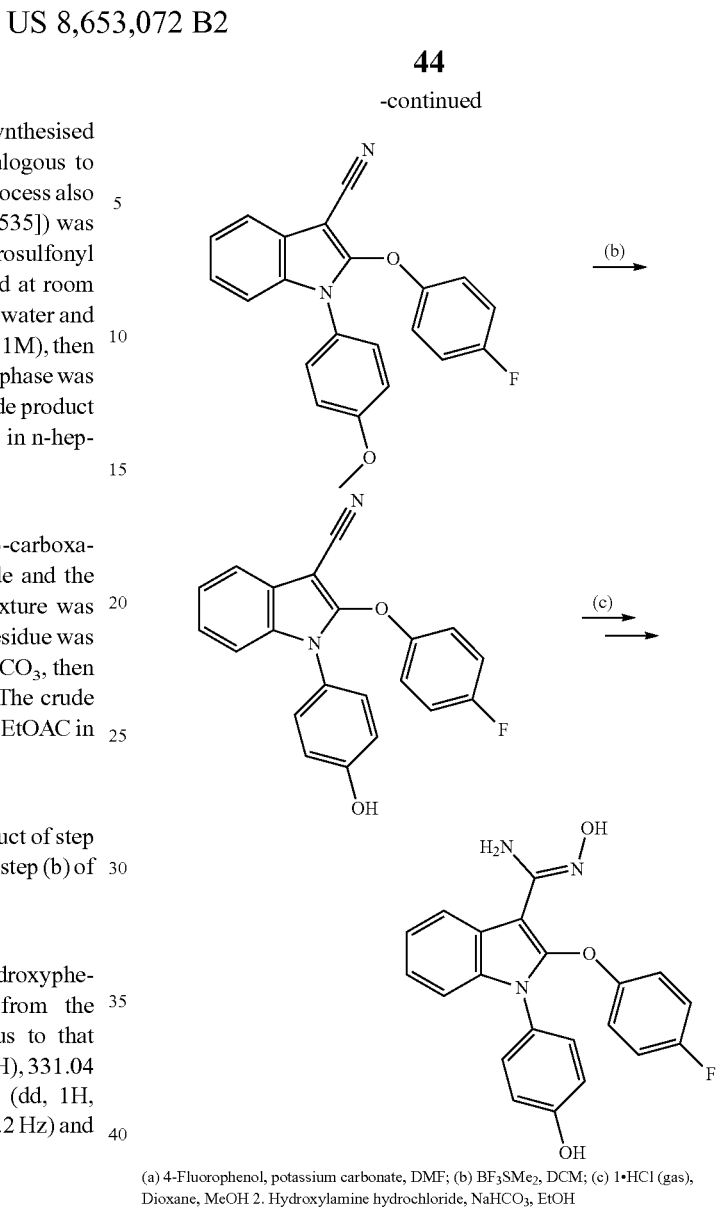

(a) 4-Fluorophenol, potassium carbonate, DMF; (b) $BF_3SMe_2$, DCM; (c) 1•HCl (gas), Dioxane, MeOH 2. Hydroxylamine hydrochloride, $NaHCO_3$, EtOH Step (a):

A mixture of 2-bromo-1-(4-methoxyphenyl)-1H-indole-3-carbonitrile (the intermediate product of step (b) from the synthesis of Example 1), 5 eq 4-fluorophenol and 5 eq potassium carbonate was heated at 200° C. for 20 minutes in a microwave reactor under inert atmosphere. The cooled mixture was diluted with water and extracted with EtOAc, the combined organic phases were dried over $Na_2SO_4$ and concentrated. The crude product was purified on a Silica column using 20% EtOAc in n-heptane as mobile phase.

Step (b):

The compound 2-bromo-4-fluoro-1-(4-hydroxyphenyl)-1H-indole-3-carbonitrile was synthesized from the product of step (a) using a procedure analogous to that described in Example 23.

Step (c):

The title compound (Z)—N'-hydroxy-1-(4-hydroxyphenyl)-2-phenoxy-1H-indole-3-carboximidamide was synthesized from the product of step (b) using procedures analogous to those described in Example 14. ES/MS m/z: 360.18 (M+H), 358.22 (M−H); $^1$H NMR (acetone-d6, 500 MHz); 8.24 (m, 1H), 7.25-7.14 (m, 6H), 7.09 (m, 1H), 7.00 (m, 1H) and 6.90-6.85 (m, 4H).

Example 26

4-(2-(3,5-Dimethylisoxazol-4-yl)-3-nitro-1H-Indol-1-yl)phenol (E26)

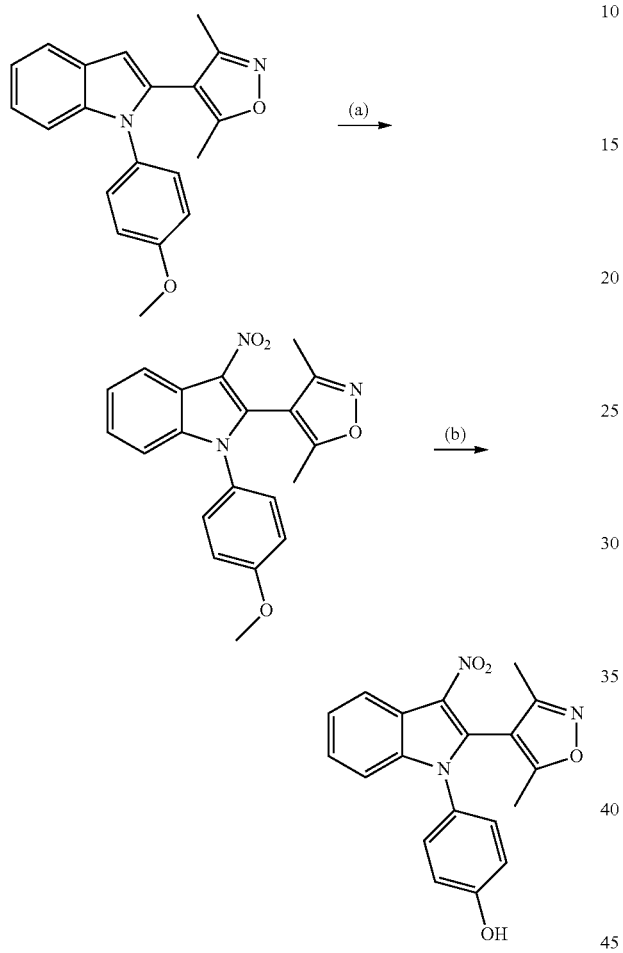

(a) Nitric acid, HOAc, DCM; (b) BF₃SMe₂, DCM

Step (a):

To a solution of 4-(1-(4-methoxyphenyl)-1H-indol-2-yl)-3,5-dimethylisoxazole (the intermediate product of step (a) from the synthesis of Example 22) in DCM was slowly added a mixture of 2 eq nitric acid and 20 eq acetic acid. After 1 hour stirring at rt, the mixture was diluted with water and the phases partitioned. The organic phase was concentrated and purified on a Silica column using 30% EtOAc in n-heptane as mobile phase.

Step (b):

The title compound 4-(2-(3,5-dimethylisoxazol-4-yl)-3-nitro-1H-indol-1-yl)phenol was synthesized from the product of step (a) using a procedure analogous to that described in Example 23. ES/MS m/z: 350.18 (M+H), 348.22 (M−H); ¹H NMR (acetone-d6, 500 MHz): 8.34 (m, 1H), 7.50 (m, 1H), 7.44-7.40 (m, 2H), 7.29 (m, 1H), 7.20 (m, 1H), 7.01 (m, 2H), 2.22 (s, 31-1) and 2.11 (s, 3H).

Example 27

4-(3-(Dihydroxyamino)-2-(3,5-dimethylisoxazol-4-yl)-1H-indol-1-yl)phenol (E27)

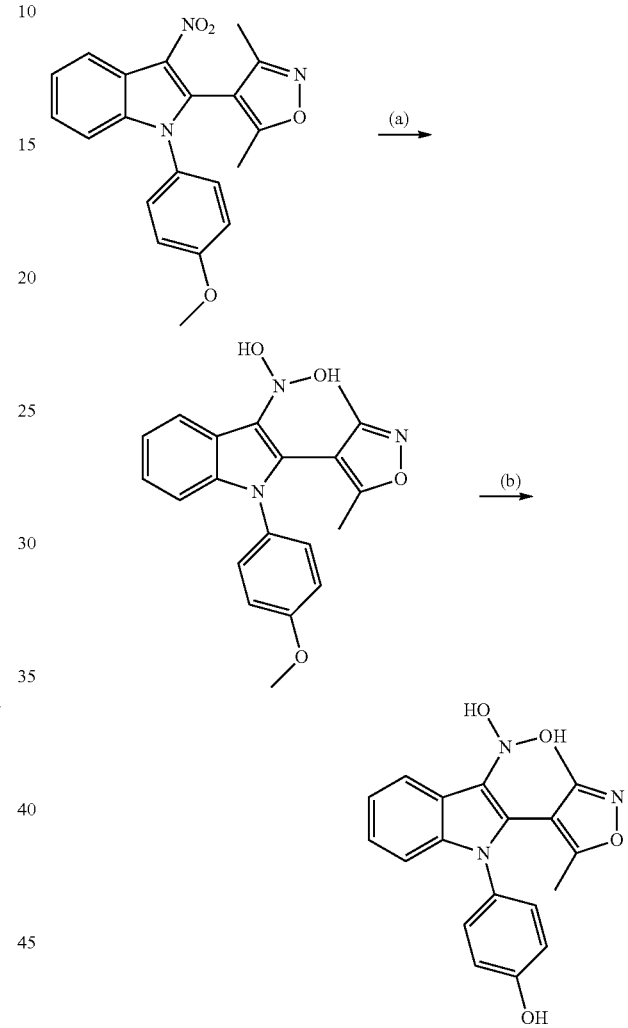

(a) Pd/C (10%), EtOH; (b) BF₃SMe₂, DCM

Step (a):

4-(1-(4-Methoxyphenyl)-3-nitro-1H-indol-2-yl)-3,5-dimethylisoxazole (the intermediate product of step (a) from the synthesis of Example 26) was dissolved in EtOH (99%), a catalytic amount of Pd/C (10%) was added and the mixture was stirred under 4 psi H₂ over night. The mixture was filtered through a plug of Celite, concentrated and purified on a Silica column using 45% EtOAc in n-heptane as mobile phase.

Step (b):

The title compound 4-(3-(dihydroxyamino)-2-(3,5-dimethylisoxazol-4-yl)-1H-indol-1-yl)phenol was synthesized from the product of step (a) using a procedure analogous to that described in Example 23. ES/MS m/z: 351.13 (M+H), 350.18 (M−H); ¹H NMR (acetone-d6, 500 MHz); 8.31 (d, 1H, J=8.2 Hz), 7.44 (t, 1H, J=7.4 Hz), 7.36 (m, 1H), 7.30 (m, 2H), 7.22 (d, 1H, J=8.2 Hz), 7.05 (m, 2H), 1.81 (s, 3H) and 1.80 (s, 3H).

Example 28

N-(2-(3,5-Dimethylisoxazol-4-yl)-1-(4-hydroxyphenyl)-1H-indol-3-yl)acetamide (E28)

Scheme 26

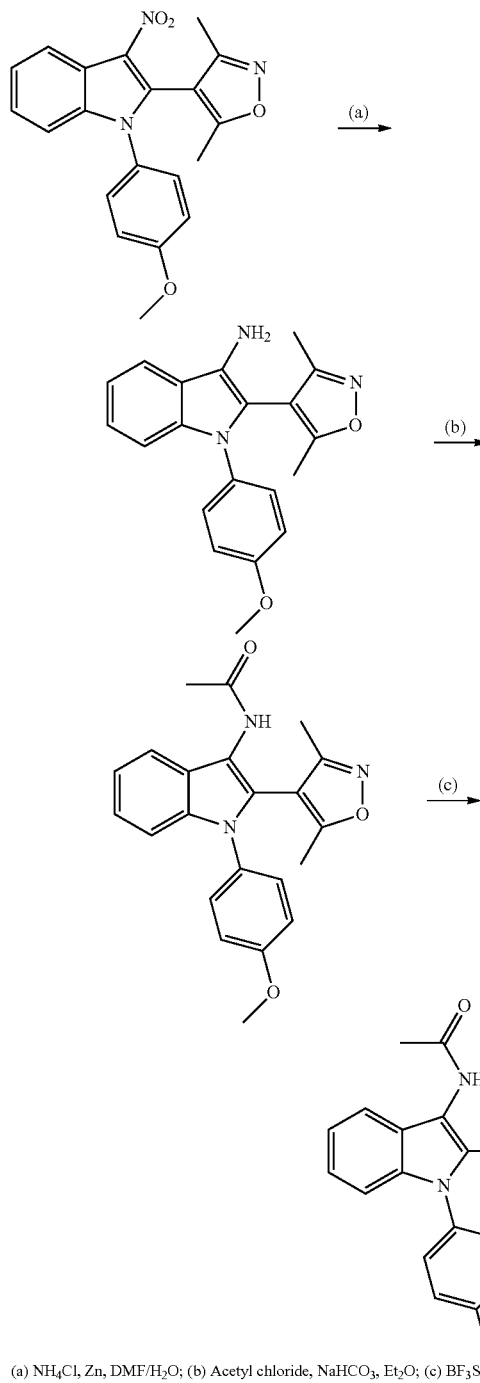

(a) NH₄Cl, Zn, DMF/H₂O; (b) Acetyl chloride, NaHCO₃, Et₂O; (c) BF₃SMe₂, DCM

Step (a):

To a solution of 4-[1-(4-methyoxyphenyl)-3-nitro-1H-indol-2-yl]-3,5-dimethylisoxazole (the intermediate product of step (a) from the synthesis of Example 26) in DMF/water (10:1) at 0° C., was added ammonium chloride (5 eq) and zinc (5 eq). The mixture was stirred for 2 hours at that temperature and then diluted with EtOAc, the formed precipitate was filtered off and the organic phase washed with brine and dried over Na₂SO₄. The mixture was concentrated and used without further purification in the next step.

Step (b):

2-(3,5-Dimethylisoxazol-4-yl)-1-(4-methoxyphenyl)-1H-indol-3-amine was dissolved in diethyl ether and cooled to 0° C., then was added NaHCO₃ (2 eq) and acetyl chloride (2 eq) as a solution in diethyl ether, the mixture was kept at 0° C. and stirred for 1 hour. The solvent was removed and the residue dissolved in EtOAc and washed with water, then subsequently with brine, then dried over Na₂SO₄. The mixture was concentrated and used without further purification in the next step.

Step (c):

The title compound N-(2-(3,5-dimethylisoxazol-4-yl)-1-(4-hydroxyphenyl)-1H-indol-3-yl)acetamide was synthesized from the product of step (b) using a procedure analogous to that described in Example 23. ES/MS m/z: 361.21 (M+H), 360.17 (M−H); ¹H NMR (acetone-d6, 500 MHz): 7.58 (m, 1H), 7.21-7.11 (m, 5H), 6.93 (m, 2H), 2.20 (s, 3H), 2.07 (s, 3H) and 1.88 (s, 3H).

Example 29

N-(2-(3,5-dimethylisoxazol-4-yl)-1-(4-hydroxyphenyl)-1H-indol-3-yl)methanesulfonamide (E29)

Scheme 27

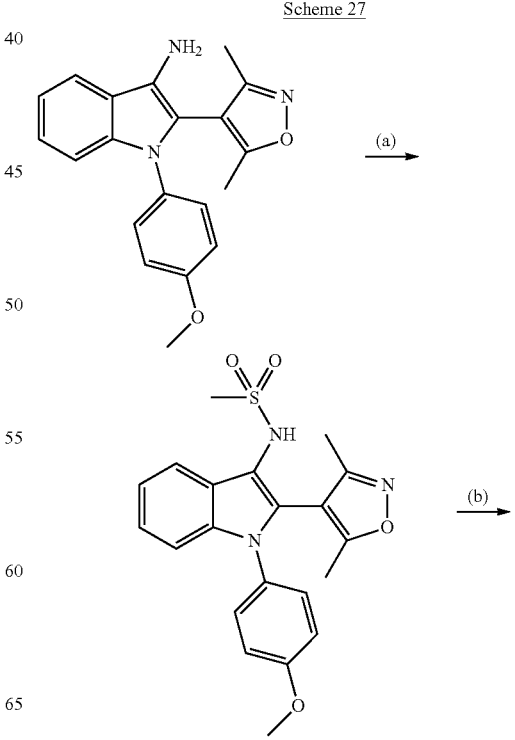

49

-continued

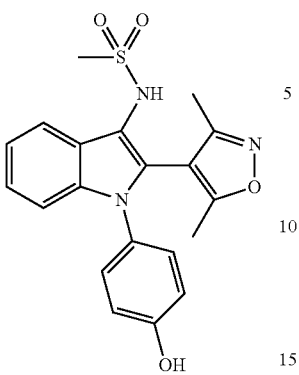

(a) Methanesulphonyl chloride, NaHCO₃, Et₂O; (b) BF₃SMe₂

Step (a):

2-(3,5-Dimethylisoxazol-4-yl)-1-(4-methoxyphenyl)-1H-indol-3-amine (the intermediate product of step (a) from the synthesis of Example 28) was dissolved in diethyl ether and cooled to 0° C., then was added NaHCO₃ (2 eq) and methanesulfonyl chloride (2 eq) as a solution in diethyl ether, the mixture was kept at 0° C. and stirred for 1 hour, then at rt over weekend. The solvent was removed and the residue dissolved in EtOAc and washed with water, then subsequently with brine, then dried over Na₂SO₄. The mixture was concentrated and used without further purification in the next step.

Step (b):

The title compound N-(2-(3,5-dimethylisoxazol-4-yl)-1-(4-hydroxyphenyl)-1H-indol-3-yl)methanesulfonamide was synthesized from the product of step (a) using a procedure analogous to that described in Example 23. ES/MS m/z: 398.17 (M+H), 396.15 (M−H); ¹H NMR (acetone-d6, 500 MHz): 7.82 (m, 1H), 7.24-7.20 (m, 3H), 7.17 (m, 2H), 6.95 (m, 2H), 2.89 (s, 3H), 2.26 (s, 3H) and 1.96 (s, 3H).

Example 30

1-(2-(3,5-Dimethylisoxazol-4-yl)-1-(4-hydroxyphenyl)-1H-indol-3-yl)urea (E30)

Scheme 28

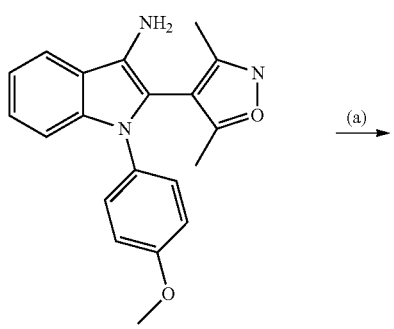

50

-continued

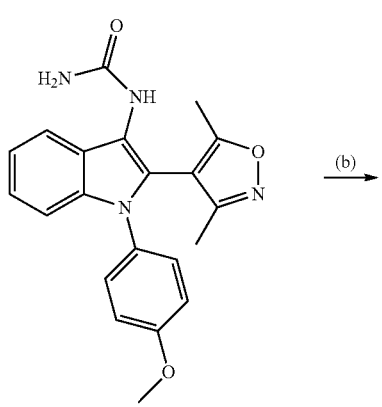

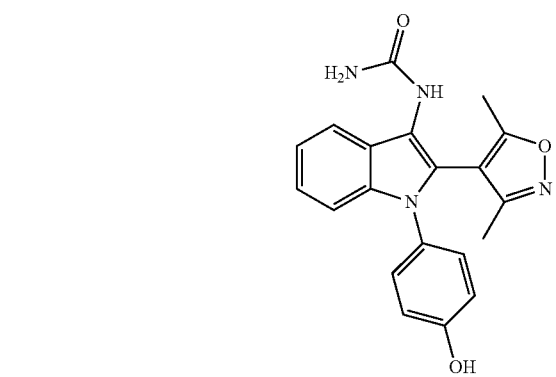

(a) Isocyanato trimethylsilane, DMF; (b) HI

Step (a):

A degassed (N₂) mixture of 2-(3,5-dimethylisoxazol-4-yl)-1-(4-methoxyphenyl)-1H-indol-3-amine (the intermediate product of step (a) from the synthesis of Example 28) and isocyanatotrimethylsilane (6 eq) in DMF was heated in a microwave reactor at 200° C. for 2×20 min. The mixture was cooled and concentrated and used without further purification in the next step.

Step (b):

1-(2-(3,5-Dimethylisoxazol-4-yl)-1-(4-methoxyphenyl)-1H-indol-3-yl)urea was heated neat in hydriodic acid (aq, 57%) at 100° C. for 3 hours. The reaction mixture was cooled and concentrated, and co-evaporated with DCM and EtOAc. The residue was subjected to reversed phase preparative HPLC. Appropriate fractions were combined and evaporated, and identified by ¹H NMR. ES/MS m/z: 363.19 (M+H), 362.18 (M−H); ¹H NMR (acetone-d6, 500 MHz): 7.65 (m, 1H), 7.22-7.09 (m, 5H), 6.93 (m, 2H), 2.25 (s, 3H) and 1.94 (s, 3H).

Examples 31 and 32

4-(2-(3,5-Dimethylisoxazol-4-yl)-3-thiocyanato-1,4-indol-1-yl)phenol (E31)

2-(3,5-Dimethylisoxazol-4-yl)-1-(4-hydroxyphenyl)-1H-indol-3-yl N'-hydroxycarbamimidothioate (E32)

Scheme 29

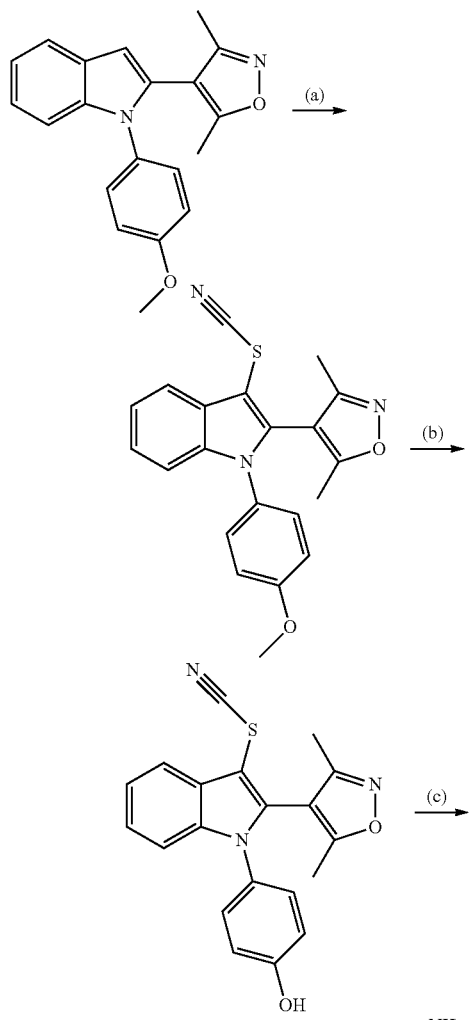

(a) NH₄SCN, Mn(OAc)₃, HOAc; (b) BBr₃, DCM; (c) Hydroxylamine, NaHCO₃ (aq), DMSO

Step (a):

4-(1-(4-Methoxyphenyl)-1H-indol-2-yl)-3,5-dimethylisoxazole (the intermediate product of step (a) from the synthesis of Example 22) was dissolved in AcOH and 1.2 eq ammonium thiocyanate was added. 3 eq Manganese (III) acetate was then added and the reaction was stirred at room temperature for 45 minutes after which monitoring on TLC showed full consumption of the starting material. Reaction mixture was diluted with EtOAc and washed with Brine. The phases were partitioned and the organic phase was washed with NaHCO₃ (aq). Organic phase was then evaporated to dryness in vacuo and the crude product was used without further purification. ES/MS m/z: 376.14 (M+H);

Step (b):

The product of step (a) was subjected to demethylation using BBr₃ according to the process described in step (c) of Example 9 to give 4-(2-(3,5-dimethylisoxazol-4-yl)-3-thiocyanato-1H-indol-1-yl)phenol (E31). ES/MS m/z: 362.14 (M+H), 360.18 (M–H); ¹H NMR (acetone-d6, 500 MHz): 7.86 (m, 1H), 7.43-7.37 (m, 2H), 7.31 (m, 1H), 7.26 (m, 2H), 6.98 (m, 2H), 2.34 (s, 3H) and 2.03 (s, 3H).

Step (c):

4-(2-(3,5-Dimethylisoxazol-4-yl)-3-thiocyanato-1H-indol-1-yl)phenol was dissolved in DMSO and 10 eq 2 M hydroxylamine/NaHCO₃ (aq) stock solution was added. The reaction was stirred at 65° C. overnight and then diluted with H₂O. A precipitation was formed after stirring for 5 min. The mixture was diluted with EtOAc and diethylether, washed with NH₄Cl (aq) and phases were partitioned. Organic phase was evaporated to dryness in vacuo and subjected to purification on reverse phase preparative HPLC to provide the title compound 2-(3,5-dimethylisoxazol-4-yl)-1-(4-hydroxyphenyl)-1H-indol-3-yl N'-hydroxycarbamimidothioate (E32). ES/MS m/z: 395.17 (M+H), 393.19 (M–H); ¹H NMR (acetone-d6, 500 MHz): 8.88 (broad s, 1H), 8.73 (broad s, 1H), 7.80-7.78 (m, 1H), 7.29-7.24 (m, 3H), 7.18 (d, 2H), 6.95 (d, 2H), 5.11 (broad s, 2H), 2.28 (s, 3H), 2.00 (s, 3H)

Example 33

4-(3-benzyl-2-phenyl-1H-indol-1-yl)phenol (E33)

Scheme 30

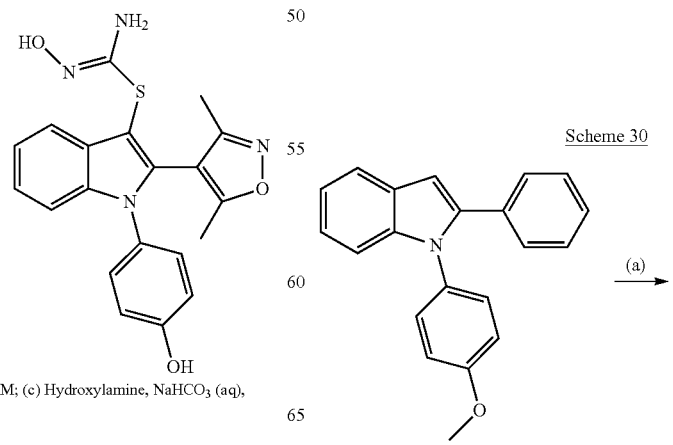

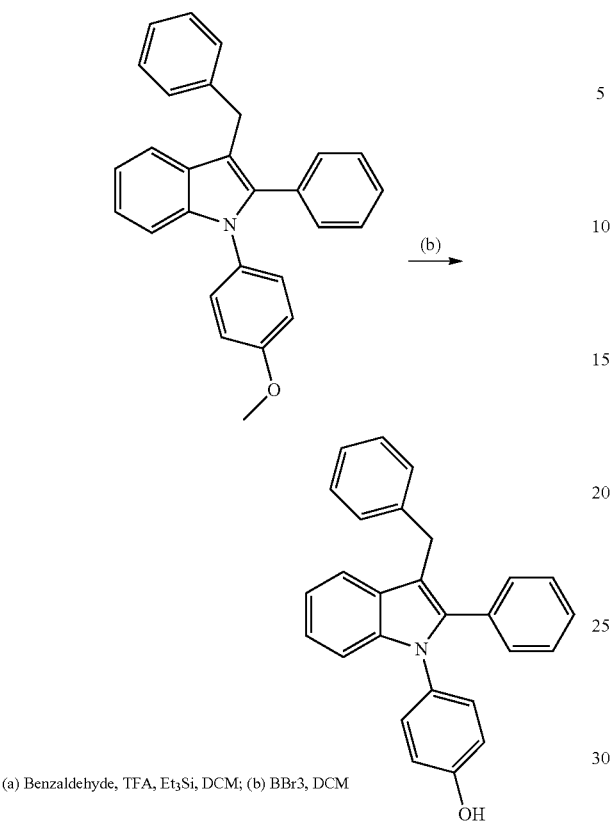

(a) Benzaldehyde, TFA, Et₃Si, DCM; (b) BBr3, DCM

Step (a):

A mixture of 19 μl TFA and 80 μl Et₃SiH in 0.5 ml dry DCM was added drop wise over 5 min. to a mixture of 47 mg 1-(4-methoxyphenyl)-2-phenyl-1H-indole (synthesised from 2-phenylindole by an arylation process as described in *J. Org. Chem.* 2001, 66 (23), 7729-7737) and 19 μl benzaldehyde in 1 ml dry DCM at 0° C. under nitrogen. The mixture was allowed to reach room temp over night after which the mixture was cooled to 0° C. and 160 μl Et₃SiH and 38 μl TFA dissolved in 1 ml CH₂Cl₂ was added. The mixture was stirred for 40 min and then basified with NaOH 2M (~pH 13) followed by addition of brine, extraction with dichloromethane (×3) and evaporation. 0.2 g Solid supported TsNHNH₂ was added to the crude product together with 3 ml dichloromethane. The mixture was stirred gently for 1 h 20 min. The polymer was filtered off and the crude product was filtered through a silica gel plug. The product was obtained pure without need for further purification.

Step (b):

The product of step (a) was subjected to demethylation using BBr₃ according to the process described in step (c) of Example 9 to give 4-(3-benzyl-2-phenyl-1H-indol-1-yl)phenol. ES/MS m/z: 376.4 (M+H), 374.2 (M−H); ¹H NMR (acetone-d6, 500 MHz): 7.86 (m, 1H), 7.43-7.37 (m, 2H), 7.31 (m, 1H), 7.26 (m, 2H), 6.98 (m, 2H), 2.34 (s, 3H) and 2.03 (s, 3H).

Examples 34 and 35

2-(2-(3,5-Dimethylisoxazol-4-yl)-1-(4-hydroxyphenyl)-1H-indol-3-yl)-2-oxoacetamide (E34)

2-(2-(3,5-Dimethylisoxazol-4-yl)-1-(4-hydroxyphenyl)-1H-indol-3-yl)-2-(hydroxyimino)acetamide (E35)

Scheme 31

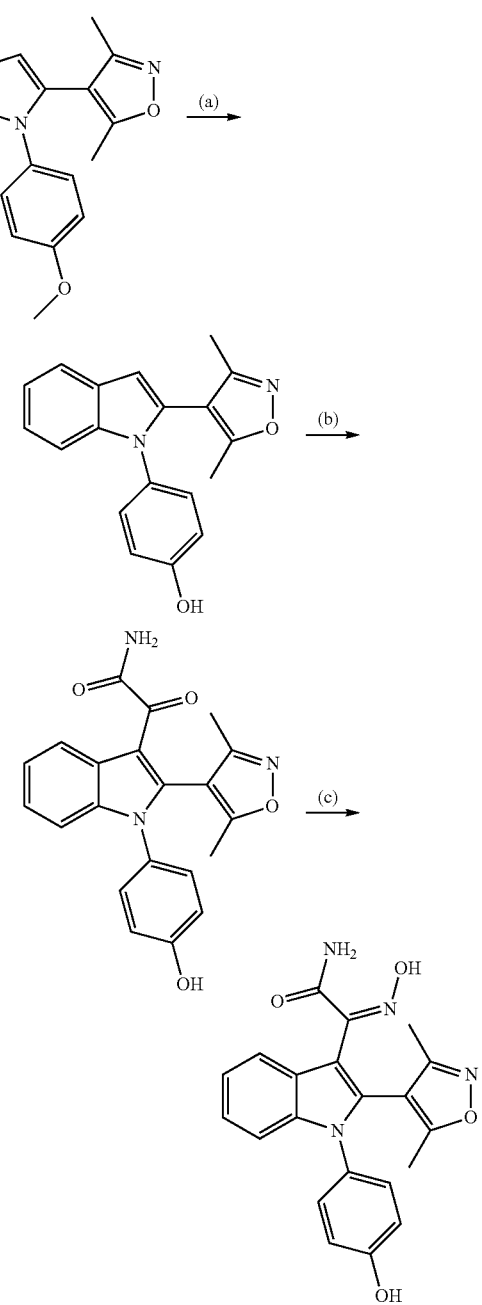

(a) BBr₃, DCM; (b) Oxalyl chloride, DCM, NH₃/MeOH, (c) NH₂OH, EtOH

Step (a):

4-(2-(3,5-Dimethylisoxazol-4-yl)-1H-indol-1-yl)phenol was synthesized from 4-(1-(4-methoxyphenyl)-1H-indol-2-yl)-3,5-dimethylisoxazole (the intermediate product of step (a) from the synthesis of Example 22) via an analogous process to that described in step (c) of Example 1.

Step (b):

4-(2-(3,5-Dimethylisoxazol-4-yl)-1H-indol-1-yl)phenol was dissolved in 1 ml dry dichloromethane under nitrogen and cooled to 0° C. 4 ml Oxalyl chloride was added and the mixture was stirred at 0° C. for 2 h 15 min. and then at room temp for 1 h 15 min. The mixture was concentrated under vacuum without heating and 1 ml NH$_3$/MeOH (sat.) added. The mixture was stirred for 1 h and then concentrated. The crude product was purified by flash chromatography (EtOAc/heptane; 4:6 to 8:2) to provide 2-(2-(3,5-dimethylisoxazol-4-yl)-1-(4-hydroxyphenyl)-1H-indol-3-yl)-2-oxoacetamide (E34). ES/MS m/z: 376.18 (M+H), 374.17 (M−H); $^1$H NMR (acetone-d6, 500 MHz): 8.33 (m, 1H), 7.37-7.15 (m, 5H), 6.98 (br s, 2H), 2.27 (s, 3H) and 2.00 (s, 3H).

Step (c):

50 µl Pyridine was added to 8.8 mg 2-(2-(3,5-dimethylisoxazol-4-yl)-1-(4-hydroxyphenyl)-1H-indol-3-yl)-2-oxoacetamide and 32.6 mg hydroxylamine hydrochloride in 1.5 ml EtOH in a microwave vial. The vial was sealed and flushed with nitrogen. The mixture was heated to 150° C. for 7.5 min. and then to 150° C. for 5 min. in a Biotage Initiator microwave oven. The mixture was concentrated in vacuo and purified by preparative HPLC (formic acid buffer/acetonitrile). 2-(2-(3,5-dimethylisoxazol-4-yl)-1-(4-hydroxyphenyl)-1H-indol-3-yl)-2(hydroxyimino)acetamide (E35) was obtained as a mixture of syn and anti oxime isomers. ES/MS m/z: 391.4 (M+H), 389.5 (M−H); $^1$H NMR (DMSO-d6, 500 MHz): 7.37 (m, 1H), 7.20-7.03 (m, 5H), 6.84 (m, 2H), 2.15 (s, 3H) and 1.77 (s, 3H).

Examples 36 and 37

2-(2-(3,5-Dimethylisoxazol-4-yl)-1-(4-hydroxyphenyl)-1H-indol-3-yl)-2-hydroxyacetamide (E36)

2-(2-(3,5-Dimethylisoxazol-4-yl)-1-(4-hydroxyphenyl)-1H-Indol-3-yl)acetamide (E37)

Scheme 32

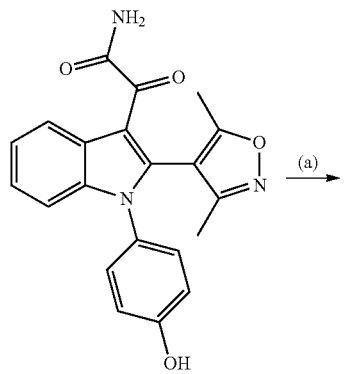

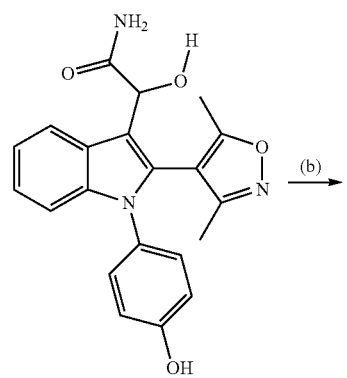

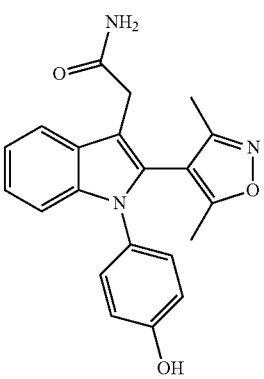

(a) NaBH$_4$, EtOH; (b) Et$_3$Si, TFA, DCM

Step (a):

9 mg 2-(2-(3,5-Dimethylisoxazol-4-yl)-1-(4-hydroxyphenyl)-1H-indol-3-yl)-2-oxoacetamide (Example 34) was mixed with 1 ml EtOH, 1.8 mg of NaBH$_4$ was added and the mixture was stirred for 1.5 h. The mixture was evaporated, water was added, followed by extraction with EtOAc. The crude product was purified by reversed phase flash chromatography (acetonitrile/water) to provide 2-(2-(3,5-dimethylisoxazol-4-yl)-1-(4-hydroxyphenyl)-1H-indol-3-yl)-2-hydroxyacetamide (E36). ES/MS m/z: 376.3 (M−H); $^1$H NMR (acetone-d6, 500 MHz): 7.78 (m, 1H), 7.13-6.93 (m, 5H), 6.79 (m, 2H), 2.23, 2.21 (two s, 3H) and 1.93, 1.90 (two s, 3H).

Step (b):

1 ml TFA and 19 µl Et$_3$SiH were added to 2-(2-(3,5-dimethylisoxazol-4-yl)-1-(4-hydroxyphenyl)-1H-indol-3-yl)-2-hydroxyacetamide at 0° C. and the mixture was stirred for 60 min. The solvent was evaporated without heating followed by short silica gel purification (EtOAc/heptane; 1:9 to 8:2) to provide 2-(2-(3,5-dimethylisoxazol-4-yl)-1-(4-hydroxyphenyl)-1H-indol-3-yl)acetamide (E37). ES/MS m/z: 362.3 (M+H); $^1$H NMR (methanol-d3, 500 MHz): 8.98 m, 1H), 8.46-8.35 (m, 5H), 8.16 (m, 2H), 4.78 (d, 21-1, J=1.9 Hz), 3.54 (s, 3H) and 3.19 (s, 3H).

Example 38

2-((Z)-But-1-enyl)-1-(4-hydroxy-phenyl)-1H-indole-3-carbonitrile (E38)

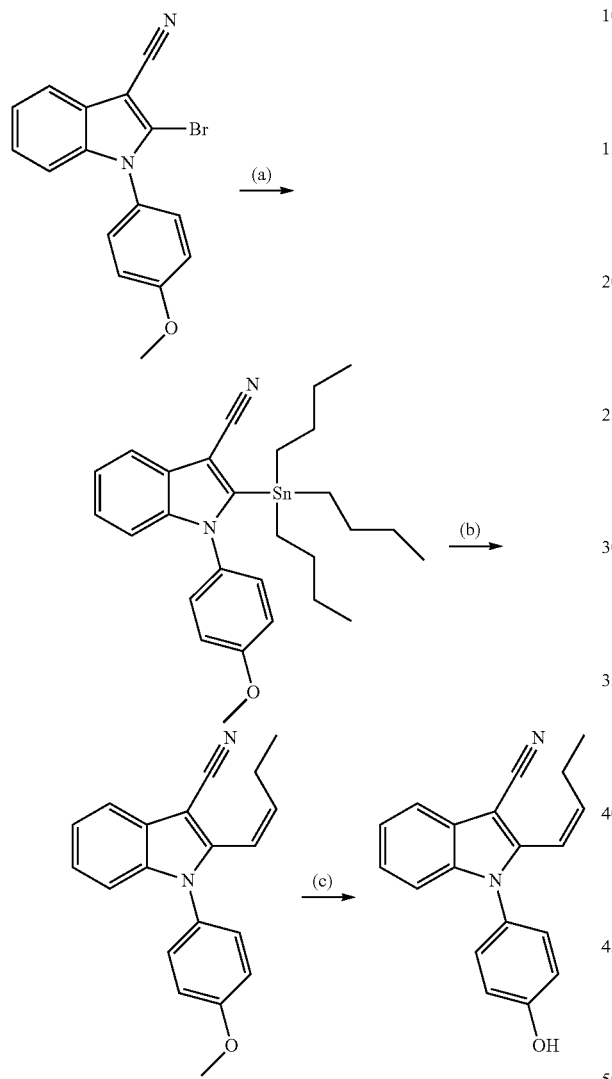

(a) BuLi, tributyltin chloride, THF; (b) (Z)-1-bromobutene, dipalladium Tri-(1E,4E)-1,5-diphenylpenta-1,4-dien-3-one, tri o-tolyphosphine, DMF; (c) BF$_3$SMe$_2$, DCM Step (a):

To a cooled solution of 2-bromo-1-(4-methoxyphenyl)-1H-indole-3-carbonitrile (the intermediate product of step (b) from the synthesis of Example 1) in dry THF at −78° C., was slowly added n-BuLi (1.6 M in hexane, 1.2 eq) and the mixture stirred for 30 min. Tributyltin chloride (1.5 eq) was added and the mixture kept at −78° C. for 1 hour, then stirred at rt over night. The mixture was quenched by addition of sat. NH$_4$Cl and then concentrated. The residue was taken up in EtOAc, washed with brine, dried over Na$_2$SO$_4$ and purified on a Silica column using 20% EtOAc in n-heptane as mobile phase.

Step (b):

A mixture of 1-(4-methoxyphenyl)-2-(tributylstannyl)-1H-indole-3-carbonitrile, (Z)-1-bromobut-1-ene (1.2 eq), Pd$_2$(dba)$_3$ (3%) and tri(o-tolyl)phosphine (17%) in DMF was degassed with N$_2$ and heated at 80° C. over night. The mixture was diluted with sat. NH$_4$Cl and EtOAc and the phases partitioned. The organic phase was washed with brine, dried over Na$_2$SO$_4$ and subjected to reversed phase preparative HPLC. Appropriate fractions were combined and evaporated, and identified by $^1$H NMR.

Step (c):

The title compound 2-((Z)-But-1-enyl)-1-(4-hydroxy-phenyl)-1H-indole-3-carbonitrile was synthesized from the product of step (b) using a procedure analogous to that described in Example 23. ES/MS m/z: 289.11 (M+H), 287.15 (M−H).

Example 39

2-(Isobut-1-enyl)-1-(4-hydroxyphenyl)-1H-indole-3-carbonitrile (E61)

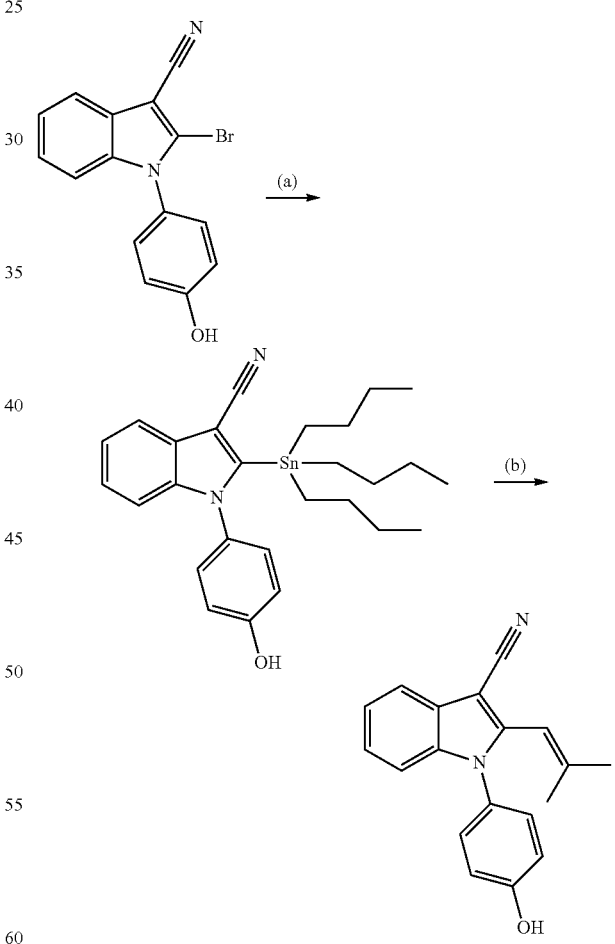

(a) Hexabutylditin, palladium di(triphenylphousphor)-Dichloride, dioxane; (b) 1-Bromo-methylprop-1-ene, Pd(PPh$_3$)$_4$, NMP/dioxane Step (a):

1 eq of 2-bromo-1-(4-hydroxyphenyl)-1H-indole-3-carbonitrile (Example 1) was dissolved in 1,4-dioxan and stirred at room temperature. 1.9 eq of hexabutylditin and 0.04 eq of palladium di(triphenylphousphor)-dichloride were added, degassed with nitrogen, and the mixture was heated to 80° C. for 4 hours. The mixture was filtered to remove catalyst, evaporated to remove most of solvent, and the residue purified on a silica column using 75:25 n-heptane:ethyl acetate as mobile phase (yield 65%).

Step (b):

1 eq of the stannyl reagent as prepared in step (a) was dissolved in a mixed solvent (1-methyl-2-pyrrolodinone and 1,4-dioxan, 2:1), stirred at room temperature, 2 eq of 1-bromo-methylprop-1-ene and 0.2% (w/w) of tetrakis(triphenylphosphine) palladium were added, degassed with nitrogen, the mixture was heated to 80° C. overnight. The mixture was filtered to remove catalyst, evaporated to remove most of the solvent, and the residue purified with preparative HPLC. ES/MS m/z: 289.11 (M+H), 287.15 (M−H); $^1$H NMR (chloroform-d, 500 MHz): 7.76 (m, 1H), 7.28 (m, 1H), 7.23 (m, 1H), 7.17 (m, 2H), 7.13 (m, 1H), 6.98 (m, 2H), 5.86 (m, 1H), 1.98 (d, 3H, J=1.3 Hz) and 1.89 (d, 3H, J=1.2 Hz).

Example 40

1-(2,3-Difluoro-4-hydroxy-phenyl)-2-(2-methylallyl)-1H-indole-3-carbonitrile (E40)

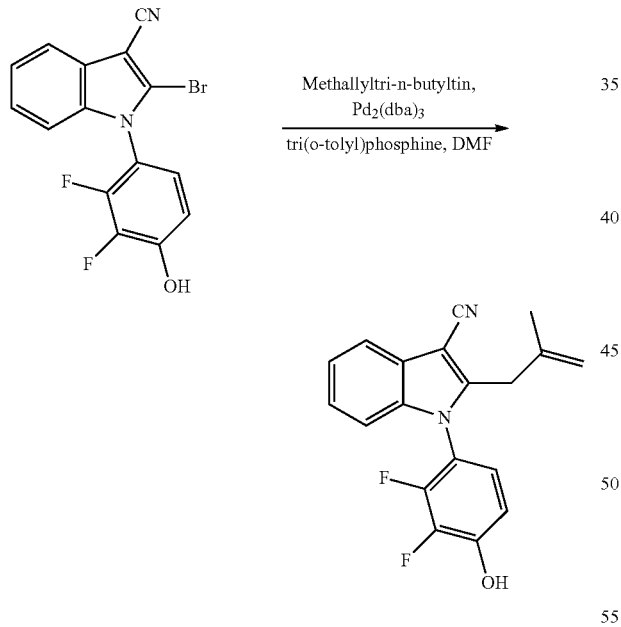

A mixture of 2-bromo-1-(2,3-difluoro-4-hydroxyphenyl)-1H-indole-3-carbonitrile (Example 103), methallyltri-n-butyltin (2 eq), Pd$_2$(dba)$_3$ (0.05%) and tri(o-tolyl)phosphine (20%) was dissolved in DMF, degassed with N$_2$ and heated at 80° C. over night. The reaction mixture was quenched by addition of sat. NH$_4$Cl, diluted with EtOAc, and washed with brine and then dried over Na$_2$SO$_4$. The residue was subjected to reversed phase preparative HPLC. Appropriate fractions were combined and evaporated, and identified by $^1$H NMR. ES/MS m/z: 289.11 (M+H), 287.15 (M−H); $^1$H NMR (chloroform-d, 500 MHz): 7.76 (m, 1H), 7.28 (m, 1H), 7.23 (m, 1H), 7.17 (m, 2H), 7.13 (m, 1H), 6.98 (m, 2H), 5.86 (m, 1H), 1.98 (d, 3H, J=1.3 Hz) and 1.89 (d, 3H, J=1.2 Hz).

Example 41

(Z)-2-(5-Ethyl-3-methylisoxazol-4-yl)-N'-hydroxy-1-(4-hydroxyphenyl)-1H-indole-3-carboximidamide (E41)

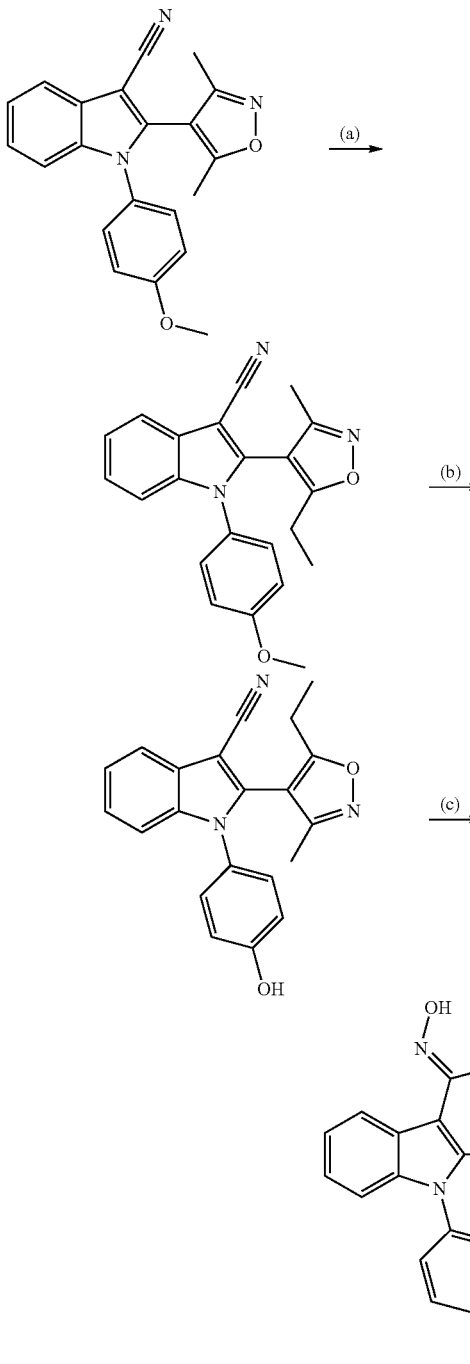

(a) n-BuLi, MeI, THF; (b) BBr$_3$, DCM; (c) NH$_2$OH, Et$_3$N, MeOH

Step (a):

38 μl of n-butyllithium (1.6M in hexanes) was added drop wise to 2-(3,5-dimethylisoxazol-4-yl)-1-(4-methoxyphenyl)-1H-indole-3-carbonitrile (synthesised by a coupling reaction of the intermediate product from step (b) of Example 1 with 3,5-dimethylisooxazole-4-boronic acid, using a process as described in Example 16) in 1 ml dry THF under argon at −78° C. The mixture was stirred at −78° C. for 45 min. 34 μl of methyl iodide was added and the mixture was allowed to reach room temp. After 4 h the mixture was concentrated in vacuo and purified by silica gel (EtOAc/heptane; 1:1).

Step (b):

The intermediate was prepared from 4-(1-(4-methoxyphenyl)-3-phenyl-1H-indol-2-yl)-3,5-dimethylisoxazole via a process analogous to that described in step (c) of Example 1.

Step (c):

The title compound was prepared from 2-(5-ethyl-3-methylisoxazol-4-yl)-1-(4-hydroxyphenyl)-1H-indole-3-carbonitrile via a process analogous to that described in Example 11, ES/MS m/z: 377.3 (M+H), 375.4 (M−H); $^1$H NMR (acetone-d6, 500 MHz): 8.06 (m, 1H), 7.22-7.10 (m, 5H), 6.94 (m, 2H), 2.56 (m, 2H), 2.02 (s, 3H) and 1.03 (t, 311, J=7.3 Hz).

Example 42

4-(2-(3,5-dimethylisoxazol-4-yl)-3-phenyl-1H-indol-1-yl)phenol (E42)

Scheme 37

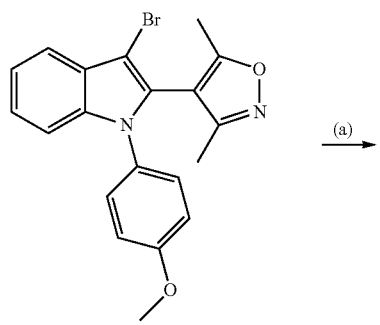

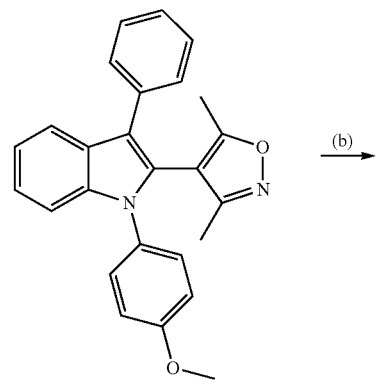

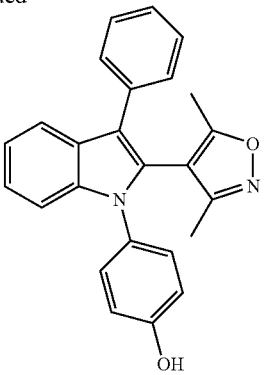

(a) Phenylboronic acid, Pd(PPh$_3$)$_4$, K$_2$CO$_3$, NaI, DME/Dioxane (b) BBr$_3$, DCM Step (a):

A mixture of DME/dioxane (1:1) was degassed by freeze-pump-thaw three times and then put under an argon atmosphere. 10 mg of 4-(3-bromo-1-(4-methoxyphenyl)-1H-indol-2-yl)-3,5-dimethylisoxazole (the intermediate product of step (b) from the synthesis of Example 22), 6.1 mg phenyl boronic acid, 2.9 mg Pd(PPh$_3$)$_4$, 21 mg potassium carbonate and 7.6 mg NaI were put in a microwave vial that was sealed and flushed with argon. 0.7 ml of the DME/water solution was cannulated to the microwave vial.

The mixture was degassed by freeze-pump-thaw twice and then flushed with argon. The mixture was heated to 150° C./15 min. in a Biotage Initiator micro wave oven, The crude product was filtered followed by evaporation and filtration through a short silica gel plug (EtOAc). Purification by flash chromatography (EtOAc/heptane; 1:9 to 2:8) gave 22.2 mg as a mixture of debrominated starting material and product plus a small amount of unreacted starting material according to LCMS. The compounds separated well on HPLC but only one spot on TLC. The crude material was used directly in the following demethylation step.

Step (b):

The title compound was prepared from 4-(1-(4-methoxyphenyl)-3-phenyl-1H-indol-2-yl)-3,5-dimethylisoxazole via a process analogous to that described in step (c) of Example 1. ES/MS m/z: 381.2 (M+H); $^1$H NMR (acetone-d6, 500 MHz): 7.78 (m, 1H), 7.43-7.37 (m, 4H), 7.30-7.19 (m, 411), 7.17 (m, 2H), 6.96 (m, 2H), 1.99 (s, 3H) and 1.77 (s, 3H).

Example 43

4-(3-chloro-2-(3,5-dimethylisoxazol-4-yl)-1H-indol-1-yl)phenol (E43)

Scheme 38

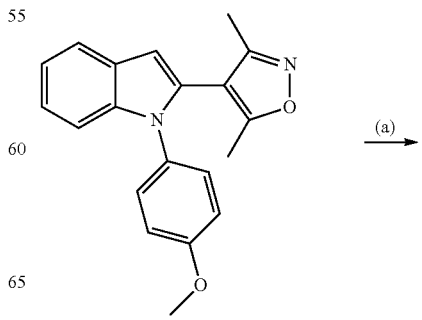

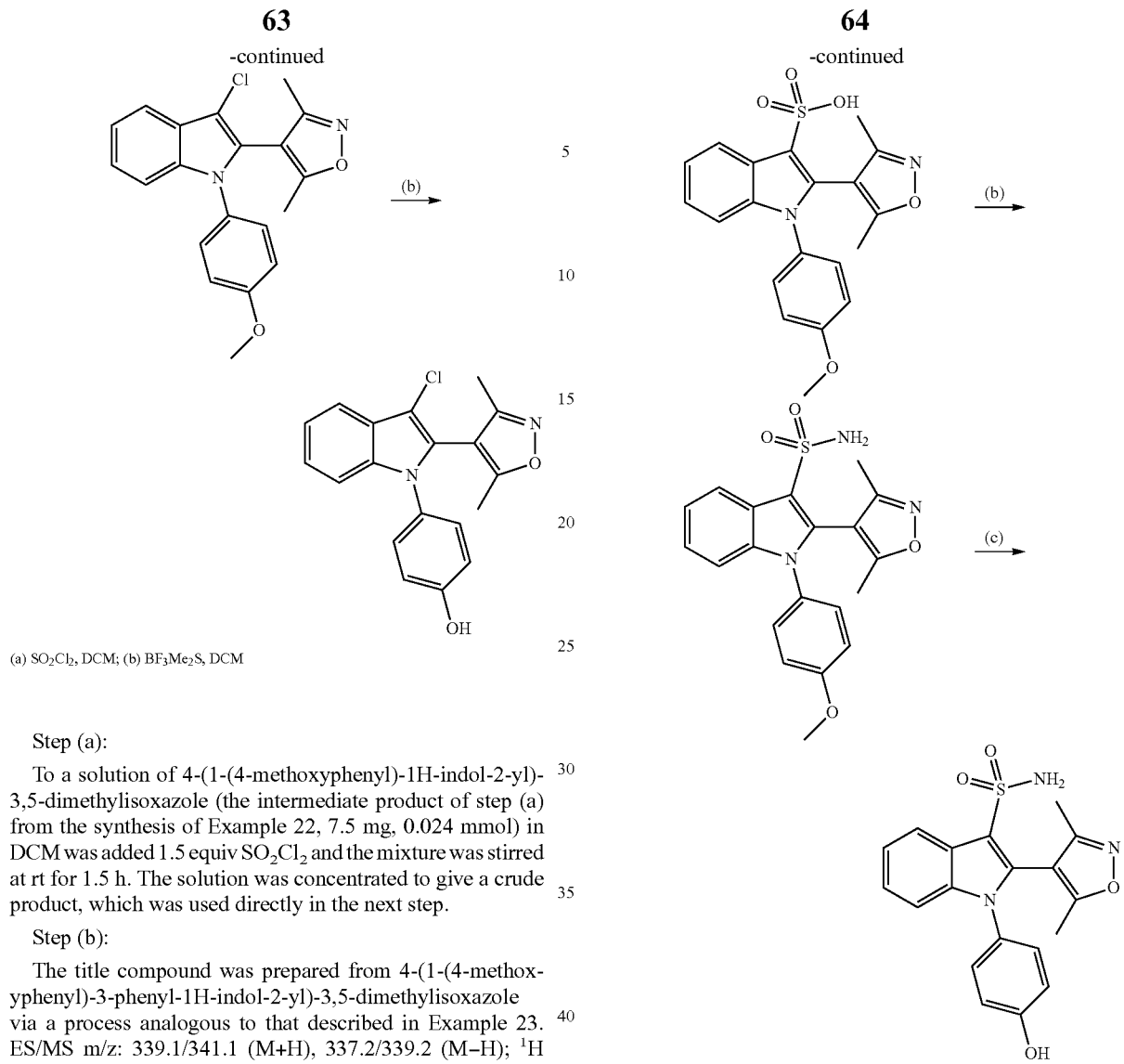

(a) SO₂Cl₂, DCM; (b) BF₃Me₂S, DCM

Step (a):

To a solution of 4-(1-(4-methoxyphenyl)-1H-indol-2-yl)-3,5-dimethylisoxazole (the intermediate product of step (a) from the synthesis of Example 22, 7.5 mg, 0.024 mmol) in DCM was added 1.5 equiv SO₂Cl₂ and the mixture was stirred at rt for 1.5 h. The solution was concentrated to give a crude product, which was used directly in the next step.

Step (b):

The title compound was prepared from 4-(1-(4-methoxyphenyl)-3-phenyl-1H-indol-2-yl)-3,5-dimethylisoxazole via a process analogous to that described in Example 23. ES/MS m/z: 339.1/341.1 (M+H), 337.2/339.2 (M−H); $^1$H NMR (acetone-d6, 500 MHz): 7.78 (m, 1H), 7.43-7.37 (m, 4H), 7.30-7.19 (m, 4H), 7.17 (m, 2H), 6.96 (m, 2H), 1.99 (s, 3H) and 1.77 (s, 3H).

Example 44

2-(3,5-dimethylisoxazol-4-yl)-1-(4-hydroxyphenyl)-1H-indole-3-sulfonamide (E44)

Scheme 39

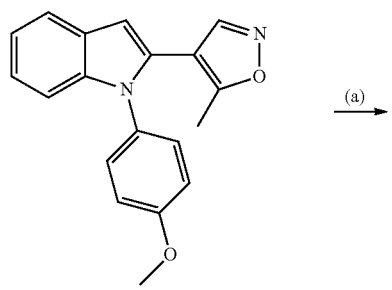

(a) HSO₃Cl, DCM; (b) 1. SOCl₂ 2. NH₃, MeOH; (c) BF₃MeS₂, DCM

Step (a):

To a solution of 4-(1-(4-methoxyphenyl)-1H-indol-2-yl)-3,5-dimethylisoxazole (the intermediate product of step (a) from the synthesis of Example 22, 7.5 mg, 0.024 mmol) in DCM was added 1.0 equiv HSO₃Cl at 0° C. and the mixture was stirred at rt for 1 h. The solution was concentrated to give a raw product, which was used in the following step.

Step (b):

To a solution of the raw product from step (a) in DCM was added 0.5 mL SOCl₂ and the mixture was stirred at 70° C. for 15 min. The solution was concentrated and 2 mL saturated NH₃ in MeOH was added and the mixture was stirred overnight. The solution was concentrated to give a raw product, which was used directly in the next step.

Step (c):

The title compound was prepared from the raw product of step (b) using the process as described in Example 23. ES/MS m/z: 384.2 (M+H), 382.2 (M−H); $^1$H NMR (acetone-d6, 500 MHz): 8.13 (m, 1H), 7.32-7.28 (m, 2H), 7.19-7.15 (m, 3H), 6.93 (m, 2H), 2.24 (s, 3H) and 2.05 (s, 3H).

Example 45

2-(3,5-Dimethylisoxazol-4-yl)-1-(2-fluoro-4-hydroxyphenyl)-1H-indole-3-carboximidamide (E45)

Scheme 40

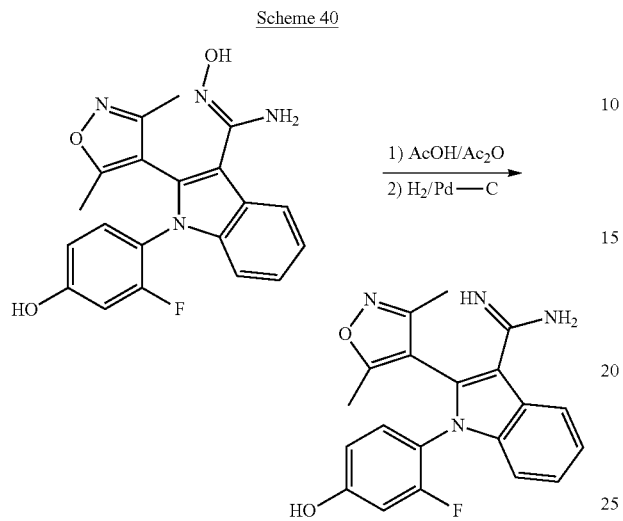

0.5 mmol (Z)-2-(3,5-dimethylisoxazol-4-yl)-1-(2-fluoro-4-hydroxyphenyl)-N'-hydroxy-1H-indole-3-carboximidamide (Example 235) was dissolved in 5 ml acetic acid. Acetic acid anhydride (4 eq) was slowly added and the mixture was stirred over night. A Pd—C catalyst (10% on carbon) was added and the mixture was placed in a hydrogenation apparatus under 50 psi $H_2$ over night. The mixture was filtered through celite and concentrated. The crude product was purified on HPLC: (Column: Sunfire, 20 min acidic gradient: 5-50% MeCN. ES/MS m/z: 365.15 (M+H), 363.18 (M−H); $^1$H NMR (MeOD, 500 MHz): 7.86 (m, 1H), 7.41-7.31 (m, 2.5H), 7.25-7.13 (m, 1.5H), 6.76 (m, 1H), 6.67 (m, 1H), 2.21, 2.15 (two s, 3H) and 2.08, 2.06 (two s, 3H).

Examples 46-95

The following compounds were prepared according to General Method 1 above. Full experimental details of the individual steps of that general method are described in Examples 1-5, 16 and 38-40 above.

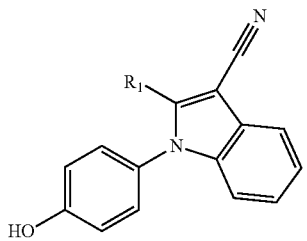

E 46  1-(4-Hydroxy-phenyl)-2-phenyl-1H-indole-3-carbonitrile
$R^1$ = phenyl
ES/MS m/z: 311.1 (pos. M + H), 309.11 (neg. M − H); $^1$H NMR (CDCl$_3$, 500 MHz): 7.74 (m, 1H), 7.31-7.15 (m, 8H), 7.00 (m, 2H) and 6.80 (m, 2H).
E 47  1-(4-Hydroxy-phenyl)-2-methyl-1H-indole-3-carbonitrile
$R^1$ = methyl
ES/MS m/z: 249.1 (pos. M + H), 247.3 (neg. M − H); $^1$H NMR (acetone-d6, 500 MHz): 7.63 (m, 1H), 7.33 (m, 2H), 7.27 (m, 1H), 7.23 (m, 1H), 7.10 (m, 2H), 7.08 (m, 1H), and 2.43 (s, 3H).
E 48  2-(3-Cyano-thiophen-2-yl)-1-(4-hydroxy-phenyl)-1H-indole-3-carbonitrile
$R^1$ = 3-cyano-thiophen-2-yl
ES/MS m/z: 342.1 (pos. M + H), 340.1 (neg. M − H); $^1$H NMR (acetone-d6, 500 MHz): 7.95 (d, 1H, J = 5.4 Hz), 7.84 (m, 1H), 7.52 (d, 1H, J = 5.4 Hz), 7.46-7.42 (m, 2H), 7.32-7.28 (m, 3H) and 7.00 (m, 2H).
E 49  1-(4-Hydroxy-phenyl)-2-((E)-propenyl)-1H-indole-3-carbonitrile
$R^1$ = (E)-propenyl
ES/MS m/z: 275.3 (pos. M + H), 273.1 (neg. M − H); $^1$H NMR (acetone-d6, 500 MHz): 7.65 (m, 1H), 7.32-7.23 (m, 4H), 7.10 (m, 2H), 7.06 (m, 1H), 6.85 (m, 1H), 6.26 (m, 1H) and 1.91 (dd, 3H, J = 1.8, 6.9 Hz).
E 50  1-(4-Hydroxy-phenyl)-2-thiophen-2-yl-1H-indole-3-carbonitrile
$R^1$ = thiophen-2-yl
ES/MS m/z: 317.0 (pos. M + H), 315.1 (neg. M − H); $^1$H NMR (acetone-d6, 500 MHz): 7.73 (m, 1H), 7.65 (dd, 1H, J = 1.1, 5.0 Hz), 7.54 (dd, 1H, J = 1.1, 3.8 Hz), 7.37-7.29 (m, 4H), 7.15 (dd, 1H, J = 3.8, 5.0 Hz), 7.11 (m, 1H) and 7.06 (m, 2H).
E 51  2-(3,5-Dimethyl-isoxazol-4-yl)-1-(4-hydroxy-phenyl)-1H-indole-3-carbonitrile
$R^1$ = 3,5-dimethyl-isoxazol-4-yl
ES/MS m/z: 330.2 (pos. M + H), 328.3 (neg. M − H); $^1$H NMR (acetone-d6, 500 MHz): 7.78 (m, 1H), 7.42-7.32 (m, 3H), 7.28 (m, 2H), 7.00 (m, 2H), 2.36 (s, 3H) and 2.02 (s, 3H).
E 52  1-(4-Hydroxy-phenyl)-2-pyridin-4-yl-1H-indole-3-carbonitrile
$R^1$ = pyridine-4-yl
ES/MS m/z: 312.2 (pos. M + H), 310.3 (neg. M − H); $^1$H NMR (acetone-d6, 500 MHz): 8.35 (m, 2H), 7.38 (m, 1H), 7.20 (m, 2H), 6.98 (m, 2H), 6.82 (m, 1H), 6.79 (m, 2H) and 6.44 (m, 2H).
E 53  1-(4-Hydroxy-phenyl)-2-(1-methyl-1H-pyrrol-2-yl)-1H-indole-3-carbonitrile
$R^1$ = 1-methyl-1H-pyrrol-2-yl

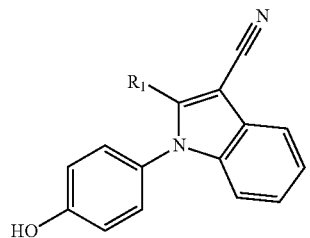

ES/MS m/z: 314.3 (pos. M + H), 312.1 (neg. M − H); $^1$H NMR (acetone-d6, 500 MHz): 7.75 (m, 1H), 7.38-7.32 (m, 2H), 7.29 (m, 1H), 7.20 (m, 2H), 6.95 (m, 2H), 6.83 (dd, 1H, J = 1.9, 2.5 Hz), 6.24 (dd, 1H, J = 1.9, 3.8 Hz), 6.09 (dd, 1H, J = 2.5, 3.8 Hz) and 3.51 (s, 3H).
E 54  1-(4-Hydroxy-phenyl)-2-(3-methyl-thiophen-2-yl)-1H-indole-3-carbonitrile
$R^1$ = 3-methyl-thiophen-2-yl
ES/MS m/z: 331.4 (pos. M + H), 329.2 (neg. M − H); $^1$H NMR (acetone-d6, 500 MHz): 7.77 (m, 1H), 7.56 (d, 1H, J = 5.1 Hz), 7.40-7.34 (m, 2H), 7.27 (m, 1H), 7.21 (m, 2H), 6.97 (d, 1H, J = 5.1 Hz), 6.95 (m, 2H) and 2.21 (s, 3H).
E 55  1-(4-Hydroxy-phenyl)-2-isopropylamino-1H-indole-3-carbonitrile
$R^1$ = isopropylamino
ES/MS m/z: 292.1 (pos. M + H), 290.2 (neg. M − H); $^1$H NMR (acetone-d6, 500 MHz): 7.34 (m, 1H), 7.25 (m, 2H), 7.09 (m, 1H), 7.06 (m, 2H), 6.95 (m, 1H), 6.70 (m, 1H), 4.33 (m, 1H) and 1.28 (d, 6H, J = 6.5 Hz).
E 56  2-Ethylamino-1-(4-hydroxy-phenyl)-1H-indole-3-carbonitrile
$R^1$ = ethylamino
ES/MS m/z: 278.3 (pos. M + H), 276.1 (neg. M − H); $^1$H NMR (acetone-d6, 500 MHz): 7.33 (m, 1H), 7.26 (m, 2H), 7.09 (m, 1H), 7.06 (m, 2H), 6.95 (m, 1H), 6.70 (m, 1H), 3.65 (q, 2H, J = 7.4 Hz) and 1.27 (t, 3H, J = 7.4 Hz).
E 57  2-Butylamino-1-(4-hydroxy-phenyl)-1H-indole-3-carbonitrile
$R^1$ = butylamino
ES/MS m/z: 306.2 (pos. M + H), 304.3 (neg. M − H); $^1$H NMR (acetone-d6, 500 MHz): 7.33 (m, 1H), 7.26 (m, 2H), 7.10-7.05 (m, 3H), 6.94 (m, 1H), 6.69 (m, 1H), 3.61 (m, 2H), 1.68 (m, 2H), 1.41 (m, 2H) and 0.92 (t, 3H, J = 7.4 Hz).
E 58  1-(4-Hydroxy-phenyl)-2-piperidin-1-yl-1H-indole-3-carbonitrile
$R^1$ = piperidin-1-yl
ES/MS m/z: 317.9 (pos. M + H), 316.3 (neg. M − H); $^1$H NMR (acetone-d6, 500 MHz): 7.45 (m, 1H), 7.36 (m, 2H), 7.18 (m, 1H), 7.12-7.07 (m, 3H), 7.01 (m, 1H), 3.27 (m, 4H), 1.54 (m, 2H) and 1.49 (m, 4H).
E 59  1-(4-Hydroxy-phenyl)-2-pyrrolidin-1-yl-1H-indole-3-carbonitrile
$R^1$ = pyrrolidin-1-yl
ES/MS m/z: 304.4 (pos. M + H), 302.2 (neg. M − H); $^1$H NMR (acetone-d6, 500 MHz): 7.33-7.29 (m, 3H), 7.11 (m, 1H), 7.04 (m, 2H), 6.96 (m, 1H), 6.73 (m, 1H), 3.40 (m, 4H) and 1.87 (m, 4H).
E 60  1-(4-Hydroxy-phenyl)-2-morpholin-4-yl-1H-indole-3-carbonitrile
$R^1$ = morpholin-4-yl
ES/MS m/z: 320.3 (pos. M + H), 317.8 (neg. M − H); $^1$H NMR (acetone-d6, 500 MHz): 7.49 (m, 1H), 7.40 (m, 2H), 7.21 (m, 1H), 7.14 (m, 1H), 7.10 (m, 2H), 7.05 (m, 1H), 3.59 (m, 4H) and 3.28 (m, 4H).
E 61  2-Diethylamino-1-(4-hydroxy-phenyl)-1H-indole-3-carbonitrile
$R^1$ = diethylamino
ES/MS m/z: 306.2 (pos. M + H), 304.3 (neg. M − H); $^1$H NMR (acetone-d6, 500 MHz): 7.47 (m, 1H), 7.31 (m, 2H), 7.19 (m, 1H), 7.10 (m, 1H), 7.08 (m, 2H), 6.96 (m, 1H), 3.28 (q, 4H, J = 6.9 Hz) and 1.05 (t, 6H, J = 6.9 Hz).
E 62  2=Ethynyl-1-(4-hydroxy-phenyl)-1H-indole-3-carbonitrile
$R^1$ = ethynyl
ES/MS m/z: 259.1 (pos. M + H), 257.0 (neg. M − H); $^1$H NMR (acetone-d6, 500 MHz): 7.74 (m, 1H), 7.44-7.37 (m, 4H), 7.26 (m, 1H), 7.10 (m, 2H) and 4.45 (s, 1H).
E 63  1-(4-Hydroxy-phenyl)-2-vinyl-1H-indole-3-carbonitrile
$R^1$ = vinyl
ES/MS m/z: 261.1 (pos. M + H), 259.0 (neg. M − H); $^1$H NMR (acetone-d6, 500 MHz): 7.70 (m, 1H), 7.34-7.27 (m, 4H), 7.13-7.09 (m, 3H), 6.56 (dd, 1H, J = 17.6, 11.6 Hz), 6.24 (dd, 1H, J = 17.6, 0.6 Hz) and 5.69 (dd, 1H, J = 11.6, 0.6 Hz).
E 64  1-(4-Hydroxy-phenyl)-1H-indole-2,3-dicarbonitrile
$R^1$ = cyano
ES/MS m/z: 258.0 (neg. M − H); $^1$H NMR (acetone-d6, 500 MHz): 7.88 (m, 1H), 7.59 (m, 1H), 7.56 (m, 2H), 7.52 (m, 1H), 7.42 (m, 1H) and 7.15 (m, 2H).
E 65  1-(4-Hydroxy-phenyl)-2-prop-1-ynyl-1H-indole-3-carbonitrile
$R^1$ = prop-1-ynyl
ES/MS m/z: 273.1 (pos. M + H), 271.1 (neg. M − H); $^1$H NMR (acetone-d6, 500 MHz): 7.68 (m, 1H), 7.38 (m, 2H), 7.36-7.33 (m, 2H), 7.22 (m, 1H), 7.08 (m, 2H) and 2.09 (s, 3H).
E 66  1-(4-Hydroxy-phenyl)-2-pyridin-2-yl-1H-indole-3-carbonitrile
$R^1$ = pyridin-2-yl
ES/MS m/z: 312.1 (pos. M + H), 310.2 (neg. M − H); $^1$H NMR (acetone-d6, 500 MHz): 8.63 (m, 1H), 7.84-7.78 (m, 2H), 7.49 (m, 1H), 7.41-7.36 (m, 3H), 7.26 (m, 1H), 7.22 (m, 2H) and 6.96 (m, 2H).
E 67  1-(4-Hydroxy-phenyl)-2-(2-methyl-allyl)-1H-indole-3-carbonitrile
$R^1$ = 2-methyl-allyl
ES/MS m/z: 289.1 (pos. M + H), 287.1 (neg. M − H); $^1$H NMR (acetone-d6, 500 MHz): 7.67 (m, 1H), 7.31-7.24 (m, 4H), 7.10-7.05 (m, 3H), 4.76 (s, 1H), 4.41 (s, 1H), 3.55 (s, 2H) and 1.66 (s, 3H).
E 68  1-(4-Hydroxy-phenyl)-2-((Z)-propenyl)-1H-indole-3-carbonitrile
$R^1$ = (Z)-propenyl -continued

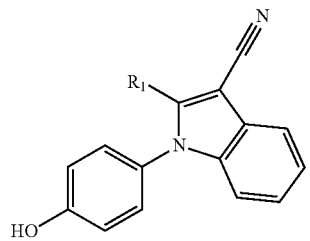

ES/MS m/z: 275.1 (pos. M + H), 273.1 (neg. M − H); $^1$H NMR (acetone-d6, 500 MHz): 7.71 (m, 1H), 7.33-7.27 (m, 4H), 7.17 (m, 1H), 7.06 (m, 2H), 6.20-6.12 (m, 2H) and 1.94 (d, 3H, J = 5.3 Hz).
E 69  2-(Butyl-methyl-amino)-1-(4-hydroxy-phenyl)-1H-indole-3-carbonitrile
$R^1$ = Butyl-methyl-amino
ES/MS m/z: 320.3 (pos. M + H), 318.1 (neg. M − H); $^1$H NMR (acetone-d6, 500 MHz): 7.43 (m, 1H), 7.31 (m, 2H), 7.17 (m, 1H), 7.09-7.06 (m, 3H), 6.93 (m, 1H), 3.15 (m, 2H), 3.00 (s, 3H), 1.45 (m, 2H), 1.20 (m, 2H) and 0.83 (t, 3H, J = 7.4 Hz).
E 70  1-(4-Hydroxy-phenyl)-2-((Z)-1-methyl-propenyl)-1H-indole-3-carbonitrile
$R^1$ = (Z)-1-methyl-propenyl
ES/MS m/z: 289.2 (pos. M + H), 287.1 (neg. M − H); $^1$H NMR (acetone-d6, 500 MHz): 7.70 (m, 1H), 7.33-7.27 (m, 4H), 7.22 (m, 1H), 7.05 (m, 2H), 5.90 (m, 1H), 1.78 (m, 3H) and 1.66 (m, 3H).
E 71  1-(4-Hydroxy-phenyl)-2-imidazol-1-yl-1H-indole-3-carbonitrile
$R^1$ = imidazol-1-yl
ES/MS m/z: 301.1 (pos. M + H), 299.2 (neg. M − H); $^1$H NMR (acetone-d6, 500 MHz): 7.85 (t, 1H, J = 0.9 Hz), 7.79 (m, 1H), 7.47-7.40 (m, 2H), 7.34-7.31 (m, 3H), 7.26 (m, 1H), 7.06 (dd, 1H, J = 0.9, 1.6 Hz) and 6.99 (m, 2H).
E 72  1-(4-Hydroxy-phenyl)-2-[1,2,4]triazol-1-yl-1H-indole-3-carbonitrile
$R^1$ = [1,2,4]triazol-1-yl
ES/MS m/z: 302.3 (pos. M + H), 300.4 (neg. M − H); $^1$H NMR (acetone-d6, 500 MHz): 8.73 (s, 1H), 8.15 (s, 1H), 7.84 (m, 1H), 7.49-7.46 (m, 2H), 7.33-7.28 (m, 3H) and 6.99 (m, 2H).
E 73  2-(3,5-Dimethyl-pyrazol-1-yl)-1-(4-hydroxy-phenyl)-1H-indole-3-carbonitrile
$R^1$ = 3,5-dimethyl-pyrazol-1-yl
ES/MS m/z: 329.3 (pos. M + H), 327.4 (neg. M − H); $^1$H NMR (acetone-d6, 500 MHz): 7.81 (m, 1H), 7.46-7.42 (m, 2H), 7.35 (m, 1H), 7.21 (m, 2H), 6.93 (m, 2H), 5.98 (s, 1H), 2.15 (s, 3H) and 2.12 (s, 3H).
E 74  1-(4-Hydroxy-phenyl)-2-pyrazol-1-yl-1H-indole-3-carbonitrile
$R^1$ = pyrrazol-1-yl
ES/MS m/z: 301.4 (pos. M + H), 299.5 (neg. M − H); $^1$H NMR (acetone-d6, 500 MHz): 7.89 (d, 1H, J = 2.6 Hz), 7.79 (m, 1H), 7.72 (d, 1H, J = 1.8 Hz), 7.45-7.39 (m, 2H), 7.29-7.23 (m, 3H), 6.97 (m, 2H) and 6.47 (dd, 1H, J = 1.8, 2.6 Hz).
E 75  1-(4-Hydroxy-phenyl)-2-(5-methyl-imidazol-1-yl)-1H-indole-3-carbonitrile
$R^1$ = 5-methyl-imidazol-1-yl
ES/MS m/z: 315.2 (pos. M + H), 313.3 (neg. M − H); $^1$H NMR (acetone-d6, 500 MHz): 7.82 (m, 1H), 7.76 (d, 1H, J = 0.9 Hz), 7.47-7.43 (m, 2H), 7.33-7.27 (m, 3H), 6.97 (m, 2H), 6.76 (m, 1H) and 2.13 (d, 3H, J = 1.1 Hz).
E 76  1-(4-Hydroxy-phenyl)-2-(5-methyl-pyrazol-1-yl)-1H-indole-3-carbonitrile
$R^1$ = 5-methyl-pyrrazol-1-yl
ES/MS m/z: 315.2 (pos. M + H), 313.3 (neg. M − H); $^1$H NMR (acetone-d6, 500 MHz): 7.83 (m, 1H), 7.55 (d, 1H, J = 1.3 Hz), 7.47-7.44 (m, 2H), 7.37 (m, 1H), 7.20 (m, 2H), 6.93 (m, 2H), 6.19 (m, 1H) and 2.22 (s, 3H).
E 77  1-(4-Hydroxy-penyl)-2-(3-methyl-pyrazol-1-yl)-1H-indole-3-carbonitrile
$R^1$ = 3-methyl-pyrrazol-1-yl
ES/MS m/z: 315.2 (pos. M + H), 313.3 (neg. M − H); $^1$H NMR (acetone-d6, 500 MHz): 7.76 (m, 1H), 7.69 (d, 1H, J = 2.5 Hz), 7.42-7.36 (m, 2H), 7.27-7.23 (m, 3H), 6.98 (m, 2H), 6.25 (d, 1H, J = 2.5 Hz) and 2.21 (s, 3H).
E 78  1-(4-Hydroxy-phenyl)-2-thiazol-2-yl-1H-indole-3-carbonitrile
$R^1$ = thiazol-2-yl
ES/MS m/z: 318.1 (pos. M + H), 316.1 (neg. M − H); $^1$H NMR (acetone-d6, 500 MHz): 7.99 (d, 1H, J = 3.2 Hz), 7.81 (m, 1H), 7.76 (d, 1H, J = 3.2 Hz), 7.42-7.37 (m, 4H) and 7.15-7.11 (m, 3H).
E 79  1-(4-Hydroxy-phenyl)-2-(2-methoxy-thiazol-4-yl)-1H-indole-3-carbonitrile
$R^1$ = 2-methoxy-thiazol-4-yl
ES/MS m/z: 348.1 (pos. M + H), 346.1 (neg. M − H); $^1$H NMR (acetone-d6, 500 MHz): 7.75 (m, 1H), 7.37-7.31 (m, 4H), 7.11 (m, 1H), 7.07 (m, 2H), 6.68 (s, 1H) and 4.04 (s, 3H).
E 80  1-(4-Hydroxy-phenyl)-2-(thiazol-4-yl-1H-indole-3-carbonitrile
$R^1$ = thiazol-4-yl
ES/MS m/z: 318.1 (pos. M + H), 316.1 (neg. M − H); $^1$H NMR (acetone-d6, 500 MHz): 9.08 (d, 1H, J = 1.9 Hz), 7.78 (m, 1H), 7.41 (d, 1H, J = 1.9 Hz), 7.39-7.33 (m, 2H), 7.29 (m, 2H), 7.17 (m, 1H) and 7.04 (m, 2H).
E 81  1-(4-Hydroxy-phenyl)-2-(3-methyl-but-2-enyl)-1H-indole-3-carbonitrile
$R^1$ = 3-methyl-but-2-enyl
ES/MS m/z: 303.1 (pos. M + H), 301.2 (neg. M − H); $^1$H NMR (acetone-d6, 500 MHz): 7.64 (m, 1H), 7.30 (m, 2H), 7.29-7.21 (m, 2H), 7.09 (m, 2H), 7.03 (m, 1H), 5.11 (m, 1H), 3.54 (m, 2), 1.62 (m, 3H) and 1.48 (s, 3H).
E 82  2-((E)-But-1-enyl)-1-(4-hydroxy-phenyl)-1H-indole-3-carbonitrile
$R^1$ = (E)-but-1-enyl
ES/MS m/z: 289.1 (pos. M + H), 287.2 (neg. M − H); $^1$H NMR (CDCl$_3$, 500 MHz): 7.73 (m, 1H), 7.28 (m, 1H), 7.22-7.19 (m, 3H), 7.04 (m, 1H), 7.02 (m, 2H), 6.92 (m, 1H), 6.11 (m, 1H), 2.23 (m, 2H) and 1.04 (t, 3H, J = 7.1 Hz).

-continued

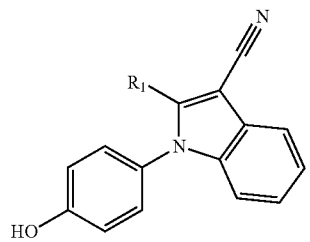

E 83   1-(4-Hydroxy-phenyl)-2-(5-methyl-thiophen-2-yl)-1H-indole-3-carbonitrile
R¹ = 5-methyl-thiophen-2-yl
ES/MS m/z: 331.1 (pos. M + H), 329.2 (neg. M − H); ¹H NMR (acetone-d6, 500 MHz): 7.70 (m, 1H),
7.35-7.28 (m, 5H), 7.09-7.05 (m, ,3H), 6.82 (m, 1H) and 2.45 (s, 3H).
E 84   2-(5-Acetyl-thiophen-2-yl)-1-(4-hydroxy-phenyl)-1H-indole-3-carbonitrile
R¹ = 5-acetyl-thiophen-2-yl
ES/MS m/z: 359.3 (pos. M + H), 357.1 (neg. M − H); ¹H NMR (acetone-d6, 500 MHz): 7.85 (d, 1H,
J = 4.1 Hz), 7.77 (m, 1H), 7.57 (d, 1H J = 4.1 Hz), 7.41-7.34 (m, 4H), 7.15 (m, 1H), 7.08 (m, 2H) and 2.54
(s, 3H).
E 85   1-(4-Hydroxy-phenyl)-2-(1-methyl-1H-pyrrazol-4-yl)-1H-indole-3-carbonitrile
R¹ = 1-methyl-1H-pyrrazol-4-yl
ES/MS m/z: 315.2 (pos. M + H), 313.3 (neg. M − H); ¹H NMR (acetone-d6, 500 MHz): 7.73 (s, 1H),
7.67 (m, 1H), 7.35 (s, 1H), 7.32-7.28 (m, 3H), 7.26 (m, 1H), 7.09 (m, 2H), 7.07 (m, 1H) and 3.90 (s,
3H).
E 86   2-(5-Chloro-thiophen-2-yl)-1-(4-hydroxy-phenyl)-1H-indole-3-carbonitrile
R¹ = 5-chloro-thiophen-2-yl
ES/MS m/z: 351.2 (pos. M + H), 349.3 (neg. M − H); ¹H NMR (acetone-d6, 500 MHz): 7.74 (m, 1H),
7.45 (d, 1H, J = 4.1 Hz), 7.39-7.32 (m, 4H) and 7.13-7.08 (m, 4H).
E 87   1-(4-Hydroxy-phenyl)-2-(4-methyl-thiophen-3-yl)-1H-indole-3-carbonitrile
R¹ = 4-methyl-thiophen-3-yl
ES/MS m/z: 331.4 (pos. M + H), 329.2 (neg. M − H); ¹H NMR (acetone-d6, 500 MHz): 7.76 (m, 1H),
7.59 (d, 1H, J = 3.2 Hz), 7.39-7.33 (m, 2H), 7.29 (m, 1H), 7.21 (m, 2H), 7.18 (m, 1H), 6.93 (m, 2H) and
2.08 (d, 3H, J = 0.9 Hz).
E 88   1-(4-Hydroxy-phenyl)-2-(4-methyl-thiophen-2-yl)-1H-indole-3-carbonitrile
R¹ = 4-methyl-thiophen-2-yl
ES/MS m/z: 331.4 (pos. M + H), 329.2 (neg. M − H); ¹H NMR (aceton-d6, 500 MHz): 7.71 (m, 1H),
7.39 (d, 1H, J = 1.3 Hz), 7.36-7.29 (m, 2H), 7.27 (m, 2H), 7.22 (m, 1H), 7.08 (m, 1H), 7.04 (m, 2H) and
2.23 (d, 3H, J = 0.9 Hz).
E 89   2-(4-Cyano-thiophen-3-yl)-1-(4-hydroxy-phenyl)-1H-indole-3-carbonitrile
R¹ = 4-cyano-thiophen-3-yl
ES/MS m/z: 342.2 (pos. M + H), 340.3 (neg. M − H); ¹H NMR (acetone-d6, 500 MHz): 8.49 (d, 1H,
J = 3.1 Hz), 7.98 (d, 1H, J = 3.1 Hz), 7.81 (m, 1), 7.44-7.39 (m, 2H), 7.31 (m, 1H), 7.26 (m, 2H) and 6.97
(m, 2H).
E 90   1-(4-Hydroxy-phenyl)-2-(2-methyl-2H-pyrrazol-3-yl)-1H-indole-3-carbonitrile
R¹ = 2-methyl-2H-pyrrazol-3-yl
ES/MS m/z: 315.2 (pos. M + H), 313.3 (neg. M − H); ¹H NMR (acetone-d6, 500 MHz): 7.80 (m, 1H),
7.45 (d, 1H, J = 2.0 Hz), 7.43-7.39 (m, 2H), 7.32 (m, 1H), 7.27 (m, 2H), 6.97 (m, 2H), 6.42 (d, 1H,
J = 2.0 Hz) and 3.77 (s, 3H).
E 91   1-(4-Hydroxy-penyl)-2-(1,3,5-trimethyl-1H-pyrrazol-4-yl)-1H-indole-3-carbonitrile
R¹ = 1,3,56-trimethyl-1H-pyrrazol-4-yl
ES/MS m/z: 343.1 (pos. M + H), 341.2 (neg. M − H); ¹H NMR (acetone-d6, 500 MHz): 7.73 (m, 1H),
7.36-7.30 (m, 3H), 7.17 (m, 2H), 6.94 (m, 2H), 3.69 (s, 3H), 2.11 (s, 3H) and 1.96 (s, 3H).
E 92   2-(2-Acetyl-pyrrol-1-yl)-1-(4-hydroxy-phenyl)-1H-indole-3-carbonitrile
R¹ = 2-acetyl-pyrrol-1-yl
ES/MS m/z: 342.2 (pos. M + H), 340.3 (neg. M − H); ¹H NMR (acetone-d6, 500 MHz): 7.76 (m, 1H),
7.44 (dd, 1H, J = 1.6, 2.8 Hz), 7.42-7.37 (m, 2H), 7.23 (m, 1H), 7.13 (dd, 1H, J = 1.6, 3.9 Hz), 7.09 (m,
2H), 6.88 (m, 2H), 6.41 (dd, 1H, J = 2.8, 3.9 Hz) and 2.23 (s, 3H).
E 93   2-(2-Ethyl-pyrrol-1-yl)-1-(4-hydroxy-phenyl)-1H-indole-3-carbonitrile
R¹ = 2-ethyl-pyrrol-1-yl
ES/MS m/z: 328.4 (pos. M + H), 326.2 (neg. M − H); ¹H NMR (acetone-d6, 500 MHz): 7.78 (m, 1H),
7.44-7.39 (m, 2H), 7.30 (m, 1H), 7.22 (m, 2H), 6.93 (m, 2H), 6.88 (dd, 1H, J = 2.9, 1.6 Hz), 6.11 (t, 1H,
J = 3.2 Hz), 5.95 (m, 1H), 2.49 (m, 1H), 2.37 (m, 1H) and 1.09 (t, 3H, J = 7.5 Hz).
E 94   2-(2-Cyano-pyrrol-1-yl)-1-(4-hydroxy-phenyl)-1H-indole-3-carbonitrile
R¹ = 2-cyano-pyrrol-1-yl
ES/MS m/z: 325.4 (pos. M + H), 323.5 (neg. M − H); ¹H NMR (acetone-d6, 500 MHz): 7.85 (m, 1H),
7.49-7.46 (m, 3H), 7.32 (m, 1H), 7.28 (m, 2H), 7.11 (dd, 1H, J = 4.1, 1.6 Hz), 6.99 (m, 2H) and 6.45 (dd,
1H, J = 4.1, 2.9 Hz).
E 95   1-(4-Hydroxy-phenyl)-2-(2-methyl-pyrrol-1-yl)-1H-indole-3-carbonitrile
R¹ = 2-methyl-pyrrol-1-yl
ES/MS m/z: 314.3 (pos. M + H), 312.4 (neg. M − H); ¹H NMR (acetone-d6, 500 MHz): 7.78 (m, 1H),
7.44-7.39 (m, 2H), 7.31 (m, 1H), 7.22 (m, 2H), 6.94 (m, 2H), 6.85 (dd, 1H, J = 3.0, 1.6 Hz), 6.07 (t, 1H,
J = 3.3 Hz), 5.92 (m, 1H) and 2.12 (d, 3H, J = 0.7 Hz).

Examples 96-159

The following compounds were prepared according to General Method 1 above. Full experimental details of the individual steps of that general method are described in Examples 1-5, 16 and 38-40 above.

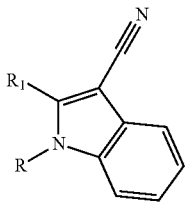

E 96  1-(3-Chloro-5-fluoro-4-hydroxy-phenyl)-2-phenyl-1H-indole-3-carbonitrile
$R^1$ = phenyl   R = 3-chloro-5-fluoro-2-hydroxy-phenyl
ES/MS m/z: 363.1 (pos. M + H), 361.1 (neg. M − H); $^1$H NMR (acetone-d6, 500 MHz): 7.77 (m, 1H), 7.56-7.53 (m, 2H), 7.50-7.45 (m, 3H), 7.41-7.34 (m, 4H) and 7.32 (dd, 1H, J = 10.8, 5.2 Hz).

E 97  1-(3-Chloro-5-fluoro-4-hydroxy-phenyl)-2-(3-cyano-thiophen-2-yl)-1H-indole-3-carbonitrile
$R^1$ = 3-cyano-thiophen-2-yl   R = 3-chloro-5-fluoro-4-hydroxy-phenyl
ES/MS m/z: 392.0, 394.0 (neg. M − H); $^1$H NMR (acetone-d6, 500 MHz): 8.00 (d, 1H, J = 5.4 Hz), 7.84 (m, 1H), 7.56 (d, 1H, J = 5.4 Hz) and 7.49-7.41 (m, 5H).

E 98  1-(3-Chloro-5-fluoro-4-hydroxy-phenyl)-2-(3-cyano-furan-2-yl)-1H-indole-3-carbonitrile
$R^1$ = 3-cyano-furan-2-yl   R = 3-chloro-5-fluoro-4-hydroxy-phenyl
ES/MS m/z: 376.0, 378.0 (neg. M − H); $^1$H NMR (acetone-d6, 500 MHz): 7.97 (d, 1H, J = 2.0 Hz), 7.86 (m, 1H), 7.52-7.44 (m, 5H) and 7.07 (d, 1H, J = 2.0 Hz).

E 99  2-Bromo-1-(3-chloro-5-fluoro-4-hydroxy-phenyl)-1H-indole-3-carbonitrile
$R^1$ = bromo   R = 3-chloro-5-fluoro-4-hydroxy-phenyl
ES/MS m/z: 362.0, 364.0, 366.0 (neg. M − H); $^1$H NMR (acetone-d6, 500 MHz): 7.70 (m, 1H), 7.54 (t, 1H, J = 2.5 Hz), 7.50 (dd, 1H, J = 2.5, 10.7 Hz), 7.39-7.34 (m, 2H) and 7.27 (m, 1H).

E 100  2-Bromo-1-(2-fluoro-4-hydroxyphenyl)-1H-indole-3-carbonitrile
$R^1$ = bromo   R = 2-fluoro-4-hydroxy-phenyl
ES/MS m/z: 331.1, 333.2 (pos. M + H), 328.9, 331.1 (neg. M − H); $^1$H NMR (acetone-d6, 500 MHz): 7.71 (m, 1H), 7.48 (m, 1H), 7.38-7.33 (m, 2H), 7.14 (m, 1H) and 6.98-6.93 (m, 2H).

E 101  1-(2-Fluoro-4-hydroxy-phenyl)-2-phenyl-1H-indole-3-carbonitrile
$R^1$ = phenyl   R = 2-fluoro-4-hydroxy-phenyl
ES/MS m/z: 329.3 (pos. M + H), 327.1 (neg. M − H); $^1$H NMR (acetone-d6, 500 MHz): 7.78 (m, 1H), 7.52-7.49 (m, 2H), 7.47-7.44 (m, 3H), 7.42-7.36 (m, 3H), 7.19 (m, 1H), 6.94 (m, 1H) and 6.7 (dd, 1H, J = 2.7, 11.1 Hz).

E 102  2-Bromo-1-(3-fluoro-4-hydroxy-phenyl)-1H-indole-3-carbonitrile
$R^1$ = bromo   R = 3-fluoro-4-hydroxy-phenyl
ES/MS m/z: 331.1, 333.2 (pos. M + H), 329.2, 331.3 (neg. M − H); $^1$H NMR (acetone-d6, 500 MHz): 7.70 (m, 1H), 7.46 (dd, 1H, J = 2.5, 11.4 Hz), 7.38-7.32 (m, 2H), 7.31-7.25 (m, 2H) and 7.21 (m, 1H).

E 103  2-Bromo-1-(2,3-difluoro-4-hydroxy-phenyl)-1H-indole-3-carbonitrile
$R^1$ = bromo   R = 2,3-difluoro-4-hydroxy-phenyl
ES/MS m/z: 349.1, 351.2 (pos. M + H), 346.9, 349.0 (neg. M − H); $^1$H NMR (acetone-d6, 500 MHz): 7.72 (m, 1H), 7.40-7.34 (m, 3H), 7.22 (m, 1H) and 7.14 (m, 1H).

E 104  2-Bromo-1-(2,5-difluoro-4-hydroxy-phenyl)-1H-indole-3-carbonitrile
$R^1$ = bromo   R = 2,5-difluoro-4-hydroxy-phenyl
ES/MS m/z: 349.1, 351.2 (pos. M + H), 346.9, 349.0 (neg. M − H); $^1$H NMR (acetone-d6, 500 MHz): 7.73 (m, 1H), 7.61 (dd, 1H, J = 7.2, 10.6 Hz), 7.41-7.35 (m, 2H), 7.23 (m, 1H) and 7.16 (dd, 1H, J = 7.6, 10.7 Hz).

E 105  2-Bromo-1-(3-chloro-4-hydroxy-phenyl)-1H-indole-3-carbonitrile
$R^1$ = bromo   R = 3-chloro-4-hydroxy-phenyl
ES/MS m/z: 347.0, 349.1 (pos. M + H), 344.8, 347.2 (neg. M − H); $^1$H NMR (acetone-d6, 500 MHz): 7.70 (m, 1H), 7.65 (d, 1H, J = 2.5 Hz), 7.39 (dd, 1H, J = 2.5, 8.5 Hz), 7.38-7.32 (m, 2H), 7.30 (d, 1H, J = 8.5 Hz) and 7.20 (m, 1H).

E 106  2-Bromo-1-(3,5-difluoro-4-hydroxy-phenyl)-1H-indole-3-carbonitrile
$R^1$ = bromo   R = 3,5-difluoro-4-hydroxy-phenyl
ES/MS m/z: 349.1, 351.2 (pos. M + H), 347.2, 349.3 (neg. M − H); $^1$H NMR (acetone-d6, 500 MHz): 7.70 (m, 1H), 7.40-7.34 (m, 4H) and 7.27 (m, 1H).

E 107  1-(3-Fluoro-4-hydroxy-phenyl)-2-phenyl-1H-indole-3-carbonitrile
$R^1$ = phenyl   R = 3-fluoro-4-hydroxy-phenyl
ES/MS m/z: 329.3 (pos. M + H), 327.1 (neg. M − H); $^1$H NMR (acetone-d6, 500 MHz): 7.77 (m, 1H), 7.51 (m, 2H), 7.46-7.43 (m, 3H), 7.40-7.35 (m, 2H), 7.31-7.26 (m, 2H) and 7.14-7.07 (m, 2H).

E 108  1-(3,5-Difluoro-4-hydroxy-phenyl)-2-phenyl-1H-indole-3-carbonitrile
$R^1$ = phenyl   R = 3,5-difluoro-4-hydroxy-phenyl
ES/MS m/z: 347.2 (pos. M + H), 344.8 (neg. M − H); $^1$H NMR (acetone-d6, 500 MHz): 7.77 (m, 1H), 7.53 (m, 2H), 7.49-7.46 (m, 3H), 7.42-7.35 (m, 3H) and 7.19 (m, 2H).

E 109  1-(3-Chloro-4-hydroxy-phenyl)-2-phenyl-1H-indole-3-carbonitrile
$R^1$ = phenyl   R = 3-chloro-4-hydroxy-phenyl

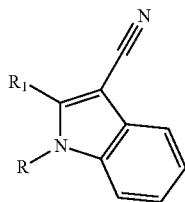

ES/MS m/z: 344.9, 347.3 (pos. M + H), 343.0 (neg. M − H); ¹H NMR (acetone-d6, 500 MHz): 7.77 (m, 1H), 7.52 (m, 2H), 7.48 (d, 1H, J = 2.5 Hz), 7.47-7.44 (m, 3H), 7.41-7.35 (m, 2H), 7.29 (m, 1H), 7.22 (dd, 1H, J = 2.5, 8.8 Hz) and 7.13 (d, 1H, J = 8.8 Hz).

E 110      1-(2,3-Difluoro-4-hydroxy-phenyl)-2-phenyl-1H-indole-3-carbonitrile
R¹ = phenyl      R = 2,3-difluoro-4-hydroxy-phenyl
ES/MS m/z: 347.2 (pos. M + H), 344.8 (neg. M − H); ¹H NMR (acetone-d6, 500 MHz): 7.80 (m, 1H), 7.52 (m, 2H), 7.49-7.46 (m, 3H), 7.43-7.38 (m, 2H), 7.29-7.25 (m, 2H) and 7.00 (m, 1H).

E 111      1-(2,5-Difluoro-4-hydroxy-phenyl)-2-phenyl-1H-indole-3-carbonitrile
R¹ = phenyl      R = 2,5-difluoro-4-hydroxy-phenyl
ES/MS m/z: 347.3 (pos. M + H), 344.8 (neg. M − H); ¹H NMR (acetone-d6, 500 MHz): 7.79 (m, 1H), 7.54-7.51 (m, 3H), 7.50-7.46 (m, 3H), 7.43-7.37 (m, 2H), 7.27 (m, 1H) and 6.96 (dd, 1H, J = 7.6, 10.7 Hz).

E112      1-(3,5-Difluoro-4-hydroxy-phenyl)-2-thiophen-3-yl-1H-indole-3-carbonitrile
R¹ = thiophen-3-yl      R = 3,5-difluoro-4-hydroxy-phenyl
ES/MS m/z: 353.0 (pos. M + H), 351.4 (neg. M − H); ¹H NMR (acetone-d6, 500 MHz): 7.74 (m, 1H), 7.71 (dd, 1H, J = 1.3, 2.9 Hz), 7.59 (dd, 1H, J = 2.9, 5.1 Hz), 7.40-7.34 (m, 2H), 7.30 (m, 1H) and 7.24-7.20 (m, 3H).

E 113      1-(3,5-Difluoro-4-hydroxy-phenyl)-2-thiophen-2-yl-1H-indole-3-carbonitrile
R¹ = thiophen-2-yl      R = 3,5-difluoro-4-hydroxy-phenyl
ES/MS m/z: 353.0 (pos. M + H), 351.4 (neg. M − H); ¹H NMR (acetone-d6, 500 MHz): 7.74 (m, 1H), 7.71 (dd, 1H, J = 1.2, 5.0 Hz), 7.54 (dd, 1H, J = 1.2, 3.8 Hz), 7.40-7.34 (m, 2H), 7.30 (m, 2H), 7.25 (m, 1H) and 7.19 (dd, 1H, J = 3.8, 5.0 Hz).

E 114      1-(3,5-Difluoro-4-hydroxy-phenyl)-2-(3,5-dimethyl-isoxazol-4-yl)-1H-indole-3-carbonitrile
R¹ = 3,5-dimethyl-isoxazol-4-yl      R = 3,5-difluoro-4-hydroxy-phenyl
ES/MS m/z: 366.2 (pos. M + H), 364.3 (neg. M − H); ¹H NMR (acetone-d6, 500 MHz): 7.78 (m, 1H), 7.45 (m, 1H), 7.44-7.40 (m, 2H), 7.22 (m, 2H), 2.41 (s, 3H) and 2.09 (s, 3H).

E 115      1-(3,5-Difluoro-4-hydroxy-phenyl)-2-(1-methyl-1H-pyrrol-2-yl)-1H-indole-3-carbonitrile
R¹ = 1-methyl-1H-pyrrol-2-yl      R = 3,5-difluoro-4-hydroxy-phenyl
ES/MS m/z: 350.3 (pos. M + H), 348.1 (neg. M − H); ¹H NMR (acetone-d6, 500 MHz): 7.76 (m, 1H), 7.41-7.36 (m, 3H), 7.15 (m, 2H), 6.90 (dd, 1H, J = 1.8, 2.6 Hz), 6.27 (dd, 1H, J = 1.8, 3.8 Hz), 6.12 (dd, 1H, J = 2.6, 3.8 Hz) and 3.61 (s, 3H).

E 116      1-(3,5-Difluoro-4-hydroxy-phenyl)-2-(3-methyl-thiophen-2-yl)-1H-indole-3-carbonitrile
R¹ = 3-methyl-thiophen-2-yl      R = 3,5-difluoro-4-hydroxy-phenyl
ES/MS m/z: 367.1 (pos. M + H), 365.2 (neg. M − H); ¹H NMR (acetone-d6, 500 MHz): 7.77 (m, 1H), 7.61 (d, 1H, J = 5.1 Hz), 7.42-7.36 (m, 3H), 7.16 (m, 2H), 7.02 (d, 1H, J = 5.1 Hz) and 2.26 (s, 3H).

E 117      1-(3,5-Difluoro-4-hydroxy-phenyl)-2-(1-methyl-1H-pyrazol-4-yl)-1H-indole-3-carbonitrile
R¹ = 1-methyl-1H-pyrrazol-4-yl      R = 3,5-difluoro-4-hydroxy-phenyl
ES/MS m/z: 351.5 (pos. M + H), 349.3 (neg. M − H); ¹H NMR (acetone-d6, 500 MHz): 7.79 (s, 1H), 7.68 (m, 1H), 7.50 (s, 1H), 7.35-7.28 (m, 2H), 7.25 (m, 2H), 7.18 (m, 1H) and 3.91 (s, 3H).

E 118      1-(3,5-Difluoro-4-hydroxy-phenyl)-2-pyridin-4-yl-1H-indole-3-carbonitrile
R¹ = pyridine-4-yl      R = 3,5-difluoro-4-hydroxy-phenyl
ES/MS m/z: 348.2 (pos. M + H); ¹H NMR (acetone-d6, 500 MHz): 8.70 (m, 2H), 7.81 (m, 1H), 7.49 (m, 2H), 7.45-7.39 (m, 3H) and 7.24 (m, 2H).

E 119      1-(3-Chloro-4-hydroxy-phenyl)-2-thiophen-3-yl-1H-indole-3-carbonitrile
R¹ = thiophen-2-yl      R = 3-chloro-4-hydroxy-phenyl
ES/MS m/z: 351.2 (pos. M + H), 349.3 (neg. M − H); ¹H NMR (acetone-d6, 500 MHz): 7.74 (m, 1H), 7.67 (dd, 1H, J = 1.3, 2.8 Hz), 7.57 (dd, 1H, J = 2.8, 5.1 Hz), 7.52 (d, 1H, J = 2.5 Hz), 7.39-7.32 (m, 2H), 7.27 (dd, 1H, J = 2.5, 6.8 Hz), 7.23 (m, 1H), 7.20 (d, 1H, J = 8.6 Hz) and 7.18 (dd, 1H, J = 1.3, 5.1 Hz).

E 120      1-(3-Chloro-4-hydroxy-phenyl)-2-thiophen-2-yl-1H-indole-3-carbonitrile
R¹ = thiophen-2-yl      R = 3-chloro-4-hydroxy-phenyl
ES/MS m/z: 351.2 (pos. M + H), 349.3 (neg. M − H); ¹H NMR (acetone-d6, 500 MHz): 7.74 (m, 1H), 7.68 (dd, 1H, J = 1.3, 5.0 Hz), 7.58 (d, 1H, J = 2.5 Hz), 7.56 (dd, 1H, J = 1.3, 3.8 Hz), 7.39-7.31 (m, 3H), 7.24 (d, 1H, J = 8.5 Hz) and 7.18-7.15 (m, 2H).

E 121      1-(3-Chloro-4-hydroxy-phenyl)-2-(3,5-dimethyl-isoxazol-4-yl)-1H-indole-3-carbonitrile
R¹ = 3,5-dimethyl-isoxazol-4-yl      R = 3-chloro-4-hydroxy-phenyl
ES/MS m/z: 364.4 (pos. M + H), 362.5 (neg. M − H); ¹H NMR (acetone-d6, 500 MHz): 7.78 (m, 1H), 7.53 (br s, 1H), 7.43-7.36 (m, 3H), 7.27 (br d, 1H, J = 7.7 Hz), 7.19 (d, 1H, J = 8.9 Hz), 2.39 (s, 3H) and 2.06 (s, 3H).

E 122      1-(3-Chloro-4-hydroxy-phenyl)-2-(1-methyl-1H-pyrrol-2-yl)-1H-indole-3-carbonitrile
R¹ = 1-methyl-1H-pyrrol-2-yl      R = 3-chloro-4-hydroxy-phenyl
ES/MS m/z: 348.2 (pos. M + H), 346.0 (neg. M − H); ¹H NMR (acetone-d6, 500 MHz): 7.75 (m, 1H), -continued

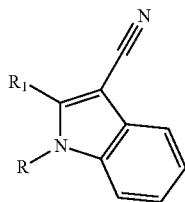

7.43 (d, 1H, J = 2.5 Hz), 7.40-7.35 (m, 2H), 7.32 (m, 1H), 7.22 (dd, 1H, J = 2.5, 8.7 Hz), 7.14 (d, 1H, J = 8.7 Hz), 6.87 (dd, 1H, J = 1.9, 2.8 Hz), 6.25 (dd, 1H, J = 1.9, 3.8 Hz), 6.10 (dd, 1H, J = 2.8, 3.8 Hz) and 3.58 (s, 3H).

E 123  1-(3-Chloro-4-hydroxy-phenyl)-2-(3-methyl-thiophen-2-yl)-1H-indole-3-carbonitrile
$R^1$ = 3-methyl-thiophen-2-yl   R = 3-chloro-4-hydroxy-phenyl
ES/MS m/z: 365.0 (pos. M + H), 363.4 (neg. M − H); $^1$H NMR (acetone-d6, 500 MHz): 7.77 (m, 1H), 7.59 (d, 1H, J = 5.1 Hz), 7.46 (d, 1H, J = 2.6 Hz), 7.41-7.36 (m, 2H), 7.30 (m, 1H), 7.22 (dd, 1H, J = 2.6, 8.5 Hz), 7.14 (d, 1H, J = 8.5 Hz), 7.00 (d, 1H, J = 5.1 Hz) and 2.24 (s, 3H).

E 124  1-(3-Chloro-4-hydroxy-phenyl)-2-pyridin-4-yl-1H-indole-3-carbonitrile
$R^1$ = pyridine-4-yl   R = 3-chloro-4-hydroxy-phenyl
ES/MS m/z: 346.1 (pos. M + H), 343.9 (neg. M − H); $^1$H NMR (acetone-d6, 500 MHz): 8.68 (m, 2H), 7.81 (m, 1H), 7.55 (d, 1H, J = 2.5 Hz), 7.47 (m, 2H), 7.44-7.41 (m, 2H), 7.34 (m, 1H), 7.27 (dd, 1H, J = 2.5, 8.6 Hz) and 7.16 (d, 1H, J = 8.6 Hz).

E 125  1-(3-Fluoro-4-hydroxy-phenyl)-2-thiophen-3-yl-1H-indole-3-carbonitrile
$R^1$ = thiophen-3-yl   R = 3-fluoro-4-hydroxy-phenyl
ES/MS m/z: 335.6 (pos. M + H), 333.1 (neg. M − H); $^1$H NMR (acetone-d6, 500 MHz): 7.74 (m, 1H), 7.67 (dd, 1H, J = 1.3, 2.8 Hz), 7.56 (dd, 1H, J = 2.8, 5.0 Hz), 7.38-7.30 (m, 3H), 7.24 (m, 1H), 7.21-7.17 (m, 2H) and 7.13 (m, 1H).

E 126  1-(3-Fluoro--hydroxy-phenyl)-2-thiophen-2-yl-1H-indole-3-carbonitrile
$R^1$ = thiophen-2-yl   R = 3-fluoro-4-hydroxy-phenyl
ES/MS m/z: 335.6 (pos. M + H), 333.1 (neg. M − H); $^1$H NMR (acetone-d6, 500 MHz): 7.73 (m, 1H), 7.68 (dd, 1H, J = 1.3, 5.0 Hz), 7.54 (dd, 1H, J = 1.3, 3.8 Hz), 7.39-7.32 (m, 3H) and 7.25-7.16 (m, 4H).

E 127  2-(3,5-Dimethyl-isoxazol-4-yl)-1-(3-fluoro-4-hydroxy-phenyl)-1H-indole-3-carbonitrile
$R^1$ = 3,5-Dimethyl-isoxazol-4-yl   R = 3-fluoro-4-hydroxy-phenyl
ES/MS m/z: 348.2 (pos. M + H), 346.0 (neg. M − H); $^1$H NMR (acetone-d6, 500 MHz): 7.79 (m, 1H), 7.43-7.39 (m, 3H), 7.32 (m, 1H), 7.20-7.13 (m, 2H), 2.39 (s, 3H) and 2.05 (s, 3H).

E 128  1-(3-Fluoro-4-hydroxy-phenyl)-2-(1-methyl-1H-pyrrol-2-yl)-1H-indole-3-carbonitrile
$R^1$ = 1-methyl-1H-pyrrol-2-yl   R = 3-fluoro-4-hydroxy-phenyl
ES/MS m/z: 332.3 (pos. M + H), 330.1 (neg. M − H); $^1$H NMR (acetone-d6, 500 MHz): 7.75 (m, 1H), 7.40-7.32 (m, 3H), 7.21 (dd, 1H, J = 2.1, 11.3 Hz), 7.15-7.08 (m, 2H), 6.87 (dd, 1H, J = 1.8, 2.5 Hz), 6.25 (dd, 1H, J = 1.8, 3.8 Hz), 6.10 (dd, 1H, J = 2.5, 3.8 Hz) and 3.56 (s, 3H).

E 129  1-(3-Fluoro-4-hydroxy-phenyl)-2-(3-methyl-thiophen-2-yl)-1H-indole-3-carbonitrile
$R^1$ = 3-methyl-thiophen-2-yl   R = 3-fluoro-4-hydroxy-phenyl
ES/MS m/z: 349.4 (pos. M + H), 347.2 (neg. M − H); $^1$H NMR (acetone-d6, 500 MHz): 7.77 (m, 1H), 7.59 (d, 1H, J = 5.1 Hz), 7.41-7.36 (m, 2H), 7.321 (m, 1H), 7.25 (dd, 1H, J = 2.4, 11.4 Hz), 7.15-7.08 (m, 2H), 7.00 (d, 1H, J = 5.1 Hz) and 2.24 (s, 3H).

E 130  1-(3-Fluoro-4-hydroxy-phenyl)-2-(1-methyl-1H-pyrrazol-4-yl)-1H-indole-3-carbonitrile
$R^1$ = 1-methyl-1H-pyrrazol-4-yl   R = 3-fluoro-4-hydroxy-phenyl
ES/MS m/z: 333.2 (pos. M + H), 331.3 (neg. M − H); $^1$H NMR (acetone-d6, 500 MHz): 7.76 (br s, 1H), 7.68 (m, 1H), 7.41 (d, 1H, J = 0.6 Hz), 7.36-7.23 (m, 4H), 7.16 (m, 1H), 7.12 (m, 1H) and 3.91 (s, 3H).

E 131  1-(3-Fluoro-4-hydroxy-phenyl)-2-pyridin-4-yl-1H-indole-3-carbonitrile
$R^1$ = pyridine-4-yl   R = 3-fluoro-4-hydroxy-phenyl
ES/MS m/z: 330.2 (pos. M + H), 328.3 (neg. M − H); $^1$H NMR (acetone-d6, 500 MHz): 8.68 (m, 2H), 7.81 (m, 1H), 7.47 (m, 2H), 7.44-7.40 (m, 2H), 7.37-7.33 (m, 2H) and 7.17-7.12 (m, 2H).

E 132  2-Dimethylamino-1-(2-fluoro-4-hydroxy-phenyl)-1H-indole-3-carbonitrile
$R^1$ = dimethylamino   R = 2-fluoro-4-hydroxy-phenyl
ES/MS m/z: 296.3 (pos. M + H), 294.1 (neg. M − H); $^1$H NMR (acetone-d6, 500 MHz): 7.45-7.41 (m, 2H), 7.19 (m, 1H), 7.10 (m, 1H), 6.69-6.85 (m, 3H) and 2.96 (s, 6H).

E 133  2-(3,5-Dimethyl-isoxazol-4-yl)-1-(2-fluoro-4-hydroxy-phenyl)-1H-indole-3-carbonitrile
$R^1$ = 3,5-dimethyl-isoxazol-4-yl   R = 2-fluoro-4-hydroxy-phenyl
ES/MS m/z: 348.2 (pos. M + H), 346.3 (neg. M − H); $^1$H NMR (acetone-d6, 500 MHz): 7.80 (m, 1H), 7.47 (m, 1H), 7.42 (m, 1H), 7.27 (m, 1H), 6.88 (m, 1H), 6.83 (m, 1H), 2.34, 2.33 (2 s, 3H) and 2.10, 2.09 (2 s, 3H).

E 134  1-(3-Fluoro-4-hydroxy-phenyl)-2-((E)-propenyl)-1H-indole-3-carbonitrile
$R^1$ = (E)-propenyl   R = 3-fluoro-4-hydroxy-phenyl
ES/MS m/z: 293.1 (pos. M + H), 291.1 (neg. M − H); $^1$H NMR (acetone-d6, 500 MHz): 7.66 (m, 1H), 7.35-7.25 (m, 4H), 7.16 (m, 1H), 7.11 (m, 1H), 6.86 (m, 1H), 6.29 (m, 1H) and 1.92 (dd, 1H, J = 1.9, 6.9 Hz).

E 135  1-(3-Fluoro-4-hydroxy-phenyl)-2-((Z)-popenyl)-1H-indole-3-carbonitrile
$R^1$ = (Z)-propenyl   R = 3-fluoro-4-hydroxy-phenyl
ES/MS m/z: 293.1 (pos. M + H), 291.1 (neg. M − H); $^1$H NMR (acetone-d6, 500 MHz): 7.71 (m, 1H), 7.35-7.29 (m, 3H), 7.25-7.21 (m, 2H), 7.16 (m, 1H), 6.23-6.16 (m, 2H) and 1.94 (m, 3H).

-continued

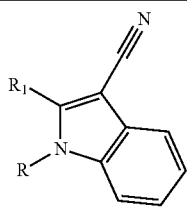

E 136　　1-(2,3-Difluoro-4-hydroxy-phenyl)-2-((Z)-propenyl)-1H-indole-3-carbonitrile
$R^1$ = (Z)-propenyl)　　R = 2,3-difluoro-4-hydroxy-phenyl
ES/MS m/z: 311.0 (pos. M + H), 309.1 (neg. M − H); $^1$H NMR (CDCl$_3$, 500 MHz): 7.79 (m, 1H), 7.35-7.28 (m, 2H), 7.08 (m, 1H), 7.05-6.96 (m, 2H), 6.17 (m, 1H), 6.10 (m, 1H) and 1.98 (dd, 3H, J = 1.5, 6.9 Hz).

E 137　　1-(2,3-Difluoro-4-hydroxy-phenyl)-2-vinyl-1H-indole-3-carbonitrile
$R^1$ = vinyl　　R = 2,3-difluoro-4-hydroxy-phenyl
ES/MS m/z: 297.0 (pos. M + H), 295.1 (neg. M − H); $^1$H NMR (CDCl$_3$, 500 MHz): 7.78 (m, 1H), 7.34-7.27 (m, 2H), 7.08-6.99 (m, 3H), 6.46 (dd, 1H, J = 11.7, 17.8 Hz), 6.31 (d, 1H, J = 17.8 Hz) and 5.67 (d, 1H, J = 11.7 Hz).

E 138　　1-(2,3-Difluoro-4-hydroxy-phenyl)-2-thiophen-3-yl-1H-indole-3-carbonitrile
$R^1$ = thiophen-3-yl　　R = 2,3-difluoro-4-hydroxy-phenyl
ES/MS m/z: 353.3 (pos. M + H), 351.4 (neg. M − H); $^1$H NMR (acetone-d6, 500 MHz): 7.77 (m, 1H), 7.70 (dd, 1H, J = 1.3, 2.8 Hz), 7.61 (dd, 1H, J = 2.8, 5.0 Hz), 7.41-7.35 (m, 2H), 7.31 (m, 1H), 7.25 (dd, 1H, J = 1.3, 5.0 Hz), 7.23 (m, 1H) and 7.06 (m, 1H).

E 139　　1-(2,3-Difluoro-4-hydroxy-phenyl)-2-thiophen-2-yl-2H-indole-3-carbonitrile
$R^1$ = thiophen-2-yl　　R = 2,3-difluoro-4-hydroxy-phenyl
ES/MS m/z: 353.3 (pos. M + H), 351.4 (neg. M − H); $^1$H NMR (acetone-d6, 500 MHz): 7.76 (m, 1H), 7.71 (m, 1H), 7.60 (m 1H), 7.42-7.32 (m, 3H), 7.21-7.19 (m, 2H) and 7.10 (m, 1H).

E 140　　1-(2,3-Difluoro-4-hydroxy-phenyl)-2-(3-methyl-thiophen-2-yl)-1H-indole-3-carbonitrile
$R^1$ = 3-methyl-thiophen-2-yl　　R = 2,3-difluoro-4-hydroxy-phenyl
ES/MS m/z: 367.1 (pos. M + H), 365.2 (neg. M − H); $^1$H NMR (acetone-d6, 500 MHz): 7.80 (m, 1H), 7.60 (d, 1H, J = 5.1 Hz), 7.44-7.39 (m, 2H9, 7.27 (m, 1H), 7.22 (m, 1H), 7.02 (d, 1H, J = 5.1 Hz), 6.99 (m, 1H) and 2.28 (s, 3H).

E 141　　1-(2,3-Difluoro-4-hydroxy-phenyl)-2-(1-methyl-1H-pyrrol-2-yl)-1H-indole-3-carbonitrile
$R^1$ = 1-methyl-1H-pyrrol-2-yl　　R = 2,3-difluoro-4-hydroxy-phenyl
ES/MS m/z: 350.3 (pos. M + H), 348.1 (neg. M − H); $^1$H NMR (acetone-d6, 500 MHz): 7.78 (m, 1H), 7.42-7.37 (m, 2H), 7.26-7.22 (m, 2H), 6.99 (m, 1H), 6.93 (dd, 1H, J = 1.5, 2.9 Hz), 6.14 (dd, 1H, J = 1.5, 3.8 Hz), 6.08 (dd, 1H, J = 2.9, 3.8 Hz) and 3.70 (s, 3H).

E 142　　2-(2-Acetyl-pyrrol-1-yl)-1-(3-fluoro-4-hydroxy-phenyl)-1H-indole-3-carbonitrile
$R^1$ = 2-acetyl-pyrrol-1-yl　　R = 3-fluoro-4-hydroxy-phenyl
ES/MS m/z: 360.2 (pos. M + H), 358.2 (neg. M − H); $^1$H NMR (acetone-d6, 500 MHz): 8.31 (m, 1H), 7.41 (d, 1H, J = 5.2 Hz), 7.32-7.26 (m, 2H), 7.18 (m, 1H), 7.16-6.96 (m, 3H), 6.85 (d, 1H, J = 5.2 Hz) and 2.09 (s, 3H).

E 143　　1-(3-Fluoro-4-hydroxy-phenyl)-2-pyrrol-1-yl-1H-indole-3-carbonitrile
$R^1$ = pyrrol-1-yl　　R = 3-fluoro-4-hydroxy-phenyl
ES/MS m/z: 317.9 (pos. M + H), 316.3 (neg. M − H); $^1$H NMR (acetone-d6, 500 MHz): 7.74 (m, 1H), 7.43-7.37 (m, 2H), 7.31-7.29 (m, 2H), 7.16-7.14 (m, 2H), 6.97 (t, 2H, J = 2.2 Hz) and 6.26 (t, 2H, J = 2.2 Hz).

E 144　　1-(2,3-Difluoro-4-hydroxy-phenyl)-2-pyrrol-1-yl-1H-indole-3-carbonitrile
$R^1$ = pyrrol-1-yl　　R = 2,3-difluoro-4-hydroxy-phenyl
ES/MS m/z: 336.5 (pos. M + H), 334.3 (neg. M − H); $^1$H NMR (acetone-d6, 500 MHz): 7.77 (m, 1H), 7.46-7.40 (m, 2H), 7.31 (m, 1H), 7.27 (m, 1H), 7.02 (m, 1H), 6.99 (t, 2H, J = 2.2 Hz) and 6.28 (t, 2H, J = 2.2 Hz).

E 145　　1-(2,3-Difluoro-4-hydroxy-phenyl)-2-prop-1-ynyl-1H-indole-3-carbonitrile
$R^1$ = prop-1-ynyl　　R = 2,3-difluoro-4-hydroxy-phenyl
ES/MS m/z: 309.1 (pos. M + H), 307.2 (neg. M − H); $^1$H NMR (CDCl$_3$, 500 MHz): 7.74 (m, 1H), 7.34-7.30 (m, 2H), 7.12 (m, 1H), 7.05 (m, 1H), 6.98 (m, 1H) and 2.08 (s, 3H).

E 146　　1-(3-Fluoro-4-hydroxy-phenyl)-2-(2-methyl-prop-1-enyl)-1H-indole-3-carbonitrile
$R^1$ = 2-methyl-prop-1-enyl　　R = 3-fluoro-4-hydroxy-phenyl
ES/MS m/z: 307.1 (pos. M + H), 305.2 (neg. M − H); $^1$H NMR (CDCl$_3$, 500 MHz): 7.76 (m, 1H), 7.40-7.36 (m, 2H), 7.18-7.13 (m, 2H), 7.07 (m, 1H), 7.02 (m, 1H), 5.86 (m, 1H), 1.98 (d, 3H, J = 1.3 Hz) and 1.91 (d, 3H, J = 1.4 Hz).

E 147　　1-(2,3-Difluoro-4-hydroxy-phenyl)-2-(2-methyl-prop-1-enyl)-1H-indole-3-carbonitrile
$R^1$ = 2-methyl-prop-1-enyl　　R = 2,3-difluoro-4-hydroxy-phenyl
ES/MS m/z: 325.1 (pos. M + H), 323.2 (neg. M − H); $^1$H NMR (CDCl$_3$, 500 MHz): 7.77 (m, 1H), 7.33-7.25 (m, 2H), 7.05-7.01 (m, 2H), 6.96 (m, 1H), 5.8 (m, 1H), 1.96 (d, 3H, J = 1.2 Hz) and 1.91 (d, 3H, J = 1.3 Hz).

E 148　　2-(2-Acetyl-pyrrol-1-yl)-1-(2,3-difluoro-4-hydroxy-phenyl)-1H-indole-3-carbonitrile
$R^1$ = 2-acetyl-pyrrol-1-yl　　R = 2,3-difluoro-4-hydroxy-phenyl
ES/MS m/z: 378.2 (pos. M + H), 376. (neg. M − H); $^1$H NMR (acetone-d6, 500 MHz): two conformations in ratio 2:1, 7.82-7.77 (m, 3H), 7.52 (dd, 1H, J = 2.9, 1.6 Hz), 7.47-7.42 (m, 6H), 7.35-7.34

-continued

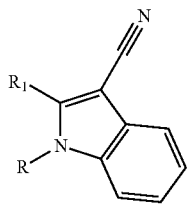

(m, 2H), 7.31 (m, 1H), 7.27-7.25 (m, 2H), 7.20 (dd, 1H, J = 4.1, 1.6 Hz), 7.16 (dd, 1H, J = 4.0, 1.6 Hz), 7.03-6.99 (m, 2H), 6.96-6.88 (m, 3H), 6.81 (m, 1H), 6.47 (dd, 1H, J = 4.0, 2.8 Hz), 6.44 (dd, 2H, J = 3.8, 2.8 Hz), 2.29 (s, 6H) and 2.21 (s, 3H).

E 149  1-(3-Fluoro-4-hydroxy-phenyl)-2-pyrazol-1-yl-1H-indole-3-carbonitrile
$R^1$ = pyrrazol-1-yl   R = 3-fluoro-4-hydroxy-phenyl
ES/MS m/z: 319.1 (pos. M + H), 317.2 (neg. M − H); $^1$H NMR (acetone-d6, 500 MHz): 7.98 (dd, 1H, J = 2.6, 6.0 Hz), 7.79 (m, 1H), 7.73 (d, 1H, J = 1.8 Hz), 7.46-7.41 (m, 2H), 7.33 (m, 1H), 7.28 (m, 1H), 7.15-7.09 (m, 2H) and 6.51 (dd, 1H, J = 2.5, 1.7 Hz).

E 150  1-(2,3-Difluoro-4-hydroxy-phenyl)-2-pyrazol-1-yl-1H-indole-3-carbonitrile
$R^1$ = pyrrazol-1-yl   R = 2,3-difluoro-4-hydroxy-phenyl
ES/MS m/z: 337.4 (pos. M + H), 335.5 (neg. M − H); $^1$H NMR (acetone-d6, 500 MHz): 8.14 (d, 1H, J = 2.6 Hz), 7.82 (m, 1H), 7.72 (d, 1H, J = 1.6 Hz), 7.48-7.43 (m, 2H), 7.31 (m, 1H), 7.20 (m, 1H), 6.96 (m, 1H) and 6.56 (dd, 1H, J = 2.6, 1.6 Hz).

E 151  2-(2,5-Dimethyl-pyrrol-1-yl)-1-(3-fluoro-4-hydroxy-phenyl)-1H-indole-3-carbonitrile
$R^1$ = 2,5-dimethyl-pyrrol-1-yl   R = 3-fluoro-4-hydroxy-penyl
ES/MS m/z: 346.1 (pos. M + H), 344.2 (neg. M − H); $^1$H NMR (acetone-d6, 500 MHz): 7.82 (m, 1H), 7.46-7.43 (m, 3H), 7.15-7.10 (m, 2H), 7.04 (m, 1H), 5.83 (s, 2H) and 2.06 (s, 6H).

E 152  2-(2-Ethyl-pyrrol-1-yl)-1-(3-fluoro-4-hydroxy-phenyl)-1H-indole-3-carbonitrile
$R^1$ = 2-ethyl-pyrrol-1-yl   R = 3-fluoro-4-hydroxy-phenyl
ES/MS m/z: 346.1 (pos. M + H), 344.2 (neg. M − H); $^1$H NMR (acetone-d6, 500 MHz): 7.79 (m, 1H), 7.45-7.41 (m, 2H), 7.37 (m, 1H), 7.22 (m, 1H), 7.13-7.09 (m, 2H), 6.92 (dd, 1H, J = 2.9, 1.6 Hz), 6.14 (t, 1H, J = 3.3 Hz), 5.98 (m, 1H), 2.50 (m, 1H), 2.40 (m, 1H) and 1.10 (t, 3H, J = 7.6 Hz).

E 153  2-(2-Cyano-pyrrol-1-yl)-1-(3-fluoro-4-hydroxy-phenyl)-1H-indole-3-carbonitrile
$R^1$ = 2-cyano-pyrrol-1-yl   R = 3-fluoro-4-hydroxy-phenyl
ES/MS m/z: 343.1 (pos. M + H), 341.2 (neg. M − H); $^1$H NMR (acetone-d6, 500 MHz): 7.86 (m, 1H), 7.52-7.48 (m, 3H), 7.39 (m, 1H), 7.32 (m, 1H), 7.19-7.12 (m, 3H) and 6.48 (dd, 1H, J = 3.9, 2.8 Hz).

E 154  1-(3-Fluoro-4-hydroxy-phenyl)-2-(2-methyl-pyrrol-1-yl)-1H-indole-3-carbonitrile
$R^1$ = 2-methyl-pyrrol-1-yl   R = 3-fluoro-4-hydroxy-phenyl
ES/MS m/z: 332.3 (pos. M + H), 330.1 (neg. M − H); $^1$H NMR (acetone-d6, 500 MHz): 7.79 (m, 1H), 7.45-7.41 (m, 2H), 7.37 (m, 1H), 7.23 (m, 1H), 7.14-7.09 (m, 2H), 6.88 (dd, 1H, J = 3.1, 1.7 Hz), 6.09 (t, 1H, J = 3.1 Hz), 5.95 (m, 1H) and 2.14 (d, 1H, J = 0.9 Hz).

E 155  1-(2,3-Difluoro-4-hydroxy-phenyl)-2-(2-ethyl-pyrrol-1-yl)-1-indole-3-carbonitrile
$R^1$ = 2-ethyl-pyrrol-1-yl   R = 2,3-difluoro-4-hydroxy-phenyl
ES/MS m/z: 364.4 (pos. M + H), 362.5 (neg. M − H); $^1$H NMR (acetone-d6, 500 MHz): two conformatiobns in ratio 1.5:1, 7.83-7.80 (m, 2.5H), 7.48-7.43 (m, 5H), 7.33-7.28 (m, 4H), 7.10 (m, 1H), 6.99-6.90 (m, 4H), 6.73 (m, 1H), 6.14-6.11 (m, 2.5H), 6.00-5.99 (m, 2.5H), 2.59-2.46 (m, 3.5H), 2.36 (m, 1.5H) and 1.17-1.13 (m, 7.5H).

E 156  2-(2-Cyano-pyrrol-1-yl)-1-(2,3-difluoro-4-hydroxy-phenyl)-1H-indole-3-carbonitrile
$R^1$ = 2-cyano-pyrrol-1-yl   R = 2,3-difluoro-4-hydroxy-phenyl
ES/MS m/z: 361.4 (pos. M + H), 359.2 (neg. M − H); $^1$H NMR (acetone-d6, 500 MHz): 7.88 (m, 1H), 7.55-7.50 (m, 2H), 7.46-7.33 (m, 3H), 7.17 (dd, 1H, J = 4.0, 1.5 Hz), 7.01 (m, 1H) and 6.49 (dd, 1H, J = 3.8, 2.9 Hz).

E 157  1-(2,3-Difluoro-4-hydroxy-phenyl)-2-(2-methyl-pyrrol-1-yl)-1H-indole-3-carbonitrile
$R^1$ = 2-methyl-pyrrol-1-yl   R = 2,3-difluoro-4-hydroxy-phenyl
ES/MS m/z: 350.3 (pos. M + H), 348.1 (neg. M − H); $^1$H NMR (acetone-d6, 500 MHz): 7.82 (m, 1H), 7.48-7.44 (m, 2H), 7.37 (m, 1H), 7.30 (m, 1H), 7.09-6.85 (m, 2H), 6.08 (m, 1H), 5.97 (m, 1H) and 1.20 (s, 3H).

E 158  1-(2-Fluoro-4-hydroxy-phenyl)-2-pyrrol-1-yl-1H-indole-3-carbonitrile
$R^1$ = pyrrol-1-yl   R = 2-fluoro-4-hydroxy-phenyl
ES/MS m/z: 317.9 (pos. M + H), 316.3 (neg. M − H); $^1$H NMR (acetone-d6, 500 MHz): 7.76 (m, 1H), 7.47 (t, 1H, J = 8.8 Hz), 7.44-7.38 (m, 2H), 7.19 (m, 1H), 6.96 (m, 2H), 6.86 (m, 1H), 6.81 (dd, 1H, J = 11.5, 2.5 Hz) and 6.27 (m, 2H).

E 159  1-(2,3-difluoro-4-hydroxyphenyl)-2-(3-methylbut-2-enyl)-1H-indole-3-carbonitrile
$R^1$ = 3-methylbut-2-enyl   R = 2,3-difluoro-4-hydroxyphenyl
ES/MS m/z: 317.9 (pos. M + H), 316.3 (neg. M − H); $^1$H NMR (acetone-d6, 500 MHz): 7.76 (m, 1H), 7.47 (t, 1H, J = 8.8 Hz), 7.44-7.38 (m, 2H), 7.19 (m, 1H), 6.96 (m, 2H), 6.86 (m, 1H), 6.81 (dd, 1H, J = 11.5, 2.5 Hz) and 6.27 (m, 2H).

Examples 160-195

Examples 160-162 below were prepared according to General Method 1 above. Full experimental details of the individual steps of that general method applicable for the synthesis of Examples 160-162 are described in Examples 1-4, 8, 16 and 38-40 above.

Examples 163-168 and 170-172 below were prepared according to General Method 4 above. Full experimental details of the individual steps of that general method are described in Examples 2-4, 9, and 20-21 above.

Examples 173-195 below were prepared according to General Method 1 above. Full experimental details of the individual steps of that general method applicable for the synthesis of Examples 173-195 are described in Examples 1-4, 10-11, 14-16, 38-40 and 45 above.

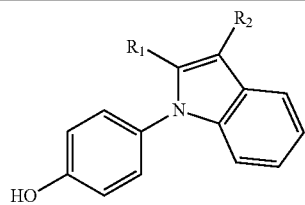

E 160 [1-(4-Hydroxy-phenyl)-2-phenyl-1H-indole-3-yl]acetonitrile
$R^1$ = phenyl $R^2$ = cyanomethyl
ES/MS m/z: 325.1 (pos. M + H), 323.2 (neg. M − H); $^1$H NMR (acetone-d6, 500 MHz): 7.81 (m, 1H), 7.41-7.32 (m, 5H), 7.25-7.22 (m, 2H), 7.19 (m, 1H), 7.11 (m, 2H), 6.88 (m, 2H) and 3.97 (s, 2H).

E 161 [1-(4-Hydroxy-phenyl)-2-phenyl-1H-indole-3-yl]-acetic acid
$R^1$ = phenyl $R^2$ = carboxymethyl
ES/MS m/z: 344.1 (pos. M + H), 342.2 (neg. M − H); $^1$H NMR (acetone-d6, 500 MHz): 7.71 (m, 1H), 7.39-7.27 (m, 5H), 7.17.7.12 (m, 3H), 7.07 (m, 2H), 6.86 (m, 2H) and 3.74 (s, 2H).

E 162 2-[1-(4-Hydroxy-phenyl)-2-phenyl-1H-indol-3-yl]acetamide
$R^1$ = phenyl $R^2$ = carbamoyl
ES/MS m/z: 313.1 (pos. M + H), 311.2 (neg. M − H); $^1$H NMR (CDCl$_3$, 500 MHz): 7.68 (m, 1H), 7.32-7.23 (m, 6H), 7.20-7.18 (m, 2H), 7.06 (m, 2H), 6.81 (m, 2H) and 3.77 (s, 1H).

E 163 4-(3-Isopropenyl-2-phenyl-indol-1-yl)-phenol
$R^1$ = phenyl $R^2$ = isopropenyl
ES/MS m/z: 326.2 (pos. M + H), 324.2 (neg. M − H); $^1$H MR (acetone-d6, 500 MHz): 7.72 (m, 1H), 7.31-7.25 (m, 5H), 7.16-7.11 (m, 3H), 7.07 (m, 2H), 6.86 (m, 2H), 5.27 (m, 1H), 5.15 (m, 1H) and 1.83 (m, 3H).

E 164 4-[3-(2-Methyl-2H-pyrazol-3-yl)-2-phenyl-indol-1-yl]-phenol
$R^1$ = phenyl $R^2$ = 2-Methyl-2H-pyrrazol-3-yl
ES/MS m/z: 366.2 (pos. M + H), 364.2 (neg. M − H); $^1$H NMR (acetone-d6, 500 MHz): 7.47-7.45 (m, 2H), 7.24-7.13 (m, 10H), 6.92 (m, 2H), 6.32 (d, 1H, J = 1.9 Hz) and 3.33 (s, 3H).

E 165 4-(2-Phenyl-3-thiazol-4-yl-indol-1-yl)-phenol
$R^1$ = phenyl $R^2$ = thiazol-4-yl
ES/MS m/z: 369.1 (pos. M + H), 367.1 (neg. M − H); $^1$H NMR (acetone-d6, 500 MHz): 9.06 (d, 1H, J = 2.0 Hz), 8.30 (m, 1H), 7.35-7.31 (m, 5H), 7.22-7.18 (m, 2H), 7.16-7.12 (m, 3H), 6.87 (m, 2H) and 6.81 (d, 1H, J = 2.2 Hz).

E 166 4-(2-Phenyl-3-prop-1-ynyl-indol-1-yl)-phenol
$R^1$ = phenyl $R^2$ = prop-1-ynyl
ES/MS m/z: 324.2 (pos. M + H), 322.2 (neg. M − H); $^1$H NMR (acetone-d6, 500 MHz): 7.70 (m, 1H), 7.48-7.46 (m, 2H), 7.34-7.26 (m, 3H), 7.21-7.18 (m, 2H), 7.16 (m, 1H), 7.11 (m, 2H), 6.91 (m, 2H) and 2.07 (s, 3H).

E 167 1-(3-Hydroxy-phenyl)-2-((E)-propenyl)-1-indole-3-carboxylic acid amide
$R^1$ = (E)-propenyl $R^2$ = carbamoyl
ES/MS m/z: 293.1 (pos. M + H), 291.2 (neg. M − H); $^1$H NMR (acetone-d6, 500 MHz): 7.99 (m, 1H), 7.19 (m, 2H), 7.16-7.10 (m, 2H), 7.05 (m, 2H), 6.94 (m, 1H), 6.73 (m, 1H), 5.91 (m, 1H) and 1.73 (dd, 3H, J = 1.3, 6.6 Hz).

E 168 1-(4-Hydroxy-phenyl)-2-(2-methyl-prop-1-enyl)-1H-indole-3-carboxylic acid amide
$R^1$ = 2-methyl-prop-1-enyl $R^2$ = carbamoyl
ES/MS m/z: 307.2 (pos. M + H), 305.2 (neg. M − H); $^1$H NMR (acetone-d6, 500 MHz): 8.36 (m, 1H), 7.20 (m, 2H), 7.17-7.12 (m, 2H), 7.05 (m, 1H), 7.01 (m, 2H), 6.17 (m, 1H), 1.83 (d, 3H, J = 1.4 Hz) and 1.65 (d, 3H, J = 1.2 Hz).

E 169 1-(4-Hydroxy-phenyl)-2-((Z)-1-methyl-propenyl)-1H-indole-3-carboxylicacid amide
$R^1$ = (Z)-1-methyl-propenyl $R^2$ = carbamoyl
ES/MS m/z: 307.1 (pos. M + H), 305.2 (neg. M − H); $^1$H NMR (acetone-d6, 500 MHz): 8.41 (m, 1H), 7.23 (br s, 2H), 7.19-7.13 (m, 2H), 7.03-7.00 (m, 3H), 5.91 (m, 1H), 1.89 (m, 3H) and 1.59 (m, 3H).

E 170 4-(2-Phenyl-3-pyrrazol-1-yl-indol-1-yl)-phenol
$R^1$ = phenyl $R^2$ = pyrrazol-1-yl
ES/MS m/z: 352.1 (pos. M + H), 350.2 (neg. M − H); $^1$H NMR (acetone-d6, 500 MHz): 7.68 (d, 1H, J = 1.3 Hz), 7.57 (m, 1H), 7.51 (dd, 1H, J = 0.6, 2.5 Hz), 7.27-7.17 (m, 10H), 6.92 (m, 2H) and 6.34 (t, 1H, J = 2.1 Hz).

E 171 4-(3-Imidazol-1-yl-2-phenyl-indol-1-yl)-phenol
$R^1$ = phenyl $R^2$ = imidazol-1-yl
ES/MS m/z: 352.2 (pos. M + H), 350.2 (neg. M − H); $^1$H NMR (acetone-d6, 500 MHz): 7.75 (br s, 1H), 7.53 (m, 1H), 7.38-7.29 (m, 7H), 7.25-7.19 (m, 5H) and 6.91 (m, 2H).

E 172 4-[3-(5-Methyl-pyrazol-1-yl)-2-phenyl-indol-1-yl]-phenol
$R^1$ = phenyl $R^2$ = 5-Methyl-pyrrazol-1-yl

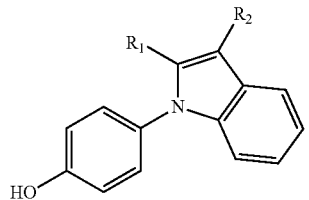

ES/MS m/z: 366.1 (pos. M + H), 364.2 (neg. M − H); $^1$H NMR (acetone-d6, 500 MHz): 7.61 (m, 1H), 7.34 (d, 1H, J = 2.1 Hz), 7.25-7.15 (m, 10H), 6.91 (m, 2H), 6.11 (d, 1H, J = 2.1 Hz) and 2.29 (s, 3H).

E 173  2-Bromo-1-(4-hydroxy-phenyl)-1H-indole-3-carboxylic acid amide
$R^1$ = bromo  $R^2$ = carbamoyl
ES/MS m/z: 331.0, 333.0 (pos. M + H), 329.0, 331.0 (neg. M − H); $^1$H NMR (acetone-d6, 500 MHz): 8.22 (m, 1H), 7.28 (m, 2H), 7.22-7.17 (m, 2H), 7.08 (m, 2H) and 7.00 (m, 1H).

E 174  1-(4-Hydroxy-phenyl)-2-((Z)-3,3,3-trifluoro-propenyl)-1H-indole-3-carbonitrile
$R^1$ = (Z)-3,3,3-trifluoro-propenyl  $R^2$ = CN
ES/MS m/z: 329.1 (pos. M + H), 327.13 (neg. M − H); $^1$H NMR (acetone-d6, 500 MHz): 7.75 (m, 1H), 7.39-7.34 (m, 2H), 7.31 (m, 2H), 7.23 (m, 1H), 7.08 (m, 2H), 7.03 (d, 1H, J = 12.2 Hz) and 6.43 (m, 1H).

E 175  (Z)-2-bromo-N'-hydroxy-1-(4-hydroxyphenyl)-1H-indole-3-carboximidamide
$R^1$ = bomo  $R^2$ = N-Hydroxycarbamimidoyl
ES/MS m/z: 346.1, 347.9 (pos. M + H), 343.9, 346.0 (eg. M − H); $^1$H NMR (acetone-d6, 500 MHz): 8.91-8.84 (s, OH), 7.98-7.95 (m, 1H), 7.27-7.23 (m, 2H), 7.17-7.10 (m, 2H), 7.09-7.05 (m, 2H), 7.00-6.97 (m, 1H), 5.49-5.38 (m, 2H).

E 176  (Z)-N'-hydroxy-1-(4-hydroxyphenyl)-2-(1H-pyrrol-1-yl)-1H-indole-3-carboximidamide
$R^1$ = pyrrol-1-yl  $R^2$ = N-Hydroxycarbamimidoyl
ES/MS m/z: 333.2 (pos. M + H), 331.3 (neg. M − H); $^1$H NMR (acetone-d6, 500 MHz): 8.25-8.22 (m, 1H), 8.14-8.12 (s, OH), 7.25-7.16 (m, 4H), 7.10-7.06 (m, 1H), 6.92-6.90 (t, 2H), 6.90-6.86 (m, 2H), 6.16-6.14 (t, 2H), 4.71-4.53 (m, 2H).

E 177  2-(3,5-Dimethyl-isoxazol-4-yl)-1-(4-hydroxy-penyl)-1H-indole-3-carboxylic acid amide
$R^1$ = 3,5-Dimethyl-isoxazol-4-yl  $R^2$ = carbamoyl
ES/MS m/z: 348.2 (pos. M + H); $^1$H NMR (acetone-d6, 500 MHz): 8.26 (m, 1H), 7.27-7.23 (m, 2H), 7.21-7.08 (m, 3H), 6.95 (m, 2H), 2.20 (s, 3H) and 2.06 (s, 3H).

E 178  (Z)-N'-hydroxy-1-(4-hydroxyphenyl)-2-(2-methylprop-1-enyl)-1H-indole-3-carboximidamide
$R^1$ = 2-methyl-prop-1-enyl  $R^2$ = N-Hydroxycarbamimidoyl
ES/MS m/z: 322.4 (pos. M + H), 320.2 (neg. M − H); $^1$H NMR (acetone-d6, 500 MHz): 8.14 (s, 1H), 7.99 (m, 1H), 7.29 (m, 2H), 7.13-7.05 (m, 5H) and 1.35 (s, 6H).

E 179  1-(4-Hydroxy-phenyl)-2-penyl-1H-indole-3-carboxylic acid hydroxyamide
$R^1$ = phenyl  $R^2$ = hydroxycarbamoyl
ES/MS m/z: 345.13 (pos. M + H), 343.13 (neg. M − H); $^1$H NMR (acetone-d6, 500 MHz): 8.04 (m, 1H), 7.38 (m, 2H), 7.34-7.31 (m, 3H), 7.23-7.20 (m, 2H), 7.13-7.08 (m, 3H) and 6.87 (m, 2H).

E 180  (Z)-N'-hydroxy-1-(4-hydroxyphenyl)-2-phenyl-1H-indole-3-carboximidamide
$R^1$ = phenyl  $R^2$ = N-Hydroxycarbamimidoyl
ES/MS m/z: 344 (pos. M + H), 342.4 (neg. M − H); $^1$H NMR (acetone-d6, 500 MHz): 8.03 (m, 1H), 7.39 (m, 2H), 7.31-7.28 (m, 3H), 7.18-7.13 (m, 2H), 7.09-7.06 (m, 3H) and 6.85 (m, 2H).

E 181  1-(4-Hydroxy-phenyl)-2-pyrrol-1-yl-1H-indole-3-carboxylic acid amide
$R^1$ = pyrrol-1-yl  $R^2$ = carbamoyl
ES/MS m/z: 318.15 (pos. M + H), 316.19 (neg. M − H); $^1$H NMR (acetone-d6, 500 MHz): 8.44 (m, 1H), 7.29-7.23 (m, 4H), 7.10 (m, 1H), 7.00 (t, 2H, J = 2.1 Hz), 6.90 (m, 2H) and 6.24 (t, 2H, J = 2.1 Hz).

E 182  [1-(4-Hydroxy-phenyl)-2-pyrrol-1-yl-1H-indole-3-yl]-carbamic acid tert-butyl ester
$R^1$ = pyrrol-1-yl  $R^2$ = tert-butoxycarbonylamino
ES/MS m/z: 390.16 (pos. M + H), 388.2 (neg. M − H); $^1$H NMR (acetone-d6, 500 MHz): 7.59 (m, 1H), 7.22-7.15 (m, 3H), 7.11 (m, 2H), 6.89 (m, 2H), 6.77 (m, 2H), 6.09 (m, 2H) and 1.45 (s, 9H).

E 183  2-(3,5-Dimethyl-isoxazol-4-yl)-1-(4-hydroxy-phenyl)-N-methyl-1H-indole-3-carboxamidine
$R^1$ = 3,5-Dimethyl-isoxazol-4-yl  $R^2$ = N-methylcarbamimidoyl
ES/MS m/z: 361.2 (pos. M + H), 359.2 (neg. M − H); $^1$H NMR (methanol-d4, 500 MHz): 7.81 (m, 1H), 7.38-7.34 (m, 3H), 7.07 (br s, 2H), 6.91 (m, 2H), 3.11 (s, 3H), 2.14 (s, 3H) and 1.96 (s, 3H).

E 184  methyl 2-(3,5-dimethylisoxazol-4-yl)-1-(4-hydroxyphenyl)-1H-indole-3-carbimidate
$R^1$ = 3,5-Dimethyl-isoxazol-4-yl  $R^2$ = imino(methoxy)methyl
ES/MS m/z: 362.3 (pos. M + H), 360.4 (neg. M − H); $^1$H NMR (acetone-d6, 500 MHz): 8.26 (m, 1H), 7.27-7.04 (m, 5H), 6.96 (m, 2H), 3.04 (s, 3H), 2.21 (s, 3H) and 2.07 (s, 3H).

E 185  N-((2-(3,5-dimethylisoxazol-4-yl)-1-(4-hydroxyphenyl)-1H-indol-3-yl)(imino)methyl)acetamide

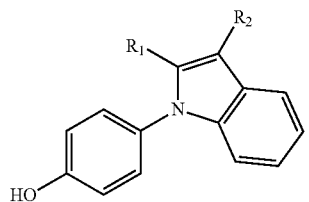

R¹ = 3,5-Dimethyl-isoxazol-4-yl   R² = (imino)methylacetamide
ES/MS m/z: ¹H NMR (acetone-d6, 500 MHz): 8.38 (m, 1H), 7.34-7.29 (m, 2H), 7.25-7.20 (m, 3H), 6.97 (m, 2H), 2.59 (s, 3H), 2.17 (s, 3H) and 1.97 (s, 3H).

E 186     2-(5-ethyl-3-methylisoxazol-4-yl)-1-(4-hydroxyphenyl)-1H-indole-3-carboxamide
R¹ = -ethyl-3-methylioxazol-4-yl   R² = carbamoyl
ES/MS m/z: 362.3 (pos. M + H), 360.4 (neg. M − H); ¹H NMR (acetone-d6, 500 MHz): 8.27 (m, 1H), 7.27-7.07 (m, 5H), 6.96 (m, 2H), 2.58 (m, 2H), 2.09 (s, 3H) and 1.04 (t, 3H, J = 7.6 Hz).

E 187     (Z)-2-(2-ethyl-1H-pyrrol-1-yl)-N'-hydroxy-1-(4-hydroxyphenyl)-1H-indole-3-carboximidamide
R¹ = 2-ethyl-1H-pyrrol-1-yl   R² = N-Hydroxycarbamimidoyl
ES/MS m/z: 361.23 (pos. M + H), 359.35 (neg. M − H); ¹H NMR (acetone-d6, 500 MHz): 8.34 (d, 1H, J = 7.9 Hz), 7.24 (m, 1H), 7.20-7.17 (m, 3H), 7.11 (m, 1H), 6.91-6.87 (m, 3H), 6.13 (t, 1H, J = 3.2 Hz), 5.91 (m, 1H), 2.35 (m, 1H), 2.25 (m, 1H) and 1.06 (t, 3H, J = 7.6 Hz).

E 188     (Z)-N'-hydroxy-1-(4-hydroxyphenyl)-2-(2-methyl-1H-pyrrol-1-yl)-1H-indole-3-carboximidamide
R¹ = 2-methyl-1H-pyrrol-1-yl   R² = N-Hydroxycarbamimidoyl
ES/MS m/z: 347.18 (pos. M + H), 345.25 (neg. M − H); ¹H NMR (acetone-d6, 500 MHz): 8.33 (d, 1H, J = 7.8 Hz), 7.24 (m, 1H), 7.20-7.17 (m, 3H), 7.12 (m, 1H), 6.91-6.87 (m, 3H), 6.08 (t, 1H, J = 3.0 Hz), 5.88 (m, 1H) and 1.99 (s, 3H).

E 189     1-(4-hydroxyphenyl)-2-(2-methyl-1H-pyrrol-1-yl)-1H-indole-3-carboxamide
R¹ = 2-methyl-1H-pyrrol-1-yl   R² = carbamoyl
ES/MS m/z: 332.16 (pos. M + H), 330.21 (neg. M − H); ¹H NMR (acetone-d6, 500 MHz): 8.50 (m, 1H), 7.31-7.27 (m, 2H), 7.25 (m, 2H), 7.14 (m, 1H), 6.98 (m, 1H), 6.93 (m, 2H), 6.16 (t, 1H, J = 3.4 Hz), 5.96 (m, 1H) and 2.00 (s, 3H).

E 190     4-(3-chloro-2-(3,5-dimethylisoxazol-4-yl)-1H-indol-1-yl)phenol
R¹ = 3,5-dimethylisoxazol-4-yl   R² = Cl
ES/MS m/z: 339.1/341.1 (pos. M + H), 337.2/339.2 (neg. M − H); ¹H NMR (CDCl₃, 500 MHz): 7.72 (m, 1H), 7.32-7.27 (m, 3H), 7.02 (m, 2H9, 6.86 (m, 2H), 2.24 (s, 3H), and 1.99 (s, 3H)

E 191     (Z)-2-((Z)-but-2-en-2-yl)-N'-hydroxy-1-(4-hydroxyphenyl)-1H-indole-3-carboximidamide
R¹ = (Z)-but-2-en-2-yl   R² = N-Hydroxycarbamimidoyl
ES/MS m/z: 322.19 (pos. M + H), 320.27 (neg. M − H); ¹H NMR (methanol-d3, 500 MHz): 7.69 (m, 1H), 7.30-7.24 (m, 2H), 7.19-7.10 (m, 3H), 6.94 (m, 2H), 5.85 (m, 1H), 1.79 (t, 3H, J = 1.3 Hz) and 1.57 (m, 3H).

E 192     (Z)-N'-hydroxy-1-(4-hydroxyphenyl)-2-(5-methyl-1H-pyrazol-1-yl)-1H-indole-3-carboximidamide
R¹ = 5-methyl-1H-pyrazol-1-yl   R² = N-hydroxycarbamimidoyl
ES/MS m/z: 348.22 (pos. M + H), 346.23 (neg. M − H); ¹H NMR (methanol-d3, 500 MHz): 8.10 (d, 1H, J = 8.1 Hz), 7.59 (d, 1H, J = 1.9 Hz), 7.32-7.21 (m, 3H), 7.08 (m, 2H), 6.78 (m, 2H), 6.14 (m, 1H) and 2.02 (s, 3H).

E 193     (Z)-N'-hydroxy-1-(4-hydroxyphenyl)-2-(4-methylthiophen-3-yl)-1H-indole-3-carboximidamide
R¹ = 4-methylthiophen-3-yl   R² = N-Hydroxycarbamimidoyl
ES/MS m/z: 364.17 (pos. M + H), 362.2 (neg. M − H); ¹H NMR (methanol-d3, 500 MHz): 7.88 (m, 1H), 7.33 (d, 1H, J = 3.2 Hz), 7.23-7.20 (m, 2H), 7.17 (m, 1H), 7.02-6.99 (m, 3H), 6.78 (m, 2H) and 1.99 (s, 3H).

E 194     (Z)-2-(2,5-dimethyl-1H-pyrrol-1-yl)-N'-hydroxy-1-(4-hydroxyphenyl)-1H-indole-3-carboximidamide
R¹ = 2,5-dimethyl-1H-pyrrol-1-yl   R² = N-Hydroxycarbamimidoyl
ES/MS m/z: 361.4 (pos. M + H), 359.5 (neg. M − H); ¹H NMR (acetone-d6, 500 MHz): 8.38 (m, 1H), 7.25 (m, 1H), 7.21-7.18 (m, 2H), 7.12 (m, 2H), 6.91 (m, 2H), 5.80 (s, 2H) and 2.00 (s, 6H).

E 195     (Z)-N'-hydroxy-1-(4-hydroxyphenyl)-2-phenoxy-1H-indole-3-carboximidamide
R¹ = phenoxy   R² = N-Hydroxycarbamimidoyl
ES/MS m/z: 360.18 (pos. M + H), 358.22 (neg. M − H); ¹H NMR (acetone-d6, 500 MHz): 8.24 (m, 1H), 7.25-7.14 (m, 6H), 7.09 (m, 1H), 7.00 (m, 1H) and 6.90-6.85 (m, 4H).

Examples 196-210

Examples 196-210 below were prepared according to General Method 1 above. Full experimental details of the individual steps of that general method applicable for the synthesis of Examples 196-210 are described in Examples 1-4, 8, 16 and 38-40 above.

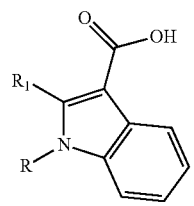

| E 196 | 1-(4-Hydroxy-phenyl)-2-phenyl-1H-indole-3-carboxylic acid |
|---|---|

$R^1$ = phenyl            $R^2$ = carboxy
ES/MS m/z: 330.1 (pos. M + H), 328.1 (neg. M − H); $^1$H NMR (acetone-d6, 500 MHz): 8.31 (m, 1H), 7.38-7.36 (m, 2H), 7.29-7.24 (m, 4H), 7.22 (m, 1H), 7.11-7.08 (m, 3H) and 6.88 (m, 2H).

| E 197 | 2-(3,5-Dimethyl-isoxazol-4-yl)-1-(3-fluoro-4-hydroxy-phenyl)-1H-indole-3-carboxylic acid |
|---|---|

$R^1$ = 3,5-Dimethyl-isoxazol-4-yl   R = 3-fluoro-4-hydroxy-phenyl
ES/MS m/z: 367.1 (pos. M + H), 365.2 (neg. M − H); $^1$H NMR (acetone-d6, 500 MHz): 8.31 (m, 1H), 7.33-7.28 (m, 2H), 7.23 (m, 1H), 7.21-6.95 (m, 3H), 2.19 (s, 3H) and 2.07 (s, 3H).

| E 198 | 2-(3,5-Dimethyl-isoxazol-4-yl)-1-(2-fluoro-4-hydroxy-phenyl)-1H-indole-3-carboxylic acid |
|---|---|

$R^1$ = 3,5-Dimethyl-isoxazol-4-yl   R = 2-fluoro-4-hydroxy-phenyl
ES/MS m/z: 367.1 (pos. M + H), 365.2 (neg. M − H); $^1$H NMR (acetone-d6, 500 MHz): 8.32 (d, 1H, J = 7.3 Hz), 7.46 (t, 1H, J = 8.8 Hz), 7.34-7.25 (m, 2H), 7.13 (m, 1H), 6.89-6.77 (m, 2H), 2.16, 2.15 (2s, 3H) and 2.07, 2.06 (2s, 3H).

| E 199 | 1-(2,3-Difluoro-4-hydroxy-phenyl)-2-(3,5-dimethyl-isoxazol-4-yl)-1H-indole-3-carboxylic acid |
|---|---|

$R^1$ = 3,5-Dimethyl-isoxazol-4-yl   R = 2,3-difluoro-4-hydroxy-phenyl
ES/MS m/z: 385.1 (pos. M + H), 383.2 (neg. M − H); $^1$H NMR (acetone-d6, 500 MHz): 8.32 (d, 1H, J = 7.6 Hz), 7.36-7.28 (m, 3H), 7.17 (m, 1H), 7.03 (m, 1H), 2.20, 2.17 (2s, 3H) and 2.08, 2.05 (2s, 3H).

| E 200 | 1-(4-Hydroxy-phenyl)-2-((Z)-propenyl)-1H-indole-3-carboxylic acid |
|---|---|

$R^1$ = (Z)-propenyl           R = 4-hydroxy-phenyl
ES/MS m/z: 294.1 (pos. M + H), 292.1 (neg. M − H); $^1$H NMR (acetone-d6, 500 MHz): 8.24 (m, 1H), 7.25 (m, 2H), 7.23 (m, 1H), 7.19 (m, 1H),k 7.14 (m, 1H), 7.03 (m, 2H), 6.42 (m, 1H), 5.86 (m, 1H) and 1.46 (dd, 3H, J = 1.9, 7.1 Hz).

| E 201 | 1-(4-Hydroxy-phenyl)-2-((E)-propenyl)-1H-indole-3-carboxylic acid |
|---|---|

$R^1$ = (E)-propenyl           R = 4-hydroxy-phenyl
ES/MS m/z: 294.1 (pos. M + H), 292.1 (neg. M − H); $^1$H NMR (acetone-d6, 500 MHz): 8.20 (m, 1H), 7.24 (m, 2H), 7.22-7.18 (m, 2H), 7.15 (m, 1H), 7.08 (m, 2H), 6.94 (m, 1H), 5.72 (m, 1H) and 1.72 (dd, 3H, J = 1.8, 6.7 Hz).

| E 202 | 1-(4-Hydroxy-phenyl)-2-(2-methyl-prop-1-enyl)-H-indole-3-carboxylic acid |
|---|---|

$R^1$ = 2-methyl-prop-1-enyl       R = 4-hydroxy-phenyl
ES/MS m/z: 308.1 (pos. M + H), 306.2 (neg. M − H); $^1$H NMR (acetone-d6, 500 MHz):8.23 (m, 1H), 7.24-7.20 (m, 3H), 7.17 (m, 1H), 7.12 (m, 1H), 7.02 (m, 2H), 6.17 (m, 1H), 1.75 (d, 3H, J = 1.3 Hz) and 1.48 (d, 3H, J = 1.2 Hz).

| E 203 | 1-(4-Hydroxy-phenyl)-2-(2-methyl-allyl)-1H-indole-3-carboxylic acid |
|---|---|

$R^1$ = 2-methyl-allyl           R = 4-hydroxy-phenyl
ES/MS m/z: 308.1 (pos. M + H), 306.2 (neg. M − H); $^1$H NMR (acetone-d6, 500 MHz): 8.21 (m, 1H), 7.24 (m, 2H), 7.21 (m, 1H), 7.15 (m, 1H), 7.05 (m, 2H), 6.97 (m, 1H), 4.65 (m, 1H), 4.24 (m, 1H), 3.83 (s, 2H) and 1.62 (s, 3H).

| E 204 | 1-(4-Hydroxy-phenyl)-2-((Z)-1-methyl-propenyl)-1H-indole-3-carboxylic acid |
|---|---|

$R^1$ = (Z)-1-methyl-propenyl       R = 4-hydroxy-phenyl
ES/MS m/z: 308.1 (pos. M + H), 306.2 (neg. M − H); $^1$H NMR (acetone-d6, 500 MHz): 8.24 (m, 1H), 7.26-7.21 (m, 3H), 7.17 (m, 1H), 7.05 (m, 1H), 7.02 (m, 2H), 5.59 (m, 1H), 1.92 (m, 3H) and 1.39 (m, 3H).

-continued

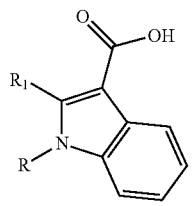

| E 205 | 1-(3-Fluoro-4-hydroxy-phenyl)-2-thiophen-3-yl-1H-indole-3-carboxylic acid |
|---|---|

$R^1$ = thiophen-3-yl    R = 3-fluoro-4-hydroxy-phenyl
ES/MS m/z: 354.2 (pos. M + H), 352.3 (neg. M − H); $^1$H NMR (acetone-d6, 500 MHz): 8.29 (m, 1H), 7.48 (dd, 1H, J = 1.3, 2.9 Hz), 7.36 (dd, 1H, J = 3.2, 1.5 Hz), 7.28 (m, 1H), 7.24 (m, 1H), 7.17-7.12 (m, 3H), 7.08 (dd, 1H, J = 8.4, 9.3 Hz) and 7.00 (m, 1H).

| E 206 | 1-(3-Fluoro-4-hydroxy-phenyl)-2-thiophen-2-yl-1H-indole-3-carboxylic acid |
|---|---|

$R^1$ = thiophen-2-yl    R = 3-fluoro-4-hydroxy-phenyl
ES/MS m/z: 354.2 (pos. M + H), 352.3 (neg. M − H); $^1$H NMR (acetone-d6, 500 MHz): 8.29 (m, 1H), 7.54 (dd, 1H, J = 1.3, 5.0 Hz), 7.31-7.25 (m, 2H), 7.22-7.19 (m, 2H), 7.13 (m, 1H), 7.09 (m, 1H), 7.04 (m, 1H) and 7.00 (dd, 1H, J = 3.5, 5.0 Hz).

| E 207 | 1-(3-Fluoro-4-hydroxy-phenyl)-2-(1-methyl-1H-pyrrol-2-yl)-1H-indole-3-carboxylic acid |
|---|---|

$R^1$ = 1-methyl-1H-pyrrol-2-yl    R = 3-fluoro-4-hydroxy-phenyl
ES/MS m/z: 351.5 (pos. M + H), 349.3 (neg. M − H); $^1$H NMR (acetone-d6, 500 MHz): 8.30 (m, 1H), 7.31-7.25 (m, 2H), 7.17 (m, 1H), 7.16-6.93 (m, 3H), 6.75 (m, 1H) and 5.96-5.93 (m, 2H).

| E 208 | 1-(3-Fluoro-4-hydroxy-phenyl)-2-(3-methyl-thiophen-2-yl)-1H-indole-3-carboxylic acid |
|---|---|

$R^1$ = 3-methyl-thiophen-2-yl    R = 3-fluoro-4-hydroxy-phenyl
ES/MS m/z: 368.0 (pos. M + H), 366.1 (neg. M − H); $^1$H NMR (acetone-d6, 500 MHz): 8.31 (m, 1H), 7.41 (d, 1H, J = 5.1 Hz), 7.32-7.26 (m, 2H), 7.18 (m, 1H), 7.16-6.97 (m, 3H), 6.85 (d, 1H, J = 5.1 Hz) and 2.09 (s, 3H).

| E 209 | 2-Bromo-1-(4-hydroxy-phenyl)-1H-indole-3-carboxylic acid |
|---|---|

$R^1$ = bromo    R = 4-hydroxy-phenyl
ES/MS m/z: 332.0, 334.0 (pos. M + H), 330.0, 332.0 (neg. M − H); $^1$H NMR (acetone-d6, 500 MHz): 8.22 (m, 1H), 7.32-7.20 (m, 4H) and 7.12-7.01 (m, 3H).

| E 210 | 1-(4-Hydroxy-phenyl)-2-pyrrol-1-yl-1H-indole-3-carboxylic acid |
|---|---|

$R^1$ = pyrrol-1-yl    $R^2$ = carboxy
ES/MS m/z: 319.15 (pos. M + H), 317.16 (neg. M − H); $^1$H NMR (acetone-d6, 500 MHz): 8.03 (m, 1H), 7.39 (m, 2H), 7.31-7.28 (m, 3H), 7.18-7.13 (m, 2H), 7.09-7.06 (m, 3H) and 6.85 (m, 2H).

Example 211

Example 211 below was prepared according to General Method 1 above. Full experimental details of the individual steps of that general method applicable for the synthesis of Example 211 are described in Examples 1-5, 16 and 38-40 above.

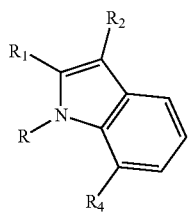

| E 211 | 2,7-Dibromo-1-(2,5-difluoro-4-hydroxy-phenyl)-1H-indole-3-carbonitrile |
|---|---|

$R^1$ = bromo    $R^2$ = cyano
R = 2,5-difluoro-4-hydroxy-phenyl    $R^4$ = bromo
ES/MS m/z: 319.15 (pos. M + H), 317.16 (neg. M − H); $^1$H NMR (acetone-d6, 500 MHz): 8.03 (m, 1H), 7.39 (m, 2H), 7.31-7.28 (m, 3H), 7.18-7.13 (m, 2H), 7.09-7.06 (m, 3H) and 6.85 (m, 2H).

Examples 212-228

Examples 212-228 below were prepared according to General Method 2 above. Full experimental details of the individual steps of that general method applicable for the synthesis of Examples 212-228 are described in Examples 2-4, 8, 16, 24 and 38-40 above.

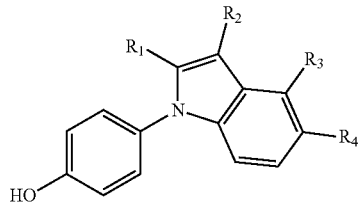

| E 212 | 2-Bromo-4-fluoro-1-(4-hydroxy-phenyl)-1H-indole-3-carbonitrile |
|---|---|
| $R^1$ = Br | $R^2$ = CN |
| $R^3$ = F | $R^4$ = H |

ES/MS m/z: 332.97 (pos. M + H), 331.01 (neg. M − H); $^1$H NMR (acetone-d6, 500 MHz): 7.40 (s, 2H), 7.30 (m, 1H), 7.12 (m, 2H), 7.07 (dd, 1H, J = 10.4, 8.2 Hz) and 6.98 (d, 1H, J = 8.2 Hz).

| E 213 | 4-Fluoro-1-(4-hydroxy-phenyl)-2-pyrrol-1-yl-1H-indole-3-carbonitrile |
|---|---|
| $R^1$ = pyrrol-1-yl | $R^2$ = CN |
| $R^3$ = F | $R^4$ = H |

ES/MS m/z: 318.1 (pos. M + H), 316.14 (neg. M − H); $^1$H NMR (acetone-d6, 500 MHz): 7.34 (m, 1H), 7.29 (m, 2H), 7.11 (dd, 1H, J = 10.4, 8.0 Hz), 7.06 (d, 1H, J = 8.3 Hz), 6.99 (m, 2H), 6.96 (t, 2H, J = 2.2 Hz) and 6.24 (t, 2H, J = 2.2 Hz).

| E 214 | 4-Fluoro-1-(4-hydroxy-phenyl)-2-phenyl-1H-indole-3-carbonitrile |
|---|---|
| $R^1$ = phenyl | $R^2$ = CN |
| $R^3$ = F | $R^4$ = H |

ES/MS m/z: 329.11 (pos. M + H), 327.15 (neg. M − H); $^1$H NMR (acetone-d6, 500 MHz): 7.51 (m, 2H), 7.45-7.42 (m, 3H), 7.31 (m, 1H), 7.25 (m, 2H), 7.09-7.06 (m, 2H) and 6.95 (m, 2H).

| E 215 | 2-(3,5-Dimethyl-isoxazol-4-yl)-4-fluoro-1-(4-hydroxy-phenyl)-1H-indole-3-carbonitrile |
|---|---|
| $R^1$ = 3,5-Dimethyl-isoxazol-4-yl | $R^2$ = CN |
| $R^3$ = F | $R^4$ = H |

ES/MS m/z: 348.11 (pos. M + H), 346.15 (neg. M − H); $^1$H NMR (acetone-d6, 500 MHz): 7.36 (m, 1H), 7.30 (br s, 2H), 7.17 (d, 1H, J = 8.3 Hz), 7.11 (dd, 1H, J = 10.4, 7.8 Hz), 7.01 (m, 2H), 2.38 (s, 3H) and 2.05 (s, 3H).

| E 216 | 4-Fluoro-1-(4-hydroxy-phenyl)-2-(2-methyl-prop-1-enyl)-1H-indole-3-carbonitrile |
|---|---|
| $R^1$ = 2-methyl-prop-1-enyl | $R^2$ = CN |
| $R^3$ = F | $R^4$ = H |

ES/MS m/z: 307.14 (pos. M + H), 305.15 (neg. M − H); $^1$H NMR (acetone-d6, 500 MHz): 7.28 (m, 2H), 7.24 (m, 1H), 7.06 (m, 2H), 7.00 (dd, 1H, J = 10.5, 8.2 Hz), 6.97 (d, 1H, J = 8.2 Hz), 5.96 (m, 1H), 1.94 (d, 3H, J = 1.2 Hz) and 1.90 (d, 3H, J = 1.4 Hz).

| E 217 | 5-Fluoro-1-(4-hydroxy-phenyl)-2-phenyl-1H-indole-3-carbonitrile |
|---|---|
| $R^1$ = phenyl | $R^2$ = CN |
| $R^3$ = H | $R^4$ = F |

ES/MS m/z: 329.3 (pos. M + H), 327.4 (neg. M − H); $^1$H NMR (acetone-d6, 500 MHz): 7.50-7.42 (m, 6H), 7.27-7.22 (m, 3H), 7.14 (m, 1H) and 6.95 (m, 2H).

| E 218 | 2-(3,5-Dimethyl-isoxazol-4-yl)-5-fluoro-1-(4-hydroxy-phenyl)-1H-indole-3-carbonitrile |
|---|---|
| $R^1$ = 3,5-Dimethyl-isoxazol-4-yl | $R^2$ = CN |
| $R^3$ = H | $R^4$ = F |

ES/MS m/z: 348.2 (pos. M + H), 346.3 (neg. M − H); $^1$H NMR (acetone-d6, 500 MHz): 7.50 (dd, 1H, J = 8.8, 2.2 Hz), 7.37 (dd, 1H, J = 9.1, 4.4 Hz), 7.29 (m, 2H), 7.19 (m, 1H), 7.00 (m, 2H), 2.36 (s, 3H) and 2.02 (s, 3H).

| E 219 | 5-Fluoro-1-(4-hydroxy-phenyl)-2-pyrrol-1-yl-1H-indole-3-carbonitrile |
|---|---|
| $R^1$ = 2-pyrrol-1-yl | $R^2$ = CN |
| $R^3$ = H | $R^4$ = F |

ES/MS m/z: 317.9 (pos. M + H), 316.3 (neg. M − H); $^1$H NMR (acetone-d6, 500 MHz): 7.46 (dd, 1H, J = 8.8, 2.5 Hz), 7.29-7.24 (m, 3H), 7.16 (m, 1H), 6.99 (m, 2H), 6.94 (t, 2H, J = 2.2 Hz) and 6.24 (t, 2H, J = 2.2 Hz).

-continued

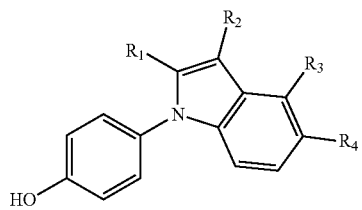

E 220      5-Fluoro-1-(4-hydroxy-penyl)-2-(2-methyl-prop-1-enyl)-1H-indole-3-carbonitrile $R^1$ = 2-methyl-prop-1-enyl      CN
$R^3$ = H      $R^4$ = F
ES/MS m/z: 307.4 (pos. M + H), 305.5 (neg. M − H); $^1$H NMR (acetone-d6, 500 MHz): 7.38 (dd, 1H,
J = 9.0, 2.5 Hz), 7.27 (m, 2H), 7.15 (dd, 1H, J = 9.0, 4.3 Hz), 7.09-7.04 (m, 3H), 5.97 (m, 1H), 1.93 (d, 3H,
J = 1.2 Hz) and 1.90 (d, 3H, J = 1.6 Hz).

E 221      (Z)-2-(3,5-dimethylisoxazol-4-yl)-5-fluoro-N'-hydroxy-1-(4-hydroxyphenyl)-1H-indole-3-carboximidamide $R^1$ = 3,5-Dimethyl-isoxazol-4-yl      $R^2$ = N-Hydroxycarbaimidoyl
$R^3$ = H      $R^4$ = F
ES/MS m/z: 381.2 (pos. M + H), 379.3 (neg. M − H); $^1$H NMR (acetone-d6, 500 MHz): 7.79 (dd, 1H,
J = 10.0, 2.5 Hz), 7.17-7.10 (m, 3H), 7.01 (m, 1H), 6.94 (m, 2H), 2.17 (s, 3H) and 2.01 (s, 3H).

E 222      (Z)-2-(3,5-dimethylisoxazol-4-yl)-4-fluoro-N'-hydroxy-1-(4-hydroxyphenyl)-1H-indole-3-carboximidamide $R^1$ = 3,5-Dimethyl-isoxazol-4-yl      $R^2$ = N-Hydroxycarbamimidoyl
$R^3$ = F      $R^4$ = H
ES/MS m/z: 381.5 (pos. M + H), 379.3 (neg. M − H).

E 223      (Z)-5-fluoro-N'-hydroxy-1-(4-hydroxyphenyl)-2-(2-methylprop-1-enyl)-1H-indole-3-carboximidamide $R^1$ = 2-methyl-prop-1-enyl      $R^2$ = N-Hydroxycarbamimidoyl
$R^3$ = H      $R^4$ = F
ES/MS m/z: 340.4 (pos. M + H), 338.2 (neg. M − H); $^1$H NMR (acetone-d6, 500 MHz): 7.84 (dd, 1H,
J = 10.4, 2.7 Hz), 7.17 (m, 2H), 7.02-6.99 (m, 3H), 6.89 (m, 1H), 6.08 (m, 1H), 1.80 (d, 3H, J = 1.4 Hz) and
1.65 (d, 3H, J = 1.1 Hz).

E 224      4-Chloro-2-(3,5-dimethyl-isoxazol-4-yl)-1-(4-hydroxy-phenyl)-1H-indole-3-carbonitrile $R^1$ = 3,5-dimethyl-isoxazol-4-yl      $R^2$ = CN
$R^3$ = Cl      $R^4$ = H
ES/MS m/z: 362.2 (neg. M − H); $^1$H NMR (acetone-d6, 500 MHz): 7.35-7.26 (m, 3H), 7.15 (br s, 2H),
6.90 (m, 2H), 2.32 (s, 3H) and 2.00 (s, 3H).

E 225      2-(3,5-dimethylisoxazol-4-yl)-4,5-difluoro-1-(4-hydroxyphenyl)-1H-indole-3-carbonitrile $R^1$ = 3,5-dimethyl-isoxazol-4-yl      $R^2$ = CN
$R^3$ = F      $R^4$ = F
ES/MS m/z: 366.2 (pos. M + H), 364.3 (neg. M − H); $^1$H NMR (acetone-d6, 500 MHz): 7.41-7.28 (m,
3H), 7.17 (m, 1H), 7.01 (m, 2H), 2.38 (s, 3H) and 2.04 (s, 3H).

E 226      2-(4-cyano-1-methyl-1H-pyrazol-5-yl)-4-fluoro-1-(4-hydroxyphenyl)-1H-indole-3-carbonitrile $R^1$ = 4-cyano-1-methyl-1H-pyrazol-5-yl      $R^2$ = CN
$R^3$ = F      $R^4$ = H
ES/MS m/z: 366.2 (pos. M + H), 364.3 (neg. M − H); $^1$H NMR (acetone-d6, 500 MHz): 7.41-7.28 (m,
3H), 7.17 (m, 1H), 7.01 (m, 2H), 2.38 (s, 3H) and 2.04 (s, 3H).

E 227      2-(3,5-dimethylisoxazol-4-yl)-5-fluoro-1-(4-hydroxyphenyl)-1H-indole-3-carboximidamide $R^1$ = 3,5-dimethylisoxazol-4-yl      $R^2$ = carbamimidoyl
$R^3$ = H      $R^4$ = F
ES/MS m/z: 365.15 (pos. M + H), 363.19 (neg. M − H); $^1$H NMR (methanol-d3, 500 MHz): 7.54 (dd,
1H, J = 9.1, 2.2 Hz), 7.34 (dd, 1H, J = 93, 4.5 Hz), 7.15 (m, 1H), 7.05 (br s, 2H), 6.91 (m, 2H), 2.15 (s, 3H)
and 2.00 (s, 3H).

E 228      2-(3,5-dimethylisoxazol-4-yl)-5-fluoro-1-(4-hydroxyphenyl)-1H-indole-3-carboxamide $R^1$ = 3,5-dimethylioxazol-4-yl      $R^2$ = carbamoyl
$R^3$ = H      $R^4$ = F
ES/MS m/z: 366.2 (pos. M + H), 364.3 (neg. M − H); $^1$H NMR (acetone-d6, 500 MHz): 7.99 (dd, 1H,
J = 10.1, 2.6 Hz), 7.26-7.03 (m, 4H), 6.96 (m, 2H9, 2.21 (s, 3H) and 2.07 (s, 3H).

Examples 229-232

Examples 229-232 below were prepared according to General Method 2 above. Full experimental details of the individual steps of that general method applicable for the synthesis of Examples 229-232 are described in Examples 2-4, 8, 16, 24 and 38-40 above.

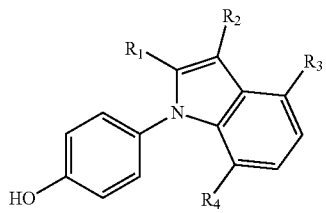

| E 229 | 2-Bromo-7-fluoro-1-(4-hydroxy-phenyl)-1H-indole-3-carbonitrile |
|---|---|

$R^1$ = Br  $R^2$ = CN
$R^3$ = H  $R^4$ = F
ES/MS m/z: 331.0; 333.0 (pos. M + H), 331.0; 329.0 (neg. M − H); 1H NMR (acetone-d6, 500 MHz):
7.45 (m, 1H), 7.28-7.22 (m, 3H), 7.00 (m, ,1H) and 6.92 (m, 2H).

| E 230 | 2-(3,5-Dimethyl-isoxazol-4-yl)-7-fluoro-1-(4-hydroxy-phenyl)-1H-indole-3-carbonitrile |
|---|---|

$R^1$ = 3,5-Dimethyl-isoxazol-4-yl  $R^2$ = CN
$R^3$ = H  $R^4$ = F
ES/MS m/z: 348.1 (pos. M + H), 346.1 (neg. M − H); 1H NMR (acetone-d6, 500 MHz): 7.55 (dd, 1H,
J = 8.2, 0.9 Hz), 7.31 (m, 1H), 7.19 (m, 1H), 7.11 (m, 1H), 7.08 (m, 1H), 6.84-6.79 (m, 2H), 2.29 (s, 3H),
and 2.00 (s, 3H).

| E 231 | 2-(3,5-Dimethyl-isoxazol-4-yl)-4,7-difluoro-01-(4-hydroxy-phenyl)-1H-indole-3-carbonitrile |
|---|---|

$R^1$ = 3,5-Dimethyl-isoxazol-4-yl  $R^2$ = CN
$R^3$ = F  $R^4$ = F
ES/MS m/z: 366.2 (pos. M + H), 364.3 (neg. M − H); 1H NMR (acetone-d6, 500 MHz): 7.39-7.32 (m,
2H), 7.13-7.04 (m, 2H), 6.96-6.90 (m, 2H), 2.37 (s, 3H) and 2.07 (s, 3H).

| E 232 | (Z)-2-(3,5-dimethylisoxazol-4-yl)-4,7-difluoro-N'-hydroxy-1-(4-hydroxyphenyl)-1H-indole-3-carboximidamide |
|---|---|

$R^1$ = 3,5-Dimethyl-isoxazol-4-yl  $R^2$ = N-Hydroxycarbamimidoyl
$R^3$ = F  $R^4$ = F
ES/MS m/z: 399.2 (pos. M + H), 397.2 (neg. M − H); 1H NMR (acetone-d6, 500 MHz): 7.06 (m, 2H),
6.87 ( m, 1H), 6.83-6.75 (m, 3H), 2.21 (s, 3H) and 2.01 (s, 3H).

Examples 233-270

Examples 233-270 below were prepared according to General Method 1 above. Full experimental details of the individual steps of that general method applicable for the synthesis of Examples 233-270 are described in Examples 1-4, 10-11, 14-16, 38-40 and 45 above.

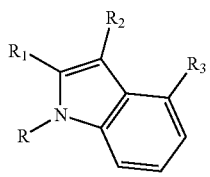

| E 233 | 1-(2,5-Difluoro-4-hydroxy-phenyl)-2-(3,5-dimethyl-isoxazol-4-yl)-1H-indole-3-carbonitrile |
|---|---|

R = 2,5-Difluoro-4-hydroxy-phenyl  $R^1$ = 3,5-Dimethyl-isoxazol-4-yl
$R^2$ = CN  $R^3$ = H
ES/MS m/z: 366.2 (pos. M + H), 364.6 (neg. M − H); $^1$H NMR (acetone-d6, 500 MHz): 7.80 (m, 1H),
7.55 (m, 1H), 7.45-7.41 (m, 2H), 7.34 (m, 1H), 7.03 (m, 1H), 2.38, 2.34 (two s, 3H) and 2.14, 2.10 (two
s, 3H).

-continued

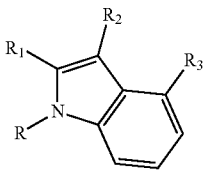

| E 234 | 1-(3-bromo-4-hydroxyphenyl)-2-(2-methylprop-1-enyl)-1H-indole-3-carboxamide |

R = 3-bromo-4-hydroxyphenyl   $R^1$ = 2-methylprop-1-enyl
$R^2$ = carbamoyl   $R^3$ = H
ES/MS m/z: 385.06/387.02 (pos. M + H); $^1$H NMR (acetone-d6, 500 MHz): 8.35 (m, 1H), 7.55 (d, 1H, J = 2.4 Hz), 7.25 (m, 1H), 7.21-7.14 (m, 3H), 7.08 (m, 1H), 6.20 (m, 1H), 1.85 (d, 3H, J = 1.4 Hz) and 1.66 (d, 3H, J = 1.0 Hz).

| E 235 | (Z)-2-(3,5-dimethylisoxazol-4-yl)-1-(2-fluoro-4-hydroxyphenyl)-N'-hydroxy-21H-indole-3-carboximidamide |

R = 2-fluoro-4-hydroxy-phenyl   $R^1$ = 3,5-Dimethyl-isoxazol-4-yl
$R^2$ = N-Hydroxycarbamimidoyl   $R^3$ = H
ES/MS m/z: 380.3 (pos. M + H), 378.4 (neg. M − H); $^1$H NMR (acetone-d6, 500 MHz): 8.06 (m, 1H), 7.34 (t, 0.5H, J = 8.7 Hz), 7.25-7.18 (m, 2.5H), 7.07 (m, 1H), 6.84-6.74 (m, 2H), 2.17, 2.15 (two s, 3H) and 2.05, 2.02 (two s, 3H).

| E 236 | (Z)-1-(2,5-difluoro-4-hydroxyphenyl)-2-(3,5-dimethylisoxazol-4-yl)-N'-hydroxy-1H-indole-3-carboximidamide |

R = 2,5-Difluoro-4-hydroxy-phenyl   $R^1$ = 3,5-Dimethyl-isoxazol-4-yl
$R^2$ = N-Hydroxycarbamimidoyl   $R^3$ = H
ES/MS m/z: 399.2 (pos. M + H), 397 (neg. M − H); $^1$H NMR (acetone-d6, 500 MHz): 1H NMR (acetone-d6, 500 MHz): 8.07 (m, 1H), 7.40 (dd, 0.5H, J = 10.0, 6.6 Hz), 7.28-7.19 (m, 2.5H), 7.12 (m, 1H), 6.96 (m, 1H), 2.23, 2.17 (two s, 3H) and 2.09, 2.02 (two s, 3H).

| E 237 | (Z)-1-(3,5-difluoro-4-hydroxypenyl)-2-(3,5-dimethylisoxazol-4-yl)-N'-hydroxy-1H-indole-3-carboximidamide |

R = 3,5-Difluoro-4-hydroxy-phenyl   $R^1$ = 3,5-Dimethyl-ioxazol-4-yl
$R^2$ = N-Hydroxycarbamimidoyl   $R^3$ = H
ES/MS m/z: 399.2 (pos. M + H), 397 (neg. M − H); $^1$H NMR (acetone-d6, 500 MHz): 1H NMR (acetone-d6, 500 MHz): 8.06 (m, 1H), 7.28-7.19 (m, 3H), 7.06-7.00 (m, 2H), 2.23 (s, 3H) and 2.05 (s, 3H).

| E 238 | (Z)-2-(3,5-dimethylisoxazol-4-yl)-1-(3-fluoro-4-hydroxyphenyl)-N'-hydroxy-1H-indole-3-carboximidamide |

R = 3-fluoro-4-hydroxy-phenyl   $R^1$ = 3,5-Dimethyl-isoxazol-4-yl
$R^2$ = N-Hydroxy carbamimidoyl   $R^3$ = H
ES/MS m/z: 381.5 (pos. M + H), 379.2 (neg. M − H); $^1$H NMR (acetone-d6, 500 MHz): 1H NMR (acetone-d6, 500 MHz): 8.06 (m, 1H), 7.25-7.17 (m, 3H9, 7.14-7.09 (m, 2H), 6.98 (m, 1H), 2.20 (s, 3H) and 2.02 (s, 3H).

| E 239 | (Z)-1-(3-chloro-4-hydroxyphenyl)-2-(3,5-dimethylisoxazol-4-yl)-N'-hydroxy-1H-indole-3-carboximidamide |

R = 3-Chloro-4-hydroxy-phenyl   $R^1$ = 3,5-Dimethyl-isoxazol-4-yl
$R^2$ = N-Hydroxycarbamimidoyl   $R^3$ = H
ES/MS m/z: 397.4/399.2 (pos. M + H), 394.9/397.0 (neg. M − H); $^1$H NMR (acetone-d6, 500 MHz): 1H NMR (acetone-d6, 500 MHz): 8.25 (m, 1H), 7.50-7.14 (m, 6H), 2.19 (s, 3H) and 2.05 (s, 3H).

| E 240 | 2-(3,5-dimethylisoxazol-4-yl)-1-(2-fluoro-4-hydroxyphenyl)-1H-indole-3-carboxamide |

R = 2-fluoro-4-hydroxyphenyl   $R^1$ = 3,5-Dimethyl-isoxazol-4-yl
$R^2$ = carbamoyl   $R^3$ = H
ES/MS m/z: 366.2 (pos. M + H), 364.2 (neg. M − H); $^1$H NMR (acetone-d6, 500 MHz): $^1$H NMR (acetone-d6, 500 MHz): 8.25 (m, 1H), 7.38 (t, 0.6H, J = 9.0 Hz), 7.29-7.25 (m, 2H), 7.21 (t, 0.4H, J = 9.0 Hz), 7.10 (m, 1H), 6.84-6.72 (m, 2H), 2.21, 2.19 (two s, 3H) and 2.09, 2.06 (two s, 3H).

| E 241 | (Z)-1-(2,3-difluoro-4-hydroxyphenyl)-2-(3,5-dimethylisoxazol-4-yl)-N'-hydroxy-1H-indole-3-carboximidamide |

R = 2,3-difluoro-4-hydroxyphenyl   $R^1$ = 3,5-Dimethyl-isoxazol-4-yl
$R^2$ = N-Hydroxycarbamimidoyl   $R^3$ = H
ES/MS m/z: 399.2 (pos. M + H), 397.2 (neg. M − H); $^1$H NMR (acetone-d6, 500 MHz): $^1$H NMR (acetone-d6, 500 MHz): 8.07 (m, 1H), 7.27-7.19 (m, 3H), 7.13 (m, 1H), 6.99 (m, 1H), 2.19, 2.18 (two s, 3H) and 2.05, 2.04 (two s, 3H).

| E 242 | 1-(2,3-difluoro-4-hydroxyphenyl)-2-(3,5-dimethylisoxazol-4-yl)-1H-indole-3-carboxamide |

R = 2,3-difluoro-4-hydroxyphenyl   $R^1$ = 3,5-Dimethyl-ioxazol-4-yl
$R^2$ = carbamoyl   $R^3$ = H
ES/MS m/z: 384.2 (pos. M + H), 382.2 (neg. M − H); $^1$H NMR (acetone-d6, 500 MHz): $^1$H NMR (acetone-d6, 500 MHz): 8.25 (m, 1H), 7.31-7.26 (m, 2.5H), 7.16 (m, 1H), 7.11 (m, 0.5H), 7.01 (m, 1H), 2.23, 2.22 (two s, 3H) and 2.09, 2.08 (two s, 3H).

-continued

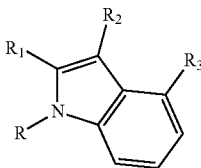

| E 243 | 1-(2-fluoro-4-hydroxyphenyl)-2-(3-methylthiophen-2-yl)-1H-indole-3-carbonitrile |
|---|---|

R = 2-fluoro-4-hydroxyphenyl   $R^1$ = 3-methylthiophen-2-yl
$R^2$ = CN   $R^3$ = H
ES/MS m/z: 349.1 (pos. M + H), 347.2 (neg. M − H); $^1$H NMR (acetone-d6, 500 MHz): $^1$H NMR
(acetone-d6, 500 MHz): 7.83 (m, 1H), 7.38-7.31 (m, 3H), 7.13-7.11 (m, 2H), 6.89 (d, 1H, J = 5.8 Hz),
6.71-6.67 (m, 2H) and 2.18 (s, 3H).

| E 244 | 2-(3,5-dimethyl-1H-pyrazol-4-yl)-1-(2-fluoro-4-hydroxyphenyl)-1H-indole-3-carbonitrile |
|---|---|

R = 2-fluoro-4-hydroxyphenyl   $R^1$ = 3,5-dimethyl-1H-pyrazol-4-yl
$R^2$ = CN   $R^3$ = H
ES/MS m/z: 347 (pos. M + H), 345.1 (neg. M − H); $^1$H NMR (acetone-d6, 500 MHz): $^1$H NMR
(acetone-d6, 500 MHz): 7.75 (m, 1H), 7.39-7.31 (m, 3H), 7.21 (m, 1H), 6.83-6.76 (m, 2H), 2.13 (s, 3H)
and 2.08 (s, 3H).

| E 245 | 1-(2-fluoro-4-hydroxyphenyl)-2-(1-methyl-1H-pyrazol-5-yl)-1H-indole-3-carbonitrile |
|---|---|

R = 2-fluoro-4-hydroxyphenyl   $R^1$ = 1-methyl-1H-pyrazol-5-yl
$R^2$ = CN   $R^3$ = H
ES/MS m/z: 333.2 (pos. M + H), 331.3 (neg. M − H); $^1$H NMR (acetone-d6, 500 MHz): $^1$H NMR
(acetone-d6, 500 MHz): 7.87 (m, 1H), 7.48 (d, 1H, J = 2.2 Hz), 7.42-7.37 (m, 2H), 7.20 (m, 1H), 7.15 (t,
1H, J = 8.6 Hz), 6.69 (m, 1H), 6.60 (dd, 1H, J = 2.5, 11.0 Hz), 6.22 (d, 1H, J = 2.2 Hz) and 3.87 (s, 3H).

| E 246 | 1-(2-fluoro-4-hydroxyphenyl)-2-(1,3,5-trimethyl-1H-pyrazol-4-yl)-1H-indole-3-carbonitrile |
|---|---|

R = 2-fluoro-4-hydroxyphenyl   $R^1$ = 1,3,5-trimethyl-1H-pyrazol-4-yl
$R^2$ = CN   $R^3$ = H
ES/MS m/z: 361.4 (pos. M + H), 359.2 (neg. M − H); $^1$H NMR (acetone-d6, 500 MHz): $^1$H NMR
(acetone-d6, 500 MHz): 7.81 (m, 1H), 7.38-7.31 (m, 2H), 7.22 (m, 1H), 7.12 (t, 0.5H, J = 8.7 Hz), 7.02 (t,
0.5H, J = 8.7 Hz), 6.59 (m, 1H), 6.45 (m, 1H), 3.73, 3.70 (two s, 3H), 2.17, 2.09 (two s, 3H) and 2.05
1.96 (two s, 3H). Two conformations

| E 247 | 1-(2-fluoro-4-hydroxyphenyl)-2-(3-(trifluoromethyl)-1H-pyrazol-4-yl)-1H-indole-3-carbonitrile |
|---|---|

R = 2-fluoro-4-hydroxyphenyl   $R^1$ = 3-(trifluoromethyl)-1H-pyrazol-4-yl
$R^2$ = CN   $R^3$ = H
ES/MS m/z: 385.3 (pos. M + H); $^1$H NMR (acetone-d6, 500 MHz): $^1$H NMR (acetone-d6, 500 MHz):
7.73 (m, 1H), 7.35-7.22 (m, 4H), 7.05 (m, 1H) and 6.87-6.83 (m, 2H).

| E 248 | (Z)-1-(2-fluoro-4-hydroxyphenyl)-N'-hydroxy-2-(3-methylthiophen-2-yl)-1H-indole-3-carboximidamide |
|---|---|

R = 2-fluoro-4-hydroxyphenyl   $R^1$ = 3-methylthiophen-2-yl
$R^2$ = N-Hydroxycarbamimidoyl   $R^3$ = H
ES/MS m/z: 382.2 (pos. M + H), 380.1 (neg. M − H); $^1$H NMR (acetone-d6, 500 MHz): $^1$H NMR
(acetone-d6, 500 MHz): 8.25 (m, 1H), 7.41 (d, 1H, J = 5.0 Hz), 7.33-7.27 (m, 3H), 7.06 (m, 1H), 6.87 (d,
1H, J = 5.0 Hz), 6.74 (br s, 2H) and 2.09 (br s, 3H).

| E 249 | (Z)-1-(2-fluoro-4-hydroxyphenyl)-N'-hydroxy-2-(1-methyl-1H-pyrazol-5-yl)-1H-indole-3-carboximidamide |
|---|---|

R = 2-fluoro-4-hydroxyphenyl   $R^1$ = 1-methyl-1H-pyrazol-5-yl
$R^2$ = N-Hydroxycarbamimidoyl   $R^3$ = H
ES/MS m/z: 366.2 (pos. M + H), 364.1 (neg. M − H); $^1$H NMR (acetone-d6, 500 MHz): $^1$H NMR
(acetone-d6, 500 MHz): 8.27 (m, 1H), 7.50 (br s, 1H), 7.37-7.31 (m, 3H), 7.12 (br s, 1H), 6.84 (br s,
1H), 6.70 (br s, 1H), 6.14 (s, 1H) and 3.71 (s, 3H).

| E 250 | (Z)-1-(2-fluoro-4-hydroxyphenyl)-N'-hydroxy-2-(1,3,5-trimethyl-1H-pyrazol-4-yl)-1H-indole-3-carboximidamide |
|---|---|

R = 2-fluoro-4-hydroxyphenyl   $R^1$ = 1,3,5-trimethyl-1H-pyrazol-4-yl
$R^2$ = N-Hydroxycarbamimidoyl   $R^3$ = H
ES/MS m/z: 394.3 (pos. M + H), 392.1 (neg. M − H); $^1$H NMR (acetone-d6, 500 MHz): $^1$H NMR
(acetone-d6, 500 MHz): 8.23 (d, 1H, J = 7.9 Hz), 7.30-7.20 (m, 3H), 7.07 (m, 1H), 6.80-6.76 (m, 2H),
3.64, 3.63 (two s, 3H), 2.05, 1.92 (two s, 3H) and 1.99, 1.88 (two s, 3H). Two conformations.

| E 251 | (Z)-4-fluoro-1-(2-fluoro-4-hydroxyphenyl)-N'-hydroxy-2-(1-methyl-1H-pyrazol-5-yl)-1H-indole-3-carboximidamide |
|---|---|

R = 2-fluoro-4-hydroxypebnyl   $R^1$ = 1-methyl-1H-pyrazol-5-yl
$R^2$ = N-Hydroxycarbamimidoyl   $R^3$ = F
ES/MS m/z: 384.16 (pos. M + H), 382.16 (neg. M − H); $^1$H NMR (acetone-d6, 500 MHz): $^1$H NMR

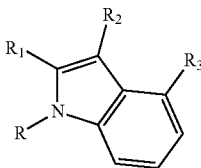

| | |
|---|---|
| (acetone-d6, 500 MHz): 7.30-7.21 (m, 3H), 6.95-6.89 (m, 2H), 6.78-6.71 (m, 2H), 6.12 (d, 1H, J = 1.9 Hz) and 3.72 (s, 3H). | |
| E 252 | (Z)-4-fluoro-1-(2-fluoro-4-hydroxyphenyl)-N'-hydroxy-2-(1,3,5-trimethyl-1H-pyrazol-4-yl)-1H-indole-3-carboximidamide |
| R = 2-fluoro-4-hydroxyphenyl  $R^1$ = 1,3,5-trimethyl-1H-pyrazol-4-yl $R^2$ = N-Hydroxycarbamimidoyl  $R^3$ = F ES/MS m/z: 412.18 (pos. M + H), 410.21 (neg. M − H); $^1$H NMR (acetone-d6, 500 MHz): $^1$H NMR (acetone-d6, 500 MHz): 7.17-7.11 (m, 2H), 6.88-6.83 (m, 2H), 6.75-6.67 (m, 2H), 3.59, 3.58 (two s, 3H), 2.08, 2.02 (two s, 3H) and 1.96, 1.91 (two s, 3H). Two conformations. | |
| E 253 | (Z)-2-(3,5-dimethyl-1H-pyrazol-4-yl)-4-fluoro-1-(2-fluoro-4-hydroxyphenyl)-N'-hydroxy-1H-indole-3-carboximidamide |
| R = 2-fluoro-4-hydroxyphenyl  $R^1$ = 3,5-dimethyl-1H-pyrazol-4-yl $R^2$ = N-Hydroxycarbamimidoyl  $R^3$ = F ES/MS m/z: 399.16 (pos. M + H), 397.18 (neg. M − H); $^1$H NMR (acetone-d6, 500 MHz): $^1$H NMR (acetone-d6, 500 MHz): 7.30 (q, 1H, J = 9.1 Hz), 7.21 (m, 1H), 6.94-6.90 (m, 2H), 6.82-6.75 (m, 2H), 2.20, 2.19 (two s, 3H) and 2.03, 2.01 (two s, 3H). Two conformations. | |
| E 254 | (Z)-4-fluoro-1-(2-fluoro-4-hydroxyphenyl)-N'-hydroxy-2-(3-methylthiophen-2-yl)-1H-indole-3-carboximidamide |
| R = 2-fluoro-4-hydroxyphenyl  $R^1$ = 3-methylthiophen-2-yl $R^2$ = N-Hydroxycarbamimidoyl  $R^3$ = F ES/MS m/z: 400.14 (pos. M + H), 398.12 (neg. M − H); $^1$H NMR (acetone-d6, 500 MHz): $^1$H NMR (acetone-d6, 500 MHz): 7.30 (q, 1H, J = 9.1 Hz), 7.21 (m, 1H), 6.94-6.90 (m, 2H), 6.82-6.75 (m, 2H), 2.20, 2.19 (two s, 3H) and 2.03, 2.01 (two s, 3H). Two conformations. | |
| E 255 | (Z)-2-(3,5-dimethylisoxazol-4-yl)-4-fluoro-1-(2-fluoro-4-hydroxyphenyl)-N'-hydroxy-1H-indole-3-carboximidamide |
| R = 2-fluoro-4-hydroxyphenyl  $R^1$ = 3,5-dimethylisoxazol-4-yl $R^2$ = N-Hydroxycarbamimidoyl  $R^3$ = F ES/MS m/z: 399.16 (pos. M + H), 397.18 (neg. M − H); $^1$H NMR (acetone-d6, 500 MHz): $^1$H NMR (acetone-d6, 500 MHz): 7.30 (q, 1H, J = 9.1 Hz), 7.21 (m, 1H), 6.94-6.90 (m, 2H), 6.82-6.75 (m, 2H), 2.20, 2.19 (two s, 3H) and 2.03, 2.01 (two s, 3H). Two conformations. | |
| E 256 | (Z)-1-(2-fluoro-4-hydroxyphenyl)-N'-hydroxy-2-(3-methylthiophen-2-yl)-1H-indole-3-carboximidamide |
| R = 2-fluoro-4-hydroxyphenyl  $R^1$ = 3-methylthiophen-2-yl $R^2$ = N-Hydroxycarbamimidoyl  $R^3$ = H ES/MS m/z: 382.16 (pos. M + H), 380.07 (neg. M − H); $^1$H NMR (acetone-d6, 500 MHz): 8.27 (m, 1H), 7.50 (br s, 0.5H), 7.37-7.31 (m, 3H), 7.15-7.09 (m, 1.5H), 6.84 (br s, 1H), 6.69 (br s, 1H), 6.14 (s, 1H) and 1.41 (s, 3H). | |
| E 257 | (Z)-1-(2-fluoro-4-hydroxyphenyl)-N'-hydroxy-2-(1-methyl-1H-pyrazol-5-yl)-1H-indole-3-carboximidamide |
| R = 2-fluoro-4-hydroxyphenyl  $R^1$ = 1-methyl-1H-pyrazol-5-yl $R^2$ = N-Hydroxycarbamimidoyl  $R^3$ = H ES/MS m/z: 366.2 (pos. M + H), 364.17 neg. M − H); $^1$H NMR (acetone-d6, 500 MHz): 8.25 (m, 1H), 7.41 (d, 1H, J = 5.0 Hz), 7.33-7.27 (m, 2.5H), 7.13 (br s, 0.5H), 7.06 (d, 1H, J = 7.8 Hz), 6.87 (d, 1H, J = 5.0 Hz), 6.75 (br s, 2H) and 3.75 (s, 3H). | |
| E 258 | (Z)-1-(2-fluoro-4-hydroxyphenyl)-N'-hydroxy-2-(1,3,5-trimethyl-1H-pyrazol-4-yl)-1H-indole-3-carboximidamide |
| R = 2-fluoro-4-hydroxyphenyl  $R^1$ = 1,3,5-trimethyl-1H-pyrazol-4-yl $R^2$ = N-Hydroxycarbamimidoyl  $R^3$ = H ES/MS m/z: 394.26 (pos. M + H), 392.17 (neg. M − H); $^1$H NMR (acetone-d6, 500 MHz): 8.23 (m, 1H), 7.30-7.20 (m, 3H), 7.07 (m, 1H), 6.80-6.70 (m, 2H), 3.64, 3.63 (two s, 3H), 2.05, 1.99 (two s, 3H) and 1.92, 1.88 (two s, 3H). | |
| E 259 | (Z)-2-(3,5-dimethyl-1H-pyrazol-4-yl)-1-(2-fluoro-4-hydroxyphenyl)-N'-hydroxy-1H-indole-3-carboximidamide |
| R = 2-fluoro-4-hydroxyphenyl  $R^1$ = 3,5-dimethyl-1H-pyrazol-4-yl $R^2$ = N-Hydroxycarbamimidoyl  $R^3$ = H ES/MS m/z: 380.16 (pos. M + H), 378.18 (neg. M − H); $^1$H NMR (acetone-d6, 500 MHz): 8.25 (m, 1H), 7.18-7.12 (m, 3H), 6.99 (m, 1H), 6.77-6.71 (m, 2H), 2.08 (s, 3H) and 2.01 (s, 3H). | |

-continued

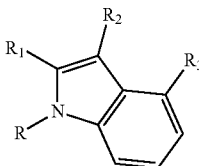

| E 260 | methyl 2-(3,5-dimethylisoxazol-4-yl)-1-(2-fluoro-4-hydroxyphenyl)-1H-indole-3-carbimidate |
|---|---|

R = 2-fluoro-4-hydroxyphenyl  $R^1$ = 3,5-dimethylioxazol-4-yl
$R^2$ = imino(methoxy)methyl  $R^3$ = H
ES/MS m/z: 380.3 (pos. M + H), 378.7 (neg. M – H).

| E 261 | 2-(3,5-dimethylisoxazol-4-yl)-1-(3-fluoro-4-hydroxyphenyl)-1H-indole-3-carboxamide |
|---|---|

R = 3-fluoro-4-hydroxyphenyl  $R^1$ = 3,5-dimethylisoxazol-4-yl
$R^2$ = carbamoyl  $R^3$ = H
ES/MS m/z: 366.2 (pos. M + H), 364.3 (neg. M – H).

| E 262 | 1-(2,5-difluoro-4-hydroxyphenyl)-2-(3,5-dimethylisoxazol-4-yl)-1H-indole-3-carboximidamide |
|---|---|

R = 2,5-difluoro-4-hydroxyphenyl  $R^1$ = 3,5-dimethylisoxazol-4-yl
$R^2$ = carbamimidoyl  $R^3$ = H
ES/MS m/z: 383.3 (pos. M + H); $^1$H NMR (acetone-d6, 500 MHz): 7.95 (m, 1H), 7.56 (m, 1H), 7.42-
7.30 (m, 3H), 7.01 (m, 1H), 2.27, 2.23 (two s, 3H) and 2.13, 2.08 (two s, 3H).

| E 263 | 2-(3,5-dimethylisoxazol-4-yl)-1-(3-fluoro-4-hydroxyphenyl)-1H-indole-3-carboximidamide |
|---|---|

R = 3-fluoro-4-hydroxyphenyl  $R^1$ = 3,5-dimethylisoxazol-4-yl
$R^2$ = carbamimidoyl  $R^3$ = H
ES/MS m/z: 365.17 (pos. M + H), 363.21 (neg. M – H); $^1$H NMR (MeOD, 500 MHz): 7.86 (m, 1H),
7.40-7.37 (m, 3H), 7.08-7.01 (m, 3H), 6.90 (br s, 1H), 2.18 (s, 3H) and 2.02 (s, 3H).

| E 264 | (Z)-1-(3-fluoro-4-hydroxyphenyl)-N'-hydroxy-2-(1H-pyrrol-1-yl)-1H-indole-3-carboximidamide-pyrrol-3-1-yl)-1H-indole-carboximidamide |
|---|---|

R = 3-fluoro-4-hydroxyphenyl  $R^1$ = 1H-pyrrol-1-yl
$R^2$ = N-Hydroxycarbamimidoyl  $R^3$ = H
ES/MS m/z: 351.16 (pos. M + H), 349.14 (neg. M – H); $^1$H NMR (acetone-d6, 500 MHz): 8.24 (d, 1H,
J = 7.9 Hz), 7.27-7.12 (m, 4H), 7.08-7.04 (m, 2H), 6.94 (t, 2H, J = 2.2 Hz) and 6.18 (t, 2H, J = 2.2 Hz).

| E 265 | 1-(3-fluoro-4-hydroxyphenyl)-2-(1H-pyrrol-1-yl)-1H-indole-3-carboxamide |
|---|---|

R = 3-fluoro-4-hydroxyphenyl  $R^1$ = 1H-pyrrol-1-yl
$R^2$ = carbamoyl  $R^3$ = H
ES/MS m/z: 336.13 (pos. M + H), 334.22 (neg. M – H); $^1$H NMR (acetone-d6, 500 MHz): 8.44 (m, 1H),
7.32-7.23 (m, 3H), 7.15 (m, 1H), 7.12-7.06 (m, 2H), 7.04 (t, 2H, J = 2.2 Hz) and 6.26 (t, 2H, J = 2.2 Hz).

| E 266 | (Z)-1-(2,3-difluoro-4-hydroxyphenyl)-N'-hydroxy-2-(1H-pyrrol-1-yl)-1H-indole-3-carboximidamide |
|---|---|

R = 2,3-difluoro-4-hydroxyphenyl  $R^1$ = 1H-pyrrol-1-yl
$R^2$ = N-Hydroxycarbamimidoyl  $R^3$ = H
ES/MS m/z: 369.14 (pos. M + H), 367.19 (neg. M – H); $^1$H NMR (acetone-d6, 500 MHz): 8.24 (d, 1H,
J = 7.9 Hz), 7.27 (m, 1H), 7.22 (m, 1H), 7.14 (m, 1H), 7.06 (d, 1H, J = 7.8 Hz), 6.92-6.88 (m, 3H) and 6.17
(t, 2H, J = 2.1 Hz).

| E 267 | 1-(2,3-difluoro-4-hydroxyphenyl)-2-(1H-pyrrol-1-yl)-1H-indole-3-carboxamide |
|---|---|

R = 2,3-difluoro-4-hydroxyphenyl  $R^1$ = 1H-pyrrol-1-yl
$R^2$ = carbamoyl  $R^3$ = H
ES/MS m/z: 354.12 (pos. M + H), 352.19 (neg. M – H); $^1$H NMR (acetone-d6, 500 MHz): 8.44 (m, 1H),
7.34-7.29 (m, 2H), 7.20 (br s, 1H), 7.11 (m, 1H), 6.99 (t, 2H, J = 2.1 Hz), 6.91 (m, 1H) and 6.26 (t, 2H,
J = 2.1 Hz).

| E 268 | (Z)-2-(2,5-dimethyl-1H-pyrrol-1-yl)-1-(3-fluoro-4-hydroxyphenyl)-N'-hydroxy-1H-indole-3-carboximidamide |
|---|---|

R = 3-fluoro-4-hydroxyphenyl  $R^1$ = 2,5-dimethyl-1H-pyrrol-1-yl
$R^2$ = N-Hydroxycarbamimidoyl  $R^3$ = H
ES/MS m/z: 379.21 (pos. M + H), 377.29 (neg. M – H); $^1$H NMR (acetone-d6, 500 MHz): 8.37 (d, 1H,
J = 8.1 Hz), 7.34-7.20 (m, 4H), 7.11-6.98 (m, 4H), 2.52 (s, 3H) and 2.01 (s, 3H).

| E 269 | (Z)-1-(3-fluoro-4-hydroxyphenyl)-N'-hydroxy-2-(2-methyl-1H-pyrrol-1-yl)-1H-indole-3-carboximidamide |
|---|---|

R = 3-fluoro-4-hydroxyphenyl  $R^1$ = 2-methyl-1H-pyrrol-1-yl
$R^2$ = N-Hydroxycarbamimidoyl  $R^3$ = H
ES/MS m/z: 365.18 (pos. M + H), 363.2 (neg. M – H); $^1$H NMR (acetone-d6, 500 MHz): 8.33 (d, 1H,

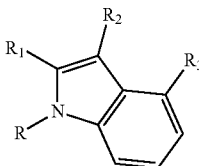

J = 8.1 Hz), 7.29-7.14 (m, 4H), 7.09-7.04 (m, 2H), 6.92 (dd, 1H, J = 2.8, 1.8 Hz), 6.10 (t, 1H, J = 3.2 Hz), 5.90 (m, 1H) and 2.01 (s, 3H).

| E 270 | 1-(3,5-difluoro-4-hydroxyphenyl)-2-(3,5-dimethylisoxazol-4-yl)-1H-indole-3-carboxamide |
|---|---|
| R = 3,5-difluoro-4-hydroxyphenyl  $R^1$ = 3,5-dimethylisoxazol-4-yl<br>$R^2$ = carbamoyl  $R^3$ = H<br>ES/MS m/z: 384.2 (pos. M + H), 382.3 (neg. M − H); $^1$H NMR (acetone-d6, 500 MHz): 8.25 (m, 1H), 7.30-7.25 (m, 3H), 7.10 (br s, 2H), 2.27 (s, 3H) and 2.11 (s, 3H). | |

Example 271

Example 271 below was prepared according to General Method 3 above. Full experimental details of the individual steps of that general method are described in Examples 2-4, 8, 16, 24 and 38-40 above.

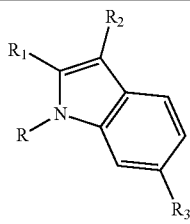

| E 271 | (Z)-2-(3,5-dimethylisoxazol-4-yl)-6-fluoro-N'-hydroxy-1-(4-hydroxyphenyl)-1H-indole-3-carboximidamide |
|---|---|
| R = 4-hydroxyphenyl  $R^1$ = 3,5-dimethylisoxazol-4-yl<br>$R^2$ = N-Hydroxycarbamimidoyl  $R^3$ = F<br>ES/MS m/z: 381.18 (pos. M + H), 379.22 (neg. M − H); $^1$H NMR (acetone-d6, 500 MHz): 8.08 (dd, 1H, J = 8.9, 1.5 Hz), 7.13 (br s, 2H), 6.99 (m, 1H), 6.95 (m, 2H), 6.87 (dd, 1H, J = 9.8k, 2.3 Hz), 2.17 (s, 3H) and 2.00 (s, 3H). | |

Binding Assay 1: Estrogen Receptor Binding Assay

The estrogen receptor ligand binding assays are designed as scintillation proximity assays (SPA), employing the use of tritiated estradiol ($^3$H-E2) and recombinant expressed biotinylated estrogen receptor binding domains. The binding domains of human ERα (ERα-LBD, pET-N-AT #1, aa 301-595) and ERβ (ERβ-LBD, pET-N-AT #1, aa 255-530) proteins are produced in E. coli ((BL21, (DE3), pBirA)) at 22 C in 2×LB medium supplemented with 50 uM biotin. After 3 h of IPTG induction (0.55 mM), cells are harvested by centrifugation at 7300×g for 15 min and cell pellets stored frozen in −20 C. Extraction of ERα and ERβ are performed using 5 g of cells suspended in 50 mL of extraction buffer (50 mM Trig, pH 8.0, 100 mM KCl, 4 mM EDTA, 4 mM DDT and 0.1 mM PMSF). The cell suspension is run twice through a Microfluidizer M-110L (Microfluidics) and centrifuged at 15,000×g for 60 min. The supernatant is aliquoted and stored in −70 C.

Dilute ERα-LBD or ERβ-LBD extracts in assay buffer (18 mM $K_2HPO_4$, 2 mM $KH_2PO_4$, 20 mM $Na_5MoO_4$, 1 mM EDTA, 1 mM TCEP) 1:676 and 1:517 for alpha and beta respectively. The diluted receptor concentrations should be 900 fmol/L. Preincubate the extracts with streptavidin coated polyvinyltoluene SPA beads (RPNQ0007, GE Healthcare) at a concentration of 0.43 mg/mL for 1 hr at room temperature.

Test compounds are evaluated over a range of concentrations from 157 μM to 37.5 pM. The test compound stock solutions should be made in 100% DMSO at 5× of the final concentration desired for testing in the assay. The amount of DMSO in the test wells of the 384 well plate will be 20%. Add 18 μl aliquots of test compounds to the assay plates followed by 35 μl of the preincubated receptor/SPA bead mix and finally add 35 μl of 3 nM $^3$H-E2. Cover the plates with a plastic sealer, centrifuge for 1 minute at 1000 rpm and equilibrate over night on a shaker at room temperature. The following morning, centrifuge the plates 5 minutes at 2000 rpm and measure on a plate scintillation counter e.g. a PerkinElmer Microbeta 1450 Trilux.

For compounds able to displace 3[H]-E2 from the receptor an $IC_{50}$-value (the concentration required to inhibit 50% of the binding of 3[H]-E2) is determined by a non-linear four parameter logistic model; b=((bmax−bmin)/(1+(I/$IC_{50}$)S))+bmin I is added concentration of binding inhibitor, $IC_{50}$ is the concentration of inhibitor at half maximal binding and S is a slope factor. The Microbeta-instrument generates the mean cpm (counts per minute) value/minute and corrects for individual variations between the detectors thus generating corrected cpm values.

Binding Assay 2: Estrogen Receptor Filter Binding Assay

The ligand binding domain of the human estrogen receptor beta (hERβ-LBD) is used in a competition binding assay with filter separation of bound and free ligand. The assay utilizes tritiated estradiol ($^3$H-E2) as beta particle emitting tracer and recombinant expressed human estrogen beta receptor binding domain. The binding domain of human ERβ (hERβ-LBD, pET-N-AT #1, aa 255-530) protein is produced in *Escherichia coli* ((BL21, (DE3), pBirA)) at 22° C. in 2×LB medium supplemented with 50 μM biotin. After 3 h of isopropyl β-D-1-thiogalactopyranoside induction (0.55 mM), cells are harvested by centrifugation at 7300×g for 15 min and cell pellets stored frozen in −20° C. Extraction of hERβ-LBD is performed using 5 g of cells suspended in 50 mL of extraction buffer (50 mM Tris, pH 8.0, 100 mM KCl, 4 mM ethylenediaminetetraacetic acid (EDTA), 4 mM dithiothreitol and 0.1 mM phenylmethanesulfonyl fluoride (TCEP). The cell suspension is run twice through a Microfluidizer M-110L (Microfluidics) and centrifuged at 15,000×g for 60 min. The supernatant is aliquoted and stored in −70° C. Estrogen receptor extract is diluted 1:400 in assay buffer (18 mM $K_2HPO_4$, 2 mM $KH_2PO_4$, 20 mM $Na_2MoO_4$, 1 mM EDTA, 1 mM TCEP, pH 8.0). Test compounds are evaluated over a range of concentrations from 2 μM to 10 pM. The test compound stock solutions should be made in 100% dimethyl sulfoxide (DMSO) at 51× of the final concentration desired for testing in the assay. The final fraction of DMSO in the wells of the 96 well assay plate will be 2%. 100 μl $^3$H-E2 is added to the assay plates followed by 4 μl aliquots of test compounds and 100 μl of the diluted receptor extract. The assay plates are stored over night at +4° C. Receptor bound and free tracer are separated over a glass fiber filter (FILTERMAT B, PerkinElmer)) on a cell harvester (TOMTECMACH3, Tomtec) with wash buffer (18 mM $K_2HPO_4$, 2 mM $KH_2PO_4$, 0.5 mM EDTA). The filters are dried at 60° C. for 1 hour and then merged by heat with a scintillating wax (MELTILEX, PerkinElmer) before measuring on a plate beta counter (Wallac Microbeta Trilux 1450-028, PerkinElmer). The Trilux-instrument generates mean counts per minute (cpm) and corrects for individual variations between the detectors, thus generating corrected cpm values (ccpm). The IC50 values, defined as the midpoint between maximum binding and minimum binding on the sigmoid binding curve, are calculated with XLfit software version 2.0 or later (IDBS) with a four parameter logistic model; $b=((bmax-bmin)/(1+(I/IC_{50})S))+bmin$ where I is added concentration of binding inhibitor, $IC_{50}$ is the concentration of inhibitor at half maximal binding and S is a slope factor.

Transactivation Assay 1: Transactivation Assay in Human Embryonic Kidney 293 Cells Stably Transfected with pERE-ALP and Human Estrogen Receptor Alpha The expression vector pMThERα contains an insert of wild type human estrogen receptor alpha with deleted leader. The pERE-ALP reporter construct contains the gene for the secreted form of placental alkaline phosphatase (ALP) and the vitellogenin estrogen response element (ERE). The human embryonic kidney 293 cells are transfected in two steps. Firstly, a stable clone mix transfected with the pERE-ALP reporter gene construct and pSV2-Neo for selection is developed. Secondly, the stable clone mix is transfected with pMThERα and a pKSV-Hyg resistance vector for selection. All transfections are performed using Lipofectamine (Invitrogen) according to supplier's recommendations. A selected clone with both pERE-ALP and pMThERα is used for the transactivation assay.

The cells are seeded in 384-well plates at 12 500 cells per well in Ham's F12 Coon's modification (without phenol red) with 10% dextran-coated charcoal treated (DCC) fetal bovine serum (FBS), 2 mM L-glutamine and 50 μg/ml gentamicin. After 24 h incubation (37° C., 5% $CO_2$) the seeding medium is discarded and replaced with 20 μl Ham's F12 Coon's modification (without phenol red) with 1.5% DCC-FCS, 2 mM L-glutamine and supplemented with 100 U/ml penicillin and 100 μg/ml streptomycin. The selected compounds are added to the wells in 12 concentrations ranging from 3.3 pM to 33 μM. The compounds are dissolved in 100% dimethylsulphoxide (DMSO) and the final concentration of DMSO in the assay is 0.1%. After 72 h incubation (37° C., 5% $CO_2$) the medium is assayed for ALP activity by a chemiluminescence assay; a 10 μl aliquot of the cell culture medium is mixed with 100 μl assay buffer (0.1 M diethanolamine, 1 mM $MgCl_2$) and 0.5 mM disodium 3-(4-methoxyspiro 1,2-dioxetane-3,2'-(5'-chloro)-tricyclo[3.3.1.13,7]decan-4-yl)phenyl phosphate (CSPD) (Tropix, Applied Biosystems) and incubated for 20 min at 37° C. and 15 min at room temperature before measurement chemiluminescent light signal (one second per well) in a Wallac Microbeta Trilux 1450-028 (PerkinElmer). The half maximal effective concentrations ($EC_{50}$) are calculated from the curves fitted to the concentration-response data with a four parameter logistic model in XLfit software version 2.0 (IDBS) or later.

Transactivation Assay 2: Transactivation Assay in Human Embryonic Kidney 293 Cells Stably Transfected with pERE2-ALP and Human Estrogen Receptor Beta Generation of stable HEK293 cell lines (CRL-1573; American Type Culture Collection) expressing the reporter vector pERE2-ALP and human estrogen receptor beta (hERβ 530) have been described (Mol Pharmacol 1998, 54, 105-112; Endocrinology 2002, 143, 1558-1561), The cells were seeded in 384-well plates at 12 500 cells per well in Ham's F12 Coon's modification (without phenol red) with 10% dextran-coated charcoal treated (DCC) fetal bovine serum (FBS), 2 mM L-glutamine and 50 μg/ml gentamicin. After 24 h incubation (37° C., 5% CO2) the seeding medium was discarded and replaced with 20 μl Ham's F12 Coon's modification (without phenol red) with 1.5 DCC-FCS, 2 mM L-glutamine and supplemented with 100 U/ml penicillin and 100 μg/ml streptomycin. The selected compounds were added to the wells in 12 concentrations ranging from 3.3 μM to 33 μM. The compounds were dissolved in 100% dimethylsulfoxide (DMSO) and the final concentration of DMSO in the assay was 0.1%. After 72 h incubation (37° C., 5% $CO_2$) the medium was assayed for ALP activity by a chemiluminescence assay; a 10 μl aliquot of the conditioned medium was mixed with 100 μl assay buffer (0.1 M diethanolamine, 1 mM MgCl2) and 0.5 mM disodium 3-(4-methoxyspiro 1,2-dioxetane-3,2'-(5'-chloro)-tricyclo[3.3.1.13,7]decan-4-yl) phenyl phosphate (CSPD) (Tropix, Applied Biosystems) and incubated for 20 min at 37° C. and 15 min at room temperature before measurement of the chemiluminescent signal (one second per well) in a Wallac Microbeta Trilux 1450-028 (PerkinElmer). The ALP activity expressed in LCPS is directly proportional to the level of ALP expressed by the cells. The half maximal effective concentrations of the test compounds (EC50) were calculated from the curves fitted to the concentration-response data with a four parameter logistic model in XLfit software version 2.0 (IDBS) or later.

The compounds of Examples 1-271 exhibit one or more of the following:

(i) a binding affinity to the estrogen receptor α-subtype in the range of $IC_{50}$ 1 to 10,000 nM in binding assay 1;

(ii) a binding affinity to the estrogen receptor β-subtype in the range of $IC_{50}$ 1 to 10,000 nM in binding assay 1;

(iii) a binding affinity to the estrogen receptor α-subtype in the range of $IC_{50}$ 1 to 10,000 nM in binding assay 2;
(iv) a binding affinity to the estrogen receptor β-subtype in the range of $IC_{50}$ 1 to 10,000 nM in binding assay 2;
(v) a potency in the range of $EC_{50}$ 1 to 10,000 nM at the estrogen receptor α-subtype in transactivation assay 1;
(vi) a potency in the range of $EC_{50}$ 1 to 10,000 nM at the estrogen receptor β-subtype in transactivation assay 2.

Preferred Example compounds of the invention are those which exhibit a binding affinity to the estrogen receptor β-subtype at lower concentrations within the $IC_{50}$ range shown above. For example, the compounds of Examples 1, 2, 4-6, 11, 23, 39, 42, 43, 46, 49-51, 53, 54, 63, 64, 68, 70, 83, 86, 87, 95, 100, 101, 107, 110, 125, 126, 128, 129, 132-141, 143, 144, 146, 147, 158, 163, 188, 191, 194, 212-217, 219-221, 223, 224, 235, 243, exhibit a binding affinity to the estrogen receptor β-subtype in the range of $IC_{50}$ 1 to 200 nM in binding assay 1.

Preferred Example compounds of the invention are those which are selective for the estrogen receptor β-subtype over the estrogen receptor α-subtype in binding assay 1. For example, the compounds of Examples 2, 4, 5, 11, 23, 43, 51, 53, 68, 70, 39, 95, 133, 134, 143, 146, 188, 191, 213, 215, 221, 224, 235, display selectivity for the estrogen receptor β-subtype of 50 or greater in the binding assay.

Preferred Example compounds of the invention are those which display a potency at the estrogen receptor β-subtype at lower concentrations within the $EC_{50}$ range shown above. For example, the compounds of Examples 11, 14, 39, 41, 42, 47, 68, 163, 176, 187, 188, 191, 194, 220, 221, 223, 235-238, 255, 266, 268, 269, 271 exhibit a potency in the range of $EC_{50}$ 1 to 50 nM at the estrogen receptor β-subtype in transactivation assay 2.

Preferred Example compounds of the invention are those which are selective for the estrogen receptor β-subtype over the estrogen receptor α-subtype in the transactivation assays 1 and 2. For example, the compounds of Examples 11, 14, 41, 42, 44, 221, 235-238, 241, 255, 260, 268, 271 display selectivity for the estrogen receptor β-subtype of 50 or greater in the transactivation assays.

Particularly preferred Example compounds of the invention are those which exhibit both a binding affinity to the estrogen receptor β-subtype at lower concentrations within the $IC_{50}$ range shown above and a potency at the estrogen receptor β-subtype at lower concentrations within the $EC_{50}$ range shown above. For example, the compounds of Examples 11, 39, 42, 68, 163, 188, 191, 194, 220, 221, 223, 235 exhibit a binding affinity to the estrogen receptor β-subtype in the range of $IC_{50}$ 1 to 200 nM in binding assay 1 and a potency in the range of $EC_{50}$ 1 to 50 nM at the estrogen receptor β-subtype in transactivation assay 2.

The invention claimed is:

1. A method for the treatment of a disease or disorder associated with estrogen receptor activity in a mammal, wherein said disease or disorder associated with estrogen receptor activity is selected from hot flashes, cardiovascular disease, impairment of cognitive functioning, age-related mild cognitive impairment, cerebral degenerative disorders, restenosis, obesity, anxiety, depression, hearing disorders, multiple sclerosis, Parkinson's disease, Alzheimer's disease, Huntington's disease, amyotrophic lateral sclerosis, stroke, IBD, IBS, hypertension, lung cancer, colon cancer, breast cancer, prostate cancer and cholangiocarcinoma, which comprises administering to the mammal a therapeutically effective amount of a compound of formula (I) or a pharmaceutically acceptable ester, amide, carbamate, solvate or salt thereof, including a salt of such an ester, amide or carbamate, and a solvate of such an ester, amide, carbamate or salt,

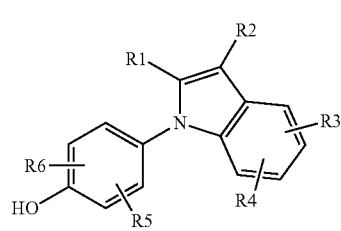

(I)

wherein $R^1$ is selected from the group consisting of halogen, cyano, nitro, $OR^A$, $N(R^B)_2$, —C(O)$C_{1-4}$alkyl, —SO$_2$C$_{1-4}$alkyl, $C_{1-6}$alkyl, $C_{2-6}$alkenyl, $C_{2-6}$alkynyl, haloC$_{1-6}$alkyl, dihaloC$_{1-6}$alkyl, trihaloC$_{1-6}$alkyl, haloC$_{2-6}$alkenyl, dihaloC$_{2-6}$alkenyl, trihaloC$_{2-6}$alkenyl, cyanoC$_{1-6}$alkyl, C$_{1-4}$alkoxyC$_{1-6}$ alkyl, C$_{3-8}$cycloalkyl, C$_{3-8}$cycloalkylC$_{1-6}$alkyl, phenyl, benzyl, and 5-10 membered heterocyclyl, wherein said phenyl, benzyl or heterocyclyl group can be either unsubstituted or substituted with from 1 to 3 substituents, each substituent being selected from the group consisting of $OR^A$, halogen, cyano, nitro, —C(O)C$_{1-4}$alkyl, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

$R^2$ is selected from the group consisting of halogen, cyano, nitro, $OR^A$, $N(R^B)_2$, $N(OH)_2$, —C(O)C$_{1-4}$alkyl optionally substituted with from 1 to 3 halogens, —SO$_2$C$_{1-4}$alkyl, —C(O)NH—OH, —C(NH$_2$)=N—OH, —C(CO$_2$H)=N—OH, —C(NH$_2$)=NH, —C(NHC$_{1-4}$alkyl)=NH, —C(O—C$_{1-4}$alkyl)=NH, —C(NH$_2$)=N—NH$_2$, —NH—C(NH$_2$)=NH, —NH—C(O)NH$_2$, —N=C(—NH—CH$_2$CH$_2$—NH—), —S—CN, —S—C(NH$_2$)=NH, —S—C(NH$_2$)=N—OH, —CO$_2$H, —CH$_2$—CO$_2$H, —CH(OH)CO$_2$H, —C(O)CO$_2$H, SO$_3$H, CH$_2$SO$_3$H, C$_{1-6}$alkyl, haloC$_{1-6}$alkyl, dihaloC$_{1-6}$alkyl, trihaloC$_{1-6}$alkyl, cyanoC$_{1-6}$alkyl, C$_{1-4}$alkoxyC$_{1-6}$ alkyl, C$_{2-6}$alkenyl, C$_{2-6}$alkynyl, C$_{3-8}$cycloalkyl, C$_{3-8}$cycloalkylC$_{1-6}$alkyl, phenyl, benzyl and 5-10 membered heterocyclyl wherein said phenyl, benzyl or heterocyclyl group can be either unsubstituted or substituted with from 1 to 3 substituents each substituent being selected from the group consisting of $OR^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl; provided that if one of $R^1$ and $R^2$ represents halogen, the other must represent a group other than halogen;

each of $R^3$, $R^4$, $R^5$ and $R^6$ is independently selected from the group consisting of hydrogen, $OR^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

each $R^A$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, C$_{6-10}$aryl and C$_{6-10}$ arylC$_{1-6}$alkyl, each optionally substituted by from 1 to 3 halogen atoms; and each $R^B$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, C$_{6-10}$aryl and C$_{6-10}$ arylC$_{1-6}$alkyl, each optionally substituted by from 1 to 3 halogen atoms;

with the proviso that the compound of formula (I) is not
4-[3-(4,5-Dihydro-1H-imidazol-2-yl)-2-(3,5-dimethyl-isoxazol-4-yl)-indol-1-yl]-phenol;
1-(4-Hydroxy-phenyl)-2-(4-methyl-imidazol-1-yl)-1H-indole-3-carbonitrile;
1-(4-Hydroxy-phenyl)-2-(1H-pyrazol-3-yl)-1H-indole-3-carbonitrile;
1-(3-Chloro-4-hydroxy-phenyl)-2-(1-methyl-1H-pyrazol-4-yl)-1H-indole-3-carbonitrile;
1-(4-Hydroxy-phenyl)-2-prop-1-ynyl-1H-indole-3-carboxylic acid amide; or
1-(4-Hydroxy-phenyl)-2-thiazol-2-yl-1H-indole-3-carboxylic acid.

2. A method as claimed in claim 1, in which each $R^A$ is independently selected from the group consisting of hydrogen, $C_{1-4}$alkyl, $C_{2-4}$alkenyl, $C_{2-4}$alkynyl, $C_{3-6}$cycloalkyl, phenyl and benzyl.

3. A method as claimed in claim 2, in which each $R^A$ independently represents hydrogen or $C_{1-4}$alkyl.

4. A method as claimed in claim 1, in which each $R^B$ is independently selected from the group consisting of hydrogen and $C_{1-4}$alkyl.

5. A method as claimed in claim 1, in which $R^1$ is selected from the group consisting of $OR^A$, $N(R^B)_2$, —C(O)$C_{1-4}$alkyl, $C_{1-6}$alkyl, $C_{2-6}$alkenyl, $C_{2-6}$alkynyl, halo$C_{1-4}$alkyl, dihalo$C_{1-4}$alkyl, trihalo$C_{1-4}$alkyl, halo$C_{2-4}$alkenyl, dihalo$C_{2-4}$alkenyl, trihalo$C_{2-4}$alkenyl, phenyl, and 5-6 membered heterocyclyl, wherein said phenyl or heterocyclyl group can either be unsubstituted or substituted by 1 to 3 substituents selected from the group consisting of $OR^A$, halogen, cyano, —C(O)$C_{1-4}$alkyl, $C_{1-4}$alkyl, $C_{2-4}$alkenyl, $C_{2-4}$alkynyl, halo$C_{1-4}$alkyl, dihalo$C_{1-4}$alkyl and trihalo$C_{1-4}$alkyl.

6. A method as claimed in claim 5, in which $R^1$ is selected from the group consisting of $OR^A$, $N(R^B)_2$, —C(O)$C_{1-4}$alkyl, $C_{1-4}$alkyl, $C_{2-4}$alkenyl, $C_{2-4}$alkynyl, phenyl, and 5-6 membered heterocyclyl, wherein said phenyl or heterocyclyl group can either be unsubstituted or substituted by 1 to 3 substituents selected from halogen, cyano, $C_{1-4}$alkyl, —C(O)$C_{1-4}$alkyl, and $OR^A$ in which $R^A$ represent hydrogen or $C_{1-4}$alkyl.

7. A method as claimed in claim 1, in which $R^2$ is selected from the group consisting of halogen, $OR^A$, $N(R^B)_2$, —C(O)$C_{1-4}$alkyl optionally substituted with from 1 to 3 halogens, —C(NH$_2$)=N—OH, —CO$_2$H, —CH$_2$—CO$_2$H, $C_{1-6}$alkyl, $C_{2-6}$alkenyl, $C_{2-6}$alkynyl, halo$C_{1-4}$alkyl, dihalo$C_{1-4}$alkyl, trihalo$C_{1-4}$alkyl, halo$C_{2-4}$alkenyl, dihalo$C_{2-4}$alkenyl, trihalo$C_{2-4}$alkenyl, phenyl, and 5-6 membered heterocyclyl, wherein said phenyl or heterocyclyl group can either be unsubstituted or substituted by 1 to 3 substituents selected from the group consisting of $OR^A$, halogen, cyano, $C_{1-4}$alkyl, $C_{2-4}$alkenyl, $C_{2-4}$alkynyl, halo$C_{1-4}$alkyl, dihalo$C_{1-4}$alkyl and trihalo$C_{1-4}$alkyl.

8. A method as claimed in claim 7, in which $R^2$ is selected from the group consisting of —C(O)$C_{1-4}$alkyl, —C(NH$_2$)—N—OH, —CO$_2$H, —CH$_2$—CO$_2$H, $C_{1-4}$alkyl, $C_{2-4}$alkenyl, $C_{2-4}$alkynyl, and 5-6 membered heterocyclyl wherein heterocyclyl group can either be unsubstituted or substituted by 1 to 3 substituents selected from halogen, cyano, $C_{1-4}$alkyl, and $OR^A$.

9. A method as claimed in claim 1, in which each of $R^3$, $R^4$, $R^5$ and $R^6$ is independently selected from the group consisting of hydrogen, $OR^A$, halogen, cyano, $C_{1-4}$alkyl, halo$C_{1-4}$alkyl, dihalo$C_{1-4}$alkyl, and trihalo$C_{1-4}$alkyl.

10. A method as claimed in claim 9, in which each of $R^3$, $R^4$, $R^5$ and $R^6$ is independently selected from the group consisting of hydrogen, OH, halogen, cyano, methyl, or trifluoromethyl.

11. A method as claimed in claim 1, in which $R^1$ is selected from the group consisting of $OR^A$, $N(R^B)_2$, —C(O)$C_{1-4}$alkyl, $C_{1-6}$alkyl, $C_{2-6}$alkenyl, $C_{2-6}$alkynyl, halo$C_{1-4}$alkyl, dihalo$C_{1-4}$alkyl, trihalo$C_{1-4}$alkyl, halo$C_{2-4}$alkenyl, dihalo$C_{2-4}$alkenyl, trihalo$C_{2-4}$alkenyl, phenyl, and 5-6 membered heterocyclyl, wherein said phenyl or heterocyclyl group may be either unsubstituted or substituted as above by 1 to 3 substituents selected from the group consisting of $OR^A$, halogen, cyano, —C(O)$C_{1-4}$alkyl, $C_{1-4}$alkyl, $C_{2-4}$alkenyl, $C_{2-4}$alkynyl, halo$C_{1-4}$alkyl, dihalo$C_{1-4}$alkyl and trihalo$C_{1-4}$alkyl;

$R^2$ is selected from the group consisting of halogen, $OR^A$, $N(R^B)_2$, —C(O)$C_{1-4}$alkyl optionally substituted with from 1 to 3 halogens, —C(NH$_2$)=N—OH, —CO$_2$H, —CH$_2$—CO$_2$H, $C_{1-6}$alkyl, $C_{2-6}$alkenyl, $C_{2-6}$alkynyl, halo$C_{1-4}$alkyl, dihalo$C_{1-4}$alkyl, trihalo$C_{1-4}$alkyl, halo$C_{1-4}$alkenyl, dihalo$C_{1-4}$alkenyl, trihalo$C_{1-4}$alkenyl, phenyl, and 5-6 membered heterocyclyl, wherein said phenyl or heterocyclyl group can either be unsubstituted or substituted by 1 to 3 substituents selected from the group consisting of $OR^A$, halogen, cyano, $C_{1-4}$alkyl, $C_{2-4}$alkenyl, $C_{2-4}$alkynyl, halo$C_{1-4}$alkyl, dihalo$C_{1-4}$alkyl and trihalo$C_{1-4}$alkyl;

each of $R^3$, $R^4$, $R^5$ and $R^6$ is independently selected from the group consisting of hydrogen, $OR^A$, halogen, cyano, $C_{1-4}$alkyl, halo$C_{1-4}$alkyl, dihalo$C_{1-4}$alkyl, and trihalo$C_{1-4}$alkyl;

each $R^A$ is independently selected from the group consisting of hydrogen, $C_{1-4}$alkyl, $C_{2-4}$alkenyl, $C_{2-4}$alkynyl, $C_{3-6}$cycloalkyl, phenyl and benzyl; and each $R^B$ is independently selected from the group consisting of hydrogen and $C_{1-4}$alkyl.

12. A method as claimed in claim 11, in which $R^1$ is selected from the group consisting of $OR^A$, $N(R^B)_2$, —C(O)$C_{1-4}$alkyl, $C_{1-4}$alkyl, $C_{2-4}$alkenyl, $C_{2-4}$alkynyl, phenyl, and 5-6 membered heterocyclyl, wherein said phenyl or heterocyclyl group can either be unsubstituted or substituted by 1 to 3 substituents selected from halogen, cyano, $C_{1-4}$alkyl, —C(O)$C_{1-4}$alkyl, and $OR^A$;

each $R^A$ independently represents hydrogen or $C_{1-4}$alkyl; and each $R^B$ is independently selected from the group consisting of hydrogen and $C_{1-4}$alkyl.

13. A method as claimed in claim 11, in which $R^2$ is selected from the group consisting of —C(O)$C_{1-4}$alkyl optionally substituted with from 1 to 3 halogens, —C(NH$_2$)=N—OH, —CO$_2$H, —CH$_2$—CO$_2$H, $C_{1-4}$alkyl, $C_{2-4}$alkenyl, $C_{2-4}$alkynyl, and 5-6 membered heterocyclyl wherein said heterocyclyl group can be either unsubstituted or substituted by 1 to 3 substituents selected from the group consisting of halogen, cyano, $C_{1-4}$alkyl, $C_{2-4}$alkenyl, $C_{2-4}$alkynyl, halo$C_{1-4}$alkyl, dihalo$C_{1-4}$alkyl and trihalo$C_{1-4}$alkyl, and $OR^A$, in which $R^A$ represents hydrogen or $C_{1-4}$alkyl.

14. A method as claimed in claim 11, in which $R^2$ is selected from the group consisting of —C(O)CH$_3$, —C(NH$_2$)=N—OH, —CO$_2$H, —CH$_2$—CO$_2$H, $C_{1-4}$alkyl, $C_{2-4}$alkenyl, $C_{2-4}$alkynyl, and 5-6 membered heterocyclyl wherein said heterocyclyl group can be either unsubstituted or substituted 1 to 3 substituents selected from halogen, cyano, $C_{1-4}$alkyl, and $OR^A$ in which $R^A$ represents hydrogen or $C_{1-4}$alkyl.

15. A method as claimed in claim 11, in which each of $R^3$, $R^4$, $R^5$ and $R^6$ is independently selected from the group consisting of hydrogen, OH, halogen, cyano, methyl, or trifluoromethyl.

16. A method as claimed in claim 1, in which $R^1$ is a 5-6 membered heterocyclyl group, wherein said heterocyclyl group is substituted with from 1 to 3 substituents selected from halogen, cyano and $C_{1-4}$alkyl; $R^2$ is selected from the group consisting of —C(O)CH$_3$, —C(NH$_2$)=N—OH, —CO$_2$H, and —CH$_2$—CO$_2$H; and each of $R^3$, $R^4$, $R^5$ and $R^6$ is independently selected from the group consisting of hydrogen and halogen.

17. A method as claimed in claim 16, in which $R^1$ is a 5-membered heterocyclyl group, wherein said heterocyclyl group is substituted with two substituents independently selected from methyl and ethyl; $R^2$ is —C(NH$_2$)=N—OH; and each of $R^3$, $R^4$, $R^5$ and $R^6$ is independently selected from the group consisting of hydrogen and halogen.

18. A method as claimed in claim 1, in which the compound of formula (I) is any one of the following compounds:

- 2-Bromo-1-(4-hydroxy-phenyl)-1H-indole-3-carbonitrile;
- 1-(4-Hydroxy-phenyl)-2-thiophen-3-yl-1H-indole-3-carbonitrile;
- 2-(3-Cyano-furan-2-yl)-1-(4-hydroxy-phenyl)-1H-indole-3-carbonitrile;
- 1-(4-Hydroxy-phenyl)-2-pyrrol-1-yl-1H-indole-3-carbonitrile;
- 2-Dimethylamino-1-(4-hydroxy-phenyl)-1H-indole-3-carbonitrile;
- 1-(4-Hydroxy-phenyl)-2-isopropyl-1H-indole-3-carbonitrile;
- 2-Acetyl-1-(4-hydroxy-phenyl)-1H-indole-3-carbonitrile;
- 2-(3,5-Dimethyl-isoxazol-4-yl)-1-(4-hydroxy-phenyl)-1H-indole-3-carboxylic acid;
- 1-[1-(4-Hydroxy-phenyl)-2-phenyl-1H-indol-3-yl]-ethanone;
- 1-(4-Hydroxy-phenyl)-2-phenyl-1H-indole-3-carboxylic acid, amide;
- (Z)-2-(3,5-dimethylisoxazol-4-yl)-N'-hydroxy-1-(4-hydroxyphenyl)-1H-indole-3-carboximidamide;
- [2-(3,5-Dimethyl-isoxazol-4-yl)-1-(4-hydroxy-phenyl)-1H-indol-3-yl]-carbamic acid tert-butyl ester;
- 4-[3-Amino-2-(3,5-dimethyl-isoxazol-4-yl)-indol-1-yl]-phenol;
- (Z)-2-(3,5-dimethylisoxazol-4-yl)-7-fluoro-N'-hydroxy-1-(4-hydroxyphenyl)-1H-indole-3-carboximidamide;
- (Z)-2-(5-chlorothiophen-2-yl)-N'-hydroxy-1-(4-hydroxyphenyl)-1H-indole-3-carboximidamide;
- 1-(2,3-Difluoro-4-hydroxy-phenyl)-2-(3,5-dimethyl-isoxazol-4-yl)-1H-indole-3-carbonitrile;
- 2-(3,5-dimethylisoxazol-4-yl)-1-(4-hydroxyphenyl)-1H-indole-3-carbohydrazonamide;
- 4-(2-(3,5-dimethylisoxazol-4-yl)-3-(1,2,4-oxadiazol-3-yl)-1H-indol-1-yl)phenol;
- 2-(3,5-Dimethyl-isoxazol-4-yl)-1-(4-hydroxy-phenyl)-1H-indole-3-carboxylic acid, methyl ester;
- 2-(3,5-Dimethyl-isoxazol-4-yl)-1-(4-hydroxy-phenyl)-1H-indole-3-carboxylic acid, hydroxyamide;
- 4-[2-(3,5-Dimethyl-isoxazol-4-yl)-3-methanesulfonyl-indol-1-yl]-phenol;
- 1-[2-(3,5-Dimethyl-isoxazol-4-yl)-1-(4-hydroxy-phenyl)-1H-indol-3-yl]-2,2,2-trifluoro-ethanone;
- 4-(3-bromo-2-(3,5-dimethylisoxazol-4-yl)-1H-indol-1-yl)phenol;
- 2-Bromo-5-fluoro-1-(4-hydroxy-phenyl)-1H-indole-3-carbonitrile;
- (Z)-2-(4-fluorophenoxy)-N'-hydroxy-1-(4-hydroxyphenyl)-1H-indole-3-carboximidamide;
- 4-(2-(3,5-dimethylisoxazol-4-yl)-3-nitro-1H-indol-1-yl)phenol;
- 4-(3-(dihydroxyamino)-2-(3,5-dimethylisoxazol-4-yl)-1H-indol-1-yl)phenol;
- N-(2-(3,5-dimethylisoxazol-4-yl)-1-(4-hydroxyphenyl)-1H-indol-3-yl)acetamide
- N-(2-(3,5-dimethylisoxazol-4-yl)-1-(4-hydroxyphenyl)-1H-indol-3-yl)methanesulfonamide;
- 1-(2-(3,5-dimethylisoxazol-4-yl)-1-(4-hydroxyphenyl)-1H-indol-3-yl)urea;
- 4-(2-(3,5-dimethylisoxazol-4-yl)-3-thiocyanato-1H-indol-1-yl)phenol;
- (E)-2-(3,5-dimethylisoxazol-4-yl)-1-(4-hydroxyphenyl)-1H-indol-3-yl N'-hydroxycarbamimidothioate;
- 4-(3-benzyl-2-phenyl-1H-indol-1-yl)phenol;
- 2-(2-(3,5-dimethylisoxazol-4-yl)-1-(4-hydroxyphenyl)-1H-indol-3-yl)-2-oxoacetamide;
- (Z)-2-(2-(3,5-dimethylisoxazol-4-yl)-1-(4-hydroxyphenyl)-1H-indol-3-yl)-2-(hydroxyimino)acetamide;
- 2-(2-(3,5-dimethylisoxazol-4-yl)-1-(4-hydroxyphenyl)-1H-indol-3-yl)-2-hydroxyacetamide;
- 2-(2-(3,5-dimethylisoxazol-4-yl)-1-(4-hydroxyphenyl)-1H-indol-3-yl)acetamide;
- 2-((Z)-But-1-enyl)-1-(4-hydroxy-phenyl)-1H-indole-3-carbonitrile;
- 1-(4-Hydroxy-phenyl)-2-(2-methyl-prop-1-enyl)-1H-indole-3-carbonitrile;
- 1-(2,3-Difluoro-4-hydroxy-phenyl)-2-(2-methyl-allyl)-1H-indole-3-carbonitrile;
- (Z)-2-(5-ethyl-3-methylisoxazol-4-yl)-N'-hydroxy-1-(4-hydroxyphenyl)-1H-indole-3-carboximidamide;
- 4-(2-(3,5-dimethylisoxazol-4-yl)-3-phenyl-1H-indol-1-yl)phenol;
- 4-(3-chloro-2-(3,5-dimethylisoxazol-4-yl)-1H-indol-1-yl)phenol;
- 2-(3,5-dimethylisoxazol-4-yl)-1-(4-hydroxyphenyl)-1H-indole-3-sulfonamide;
- 2-(3,5-dimethylisoxazol-4-yl)-1-(2-fluoro-4-hydroxyphenyl)-1H-indole-3-carboximidamide;
- 1-(4-Hydroxy-phenyl)-2-phenyl-1H-indole-3-carbonitrile;
- 1-(4-Hydroxy-phenyl)-2-methyl-1H-indole-3-carbonitrile;
- 2-(3-Cyano-thiophen-2-yl)-1-(4-hydroxy-phenyl)-1H-indole-3-carbonitrile;
- 1-(4-Hydroxy-phenyl)-2-((E)-propenyl)-1H-indole-3-carbonitrile;
- 1-(4-Hydroxy-phenyl)-2-thiophen-2-yl-1H-indole-3-carbonitrile;
- 2-(3,5-Dimethyl-isoxazol-4-yl)-1-(4-hydroxy-phenyl)-1H-indole-3-carbonitrile;
- 1-(4-Hydroxy-phenyl)-2-pyridin-4-yl-1H-indole-3-carbonitrile;
- 1-(4-Hydroxy-phenyl)-2-(1-methyl-1H-pyrrol-2-yl)-1H-indole-3-carbonitrile;
- 1-(4-Hydroxy-phenyl)-2-(3-methyl-thiophen-2-yl)-1H-indole-3-carbonitrile;
- 1-(4-Hydroxy-phenyl)-2-isopropylamino-1H-indole-3-carbonitrile;
- 2-Ethylamino-1-(4-hydroxy-phenyl)-1H-indole-3-carbonitrile;
- 2-Butylamino-1-(4-hydroxy-phenyl)-1H-indole-3-carbonitrile;
- 1-(4-Hydroxy-phenyl)-2-piperidin-1-yl-1H-indole-3-carbonitrile;
- 1-(4-Hydroxy-phenyl)-2-pyrrolidin-1-yl-1H-indole-3-carbonitrile;
- 1-(4-Hydroxy-phenyl)-2-morpholin-4-yl-1H-indole-3-carbonitrile;
- 2-Diethylamino-1-(4-hydroxy-phenyl)-1H-indole-3-carbonitrile;

2-Ethynyl-1-(4-hydroxy-phenyl)-1H-indole-3-carbonitrile;
1-(4-Hydroxy-phenyl)-2-vinyl-1H-indole-3-carbonitrile;
1-(4-Hydroxy-phenyl)-1H-indole-2,3-dicarbonitrile;
1-(4-Hydroxy-phenyl)-2-prop-1-ynyl-1H-indole-3-carbonitrile;
1-(4-Hydroxy-phenyl)-2-pyridin-2-yl-1H-indole-3-carbonitrile;
1-(4-Hydroxy-phenyl)-2-(2-methyl-allyl)-1H-indole-3-carbonitrile;
1-(4-Hydroxy-phenyl)-2-((Z)-propenyl)-1H-indole-3-carbonitrile;
2-(Butyl-methyl-amino)-1-(4-hydroxy-phenyl)-1H-indole-3-carbonitrile;
1-(4-Hydroxy-phenyl)-2-((Z)-1-methyl-propenyl)-1H-indole-3-carbonitrile;
1-(4-Hydroxy-phenyl)-2-imidazol-1-yl-1H-indole-3-carbonitrile;
1-(4-Hydroxy-phenyl)-2-[1,2,4]triazol-1-yl-1H-indole-3-carbonitrile;
2-(3,5-Dimethyl-pyrazol-1-yl)-1-(4-hydroxy-phenyl)-1H-indole-3-carbonitrile;
1-(4-Hydroxy-phenyl)-2-pyrazol-1-yl-1H-indole-3-carbonitrile;
1-(4-Hydroxy-phenyl)-2-(5-methyl-imidazol-1-yl)-1H-indole-3-carbonitrile;
1-(4-Hydroxy-phenyl)-2-(5-methyl-pyrazol-1-yl)-1H-indole-3-carbonitrile;
1-(4-Hydroxy-phenyl)-2-(3-methyl-pyrazol-1-yl)-1H-indole-3-carbonitrile;
1-(4-Hydroxy-phenyl)-2-thiazol-2-yl-1H-indole-3-carbonitrile;
1-(4-Hydroxy-phenyl)-2-(2-methoxy-thiazol-4-yl)-1H-indole-3-carbonitrile;
1-(4-Hydroxy-phenyl)-2-thiazol-4-yl-1H-indole-3-carbonitrile;
1-(4-Hydroxy-phenyl)-2-(3-methyl-but-2-enyl)-1H-indole-3-carbonitrile;
2-((E)-But-1-enyl)-1-(4-hydroxy-phenyl)-1H-indole-3-carbonitrile;
1-(4-Hydroxy-phenyl)-2-(5-methyl-thiophen-2-yl)-1H-indole-3-carbonitrile;
2-(5-Acetyl-thiophen-2-yl)-1-(4-hydroxy-phenyl)-1H-indole-3-carbonitrile;
1-(4-Hydroxy-phenyl)-2-(1-methyl-1H-pyrazol-4-yl)-1H-indole-3-carbonitrile;
2-(5-Chloro-thiophen-2-yl)-1-(4-hydroxy-phenyl)-1H-indole-3-carbonitrile;
1-(4-Hydroxy-phenyl)-2-(4-methyl-thiophen-3-yl)-1H-indole-3-carbonitrile;
1-(4-Hydroxy-phenyl)-2-(4-methyl-thiophen-2-yl)-1H-indole-3-carbonitrile;
2-(4-Cyano-thiophen-3-yl)-1-(4-hydroxy-phenyl)-1H-indole-3-carbonitrile;
1-(4-Hydroxy-phenyl)-2-(2-methyl-2H-pyrazol-3-yl)-1H-indole-3-carbonitrile;
1-(4-Hydroxy-phenyl)-2-(1,3,5-trimethyl-1H-pyrazol-4-yl)-1H-indole-3-carbonitrile;
2-(2-Acetyl-pyrrol-1-yl)-1-(4-hydroxy-phenyl)-1H-indole-3-carbonitrile;
2-(2-Ethyl-pyrrol-1-yl)-1-(4-hydroxy-phenyl)-1H-indole-3-carbonitrile;
2-(2-Cyano-pyrrol-1-yl)-1-(4-hydroxy-phenyl)-1H-indole-3-carbonitrile;
1-(4-Hydroxy-phenyl)-2-(2-methyl-pyrrol-1-yl)-1H-indole-3-carbonitrile;
1-(3-Chloro-5-fluoro-4-hydroxy-phenyl)-2-phenyl-1H-indole-3-carbonitrile;
1-(3-Chloro-5-fluoro-4-hydroxy-phenyl)-2-(3-cyano-thiophen-2-yl)-1H-indole-3-carbonitrile;
1-(3-Chloro-5-fluoro-4-hydroxy-phenyl)-2-(3-cyano-furan-2-yl)-1H-indole-3-carbonitrile;
2-Bromo-1-(3-chloro-5-fluoro-4-hydroxy-phenyl)-1H-indole-3-carbonitrile;
2-Bromo-1-(2-fluoro-4-hydroxy-phenyl)-1H-indole-3-carbonitrile;
1-(2-Fluoro-4-hydroxy-phenyl)-2-phenyl-1H-indole-3-carbonitrile;
2-Bromo-1-(3-fluoro-4-hydroxy-phenyl)-1H-indole-3-carbonitrile;
2-Bromo-1-(2,3-difluoro-4-hydroxy-phenyl)-1H-indole-3-carbonitrile;
2-Bromo-1-(2,5-difluoro-4-hydroxy-phenyl)-1H-indole-3-carbonitrile;
2-Bromo-1-(3-chloro-4-hydroxy-phenyl)-1H-indole-3-carbonitrile;
2-Bromo-1-(3,5-difluoro-4-hydroxy-phenyl)-1H-indole-3-carbonitrile;
1-(3-Fluoro-4-hydroxy-phenyl)-2-phenyl-1H-indole-3-carbonitrile;
1-(3,5-Difluoro-4-hydroxy-phenyl)-2-phenyl-1H-indole-3-carbonitrile;
1-(3-Chloro-4-hydroxy-phenyl)-2-phenyl-1H-indole-3-carbonitrile;
1-(2,3-Difluoro-4-hydroxy-phenyl)-2-phenyl-1H-indole-3-carbonitrile;
1-(2,5-Difluoro-4-hydroxy-phenyl)-2-phenyl-1H-indole-3-carbonitrile;
1-(3,5-Difluoro-4-hydroxy-phenyl)-2-thiophen-3-yl-1H-indole-3-carbonitrile;
1-(3,5-Difluoro-4-hydroxy-phenyl)-2-thiophen-2-yl-1H-indole-3-carbonitrile;
1-(3,5-Difluoro-4-hydroxy-phenyl)-2-(3,5-dimethyl-isoxazol-4-yl)-1H-indole-3-carbonitrile;
1-(3,5-Difluoro-4-hydroxy-phenyl)-2-(1-methyl-1H-pyrrol-2-yl)-1H-indole-3-carbonitrile;
1-(3,5-Difluoro-4-hydroxy-phenyl)-2-(3-methyl-thiophen-2-yl)-1H-indole-3-carbonitrile;
1-(3,5-Difluoro-4-hydroxy-phenyl)-2-(1-methyl-1H-pyrazol-4-yl)-1H-indole-3-carbonitrile;
1-(3,5-Difluoro-4-hydroxy-phenyl)-2-pyridin-4-yl-1H-indole-3-carbonitrile;
1-(3-Chloro-4-hydroxy-phenyl)-2-thiophen-3-yl-1H-indole-3-carbonitrile;
1-(3-Chloro-4-hydroxy-phenyl)-2-thiophen-2-yl-1H-indole-3-carbonitrile;
1-(3-Chloro-4-hydroxy-phenyl)-2-(3,5-dimethyl-isoxazol-4-yl)-1H-indole-3-carbonitrile;
1-(3-Chloro-4-hydroxy-phenyl)-2-(1-methyl-1H-pyrrol-2-yl)-1H-indole-3-carbonitrile;
1-(3-Chloro-4-hydroxy-phenyl)-2-(3-methyl-thiophen-2-yl)-1H-indole-3-carbonitrile;
1-(3-Chloro-4-hydroxy-phenyl)-2-pyridin-4-yl-1H-indole-3-carbonitrile;
1-(3-Fluoro-4-hydroxy-phenyl)-2-thiophen-3-yl-1H-indole-3-carbonitrile;
1-(3-Fluoro-4-hydroxy-phenyl)-2-thiophen-2-yl-1H-indole-3-carbonitrile;
2-(3,5-Dimethyl-isoxazol-4-yl)-1-(3-fluoro-4-hydroxy-phenyl)-1H-indole-3-carbonitrile;
1-(3-Fluoro-4-hydroxy-phenyl)-2-(1-methyl-1H-pyrrol-2-yl)-1H-indole-3-carbonitrile;

1-(3-Fluoro-4-hydroxy-phenyl)-2-(3-methyl-thiophen-2-yl)-1H-indole-3-carbonitrile;
1-(3-Fluoro-4-hydroxy-phenyl)-2-(1-methyl-1H-pyrazol-4-yl)-1H-indole-3-carbonitrile;
1-(3-Fluoro-4-hydroxy-phenyl)-2-pyridin-4-yl-1H-indole-3-carbonitrile;
2-Dimethylamino-1-(2-fluoro-4-hydroxy-phenyl)-1H-indole-3-carbonitrile;
2-(3,5-Dimethyl-isoxazol-4-yl)-1-(2-fluoro-4-hydroxyphenyl)-1H-indole-3-carbonitrile;
1-(3-Fluoro-4-hydroxy-phenyl)-2-((E)-propenyl)-1H-indole-3-carbonitrile;
1-(3-Fluoro-4-hydroxy-phenyl)-2-((Z)-propenyl)-1H-indole-3-carbonitrile;
1-(2,3-Difluoro-4-hydroxy-phenyl)-2-((Z)-propenyl)-1H-indole-3-carbonitrile;
1-(2,3-Difluoro-4-hydroxy-phenyl)-2-vinyl-1H-indole-3-carbonitrile;
1-(2,3-Difluoro-4-hydroxy-phenyl)-2-thiophen-3-yl-1H-indole-3-carbonitrile;
1-(2,3-Difluoro-4-hydroxy-phenyl)-2-thiophen-2-yl-1H-indole-3-carbonitrile;
1-(2,3-Difluoro-4-hydroxy-phenyl)-2-(3-methyl-thiophen-2-yl)-1H-indole-3-carbonitrile;
1-(2,3-Difluoro-4-hydroxy-phenyl)-2-(1-methyl-1H-pyrrol-2-yl)-1H-indole-3-carbonitrile;
2-(2-Acetyl-pyrrol-1-yl)-1-(3-fluoro-4-hydroxy-phenyl)-1H-indole-3-carbonitrile;
1-(3-Fluoro-4-hydroxy-phenyl)-2-pyrrol-1-yl-1H-indole-3-carbonitrile;
1-(2,3-Difluoro-4-hydroxy-phenyl)-2-pyrrol-1-yl-1H-indole-3-carbonitrile;
1-(2,3-Difluoro-4-hydroxy-phenyl)-2-prop-1-ynyl-1H-indole-3-carbonitrile;
1-(3-Fluoro-4-hydroxy-phenyl)-2-(2-methyl-prop-1-enyl)-1H-indole-3-carbonitrile;
1-(2,3-Difluoro-4-hydroxy-phenyl)-2-(2-methyl-prop-1-enyl)-1H-indole-3-carbonitrile;
2-(2-Acetyl-pyrrol-1-yl)-1-(2,3-difluoro-4-hydroxy-phenyl)-1H-indole-3-carbonitrile;
1-(3-Fluoro-4-hydroxy-phenyl)-2-pyrazol-1-yl-1H-indole-3-carbonitrile;
1-(2,3-Difluoro-4-hydroxy-phenyl)-2-pyrazol-1-yl-1H-indole-3-carbonitrile;
2-(2,5-Dimethyl-pyrrol-1-yl)-1-(3-fluoro-4-hydroxy-phenyl)-1H-indole-3-carbonitrile;
2-(2-Ethyl-pyrrol-1-yl)-1-(3-fluoro-4-hydroxy-phenyl)-1H-indole-3-carbonitrile;
2-(2-Cyano-pyrrol-1-yl)-1-(3-fluoro-4-hydroxy-phenyl)-1H-indole-3-carbonitrile;
1-(3-Fluoro-4-hydroxy-phenyl)-2-(2-methyl-pyrrol-1-yl)-1H-indole-3-carbonitrile;
1-(2,3-Difluoro-4-hydroxy-phenyl)-2-(2-ethyl-pyrrol-1-yl)-1H-indole-3-carbonitrile;
2-(2-Cyano-pyrrol-1-yl)-1-(2,3-difluoro-4-hydroxy-phenyl)-1H-indole-3-carbonitrile;
1-(2,3-Difluoro-4-hydroxy-phenyl)-2-(2-methyl-pyrrol-1-yl)-1H-indole-3-carbonitrile;
1-(2-Fluoro-4-hydroxy-phenyl)-2-pyrrol-1-yl-1H-indole-3-carbonitrile;
1-(2,3-difluoro-4-hydroxyphenyl)-2-(3-methylbut-2-enyl)-1H-indole-3-carbonitrile;
[1-(4-Hydroxy-phenyl)-2-phenyl-1H-indol-3-yl]-acetonitrile;
[1-(4-Hydroxy-phenyl)-2-phenyl-1H-indol-3-yl]-acetic acid;
2-[1-(4-Hydroxy-phenyl)-2-phenyl-1H-indol-3-yl]-acetamide;
4-(3-Isopropenyl-2-phenyl-indol-1-yl)-phenol;
4-[3-(2-Methyl-2H-pyrazol-3-yl)-2-phenyl-indol-1-yl]-phenol;
4-(2-Phenyl-3-thiazol-4-yl-indol-1-yl)-phenol;
4-(2-Phenyl-3-prop-1-ynyl-indol-1-yl)-phenol;
1-(4-Hydroxy-phenyl)-2-((E)-propenyl)-1H-indole-3-carboxylic acid, amide;
1-(4-Hydroxy-phenyl)-2-(2-methyl-prop-1-enyl)-1H-indole-3-carboxylic acid, amide;
1-(4-Hydroxy-phenyl)-2-((Z)-1-methyl-propenyl)-1H-indole-3-carboxylic acid, amide;
4-(2-Phenyl-3-pyrazol-1-yl-indol-1-yl)-phenol;
4-(3-Imidazol-1-yl-2-phenyl-indol-1-yl)-phenol;
4-[3-(5-Methyl-pyrazol-1-yl)-2-phenyl-indol-1-yl]-phenol;
2-Bromo-1-(4-hydroxy-phenyl)-1H-indole-3-carboxylic acid, amide;
1-(4-Hydroxy-phenyl)-2-((Z)-3,3,3-trifluoro-propenyl)-1H-indole-3-carbonitrile;
(Z)-2-bromo-N'-hydroxy-1-(4-hydroxyphenyl)-1H-indole-3-carboximidamide;
(Z)—N'-hydroxy-1-(4-hydroxyphenyl)-2-(1H-pyrrol-1-yl)-1H-indole-3-carboximidamide;
2-(3,5-Dimethyl-isoxazol-4-yl)-1-(4-hydroxy-phenyl)-1H-indole-3-carboxylic acid, amide;
(Z)—N'-hydroxy-1-(4-hydroxyphenyl)-2-(2-methylprop-1-enyl)-1H-indole-3-carboximidamide;
1-(4-Hydroxy-phenyl)-2-phenyl-1H-indole-3-carboxylic acid; hydroxyamide;
(Z)—N'-hydroxy-1-(4-hydroxyphenyl)-2-phenyl-1H-indole-3-carboximidamide;
1-(4-Hydroxy-phenyl)-2-pyrrol-1-yl-1H-indole-3-carboxylic acid, amide;
[1-(4-Hydroxy-phenyl)-2-pyrrol-1-yl-1H-indol-3-yl]-carbamic acid tert-butyl ester;
2-(3,5-Dimethyl-isoxazol-4-yl)-1-(4-hydroxy-phenyl)-N-methyl-1H-indole-3-carboxamidine;
Methyl 2-(3,5-dimethylisoxazol-4-yl)-1-(4-hydroxyphenyl)-1H-indole-3-carbimidate;
N-((2-(3,5-dimethylisoxazol-4-yl)-1-(4-hydroxyphenyl)-1H-indol-3-yl)(imino)methyl)acetamide;
2-(5-ethyl-3-methylisoxazol-4-yl)-1-(4-hydroxyphenyl)-1H-indole-3-carboxamide;
(Z)-2-(2-ethyl-1H-pyrrol-1-yl)-N'-hydroxy-1-(4-hydroxyphenyl)-1H-indole-3-carboximidamide;
(Z)—N'-hydroxy-1-(4-hydroxyphenyl)-2-(2-methyl-1H-pyrrol-1-yl)-1H-indole-3-carboximidamide;
1-(4-hydroxyphenyl)-2-(2-methyl-1H-pyrrol-1-yl)-1H-indole-3-carboxamide;
4-(3-chloro-2-(3,5-dimethylisoxazol-4-yl)-1H-indol-1-yl)phenol;
(Z)-2-((Z)-but-2-en-2-yl)-N'-hydroxy-1-(4-hydroxyphenyl)-1H-indole-3-carboximidamide;
(Z)—N'-hydroxy-1-(4-hydroxyphenyl)-2-(5-methyl-1H-pyrazol-1-yl)-1H-indole-3-carboximidamide;
(Z)—N'-hydroxy-1-(4-hydroxyphenyl)-2-(4-methylthiophen-3-yl)-1H-indole-3-carboximidamide;
(Z)-2-(2,5-dimethyl-1H-pyrrol-1-yl)-N'-hydroxy-1-(4-hydroxyphenyl)-1H-indole-3-carboximidamide;
(Z)—N'-hydroxy-1-(4-hydroxyphenyl)-2-phenoxy-1H-indole-3-carboximidamide;
1-(4-Hydroxy-phenyl)-2-phenyl-1H-indole-3-carboxylic acid;
2-(3,5-Dimethyl-isoxazol-4-yl)-1-(3-fluoro-4-hydroxyphenyl)-1H-indole-3-carboxylic acid;

2-(3,5-Dimethyl-isoxazol-4-yl)-1-(2-fluoro-4-hydroxy-phenyl)-1H-indole-3-carboxylic acid;
1-(2,3-Difluoro-4-hydroxy-phenyl)-2-(3,5-dimethyl-isoxazol-4-yl)-1H-indole-3-carboxylic acid;
1-(4-Hydroxy-phenyl)-2-((Z)-propenyl)-1H-indole-3-carboxylic acid;
1-(4-Hydroxy-phenyl)-2-((E)-propenyl)-1H-indole-3-carboxylic acid;
1-(4-Hydroxy-phenyl)-2-(2-methyl-prop-1-enyl)-1H-indole-3-carboxylic acid;
1-(4-Hydroxy-phenyl)-2-(2-methyl-allyl)-1H-indole-3-carboxylic acid;
1-(4-Hydroxy-phenyl)-2-((Z)-1-methyl-propenyl)-1H-indole-3-carboxylicacid;
1-(3-Fluoro-4-hydroxy-phenyl)-2-thiophen-3-yl-1H-indole-3-carboxylic acid;
1-(3-Fluoro-4-hydroxy-phenyl)-2-thiophen-2-yl-1H-indole-3-carboxylic acid;
1-(3-Fluoro-4-hydroxy-phenyl)-2-(1-methyl-1H-pyrrol-2-yl)-1H-indole-3-carboxylic acid;
1-(3-Fluoro-4-hydroxy-phenyl)-2-(3-methyl-thiophen-2-yl)-1H-indole-3-carboxylic acid;
2-Bromo-1-(4-hydroxy-phenyl)-1H-indole-3-carboxylic acid;
1-(4-Hydroxy-phenyl)-2-pyrrol-1-yl-1H-indole-3-carboxylic acid;
2,7-Dibromo-1-(2,5-difluoro-4-hydroxy-phenyl)-1H-indole-3-carbonitrile;
2-Bromo-4-fluoro-1-(4-hydroxy-phenyl)-1H-indole-3-carbonitrile;
4-Fluoro-1-(4-hydroxy-phenyl)-2-pyrrol-1-yl-1H-indole-3-carbonitrile;
4-Fluoro-1-(4-hydroxy-phenyl)-2-phenyl-1H-indole-3-carbonitrile;
2-(3,5-Dimethyl-isoxazol-4-yl)-4-fluoro-1-(4-hydroxy-phenyl)-1H-indole-3-carbonitrile;
4-Fluoro-1-(4-hydroxy-phenyl)-2-(2-methyl-prop-1-enyl)-1H-indole-3-carbonitrile;
5-Fluoro-1-(4-hydroxy-phenyl)-2-phenyl-1H-indole-3-carbonitrile;
2-(3,5-Dimethyl-isoxazol-4-yl)-5-fluoro-1-(4-hydroxy-phenyl)-1H-indole-3-carbonitrile;
5-Fluoro-1-(4-hydroxy-phenyl)-2-pyrrol-1-yl-1H-indole-3-carbonitrile;
5-Fluoro-1-(4-hydroxy-phenyl)-2-(2-methyl-prop-1-enyl)-1H-indole-3-carbonitrile;
(Z)-2-(3,5-dimethylisoxazol-4-yl)-5-fluoro-N'-hydroxy-1-(4-hydroxyphenyl)-1H-indole-3-carboximidamide;
(Z)-2-(3,5-dimethylisoxazol-4-yl)-4-fluoro-N'-hydroxy-1-(4-hydroxyphenyl)-1H-indole-3-carboximidamide;
(Z)-5-fluoro-N'-hydroxy-1-(4-hydroxyphenyl)-2-(2-methylprop-1-enyl)-1H-indole-3-carboximidamide;
4-Chloro-2-(3,5-dimethyl-isoxazol-4-yl)-1-(4-hydroxy-phenyl)-1H-indole-3-carbonitrile;
2-(3,5-dimethylisoxazol-4-yl)-4,5-difluoro-1-(4-hydroxyphenyl)-1H-indole-3-carbonitrile;
2-(4-cyano-1-methyl-1H-pyrazol-5-yl)-4-fluoro-1-(4-hydroxyphenyl)-1H-indole-3-carbonitrile;
2-(3,5-dimethylisoxazol-4-yl)-5-fluoro-1-(4-hydroxyphenyl)-1H-indole-3-carboximidamide;
2-(3,5-dimethylisoxazol-4-yl)-5-fluoro-1-(4-hydroxyphenyl)-1H-indole-3-carboxamide;
2-Bromo-7-fluoro-1-(4-hydroxy-phenyl)-1H-indole-3-carbonitrile;
2-(3,5-Dimethyl-isoxazol-4-yl)-7-fluoro-1-(4-hydroxy-phenyl)-1H-indole-3-carbonitrile;
2-(3,5-Dimethyl-isoxazol-4-yl)-4,7-difluoro-1-(4-hydroxy-phenyl)-1H-indole-3-carbonitrile;
(Z)-2-(3,5-dimethylisoxazol-4-yl)-4,7-difluoro-N'-hydroxy-1-(4-hydroxyphenyl)-1H-indole-3-carboximidamide;
1-(2,5-Difluoro-4-hydroxy-phenyl)-2-(3,5-dimethyl-isoxazol-4-yl)-1H-indole-3-carbonitrile;
1-(3-bromo-4-hydroxyphenyl)-2-(2-methylprop-1-enyl)-1H-indole-3-carboxamide;
(Z)-2-(3,5-dimethylisoxazol-4-yl)-1-(2-fluoro-4-hydroxyphenyl)-N'-hydroxy-1H-indole-3-carboximidamide;
(Z)-1-(2,5-difluoro-4-hydroxyphenyl)-2-(3,5-dimethyl-isoxazol-4-yl)-N'-hydroxy-1H-indole-3-carboximidamide;
(Z)-1-(3,5-difluoro-4-hydroxyphenyl)-2-(3,5-dimethyl-isoxazol-4-yl)-N'-hydroxy-1H-indole-3-carboximidamide;
(Z)-2-(3,5-dimethylisoxazol-4-yl)-1-(3-fluoro-4-hydroxyphenyl)-N'-hydroxy-1H-indole-3-carboximidamide;
(Z)-1-(3-chloro-4-hydroxyphenyl)-2-(3,5-dimethylisoxazol-4-yl)-N'-hydroxy-1H-indole-3-carboximidamide;
2-(3,5-dimethylisoxazol-4-yl)-1-(2-fluoro-4-hydroxyphenyl)-1H-indole-3-carboxamide;
(Z)-1-(2,3-difluoro-4-hydroxyphenyl)-2-(3,5-dimethyl-isoxazol-4-yl)-N'-hydroxy-1H-indole-3-carboximidamide;
1-(2,3-difluoro-4-hydroxyphenyl)-2-(3,5-dimethylisoxazol-4-yl)-1H-indole-3-carboxamide;
1-(2-fluoro-4-hydroxyphenyl)-2-(3-methylthiophen-2-yl)-1H-indole-3-carbonitrile;
2-(3,5-dimethyl-1H-pyrazol-4-yl)-1-(2-fluoro-4-hydroxyphenyl)-1H-indole-3-carbonitrile;
1-(2-fluoro-4-hydroxyphenyl)-2-(1-methyl-1H-pyrazol-5-yl)-1H-indole-3-carbonitrile;
1-(2-fluoro-4-hydroxyphenyl)-2-(1,3,5-trimethyl-1H-pyrazol-4-yl)-1H-indole-3-carbonitrile;
1-(2-fluoro-4-hydroxyphenyl)-2-(3-(trifluoromethyl)-1H-pyrazol-4-yl)-1H-indole-3-carbonitrile;
(Z)-1-(2-fluoro-4-hydroxyphenyl)-N'-hydroxy-2-(3-methylthiophen-2-yl)-1H-indole-3-carboximidamide;
(Z)-1-(2-fluoro-4-hydroxyphenyl)-N'-hydroxy-2-(1-methyl-1H-pyrazol-5-yl)-1H-indole-3-carboximidamide;
(Z)-1-(2-fluoro-4-hydroxyphenyl)-N'-hydroxy-2-(1,3,5-trimethyl-1H-pyrazol-4-yl)-1H-indole-3-carboximidamide;
(Z)-4-fluoro-1-(2-fluoro-4-hydroxyphenyl)-N'-hydroxy-2-(1-methyl-1H-pyrazol-5-yl)-1H-indole-3-carboximidamide;
(Z)-4-fluoro-1-(2-fluoro-4-hydroxyphenyl)-N'-hydroxy-2-(1,3,5-trimethyl-1H-pyrazol-4-yl)-1H-indole-3-carboximidamide;
(Z)-2-(3,5-dimethyl-1H-pyrazol-4-yl)-4-fluoro-1-(2-fluoro-4-hydroxyphenyl)-N'-hydroxy-1H-indole-3-carboximidamide;
(Z)-4-fluoro-1-(2-fluoro-4-hydroxyphenyl)-N'-hydroxy-2-(3-methylthiophen-2-yl)-1H-indole-3-carboximidamide;
(Z)-2-(3,5-dimethylisoxazol-4-yl)-4-fluoro-1-(2-fluoro-4-hydroxyphenyl)-N'-hydroxy-1H-indole-3-carboximidamide;
(Z)-1-(2-fluoro-4-hydroxyphenyl)-N'-hydroxy-2-(3-methylthiophen-2-yl)-1H-indole-3-carboximidamide;
(Z)-1-(2-fluoro-4-hydroxyphenyl)-N'-hydroxy-2-(1-methyl-1H-pyrazol-5-yl)-1H-indole-3-carboximidamide;
(Z)-1-(2-fluoro-4-hydroxyphenyl)-N'-hydroxy-2-(1,3,5-trimethyl-1H-pyrazol-4-yl)-1H-indole-3-carboximidamide;

(Z)-2-(3,5-dimethyl-1H-pyrazol-4-yl)-1-(2-fluoro-4-hydroxyphenyl)-N'-hydroxy-1H-indole-3-carboximidamide;
methyl 2-(3,5-dimethylisoxazol-4-yl)-1-(2-fluoro-4-hydroxyphenyl)-1H-indole-3-carbimidate;
2-(3,5-dimethylisoxazol-4-yl)-1-(3-fluoro-4-hydroxyphenyl)-1H-indole-3-carboxamide;
1-(2,5-difluoro-4-hydroxyphenyl)-2-(3,5-dimethylisoxazol-4-yl)-1H-indole-3-carboximidamide;
2-(3,5-dimethylisoxazol-4-yl)-1-(3-fluoro-4-hydroxyphenyl)-1H-indole-3-carboximidamide;
(Z)-1-(3-fluoro-4-hydroxyphenyl)-N'-hydroxy-2-(1H-pyrrol-1-yl)-1H-indole-3-carboximidamide;
1-(3-fluoro-4-hydroxyphenyl)-2-(1H-pyrrol-1-yl)-1H-indole-3-carboxamide;
(Z)-1-(2,3-difluoro-4-hydroxyphenyl)-N'-hydroxy-2-(1H-pyrrol-1-yl)-1H-indole-3-carboximidamide;
1-(2,3-difluoro-4-hydroxyphenyl)-2-(1H-pyrrol-1-yl)-1H-indole-3-carboxamide;
(Z)-2-(2,5-dimethyl-1H-pyrrol-1-yl)-1-(3-fluoro-4-hydroxyphenyl)-N'-hydroxy-1H-indole-3-carboximidamide;
(Z)-1-(3-fluoro-4-hydroxyphenyl)-N'-hydroxy-2-(2-methyl-1H-pyrrol-1-yl)-1H-indole-3-carboximidamide;
1-(3,5-difluoro-4-hydroxyphenyl)-2-(3,5-dimethylisoxazol-4-yl)-1H-indole-3-carboxamide; and
(Z)-2-(3,5-dimethylisoxazol-4-yl)-6-fluoro-N'-hydroxy-1-(4-hydroxyphenyl)-1H-indole-3-carboximidamide.

19. A method for the treatment of a disease or disorder associated with estrogen receptor activity in a mammal, wherein said disease or disorder associated with estrogen receptor activity is selected from hot flashes, cardiovascular disease, impairment of cognitive functioning, age-related mild cognitive impairment, cerebral degenerative disorders, restenosis, obesity, anxiety, depression, hearing disorders, multiple sclerosis, Parkinson's disease, Alzheimer's disease, Huntington's disease, amyotrophic lateral sclerosis, stroke, IBD, IBS, hypertension, lung cancer, colon cancer, breast cancer, prostate cancer and cholangiocarcinoma, which comprises administering to the mammal a therapeutically effective amount of a pharmaceutical composition which comprises a compound of formula (I) as defined in claim 1, or a pharmaceutically acceptable ester, amide, carbamate, solvate or salt thereof, including a salt of such an ester, amide or carbamate, and a solvate of such an ester, amide, carbamate or salt, together with a pharmaceutically acceptable carrier.

* * * * *